(12) United States Patent
Lian et al.

(10) Patent No.: US 12,396,458 B2
(45) Date of Patent: Aug. 26, 2025

(54) FUSED RING SUBSTITUTED AROMATIC COMPOUND AND PREPARATION METHOD THEREFOR, HERBICIDAL COMPOSITION, AND USE THEREOF

(71) Applicant: Qingdao Kingagroot Chemical Compound Co., Ltd., Qingdao (CN)

(72) Inventors: Lei Lian, Qingdao (CN); Xuegang Peng, Qingdao (CN); Rongbao Hua, Qingdao (CN); De Zhao, Qingdao (CN); Qi Cui, Qingdao (CN)

(73) Assignee: Qingdao Kingagroot Chemical Compound Co., Ltd., Qingdao (CN)

( * ) Notice: Subject to any disclaimer, the term of this patent is extended or adjusted under 35 U.S.C. 154(b) by 314 days.

(21) Appl. No.: 17/437,192

(22) PCT Filed: Jan. 12, 2021

(86) PCT No.: PCT/CN2021/071289
§ 371 (c)(1),
(2) Date: Sep. 8, 2021

(87) PCT Pub. No.: WO2021/143677
PCT Pub. Date: Jul. 22, 2021

(65) Prior Publication Data
US 2023/0091467 A1 Mar. 23, 2023

(30) Foreign Application Priority Data

Jan. 16, 2020 (CN) .......................... 202010056836.9
Feb. 28, 2020 (CN) ......................... 202010131605.X

(51) Int. Cl.
| | | |
|---|---|---|
| C07D 413/10 | (2006.01) | |
| A01N 43/80 | (2006.01) | |
| A01N 43/90 | (2006.01) | |
| C07D 413/14 | (2006.01) | |
| C07D 417/12 | (2006.01) | |
| C07D 471/04 | (2006.01) | |
| C07D 498/04 | (2006.01) | |
| C07D 513/04 | (2006.01) | |

(52) U.S. Cl.
CPC ............. *A01N 43/80* (2013.01); *A01N 43/90* (2013.01); *C07D 413/10* (2013.01); *C07D 413/14* (2013.01); *C07D 417/12* (2013.01); *C07D 471/04* (2013.01); *C07D 498/04* (2013.01); *C07D 513/04* (2013.01)

(58) Field of Classification Search
CPC .................................................. C07D 413/10
See application file for complete search history.

(56) References Cited

U.S. PATENT DOCUMENTS

| | | | |
|---|---|---|---|
| 5,013,659 | A | 5/1991 | Bedbrook et al. |
| 5,679,791 | A | 10/1997 | Crews, Jr. et al. |
| 2004/0110749 | A1 | 6/2004 | Nakatani et al. |

FOREIGN PATENT DOCUMENTS

| | | |
|---|---|---|
| CN | 1474694 A | 2/2004 |
| CN | 102875569 A | 1/2013 |
| CN | 105753853 A | 7/2016 |
| CN | 105777733 B | 12/2018 |
| CN | 109293640 A | 2/2019 |
| CN | 109864067 A | 6/2019 |
| CN | 111961041 A | 11/2020 |
| CN | 112745269 A | 5/2021 |
| EP | 0013111 A2 | 7/1980 |
| EP | 0131624 A1 | 1/1985 |
| EP | 0142924 A2 | 5/1985 |
| EP | 0193259 A1 | 9/1986 |
| EP | 0221044 A1 | 5/1987 |
| EP | 0242236 A1 | 10/1987 |
| EP | 0242246 A1 | 10/1987 |
| EP | 0257993 A2 | 3/1988 |
| JP | 2001288175 A | 10/2001 |
| JP | 2004517878 A1 | 6/2004 |
| RU | 2286989 C2 | 11/2006 |
| WO | WO 9113972 A1 | 9/1991 |
| WO | WO 9119806 A1 | 12/1991 |
| WO | WO 9200377 A1 | 1/1992 |

(Continued)

OTHER PUBLICATIONS

Wang, Da-Wei, et al. "Discovery of Novel N-Isoxazolinylphenyltriazinones as Promising Protoporphyrinogen IX Oxidase Inhibitors." J. Ag. and Food Chemistry. (2019), vol. 67, pp. 12382-12392). (Year: 2019).*

R. Zhang et al., Design, Synthesis, and Molecular Mechanism Studies of N-Phenylisoxazoline-thiadiazolo[3,4-a] Pyridazine Hybrids as Protoporphyrinogen IX Oxidase Inhibitors, Journal of Agricultural and Food Chemistry, vol. 68, pp. 13672-13684 (2020).

(Continued)

*Primary Examiner* — John S Kenyon
(74) *Attorney, Agent, or Firm* — FINNEGAN, HENDERSON, FARABOW, GARRETT & DUNNER LLP

(57) ABSTRACT

The disclosure relates to the field of pesticide technology, and in particular a type of fused-ring substituted aromatic compound represented by general formula I, preparation method, herbicidal composition and use thereof.

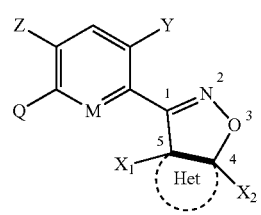

16 Claims, No Drawings

(56) References Cited

FOREIGN PATENT DOCUMENTS

| | | |
|---|---|---|
| WO | WO 9211376 A1 | 7/1992 |
| WO | WO 9214827 A1 | 9/1992 |
| WO | WO 1999055693 A2 | 11/1999 |
| WO | WO 0050409 A1 | 8/2000 |
| WO | WO 2011045224 A1 | 4/2011 |
| WO | WO 2012041789 A1 | 4/2012 |
| WO | WO 2018118781 A1 | 6/2018 |
| WO | WO 2019101551 A1 | 5/2019 |

OTHER PUBLICATIONS

P. Christou, Transformation Technology, *Trends in Plant Science*, 1:423-431 (1996).

H. Braun et al., The General Mitochondrial Processing Peptidase from Potato is an Integral Part of Cytochrome C Reductase of The Respiratory Chain, *EMBO J.* 11:3219-3227 (1992).

F. Wolter et al., Rbcs Genes in Solanum Tuberosum: Conservation of Transit Peptide and Exon Shuffling During Evolution, *Proc. Natl. Acad. Sci. USA*, 85:846-850 (1988).

U. Sonnewald et al., Transgenic Tobacco Plants Expressing Yeast-Derived Invertase in Either the Cytosol, Vacuole or Apoplast: A Powerful Tool for Studying Sucrose Metabolism and Sink/Source Interactions, *Plant J.* 1:95-106 (1991).

International Search Report and Written Opinion of counterpart International Application No. PCT/CN2021/071289, mailed Mar. 18, 2021.

D. Wang et al., Discovery of Novel N-Isoxazolinylphenyltriazinones as Promising Protoporphyrinogen IX Oxidase Inhibitors, *Journal of Agricultural and Food Chemistry*, vol. 67, No. 45, pp. 12382-12392 (2019).

Extended Search Report in counterpart European Patent Application No. 21740729.5 dated Feb. 5, 2024.

\* cited by examiner

FUSED RING SUBSTITUTED AROMATIC COMPOUND AND PREPARATION METHOD THEREFOR, HERBICIDAL COMPOSITION, AND USE THEREOF

CROSS REFERENCE TO RELATED APPLICATION

This application is a national stage filing under 35 U.S.C. § 371 of International Application No. PCT/CN2021/071289, filed Jan. 12, 2021, and claims the priority to and benefits of Chinese Application No. 202010056836.9, filed Jan. 16, 2020, and Chinese Application No. 02010131605.X, filed Feb. 28, 2020, which are incorporated herein by reference in their entireties.

TECHNICAL FIELD

The invention relates to the field of pesticide technology, and in particular a type of fused-ring substituted aromatic compound, preparation method, herbicidal composition and use thereof.

TECHNICAL BACKGROUND

Weed control is one of the most important links in the course of achieving high-efficiency agriculture. Various herbicides are available in the market, for example, patents WO00/50409 etc. disclose a use of a compound of general formula 1-aryl-4-thiotriazine as a herbicide; CN105753853A discloses an isoxazoline-containing uracil compound and its use as a herbicide. However, the herbicidal properties of these known compounds against harmful plants and their selectivity to crops are not completely satisfactory. And scientists still need to do continuously research and develop new herbicides with high efficacy, safety, economics and different modes of action due to problems such as the growing market, weed resistance, the service life and economics of pesticides as well as people's increasing concern on environment.

INVENTION CONTENTS

The present invention provides a type of fused-ring substituted aromatic compound, preparation method, herbicidal composition and application thereof. The compound has excellent herbicidal activity against gramineous weeds, broadleaf weeds, etc. even at low application rates, and has high selectivity for crops.

The technical solution adopted by the invention is as follows:

A fused-ring substituted aromatic compound, represented by general formula I:

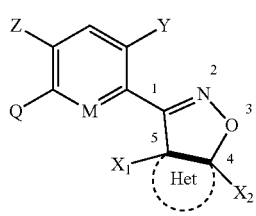

I wherein,

Q represents

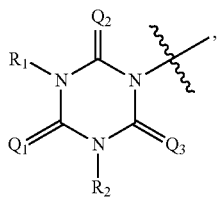

Q-1

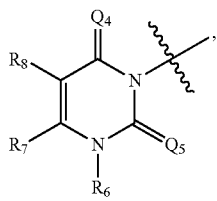

Q-2

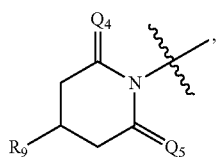

Q-3

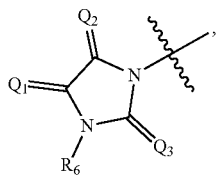

Q-4

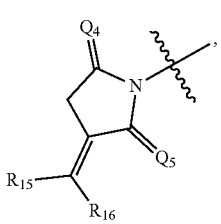

Q-5

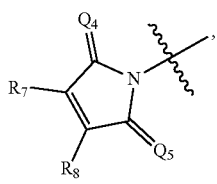

Q-6

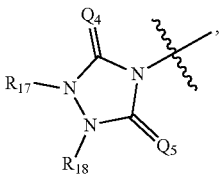

Q-7

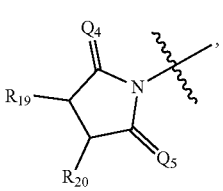

Q-8

-continued
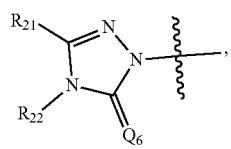 Q-9
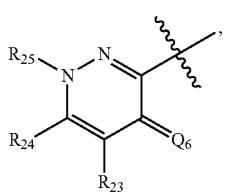 Q-10
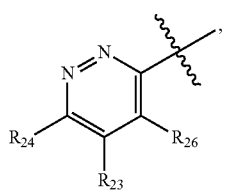 Q-11
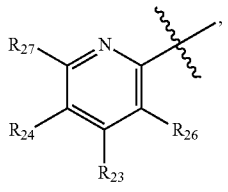 Q-12
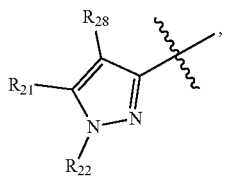 Q-13
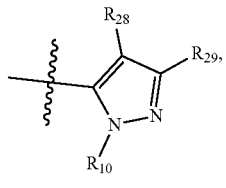 Q-14
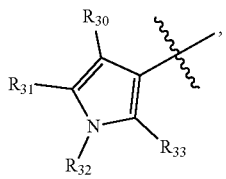 Q-15
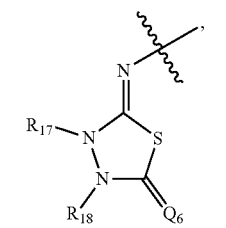 Q-16
-continued
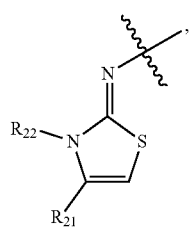 Q-17
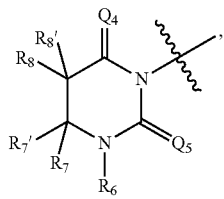 Q-18
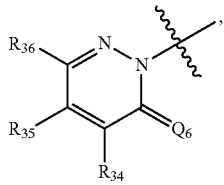 Q-19
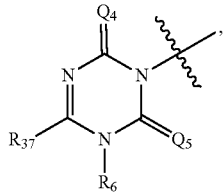 Q-20
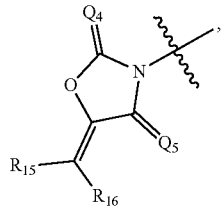 Q-21
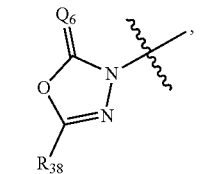 Q-22
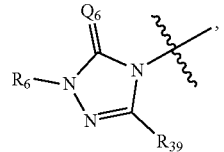 Q-23
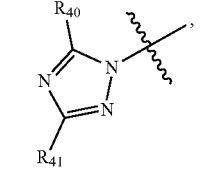 Q-24

-continued

Q-25 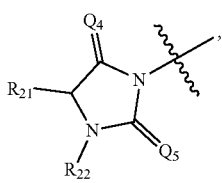

Q-26 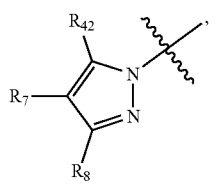

Q-27 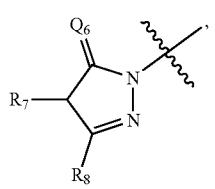

Q-28 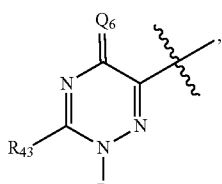

Q-29 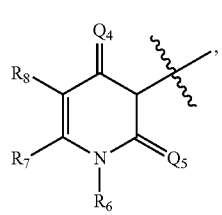

Q-30 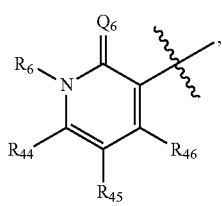

Q-31 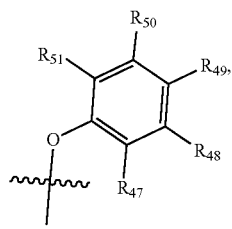

Q-32 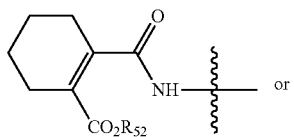

-continued

Q-33 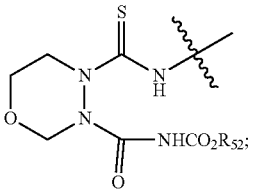

Y represents halogen, haloalkyl, cyano, nitro or amino;
Z represents H, halogen or hydroxy;
M represents CH or N;
$Q_1$, $Q_2$, $Q_3$, $Q_4$, $Q_5$, $Q_6$ each independently represent O or S;
Het represents a cyclic structure that shares two carbon atoms at 4- and 5-positions with isoxazoline ring to form a fused ring; the cyclic structure is 3~8 member saturated or unsaturated carbocyclyl or saturated or unsaturated heterocyclyl containing 1, 2 or 3 heteroatoms selected from O, S, N, NH, CO, $SO_2$ or C=N—O—$R_{14}$; except for the 4- and 5-positions that are respectively substituted by $X_2$ or $X_1$, other positions on the Het are each independently unsubstituted or substituted by at least one group selected from halogen, cyano, nitro, alkyl, alkenyl, alkynyl, cycloalkyl, haloalkyl, haloalkenyl, haloalkynyl, halo cycloalkyl, alkyl-substituted cycloalkyl, —$OR_{14}$, —$SR_{14}$, —$SOR_{14}$, —(CO)$OR_{14}$, —($SO_2$)$R_{14}$, —N($R_{14}$)$_2$ or —O—(CO)$OR_{14}$;

$X_1$, $X_2$ each independently represent H, halogen, nitro, cyano, thiocyano, hydroxy, mercapto, sulfo, formyl, haloformyl, azido, alkyl, alkenyl, alkynyl, cycloalkyl, cycloalkylalkyl, cycloalkenyl, cycloalkenylalkyl, —PO(OR')$_2$, —OR", —(CO)R", —SR", —(SO)R", —($SO_2$)R", —Si(R")$_3$, —O(CO)R", —O—($SO_2$)R", —S(CO)R", —($SO_2$)OR", —O(CO)OR", —(CO)(CO) OR",

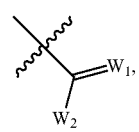

—CR'=N—OH, —CR'=N—O—R", heterocyclyl, heterocyclylalkyl, aryl, arylalkyl, amino, aminoalkyl, amino carbonyl alkyl, amino carbonyloxy alkyl, amino thio carbonyloxy alkyl, amino sulfonyl or amino sulfonyloxy alkyl, wherein, the groups "alkyl", "alkenyl" and "alkynyl" are each independently unsubstituted or substituted by at least one group selected from halogen, cyano, hydroxy, mercapto, carboxyl, —OR", —(CO)R", —SR", —($SO_2$)R", —O(CO)H, —O(CO)R", —O—($SO_2$)R", —(CO)OR", —O(CO)OR", —O(CO)(CO)OH, —O(CO)(CO)OR", —O-alkyl-(CO)OH or —O-alkyl-(CO)OR", the groups "cycloalkyl", "cycloalkylalkyl", "cycloalkenyl", "cycloalkenylalkyl", "heterocyclyl", "heterocyclylalkyl", "aryl" and "arylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —OR$_{14}$, —SR$_{14}$, —(CO)OR$_{14}$, —(SO$_2$)R$_{14}$, —N(R$_{14}$)$_2$ or —O-alkyl-(CO)OR$_{14}$, or two adjacent carbon atoms on the ring together with unsubstituted or halogen-substituted —OCH$_2$CH$_2$— or —OCH$_2$O— form a fused ring, the groups "amino", "aminoalkyl", "amino carbonyl alkyl", "amino carbonyloxy alkyl", "amino thio carbonyloxy alkyl", "amino sulfonyl" and "amino sulfonyloxy alkyl" are each independently unsubstituted or substituted by one or two groups selected from —R$_{11}$, —OR$_{11}$, —(CO)R$_{11}$, —(CO)OR$_{11}$, -alkyl-(CO)OR$_{11}$, —(SO$_2$)R$_{11}$, —(SO$_2$)OR$_{11}$, -alkyl-(SO$_2$)R$_{11}$, —(CO)N(R$_{12}$)$_2$ or —(SO$_2$)N(R$_{12}$)$_2$;

R' independently represents H, halogen, alkoxy, alkoxyalkyl, alkyl, alkenyl, alkynyl, cycloalkyl, cycloalkylalkyl, cycloalkenyl, cycloalkenylalkyl, aryl, arylalkyl, heterocyclyl or heterocyclylalkyl; wherein, the groups "alkyl", "alkenyl" and "alkynyl" are each independently unsubstituted or substituted by halogen; the groups "cycloalkyl", "cycloalkylalkyl", "cycloalkenyl", "cycloalkenylalkyl", "aryl", "arylalkyl", "heterocyclyl" and "heterocyclylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —OR$_{14}$, —SR$_{14}$, —(CO)OR$_{14}$, —(SO$_2$)R$_{14}$, —N(R$_{14}$)$_2$ or —O-alkyl-(CO)OR$_{14}$, or two adjacent carbon atoms on the ring together with unsubstituted or halogen-substituted —OCH$_2$CH$_2$— or —OCH$_2$O— form a fused ring;

R" independently represents alkyl, alkenyl, alkynyl, cycloalkyl, cycloalkylalkyl, cycloalkenyl, cycloalkenylalkyl, aryl, arylalkyl, arylalkenyl, heterocyclyl, heterocyclylalkyl or heterocyclylalkenyl; wherein, the groups "alkyl", "alkenyl" and "alkynyl" are each independently unsubstituted or substituted by at least one group selected from halogen, cyano, trialkylsilyl, —OR$_{13}$, —SR$_{13}$, —O(CO)R$_{13}$, —(CO)R$_{13}$, —(CO)OR$_{13}$ or —O(CO)OR$_{13}$; the groups "cycloalkyl", "cycloalkylalkyl", "cycloalkenyl", "cycloalkenylalkyl", "aryl", "arylalkyl", "arylalkenyl", "heterocyclyl", "heterocyclylalkyl" and "heterocyclylalkenyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —OR$_{14}$, —SR$_{14}$, —(CO)OR$_{14}$, —(SO$_2$)R$_{14}$, —N(R$_{14}$)$_2$ or —O-alkyl-(CO)OR$_{14}$, or two adjacent carbon atoms on the ring together with unsubstituted or halogen-substituted —OCH$_2$CH$_2$— or —OCH$_2$O— form a fused ring;

W$_1$ represents O, S, NH or N-alkyl;

W$_2$ represents OW$_3$, SW$_3$ or N(W$_3$)$_2$;

W$_3$ independently represents H, alkyl, alkenyl, alkynyl, cycloalkyl, cycloalkenyl, heterocyclyl, aryl,

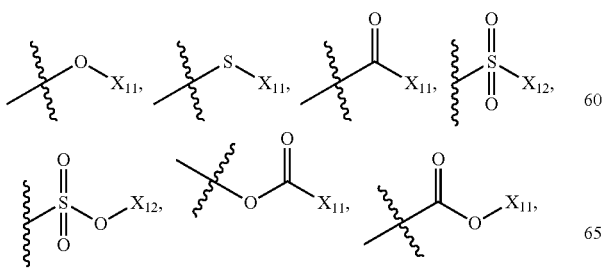

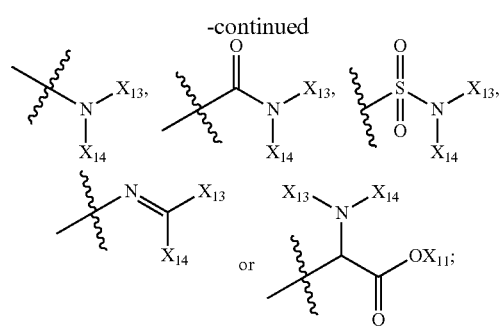

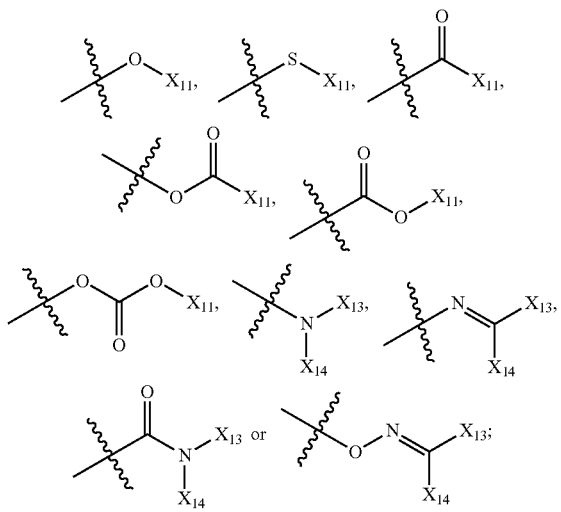

wherein, the groups "alkyl", "alkenyl" and "alkynyl" are each independently unsubstituted or substituted by at least one group selected from halogen, cyano, nitro, cycloalkyl, trialkylsilyl, cycloalkenyl, heterocyclyl, aryl, the groups "cycloalkyl", "cycloalkenyl", "heterocyclyl" and "aryl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —OR$_{14}$, —SR$_{14}$, —(CO)OR$_{14}$, —(SO$_2$)R$_{14}$, —N(R$_{14}$)$_2$ or —O-alkyl-(CO)OR$_{14}$, or two adjacent carbon atoms on the ring together with unsubstituted or halogen-substituted —OCH$_2$CH$_2$— or —OCH$_2$O— form a fused ring;

or N(W$_3$)$_2$ represents unsubstituted or substituted heterocyclyl with nitrogen atom at 1-position;

X$_{11}$ independently represents H, alkyl, alkenyl, alkynyl, cycloalkyl, cycloalkylalkyl, cycloalkenyl, cycloalkenylalkyl, heterocyclyl, heterocyclylalkyl, aryl or arylalkyl; wherein, the groups "cycloalkyl", "cycloalkylalkyl", "cycloalkenyl", "cycloalkenylalkyl", "heterocyclyl", "heterocyclylalkyl", "aryl" and "arylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —OR$_{14}$, —SR$_{14}$, —(CO)OR$_{14}$, —(SO$_2$)R$_{14}$, —N(R$_{14}$)$_2$ or —O-alkyl-(CO)OR$_{14}$, or two adjacent carbon atoms on the ring together with unsubstituted or halogen-substituted —OCH$_2$CH$_2$— or —OCH$_2$O— form a fused ring;

X$_{12}$ independently represents alkyl, alkenyl, alkynyl, cycloalkyl, cycloalkylalkyl, cycloalkenyl, cycloalkenylalkyl, heterocyclyl, heterocyclylalkyl, aryl or arylalkyl; wherein, the groups "cycloalkyl", "cycloalkylalkyl", "cycloalkenyl", "cycloalkenylalkyl", "heterocyclyl", "heterocyclylalkyl", "aryl" and "arylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —OR$_{14}$, —SR$_{14}$, —(CO)OR$_{14}$, —(SO$_2$)R$_{14}$, —N(R$_{14}$)$_2$ or —O-alkyl-(CO)OR$_{14}$, or two adjacent carbon atoms on the ring together with unsubstituted or halogen-substituted —OCH$_2$CH$_2$— or —OCH$_2$O— form a fused ring;

X$_{13}$, X$_{14}$ each independently represent H, halogen, cyano, alkoxy, alkoxyalkyl, alkyl carbonyl, alkoxy carbonyl, alkyl sulfonyl, alkyl, alkenyl, alkynyl, cycloalkyl, cycloalkylalkyl, cycloalkenyl, cycloalkenylalkyl, aryl, arylalkyl, heterocyclyl or heterocyclylalkyl, or the group CX$_{13}$X$_{14}$, taken together, forms unsubstituted or substituted cyclic structure, or the group NX$_{13}$X$_{14}$, taken together, forms unsubstituted or substituted heterocyclyl with nitrogen atom at 1-position; wherein, the groups "alkyl", "alkenyl" and "alkynyl" are each independently unsubstituted or substituted by halogen; the groups "cycloalkyl", "cycloalkylalkyl", "cycloalkenyl", "cycloalkenylalkyl", "aryl", "arylalkyl", "heterocyclyl" and "heterocyclylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —OR$_{14}$, —SR$_{14}$, —(CO)OR$_{14}$, —(SO$_2$)R$_{14}$, —N(R$_{14}$)$_2$ or —O-alkyl-(CO)OR$_{14}$, or two adjacent carbon atoms on the ring together with unsubstituted or halogen-substituted —OCH$_2$CH$_2$— or —OCH$_2$O— form a fused ring;

R$_1$, R$_2$, R$_6$, R$_{10}$, R$_{17}$, R$_{18}$, R$_{22}$, R$_{25}$, R$_{32}$ each independently represent H, cyano, alkyl, alkenyl, alkynyl, formylalkyl, cyanoalkyl, amino, aminoalkyl, amino carbonyl, amino carbonyl alkyl, amino sulfonyl, cycloalkyl, cycloalkylalkyl, cycloalkenyl, cycloalkenylalkyl, heterocyclyl, heterocyclylalkyl, aryl, arylalkyl, R$_4$R$_5$N—(CO)—NR$_3$—,

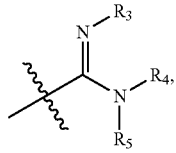

R$_3$—S(O)$_m$-(alkyl)$_n$-, R$_3$—O-(alkyl)$_n$-, R$_3$—(CO)-(alkyl)$_n$-, R$_3$—O-(alkyl)$_n$-(CO)—, R$_3$—(CO)—O-(alkyl)$_n$-, R$_3$—S—(CO)-(alkyl)$_n$-, R$_3$—O—(CO)-alkyl- or R$_3$—O—(CO)—O-alkyl-, wherein, the groups "alkyl", "alkenyl" and "alkynyl" are each independently unsubstituted or substituted by halogen, the groups "amino", "aminoalkyl", "amino carbonyl", "amino carbonyl alkyl" and "amino sulfonyl" are each independently unsubstituted or substituted by one or two groups selected from —R$_{11}$, —OR$_{11}$, —(CO)R$_{11}$, —(CO)OR$_{11}$, -alkyl-(CO)OR$_{11}$, —(SO$_2$)R$_{11}$, —(SO$_2$)OR$_{11}$, -alkyl-(SO$_2$)R$_{11}$, —(CO)N(R$_{12}$)$_2$ or —(SO$_2$)N(R$_{12}$)$_2$, the groups "cycloalkyl", "cycloalkylalkyl", "cycloalkenyl", "cycloalkenylalkyl", "heterocyclyl", "heterocyclylalkyl", "aryl" and "arylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —OR$_{14}$, —SR$_{14}$, —(CO)OR$_{14}$, —(SO$_2$)R$_{14}$, —N(R$_{14}$)$_2$ or —O-alkyl-(CO)OR$_{14}$, or two adjacent carbon atoms on the ring together with unsubstituted or halogen-substituted —OCH$_2$CH$_2$— or —OCH$_2$O— form a fused ring;

or R$_{17}$, R$_{18}$, taken together, forms —CH$_2$CH$_2$CH$_2$CH$_2$— or —CH$_2$CH$_2$OCH$_2$— that is unsubstituted or substituted by at least one group selected from halogen, alkyl or haloalkyl;

R$_3$, R$_4$, R$_5$ each independently represent H, alkyl, alkenyl, alkynyl, cycloalkyl, cycloalkylalkyl, cycloalkenyl, cycloalkenylalkyl, heterocyclyl, heterocyclylalkyl, aryl or arylalkyl; wherein, the groups "alkyl", "alkenyl" and "alkynyl" are each independently unsubstituted or substituted by halogen; the groups "cycloalkyl", "cycloalkylalkyl", "cycloalkenyl", "cycloalkenylalkyl", "heterocyclyl", "heterocyclylalkyl", "aryl" and "arylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —OR$_{14}$, —SR$_{14}$, —(CO)OR$_{14}$, —(SO$_2$)R$_{14}$, —N(R$_{14}$)$_2$ or —O-alkyl-(CO)OR$_{14}$, or two adjacent carbon atoms on the ring together with unsubstituted or halogen-substituted —OCH$_2$CH$_2$— or —OCH$_2$O— form a fused ring;

R$_7$, R$_8$, R$_7'$, R$_8'$, R$_9$, R$_{19}$, R$_{20}$, R$_{21}$, R$_{23}$, R$_{24}$, R$_{26}$, R$_{27}$, R$_{28}$, R$_{29}$, R$_{30}$, R$_{31}$, R$_{33}$, R$_{34}$, R$_{35}$, R$_{36}$, R$_{37}$, R$_{38}$, R$_{39}$, R$_{40}$, R$_{41}$, R$_{42}$, R$_{43}$, R$_{44}$, R$_{45}$, R$_{46}$, R$_{47}$, R$_{48}$, R$_{49}$, R$_{50}$, R$_{51}$ each independently represent H, halogen, hydroxy, mercapto, formyl, hydroxyalkyl, nitro, cyano, alkyl, alkenyl, alkynyl, cycloalkyl, cycloalkylalkyl, cycloalkenyl, cycloalkenylalkyl, —OR$_{11}$, —SR$_{11}$, —(SO)R$_{11}$, —(SO$_2$)R$_{11}$, —(SO$_2$)OR$_{11}$, —O(SO$_2$)R$_{11}$, —N(R$_{12}$)$_2$, phenyl or benzyl, wherein, the groups "alkyl", "alkenyl", "alkynyl", "cycloalkyl", "cycloalkylalkyl", "cycloalkenyl" and "cycloalkenylalkyl" are each independently unsubstituted or substituted by halogen; the groups "phenyl" and "benzyl" are each independently unsubstituted or substituted by at least one group selected from halogen, cyano, nitro, alkyl, haloalkyl, alkoxy carbonyl, alkylthio, alkyl sulfonyl, alkoxy or haloalkoxy;

or R$_7$, R$_8$, taken together, form —CH$_2$CH$_2$CH$_2$CH$_2$— or —CH═CH—CH═CH— that is unsubstituted or substituted by at least one group selected from halogen, alkyl or haloalkyl;

or R$_{19}$, R$_{20}$, taken together, form —CH$_2$CH$_2$CH$_2$CH$_2$— or —CH$_2$CH═CHCH$_2$— that is unsubstituted or substituted by at least one group selected from halogen, alkyl or haloalkyl;

or R$_{21}$, R$_{22}$, taken together, form —CH$_2$CH$_2$CH$_2$—, —CH$_2$OCH$_2$CH$_2$— or —CH$_2$CH$_2$CH$_2$CH$_2$— that is unsubstituted or substituted by at least one group selected from halogen, alkyl or haloalkyl;

R$_{11}$ independently represents alkyl, alkenyl, alkynyl, cycloalkyl, cycloalkylalkyl, cycloalkenyl, cycloalkenylalkyl, phenyl or benzyl; wherein, the groups "alkyl", "alkenyl" and "alkynyl" are each independently unsubstituted or substituted by halogen; the groups "phenyl" and "benzyl" are each independently unsubstituted or substituted by at least one group selected from halogen, cyano, nitro, alkyl, haloalkyl, alkoxy carbonyl, alkylthio, alkyl sulfonyl, alkoxy or haloalkoxy;

$R_{12}$ independently represents H, alkyl, alkenyl, alkynyl, alkoxy, alkyl sulfonyl, cycloalkyl, cycloalkylalkyl, cycloalkenyl or cycloalkenylalkyl, or the group $N(R_{12})_2$ in $-(CO)N(R_{12})_2$ or $-(SO_2)N(R_{12})_2$ independently represents unsubstituted or substituted heterocyclyl with nitrogen atom at 1-position;

$R_{13}$ independently represents alkyl, alkenyl, alkynyl, cycloalkyl, phenyl or phenyl substituted by at least one group selected from: halogen, cyano, nitro, alkyl, haloalkyl, alkoxy, haloalkoxy, alkoxy carbonyl, alkylthio, alkyl sulfonyl or phenoxy substituted by at least one group selected from halogen, cyano, nitro, alkyl, haloalkyl, alkoxy or haloalkoxy;

$R_{14}$ independently represents H, alkyl, haloalkyl, phenyl or phenyl substituted by at least one group selected from halogen, cyano, nitro, alkyl, haloalkyl, alkoxy carbonyl, alkylthio, alkyl sulfonyl, alkoxy or haloalkoxy;

$R_{15}$, $R_{16}$, $R_{52}$ each independently represent H, halogen, alkyl, alkenyl, alkynyl, cycloalkyl, cycloalkylalkyl, cycloalkenyl or cycloalkenylalkyl, wherein, the groups "alkyl", "alkenyl", "alkynyl", "cycloalkyl", "cycloalkylalkyl", "cycloalkenyl" and "cycloalkenylalkyl" are each independently unsubstituted or substituted by halogen;

m represents 0, 1 or 2; n independently represents 0 or 1.

Preferably, Y represents halogen, halo C1-C8 alkyl, cyano, nitro or amino;

Het represents a cyclic structure that shares two carbon atoms at 4- and 5-positions with isoxazoline ring to form a fused ring; the cyclic structure is 3~8 member saturated or unsaturated carbocyclyl or saturated or unsaturated heterocyclyl containing 1, 2 or 3 heteroatoms selected from O, S, N, NH, CO, $SO_2$ or C=N—O—$R_{14}$; except for the 4- and 5-positions that are respectively substituted by $X_2$ or $X_1$, other positions on the Het are each independently unsubstituted or substituted by at least one group selected from halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, $-OR_{14}$, $-SR_{14}$, $-SOR_{14}$, $-(CO)OR_{14}$, $-(SO_2)R_{14}$, $-N(R_{14})_2$ or $-O-(CO)OR_{14}$;

$X_1$, $X_2$ each independently represent H, halogen, nitro, cyano, thiocyano, hydroxy, mercapto, sulfo, formyl, haloformyl, azido, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, $-PO(OR')_2$, $-OR"$, $-(CO)R"$, $-SR"$, $-(SO)R"$, $-(SO_2)R"$, $-Si(R")$, $-O(CO)R"$, $-O-(SO_2)R"$, $-S(CO)R"$, $-(SO_2)OR"$, $-O(CO)OR"$, $-(CO)(CO)OR"$,

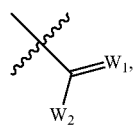

$-CR'=N-OH$, $-CR'=N-O-R"$, heterocyclyl, heterocyclyl C1-C8 alkyl, aryl, aryl C1-C8 alkyl, amino, amino C1-C8 alkyl, amino carbonyl C1-C8 alkyl, amino carbonyloxy C1-C8 alkyl, amino thio carbonyloxy C1-C8 alkyl, amino sulfonyl or amino sulfonyloxy C1-C8 alkyl, wherein, the groups "C1-C8 alkyl", "C2-C8 alkenyl" and "C2-C8 alkynyl" are each independently unsubstituted or substituted by at least one group selected from halogen, cyano, hydroxy, mercapto, carboxyl, $-OR"$, $-(CO)R"$, $-SR"$, $-(SO_2)R"$, $-O(CO)H$, $-O(CO)R"$, $-O-(SO_2)R"$, $-(CO)OR"$, $-O(CO)OR"$, $-O(CO)(CO)OH$, $-O(CO)(CO)OR"$, $-O-(C1-C8\ alkyl)-(CO)OH$ or $-O-(C1-C8\ alkyl)-(CO)OR"$, the groups "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" and "aryl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, $-OR_{14}$, $-SR_{14}$, $-(CO)OR_{14}$, $-(SO_2)R_{14}$, $-N(R_{14})_2$ or $-O-(C1-C8\ alkyl)-(CO)OR_{14}$, or two adjacent carbon atoms on the ring together with unsubstituted or halogen-substituted $-OCH_2CH_2-$ or $-OCH_2O-$ form a fused ring, the groups "amino", "amino C1-C8 alkyl", "amino carbonyl C1-C8 alkyl", "amino carbonyloxy C1-C8 alkyl", "amino thio carbonyloxy C1-C8 alkyl", "amino sulfonyl" and "amino sulfonyloxy C1-C8 alkyl" are each independently unsubstituted or substituted by one or two groups selected from $-R_{11}$, $-OR_{11}$, $-(CO)R_{11}$, $-(CO)OR_{11}$, $-(C1-C8\ alkyl)-(CO)OR_{11}$, $-(SO_2)R_{11}$, $-(SO_2)OR_{11}$, $-(C1-C8\ alkyl)-(SO_2)R_{11}$, $-(CO)N(R_{12})_2$ or $-(SO_2)N(R_{12})_2$;

R' independently represents H, halogen, C1-C8 alkoxy, C1-C8 alkoxy C1-C8 alkyl, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, heterocyclyl or heterocyclyl C1-C8 alkyl, wherein, the groups "C1-C8 alkyl", "C2-C8 alkenyl" and "C2-C8 alkynyl" are each independently unsubstituted or substituted by halogen; the groups "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "heterocyclyl" and "heterocyclyl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, $-OR_{14}$, $-SR_{14}$, $-(CO)OR_{14}$, $-(SO_2)R_{14}$, $-N(R_{14})_2$ or $-O-(C1-C8\ alkyl)-(CO)OR_{14}$, or two adjacent carbon atoms on the ring together with unsubstituted or halogen-substituted $-OCH_2CH_2-$ or $-OCH_2O-$ form a fused ring;

R" independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, aryl C2-C8 alkenyl, heterocyclyl, heterocyclyl C1-C8 alkyl or heterocyclyl C2-C8 alkenyl; wherein, the groups "C1-C8 alkyl", "C2-C8 alkenyl" and "C2-C8 alkynyl" are each independently unsubstituted or substituted by at least one group selected from halogen, cyano, tri C1-C8 alkylsilyl, —OR$_{13}$, —SR$_{13}$, —O(CO)R$_{13}$, —(CO)R$_{13}$, —(CO)OR$_{13}$ or —O(CO)OR$_{13}$; the groups "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "aryl C2-C8 alkenyl", "heterocyclyl", "heterocyclyl C1-C8 alkyl" and "heterocyclyl C2-C8 alkenyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —OR$_{14}$, —SR$_{14}$, —(CO)OR$_{14}$, —(SO$_2$)R$_{14}$, —N(R$_{14}$)$_2$ or —O—(C1-C8 alkyl)-(CO)OR$_{14}$, or two adjacent carbon atoms on the ring together with unsubstituted or halogen-substituted —OCH$_2$CH$_2$— or —OCH$_2$O— form a fused ring;

W$_1$ represents O, S, NH or N—(C1-C8 alkyl);

W$_3$ independently represents H, C1-C8 alkyl, C2-C8 alkenyl, C2-C8 alkynyl, C3-C8 cycloalkyl, C3-C8 cycloalkenyl, heterocyclyl, aryl,

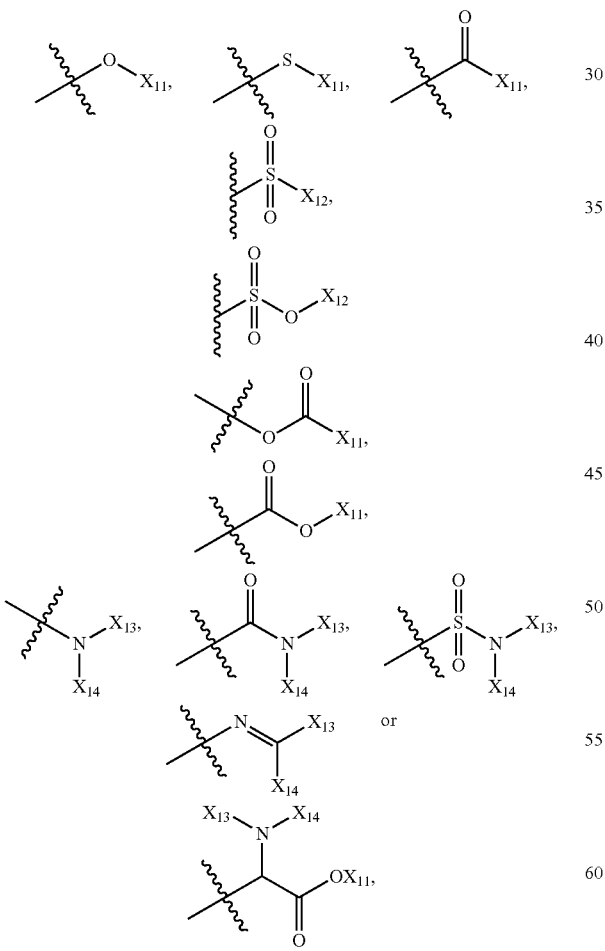

wherein, the groups "C1-C8 alkyl", "C2-C8 alkenyl" and "C2-C8 alkynyl" are each independently unsubstituted or substituted by at least one group selected from halogen, cyano, nitro, C3-C8 cycloalkyl, tri C1-C8 alkylsilyl, C3-C8 cycloalkenyl, heterocyclyl, aryl,

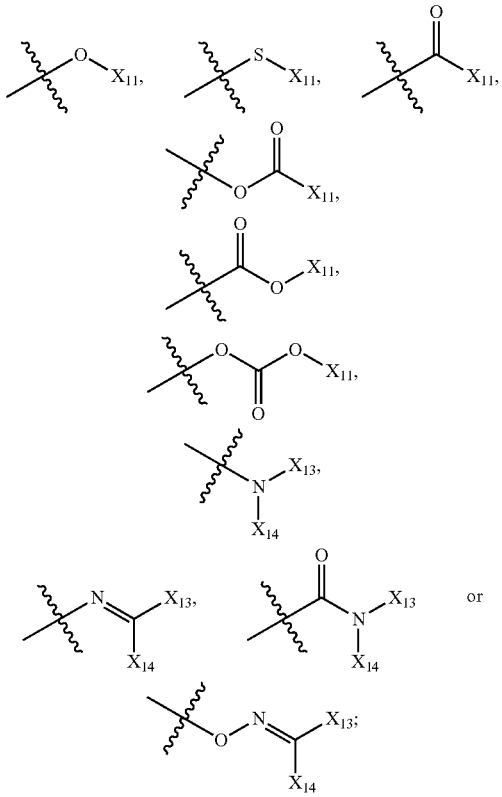

the groups "C3-C8 cycloalkyl", "C3-C8 cycloalkenyl", "heterocyclyl" and "aryl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —OR$_{14}$, —SR$_{14}$, —(CO)OR$_{14}$, —(SO$_2$)R$_{14}$, —N(R$_{14}$)$_2$ or —O—(C1-C8 alkyl)-(CO)OR$_{14}$, or two adjacent carbon atoms on the ring together with unsubstituted or halogen-substituted —OCH$_2$CH$_2$— or —OCH$_2$O— form a fused ring;

or N(W$_3$)$_2$ represents

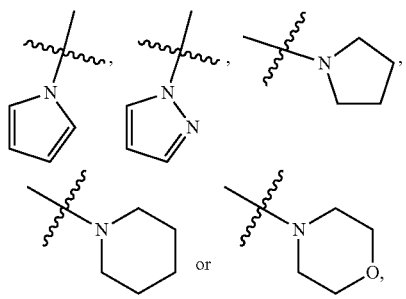

which is unsubstituted or substituted by at least one group selected from oxo, C1-C8 alkyl or C1-C8 alkoxy carbonyl;

X$_{11}$ independently represents H, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocyclyl C1-C8 alkyl, aryl or aryl C1-C8 alkyl; wherein, the groups "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" and "aryl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —OR$_{14}$, —SR$_{14}$, —(CO)OR$_{14}$, —(SO$_2$)R$_{14}$, —N(R$_{14}$)$_2$ or —O—(C1-C8 alkyl)-(CO)OR$_{14}$, or two adjacent carbon atoms on the ring together with unsubstituted or halogen-substituted —OCH$_2$CH$_2$— or —OCH$_2$O— form a fused ring;

X$_{12}$ independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocyclyl C1-C8 alkyl, aryl or aryl C1-C8 alkyl; wherein, the groups "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" and "aryl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —OR$_{14}$, —SR$_{14}$, —(CO)OR$_{14}$, —(SO$_2$)R$_{14}$, —N(R$_{14}$)$_2$ or —O—(C1-C8 alkyl)-(CO)OR$_{14}$, or two adjacent carbon atoms on the ring together with unsubstituted or halogen-substituted —OCH$_2$CH$_2$— or —OCH$_2$O— form a fused ring;

X$_{13}$, X$_{14}$ each independently represent H, halogen, cyano, C1-C8 alkoxy, C1-C8 alkoxy C1-C8 alkyl, C1-C8 alkyl carbonyl, C1-C8 alkoxy carbonyl, C1-C8 alkyl sulfonyl, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, heterocyclyl or heterocyclyl C1-C8 alkyl, or the group CX$_{13}$X$_{14}$, taken together, forms 5-8 membered carbocyclyl or oxygen-, sulfur- or nitrogen-containing heterocyclyl, or the group NX$_{13}$X$_{14}$, taken together, forms

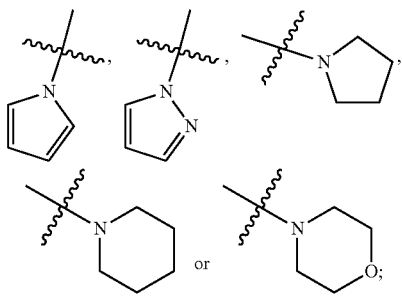

wherein, the groups "C1-C8 alkyl", "C2-C8 alkenyl" and "C2-C8 alkynyl" are each independently unsubstituted or substituted by halogen; the groups "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "heterocyclyl" and "heterocyclyl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —OR$_{14}$, —SR$_{14}$, —(CO)OR$_{14}$, —(SO$_2$)R$_{14}$, —N(R$_{14}$)$_2$ or —O—(C1-C8 alkyl)-(CO)OR$_{14}$, or two adjacent carbon atoms on the ring together with unsubstituted or halogen-substituted —OCH$_2$CH$_2$— or —OCH$_2$O— form a fused ring; the groups "5-8 membered carbocyclyl or oxygen-, sulfur- or nitrogen-containing heterocyclyl" are unsubstituted or substituted by at least one group selected from C1-C8 alkyl, C1-C8 alkoxy carbonyl or benzyl, or together with aryl or heterocyclyl form a fused ring; the groups

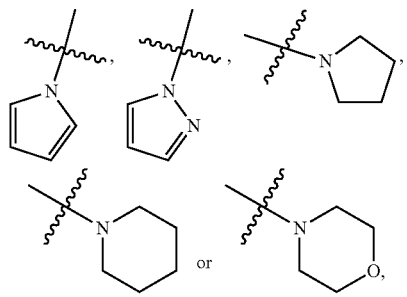

are unsubstituted or substituted by at least one group selected from oxo, C1-C8 alkyl or C1-C8 alkoxy carbonyl;

R$_1$, R$_2$, R$_6$, R$_{10}$, R$_{17}$, R$_{18}$, R$_{22}$, R$_{25}$, R$_{32}$ each independently represent H, cyano, C1-C8 alkyl, C2-C8 alkenyl, C2-C8 alkynyl, formyl C1-C8 alkyl, cyano C1-C8 alkyl, amino, amino C1-C8 alkyl, amino carbonyl, amino carbonyl C1-C8 alkyl, amino sulfonyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocyclyl C1-C8 alkyl, aryl, aryl C1-C8 alkyl, R$_4$R$_5$N—(CO)—NR$_3$—,

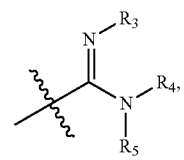

R$_3$—S(O)$_m$—(C1-C8 alkyl)$_n$-, R$_3$—O—(C1-C8 alkyl)$_n$-, R$_3$—(CO)—(C1-C8 alkyl)$_n$-, R$_3$—O—(C1-C8 alkyl)$_n$-(CO)—, R$_3$—(CO)—O—(C1-C8 alkyl)$_n$-, R$_3$—S—(CO)—(C1-C8 alkyl)$_n$-, R$_3$—O—(CO)—(C1-C8 alkyl)- or R$_3$—O—(CO)—O—(C1-C8 alkyl)-, wherein, the groups "C1-C8 alkyl", "C2-C8 alkenyl" and "C2-C8 alkynyl" are each independently unsubstituted or substituted by halogen, the groups "amino", "amino C1-C8 alkyl", "amino carbonyl", "amino carbonyl C1-C8 alkyl" and "amino sulfonyl" are each independently unsubstituted or substituted by one or two groups selected from —R$_{11}$, —OR$_{11}$, —(CO)R$_{11}$, —(CO)OR$_{11}$, —(C1-C8 alkyl)-

(CO)OR$_{11}$, —(SO$_2$)R$_{11}$, —(SO$_2$)OR$_{11}$, —(C1-C8 alkyl)-(SO$_2$)R$_{11}$, —(CO)N(R$_{12}$)$_2$ or —(SO$_2$)N(R$_{12}$)$_2$, the groups "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" and "aryl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —OR$_{14}$, —SR$_{14}$, —(CO)OR$_{14}$, —(SO$_2$)R$_{14}$, —N(R$_{14}$)$_2$ or —O—(C1-C8 alkyl)-(CO)OR$_{14}$, or two adjacent carbon atoms on the ring together with unsubstituted or halogen-substituted —OCH$_2$CH$_2$— or —OCH$_2$O— form a fused ring;

or R$_{17}$, R$_{18}$, taken together, form —CH$_2$CH$_2$CH$_2$CH$_2$— or —CH$_2$CH$_2$OCH$_2$— that is unsubstituted or substituted by at least one group selected from halogen, C1-C8 alkyl or halo C1-C8 alkyl;

R$_3$, R$_4$, R$_5$ each independently represent H, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocyclyl C1-C8 alkyl, aryl or aryl C1-C8 alkyl, wherein, the groups "C1-C8 alkyl", "C2-C8 alkenyl" and "C2-C8 alkynyl" are each independently unsubstituted or substituted by halogen, the groups "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" and "aryl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —OR$_{14}$, —SR$_{14}$, —(CO)OR$_{14}$, —(SO$_2$)R$_{14}$, —N(R$_{14}$)$_2$ or —O—(C1-C8 alkyl)-(CO)OR$_{14}$, or two adjacent carbon atoms on the ring together with unsubstituted or halogen-substituted —OCH$_2$CH$_2$— or —OCH$_2$O— form a fused ring;

R$_7$, R$_8$, R$_7$', R$_8$', R$_9$, R$_{19}$, R$_{20}$, R$_{21}$, R$_{23}$, R$_{24}$, R$_{26}$, R$_{27}$, R$_{28}$, R$_{29}$, R$_{30}$, R$_{31}$, R$_{33}$, R$_{34}$, R$_{35}$, R$_{36}$, R$_{37}$, R$_{38}$, R$_{39}$, R$_{40}$, R$_{41}$, R$_{42}$, R$_{43}$, R$_{44}$, R$_{45}$, R$_{46}$, R$_{47}$, R$_{48}$, R$_{49}$, R$_{50}$, R$_{51}$ each independently represent H, halogen, hydroxy, mercapto, formyl, hydroxy C1-C8 alkyl, nitro, cyano, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, —OR$_{11}$, —SR$_{11}$, —(SO)R$_{11}$, —(SO$_2$)R$_{11}$, —(SO$_2$)OR$_{11}$, —O(SO$_2$)R$_{11}$, —N(R$_{12}$)$_2$, phenyl or benzyl, wherein, the groups "C1-C8 alkyl", "C2-C8 alkenyl", "C2-C8 alkynyl", "C3-C8 cycloalkyl", "C3-C8 cycloalkyl C1-C8 alkyl", "C3-C8 cycloalkenyl" and "C3-C8 cycloalkenyl C1-C8 alkyl" are each independently unsubstituted or substituted by halogen, the groups "phenyl" and "benzyl" are each independently unsubstituted or substituted by at least one group selected from halogen, cyano, nitro, C1-C8 alkyl, halo C1-C8 alkyl, C1-C8 alkoxy carbonyl, C1-C8 alkylthio, C1-C8 alkyl sulfonyl, C1-C8 alkoxy or halo C1-C8 alkoxy;

or R$_7$, R$_8$, taken together, form —CH$_2$CH$_2$CH$_2$CH$_2$— or —CH=CH—CH=CH— that is unsubstituted or substituted by at least one group selected from halogen, C1-C8 alkyl or halo C1-C8 alkyl;

or R$_{19}$, R$_{20}$, taken together, form —CH$_2$CH$_2$CH$_2$CH$_2$— or —CH$_2$CH=CHCH$_2$— that is unsubstituted or substituted by at least one group selected from halogen, C1-C8 alkyl or halo C1-C8 alkyl;

or R$_{21}$, R$_{22}$, taken together, form —CH$_2$CH$_2$CH$_2$—, —CH$_2$OCH$_2$CH$_2$— or —CH$_2$CH$_2$CH$_2$CH$_2$— that is unsubstituted or substituted by at least one group selected from halogen, C1-C8 alkyl or halo C1-C8 alkyl;

R$_{11}$ independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, phenyl or benzyl; wherein, the groups "C1-C8 alkyl", "C2-C8 alkenyl" and "C2-C8 alkynyl" are each independently unsubstituted or substituted by halogen; the groups "phenyl" and "benzyl" are each independently unsubstituted or substituted by at least one group selected from halogen, cyano, nitro, C1-C8 alkyl, halo C1-C8 alkyl, C1-C8 alkoxy carbonyl, C1-C8 alkylthio, C1-C8 alkyl sulfonyl, C1-C8 alkoxy or halo C1-C8 alkoxy;

R$_{12}$ independently represents H, C1-C8 alkyl, C2-C8 alkenyl, C2-C8 alkynyl, C1-C8 alkoxy, C1-C8 alkyl sulfonyl, C3-C8 cycloalkyl, C3-C8 cycloalkyl C1-C8 alkyl, C3-C8 cycloalkenyl or C3-C8 cycloalkenyl C1-C8 alkyl, or the group N(R$_{12}$)$_2$ in —(CO)N(R$_{12}$)$_2$ or —(SO$_2$)N(R$_{12}$)$_2$ independently represents

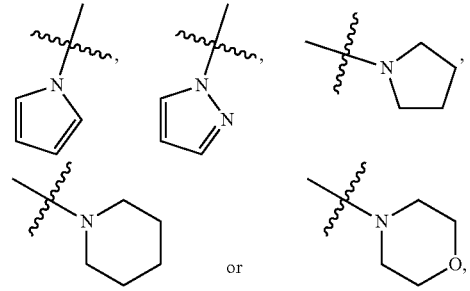

which is unsubstituted or substituted by at least one group selected from oxo, C1-C8 alkyl or C1-C8 alkoxy carbonyl;

R$_{13}$ independently represents C1-C8 alkyl, C2-C8 alkenyl, C2-C8 alkynyl, C3-C8 cycloalkyl, phenyl or phenyl substituted by at least one group selected from: halogen, cyano, nitro, C1-C8 alkyl, halo C1-C8 alkyl, C1-C8 alkoxy, halo C1-C8 alkoxy, C1-C8 alkoxy carbonyl, C1-C8 alkylthio, C1-C8 alkyl sulfonyl or phenoxy substituted by at least one group selected from halogen, cyano, nitro, C1-C8 alkyl, halo C1-C8 alkyl, C1-C8 alkoxy or halo C1-C8 alkoxy;

R$_{14}$ independently represents H, C1-C8 alkyl, halo C1-C8 alkyl, phenyl or phenyl substituted by at least one group selected from halogen, cyano, nitro, C1-C8 alkyl, halo C1-C8 alkyl, C1-C8 alkoxy carbonyl, C1-C8 alkylthio, C1-C8 alkyl sulfonyl, C1-C8 alkoxy or halo C1-C8 alkoxy;

R$_{15}$, R$_{16}$, R$_{52}$ each independently represent H, halogen, C1-C8 alkyl, C2-C8 alkenyl, C2-C8 alkynyl, C3-C8 cycloalkyl, C3-C8 cycloalkyl C1-C8 alkyl, C3-C8 cycloalkenyl or C3-C8 cycloalkenyl C1-C8 alkyl, wherein, the groups "C1-C8 alkyl", "C2-C8 alkenyl", "C2-C8 alkynyl", "C3-C8 cycloalkyl", "C3-C8 cycloalkyl C1-C8 alkyl", "C3-C8 cycloalkenyl" and "C3-C8 cycloalkenyl C1-C8 alkyl" are each independently unsubstituted or substituted by halogen.

More preferably, Y represents halogen, halo C1-C6 alkyl, cyano, nitro or amino;

Het represents a cyclic structure that shares two carbon atoms at 4- and 5-positions with isoxazoline ring to form a fused ring; the cyclic structure is 3~8 member saturated or unsaturated carbocyclyl or saturated or unsaturated heterocyclyl containing 1, 2 or 3 heteroatoms selected from O, S, N, NH, CO, $SO_2$ or C=N—O—$R_{14}$; except for the 4- and 5-positions that are respectively substituted by $X_2$ or $X_1$, other positions on the Het are each independently unsubstituted or substituted by at least one group selected from halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —$OR_{14}$, —$SR_{14}$, —$SOR_{14}$, —$(CO)OR_{14}$, —$(SO_2)R_{14}$, —$N(R_{14})_2$ or —O—$(CO)OR_{14}$;

$X_1$, $X_2$ each independently represent H, halogen, nitro, cyano, thiocyano, hydroxy, mercapto, sulfo, formyl, haloformyl, azido, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, —PO(OR')$_2$, —OR", —(CO)R", —SR", —(SO)R", —$(SO_2)$R", —Si(R")$_3$, —O(CO)R", —O—$(SO_2)$R", —S(CO)R", —$(SO_2)$OR", —O(CO)OR", —(CO)(CO)OR",

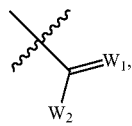

—CR'=N—OH, —CR'=N—O—R", heterocyclyl, heterocyclyl C1-C6 alkyl, aryl, aryl C1-C6 alkyl, amino, amino C1-C6 alkyl, amino carbonyl C1-C6 alkyl, amino carbonyloxy C1-C6 alkyl, amino thio carbonyloxy C1-C6 alkyl, amino sulfonyl or amino sulfonyloxy C1-C6 alkyl, wherein, the groups "C1-C6 alkyl", "C2-C6 alkenyl" and "C2-C6 alkynyl" are each independently unsubstituted or substituted by 1, 2 or 3 groups selected from halogen, cyano, hydroxy, mercapto, carboxyl, —OR", —(CO)R", —SR", —$(SO_2)$R", —O(CO)H, —O(CO)R", —O—$(SO_2)$R", —(CO)OR", —O(CO)OR", —O(CO)(CO)OH, —O(CO)(CO)OR", —O—(C1-C6 alkyl)-(CO)OH or —O—(C1-C6 alkyl)-(CO)OR", the groups "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" and "aryl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —$OR_{14}$, —$SR_{14}$, —$(CO)OR_{14}$, —$(SO_2)R_{14}$, —$N(R_{14})_2$ or —O—(C1-C6 alkyl)-(CO)OR$_{14}$, or two adjacent carbon atoms on the ring together with unsubstituted or halogen-substituted —$OCH_2CH_2$— or —$OCH_2O$— form a fused ring, the groups "amino", "amino C1-C6 alkyl", "amino carbonyl C1-C6 alkyl", "amino carbonyloxy C1-C6 alkyl", "amino thio carbonyloxy C1-C6 alkyl", "amino sulfonyl" and "amino sulfonyloxy C1-C6 alkyl" are each independently unsubstituted or substituted by one or two groups selected from —$R_{11}$, —$OR_{11}$, —(CO)R$_{11}$, —(CO)OR$_{11}$, —(C1-C6 alkyl)-(CO)OR$_{11}$, —$(SO_2)R_{11}$, —$(SO_2)OR_{11}$, —(C1-C6 alkyl)-$(SO_2)R_{11}$, —(CO)N(R$_{12}$)$_2$ or —$(SO_2)$N(R$_{12}$)$_2$;

R' independently represents H, halogen, C1-C6 alkoxy, C1-C6 alkoxy C1-C6 alkyl, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, heterocyclyl or heterocyclyl C1-C6 alkyl; wherein, the groups "C1-C6 alkyl", "C2-C6 alkenyl" and "C2-C6 alkynyl" are each independently unsubstituted or substituted by halogen; the groups "C3-C6 cycloalkyl", "C3-C6 cycloalkyl C1-C6 alkyl", "C3-C6 cycloalkenyl", "C3-C6 cycloalkenyl C1-C6 alkyl", "aryl", "aryl C1-C6 alkyl", "heterocyclyl" and "heterocyclyl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —$OR_{14}$, —$SR_{14}$, —(CO)OR$_{14}$, —$(SO_2)R_{14}$, —N(R$_{14}$)$_2$ or —O—(C1-C6 alkyl)-(CO)OR$_{14}$, or two adjacent carbon atoms on the ring together with unsubstituted or halogen-substituted —$OCH_2CH_2$— or —$OCH_2O$— form a fused ring;

R" independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, aryl C2-C6 alkenyl, heterocyclyl, heterocyclyl C1-C6 alkyl or heterocyclyl C2-C6 alkenyl; wherein, the groups "C1-C6 alkyl", "C2-C6 alkenyl" and "C2-C6 alkynyl" are each independently unsubstituted or substituted by 1, 2 or 3 groups selected from halogen, cyano, tri C1-C6 alkyl-silyl, —$OR_{13}$, —$SR_{13}$, —O(CO)R$_{13}$, —(CO)R$_{13}$, —(CO)OR$_{13}$ or —O(CO)OR$_{13}$; the groups "C3-C6 cycloalkyl", "C3-C6 cycloalkyl C1-C6 alkyl", "C3-C6 cycloalkenyl", "C3-C6 cycloalkenyl C1-C6 alkyl", "aryl", "aryl C1-C6 alkyl", "aryl C2-C6 alkenyl", "heterocyclyl", "heterocyclyl C1-C6 alkyl" and "heterocyclyl C2-C6 alkenyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —$OR_{14}$, —$SR_{14}$, —(CO)OR$_{14}$, —$(SO_2)R_{14}$, —N(R$_{14}$)$_2$ or —O—(C1-C6 alkyl)-(CO)OR$_{14}$, or two adjacent carbon atoms on the ring together with unsubstituted or halogen-substituted —$OCH_2CH_2$— or —$OCH_2O$— form a fused ring;

$W_1$ represents O, S, NH or N—(C1-C6 alkyl);

$W_3$ independently represents H, C1-C6 alkyl, C2-C6 alkenyl, C2-C6 alkynyl, C3-C6 cycloalkyl, C3-C6 cycloalkenyl, heterocyclyl, aryl,

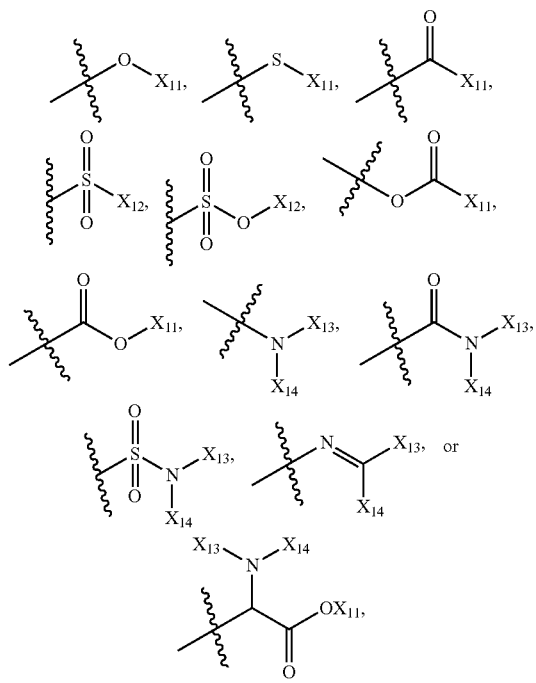

wherein, the groups "C1-C6 alkyl", "C2-C6 alkenyl" and "C2-C6 alkynyl" are each independently unsubstituted or substituted by 1, 2 or 3 groups selected from halogen, cyano, nitro, C3-C6 cycloalkyl, tri C1-C6 alkylsilyl, C3-C6 cycloalkenyl, heterocyclyl, aryl,

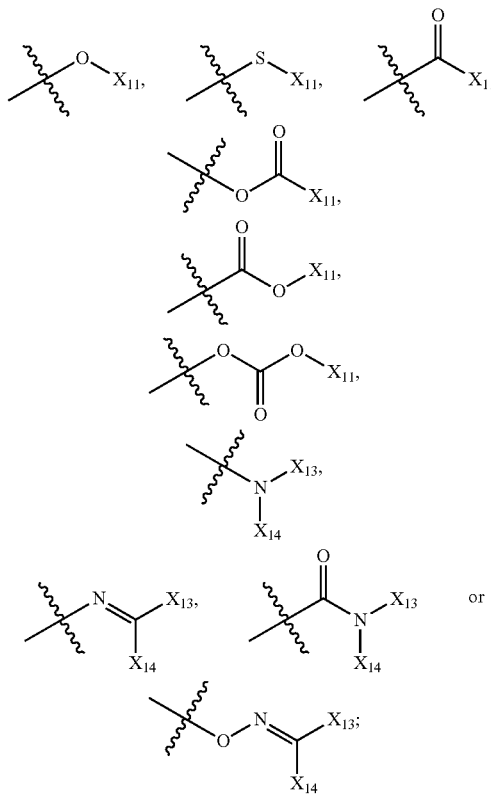

the groups "C3-C6 cycloalkyl", "C3-C6 cycloalkenyl", "heterocyclyl" and "aryl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C6 alkyl)-(CO)OR$_{14}$, or two adjacent carbon atoms on the ring together with unsubstituted or halogen-substituted —OCH$_2$CH$_2$— or —OCH$_2$O— form a fused ring;

or N(W$_3$)$_2$ represents

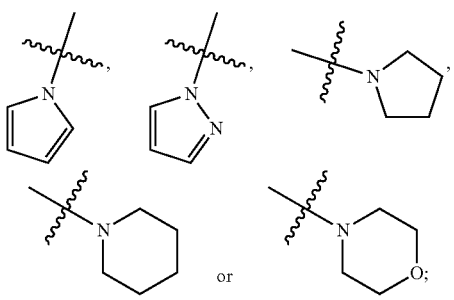

which is unsubstituted or substituted by 1, 2 or 3 groups selected from oxo, C1-C6 alkyl or C1-C6 alkoxy carbonyl;

$X_{11}$ independently represents H, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl or aryl C1-C6 alkyl, wherein, the groups "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" and "aryl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C6 alkyl)-(CO)OR$_{14}$, or two adjacent carbon atoms on the ring together with unsubstituted or halogen-substituted —OCH$_2$CH$_2$— or —OCH$_2$O— form a fused ring;

$X_{12}$ independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl or aryl C1-C6 alkyl; wherein, the groups "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" and "aryl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C6 alkyl)-(CO)OR$_{14}$, or two adjacent carbon atoms on the ring together with unsubstituted or halogen-substituted —OCH₂CH₂— or —OCH₂O— form a fused ring;

X₁₃, X₁₄ each independently represent H, halogen, cyano, C1-C6 alkoxy, C1-C6 alkoxy C1-C6 alkyl, C1-C6 alkyl carbonyl, C1-C6 alkoxy carbonyl, C1-C6 alkyl sulfonyl, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, heterocyclyl or heterocyclyl C1-C6 alkyl, or the group CX₁₃X₁₄, taken together, forms 5-8 membered saturated carbocyclyl,

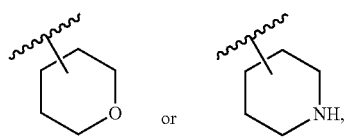

or the group NX₁₃X₁₄, taken together, forms

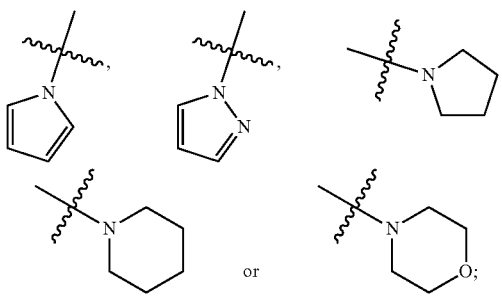

wherein, the groups "C1-C6 alkyl", "C2-C6 alkenyl" and "C2-C6 alkynyl" are each independently unsubstituted or substituted by halogen; the groups "C3-C6 cycloalkyl", "C3-C6 cycloalkyl C1-C6 alkyl", "C3-C6 cycloalkenyl", "C3-C6 cycloalkenyl C1-C6 alkyl", "aryl", "aryl C1-C6 alkyl", "heterocyclyl" and "heterocyclyl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR₁₄, —SR₁₄, —(CO)OR₁₄, —(SO₂)R₁₄, —N(R₁₄)₂ or —O—(C1-C6 alkyl)-(CO)OR₁₄, or two adjacent carbon atoms on the ring together with unsubstituted or halogen-substituted —OCH₂CH₂— or —OCH₂O— form a fused ring; the groups "5-8 membered saturated carbocyclyl,

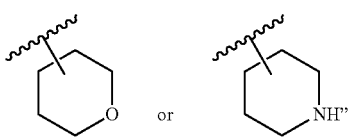

are unsubstituted or substituted by 1, 2 or 3 groups selected from C1-C6 alkyl, C1-C6 alkoxy carbonyl or benzyl, or together with aryl or heterocyclyl form a fused ring; the groups

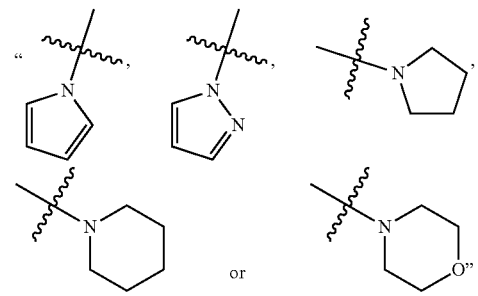

are unsubstituted or substituted by 1, 2 or 3 groups selected from oxo, C1-C6 alkyl or C1-C6 alkoxy carbonyl;

R₁, R₂, R₆, R₁₀, R₁₇, R₁₈, R₂₂, R₂₅, R₃₂ each independently represent H, cyano, C1-C6 alkyl, C2-C6 alkenyl, C2-C6 alkynyl, formyl C1-C6 alkyl, cyano C1-C6 alkyl, amino, amino C1-C6 alkyl, amino carbonyl, amino carbonyl C1-C6 alkyl, amino sulfonyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl, aryl C1-C6 alkyl, R₄R₅N—(CO)—NR₃—,

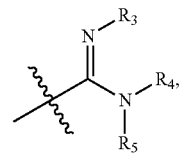

R₃—S(O)ₘ—(C1-C6 alkyl)ₙ-, R₃—O—(C1-C6 alkyl)ₙ-, R₃—(CO)—(C1-C6 alkyl)ₙ-, R₃—O—(C1-C6 alkyl)ₙ-(CO)—, R₃—(CO)—O—(C1-C6 alkyl)ₙ-, R₃—S—(CO)—(C1-C6 alkyl)ₙ-, R₃—O—(CO)—(C1-C6 alkyl)- or R₃—O—(CO)—O—(C1-C6 alkyl)-, wherein, the groups "C1-C6 alkyl", "C2-C6 alkenyl" and "C2-C6 alkynyl" are each independently unsubstituted or substituted by halogen, the groups "amino", "amino C1-C6 alkyl", "amino carbonyl", "amino carbonyl C1-C6 alkyl" and "amino sulfonyl" are each independently unsubstituted or substituted by one or two groups selected from —R₁₁, —OR₁₁, —(CO)R₁₁, —(CO)OR₁₁, —(C1-C6 alkyl)-(CO)OR₁₁, —(SO₂)R₁₁, —(SO₂)OR₁₁, —(C1-C6 alkyl)-(SO₂)R₁₁, —(CO)N(R₁₂)₂ or —(SO₂)N(R₁₂)₂, the groups "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" and "aryl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR₁₄, —SR₁₄, —(CO)OR₁₄, —(SO₂)R₁₄, —N(R₁₄)₂ or —O—(C1-C6 alkyl)-(CO)OR₁₄, or two adjacent carbon atoms on the ring together with unsubstituted or halogen-substituted —OCH₂CH₂— or —OCH₂O— form a fused ring;

or R₁₇, R₁₈, taken together, form —CH₂CH₂CH₂CH₂— or —CH₂CH₂OCH₂— that is unsubstituted or substituted by at least one group selected from halogen, C1-C6 alkyl or halo C1-C6 alkyl;

R₃, R₄, R₅ each independently represent H, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl or aryl C1-C6 alkyl; wherein, the groups "C1-C6 alkyl", "C2-C6 alkenyl" and "C2-C6 alkynyl" are each independently unsubstituted or substituted by halogen; the groups "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" and "aryl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR₁₄, —SR₁₄, —(CO)OR₁₄, —(SO₂)R₁₄, —N(R₁₄)₂ or —O—(C1-C6 alkyl)-(CO)OR₁₄, or two adjacent carbon atoms on the ring together with unsubstituted or halogen-substituted —OCH₂CH₂— or —OCH₂O— form a fused ring;

R₇, R₈, R₇', R₈', R₉, R₁₉, R₂₀, R₂₁, R₂₃, R₂₄, R₂₆, R₂₇, R₂₈, R₂₉, R₃₀, R₃₁, R₃₃, R₃₄, R₃₅, R₃₆, R₃₇, R₃₈, R₃₉, R₄₀, R₄₁, R₄₂, R₄₃, R₄₄, R₄₅, R₄₆, R₄₇, R₄₈, R₄₉, R₅₀, R₅₁ each independently represent H, halogen, hydroxy, mercapto, formyl, hydroxy C1-C6 alkyl, nitro, cyano, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, —OR₁₁, —SR₁₁, —(SO)R₁₁, —(SO₂)R₁₁, —(SO₂)OR₁₁, —O(SO₂)R₁₁, —N(R₁₂)₂, phenyl or benzyl, wherein,
the groups "C1-C6 alkyl", "C2-C6 alkenyl", "C2-C6 alkynyl", "C3-C6 cycloalkyl", "C3-C6 cycloalkyl C1-C6 alkyl", "C3-C6 cycloalkenyl" and "C3-C6 cycloalkenyl C1-C6 alkyl" are each independently unsubstituted or substituted by halogen; the groups "phenyl" and "benzyl" are each independently unsubstituted or substituted by at least one group selected from halogen, cyano, nitro, C1-C6 alkyl, halo C1-C6 alkyl, C1-C6 alkoxy carbonyl, C1-C6 alkylthio, C1-C6 alkyl sulfonyl, C1-C6 alkoxy or halo C1-C6 alkoxy;

or R₇, R₈, taken together, form —CH₂CH₂CH₂CH₂— or —CH=CH—CH=CH— that is unsubstituted or substituted by at least one group selected from halogen, C1-C6 alkyl or halo C1-C6 alkyl;

or R₁₉, R₂₀, taken together, form —CH₂CH₂CH₂CH₂— or —CH₂CH=CHCH₂— that is unsubstituted or substituted by at least one group selected from halogen, C1-C6 alkyl or halo C1-C6 alkyl;

or R₂₁, R₂₂, taken together, form —CH₂CH₂CH₂—, —CH₂OCH₂CH₂— or —CH₂CH₂CH₂CH₂— that is unsubstituted or substituted by at least one group selected from halogen, C1-C6 alkyl or halo C1-C6 alkyl;

R₁₁ independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, phenyl or benzyl; wherein, the groups "C1-C6 alkyl", "C2-C6 alkenyl" and "C2-C6 alkynyl" are each independently unsubstituted or substituted by halogen; the groups "phenyl" and "benzyl" are each independently unsubstituted or substituted by 1, 2 or 3 groups selected from halogen, cyano, nitro, C1-C6 alkyl, halo C1-C6 alkyl, C1-C6 alkoxy carbonyl, C1-C6 alkylthio, C1-C6 alkyl sulfonyl, C1-C6 alkoxy or halo C1-C6 alkoxy;

R₁₂ independently represents H, C1-C6 alkyl, C2-C6 alkenyl, C2-C6 alkynyl, C1-C6 alkoxy, C1-C6 alkyl sulfonyl, C3-C6 cycloalkyl, C3-C6 cycloalkyl C1-C6 alkyl, C3-C6 cycloalkenyl or C3-C6 cycloalkenyl C1-C6 alkyl, or the group N(R₁₂)₂ in —(CO)N(R₁₂)₂ or —(SO₂)N(R₁₂)₂ independently represent

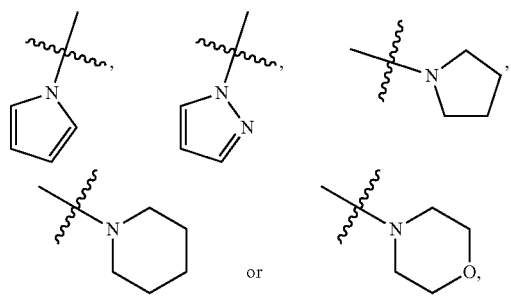

or which is unsubstituted or substituted by 1, 2 or 3 groups selected from oxo, C1-C6 alkyl or C1-C6 alkoxy carbonyl;

R₁₃ independently represents C1-C6 alkyl, C2-C6 alkenyl, C2-C6 alkynyl, C3-C6 cycloalkyl, phenyl or phenyl substituted by 1, 2 or 3 groups selected from: halogen, cyano, nitro, C1-C6 alkyl, halo C1-C6 alkyl, C1-C6 alkoxy, halo C1-C6 alkoxy, C1-C6 alkoxy carbonyl, C1-C6 alkylthio, C1-C6 alkyl sulfonyl or phenoxy substituted by 1, 2 or 3 groups selected from halogen, cyano, nitro, C1-C6 alkyl, halo C1-C6 alkyl, C1-C6 alkoxy or halo C1-C6 alkoxy;

R₁₄ independently represents H, C1-C6 alkyl, halo C1-C6 alkyl, phenyl or phenyl substituted by 1, 2 or 3 groups selected from halogen, cyano, nitro, C1-C6 alkyl, halo C1-C6 alkyl, C1-C6 alkoxy carbonyl, C1-C6 alkylthio, C1-C6 alkyl sulfonyl, C1-C6 alkoxy or halo C1-C6 alkoxy;

R₁₅, R₁₆, R₅₂ each independently represent H, halogen, C1-C6 alkyl, C2-C6 alkenyl, C2-C6 alkynyl, C3-C6 cycloalkyl, C3-C6 cycloalkyl C1-C6 alkyl, C3-C6 cycloalkenyl or C3-C6 cycloalkenyl C1-C6 alkyl, wherein, the groups "C1-C6 alkyl", "C2-C6 alkenyl", "C2-C6 alkynyl", "C3-C6 cycloalkyl", "C3-C6 cycloalkyl C1-C6 alkyl", "C3-C6 cycloalkenyl" and "C3-C6 cycloalkenyl C1-C6 alkyl" are each independently unsubstituted or substituted by halogen.

Further preferably, X₁, X₂ each independently represent H, halogen, nitro, cyano, thiocyano, hydroxy, mercapto, sulfo, formyl, haloformyl, azido, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, —PO(OR')₂, —OR", —(CO)R", —SR", —(SO)R", —(SO₂)R", —Si(R")₃, —O(CO)R", —O—(SO₂)R", —S(CO)R", —(SO₂)OR", —O(CO)OR", —(CO)(CO)OR",

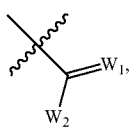

—CR'=N—OH, —CR'=N—O—R", heterocyclyl, heterocyclyl C1-C3 alkyl, aryl, aryl C1-C3 alkyl, amino, amino C1-C3 alkyl, amino carbonyl C1-C3 alkyl, amino carbonyloxy C1-C3 alkyl, amino thio carbonyloxy C1-C3 alkyl, amino sulfonyl or amino sulfonyloxy C1-C3 alkyl, wherein, the groups "C1-C6 alkyl", "C2-C6 alkenyl" and "C2-C6 alkynyl" are each independently unsubstituted or substituted by 1, 2 or 3 groups selected from halogen, cyano, hydroxy, mercapto, carboxyl, —OR", —(CO)R", —SR", —(SO$_2$)R", —O(CO)H, —O(CO)R", —O—(SO$_2$)R", —(CO)OR", —O(CO)OR", —O(CO)(CO)OH, —O(CO)(CO)OR", —O—(C1-C3 alkyl)-(CO)OH or —O—(C1-C3 alkyl)-(CO)OR", the groups "C3-C6 cycloalkyl", "C3-C6 cycloalkyl C1-C3 alkyl", "C3-C6 cycloalkenyl", "C3-C6 cycloalkenyl C1-C3 alkyl", "heterocyclyl", "heterocyclyl C1-C3 alkyl", "aryl" and "aryl C1-C3 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C3 alkyl)-(CO)OR$_{14}$, or two adjacent carbon atoms on the ring together with unsubstituted or halogen-substituted —OCH$_2$CH$_2$— or —OCH$_2$O— form a fused ring, the groups "amino", "amino C1-C3 alkyl", "amino carbonyl C1-C3 alkyl", "amino carbonyloxy C1-C3 alkyl", "amino thio carbonyloxy C1-C3 alkyl", "amino sulfonyl" and "amino sulfonyloxy C1-C3 alkyl" are each independently unsubstituted or substituted by one or two groups selected from —R$_{11}$, —OR$_{11}$, —(CO)R$_{11}$, —(CO)OR$_{11}$, —(C1-C3 alkyl)-(CO)OR$_{11}$, —(SO$_2$)R$_{11}$, —(SO$_2$)OR$_{11}$, —(C1-C3 alkyl)-(SO$_2$)R$_{11}$, —(CO)N(R$_{12}$)$_2$ or —(SO$_2$)N(R$_{12}$)$_2$;

R' independently represents H, halogen, C1-C6 alkoxy, C1-C6 alkoxy C1-C3 alkyl, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, aryl, aryl C1-C3 alkyl, heterocyclyl or heterocyclyl C1-C3 alkyl; wherein, the groups "C1-C6 alkyl", "C2-C6 alkenyl" and "C2-C6 alkynyl" are each independently unsubstituted or substituted by halogen; the groups "C3-C6 cycloalkyl", "C3-C6 cycloalkyl C1-C3 alkyl", "C3-C6 cycloalkenyl", "C3-C6 cycloalkenyl C1-C3 alkyl", "aryl", "aryl C1-C3 alkyl", "heterocyclyl" and "heterocyclyl C1-C3 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C3 alkyl)-(CO)OR$_{14}$; or two adjacent carbon atoms on the ring together with unsubstituted or halogen-substituted —OCH$_2$CH$_2$— or —OCH$_2$O— form a fused ring;

R" independently represents C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, aryl, aryl C1-C3 alkyl, aryl C2-C3 alkenyl, heterocyclyl, heterocyclyl C1-C3 alkyl or heterocyclyl C2-C3 alkenyl; wherein, the groups "C1-C6 alkyl", "C2-C6 alkenyl" and "C2-C6 alkynyl" are each independently unsubstituted or substituted by 1, 2 or 3 groups selected from halogen, cyano, tri C1-C6 alkylsilyl, —OR$_{13}$, —SR$_{13}$, —O(CO)R$_{13}$, —(CO)R$_{13}$, —(CO)OR$_{13}$ or —O(CO)OR$_{13}$; the groups "C3-C6 cycloalkyl", "C3-C6 cycloalkyl C1-C3 alkyl", "C3-C6 cycloalkenyl", "C3-C6 cycloalkenyl C1-C3 alkyl", "aryl", "aryl C1-C3 alkyl", "aryl C2-C3 alkenyl", "heterocyclyl", "heterocyclyl C1-C3 alkyl" and "heterocyclyl C2-C3 alkenyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C3 alkyl)-(CO)OR$_{14}$, or two adjacent carbon atoms on the ring together with unsubstituted or halogen-substituted —OCH$_2$CH$_2$— or —OCH$_2$O— form a fused ring;

W$_3$ independently represents H, C1-C6 alkyl, C2-C6 alkenyl, C2-C6 alkynyl, C3-C6 cycloalkyl, C3-C6 cycloalkenyl, heterocyclyl, aryl,

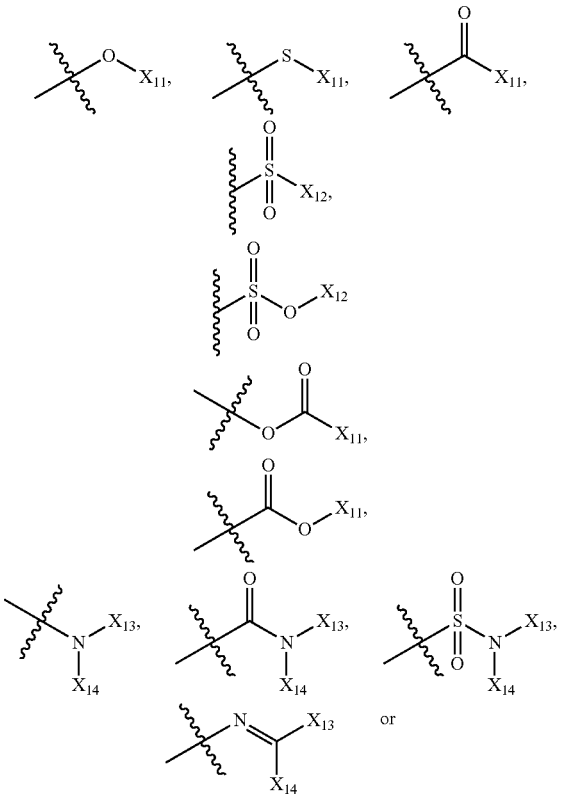

-continued

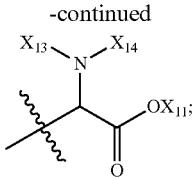

wherein, the groups "C1-C6 alkyl", "C2-C6 alkenyl" and "C2-C6 alkynyl" are each independently unsubstituted or substituted by 1, 2 or 3 groups selected from halogen, cyano, nitro, C3-C6 cycloalkyl, tri C1-C6 alkylsilyl, C3-C6 cycloalkenyl, heterocyclyl, aryl,

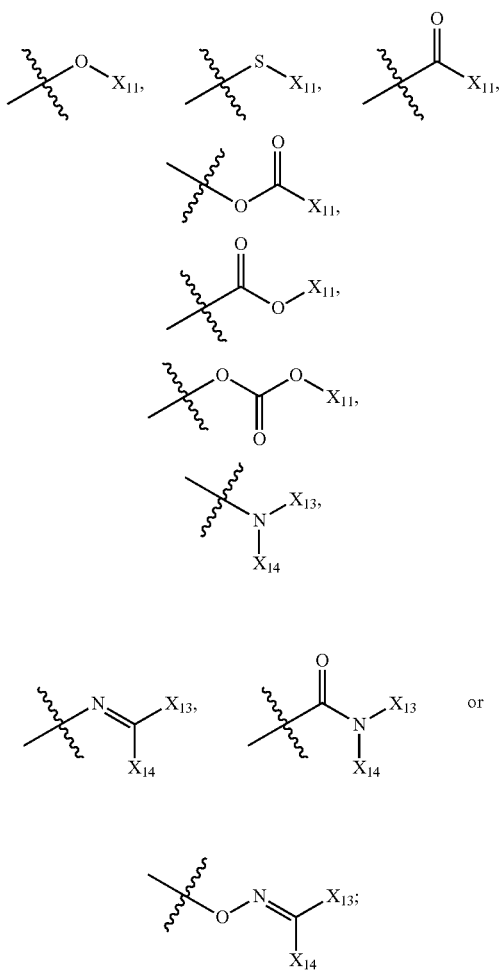

the groups "C3-C6 cycloalkyl", "C3-C6 cycloalkenyl", "heterocyclyl" and "aryl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C3 alkyl)-(CO)OR$_{14}$, or two adjacent carbon atoms on the ring together with unsubstituted or halogen-substituted —OCH$_2$CH$_2$— or —OCH$_2$O— form a fused ring;

or N(W$_3$)$_2$ represents

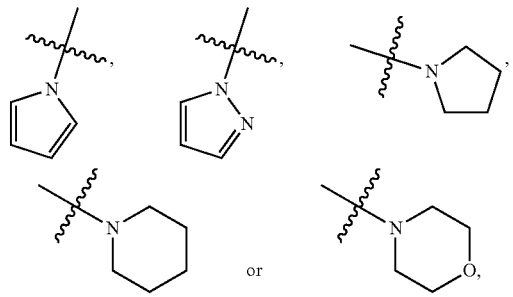

or which is unsubstituted or substituted by 1, 2 or 3 groups selected from oxo, C1-C6 alkyl or C1-C6 alkoxy carbonyl;

X$_{11}$ independently represents H, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, heterocyclyl, heterocyclyl C1-C3 alkyl, aryl or aryl C1-C3 alkyl; wherein, the groups "C3-C6 cycloalkyl", "C3-C6 cycloalkyl C1-C3 alkyl", "C3-C6 cycloalkenyl", "C3-C6 cycloalkenyl C1-C3 alkyl", "heterocyclyl", "heterocyclyl C1-C3 alkyl", "aryl" and "aryl C1-C3 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C3 alkyl)-(CO)OR$_{14}$, or two adjacent carbon atoms on the ring together with unsubstituted or halogen-substituted —OCH$_2$CH$_2$— or —OCH$_2$O— form a fused ring;

X$_{12}$ independently represents C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, heterocyclyl, heterocyclyl C1-C3 alkyl, aryl or aryl C1-C3 alkyl; wherein, the groups "C3-C6 cycloalkyl", "C3-C6 cycloalkyl C1-C3 alkyl", "C3-C6 cycloalkenyl", "C3-C6 cycloalkenyl C1-C3 alkyl", "heterocyclyl", "heterocyclyl C1-C3 alkyl", "aryl" and "aryl C1-C3 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C3 alkyl)-(CO)OR$_{14}$, or two adjacent carbon atoms on the ring together with unsubstituted or halogen-substituted —OCH$_2$CH$_2$— or —OCH$_2$O— form a fused ring;

X$_{13}$, X$_{14}$ each independently represent H, halogen, cyano, C1-C6 alkoxy, C1-C6 alkoxy C1-C3 alkyl, C1-C6 alkyl carbonyl, C1-C6 alkoxy carbonyl, C1-C6 alkyl sulfonyl, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, aryl, aryl C1-C3 alkyl, heterocyclyl or heterocyclyl C1-C3 alkyl, or the group CX$_{13}$X$_{14}$, taken together, forms 5-8 membered saturated carbocyclyl,

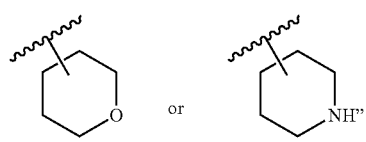

or the group NX$_{13}$X$_{14}$, taken together, forms

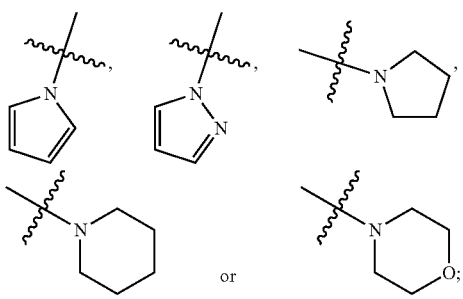

wherein, the groups "C1-C6 alkyl", "C2-C6 alkenyl" and "C2-C6 alkynyl" are each independently unsubstituted or substituted by halogen; the groups "C3-C6 cycloalkyl", "C3-C6 cycloalkyl C1-C3 alkyl", "C3-C6 cycloalkenyl", "C3-C6 cycloalkenyl C1-C3 alkyl", "aryl", "aryl C1-C3 alkyl", "heterocyclyl" and "heterocyclyl C1-C3 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C3 alkyl)-(CO)OR$_{14}$, or two adjacent carbon atoms on the ring together with unsubstituted or halogen-substituted —OCH$_2$CH$_2$— or —OCH$_2$O— form a fused ring; the groups "5-8 membered saturated carbocyclyl

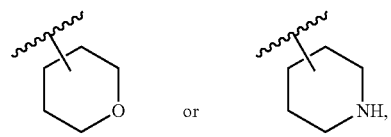

are unsubstituted or substituted by 1, 2 or 3 groups selected from C1-C6 alkyl, C1-C6 alkoxy carbonyl or benzyl, or together with phenyl or thienyl form a fused ring; the groups

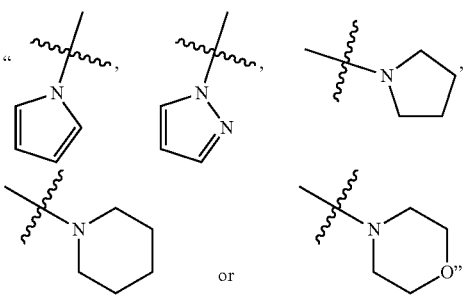

are unsubstituted or substituted by 1, 2 or 3 groups selected from oxo, C1-C6 alkyl or C1-C6 alkoxy carbonyl;

R$_{11}$ independently represents C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, phenyl, benzyl; wherein, the groups "C1-C6 alkyl", "C2-C6 alkenyl" and "C2-C6 alkynyl" are each independently unsubstituted or substituted by halogen; the groups "phenyl" and "benzyl" are each independently unsubstituted or substituted by 1, 2 or 3 groups selected from halogen, cyano, nitro, C1-C6 alkyl, halo C1-C6 alkyl, C1-C6 alkoxy carbonyl, C1-C6 alkylthio, C1-C6 alkyl sulfonyl, C1-C6 alkoxy or halo C1-C6 alkoxy;

R$_{12}$ independently represents H, C1-C6 alkyl, C2-C6 alkenyl, C2-C6 alkynyl, C1-C6 alkoxy, C1-C6 alkyl sulfonyl, C3-C6 cycloalkyl, C3-C6 cycloalkyl C1-C3 alkyl, C3-C6 cycloalkenyl or C3-C6 cycloalkenyl C1-C3 alkyl, or the group N(R$_{12}$)$_2$ in —(CO)N(R$_{12}$)$_2$ or —(SO$_2$)N(R$_{12}$)$_2$ independently represents, which is unsubstituted or substituted by 1, 2 or 3 groups selected from oxo, C1-C6 alkyl or C1-C6 alkoxy carbonyl;

R$_{13}$ independently represents C1-C6 alkyl, C2-C6 alkenyl, C2-C6 alkynyl, C3-C6 cycloalkyl, phenyl or phenyl substituted by 1, 2 or 3 groups selected from: halogen, cyano, nitro, C1-C6 alkyl, halo C1-C6 alkyl, C1-C6 alkoxy, halo C1-C6 alkoxy, C1-C6 alkoxy carbonyl, C1-C6 alkylthio, C1-C6 alkyl sulfonyl or phenoxy substituted by 1, 2 or 3 groups selected from halogen, cyano, nitro, C1-C6 alkyl, halo C1-C6 alkyl, C1-C6 alkoxy or halo C1-C6 alkoxy;

R$_{14}$ independently represents H, C1-C6 alkyl, halo C1-C6 alkyl, phenyl or phenyl substituted by 1, 2 or 3 groups selected from halogen, cyano, nitro, C1-C6 alkyl, halo C1-C6 alkyl, C1-C6 alkoxy carbonyl, C1-C6 alkylthio, C1-C6 alkyl sulfonyl, C1-C6 alkoxy or halo C1-C6 alkoxy.

More preferably, Het represent

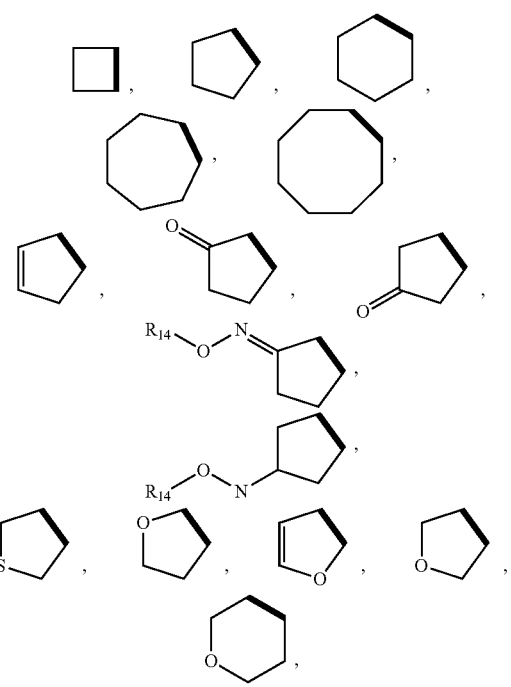

-continued

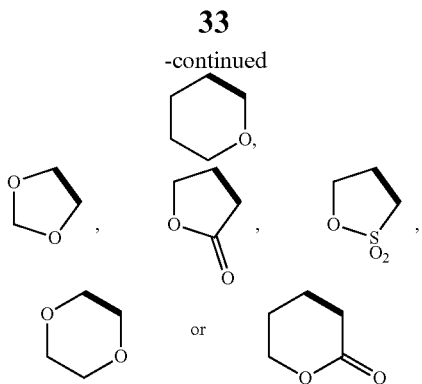

wherein, the bold chemical bond corresponds to the bold chemical bond in the general formula, and the carbon atoms at the ends of the bold chemical bond respectively correspond to C4 and C5 in the general formula without a determined order; for example, when Het is

the general formula is

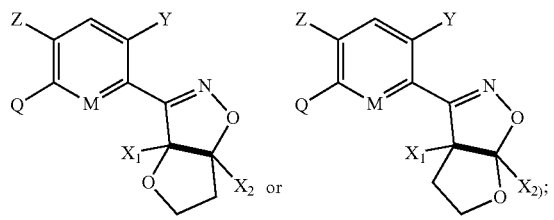

except for the 4- and 5-positions that are respectively substituted by $X_2$ or $X_1$ in the general formula I, other positions on the Het are each independently unsubstituted or substituted by 1, 2 or 3 groups selected from halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —$OR_{14}$, —$SR_{14}$, —$SOR_{14}$, —$(CO)OR_{14}$, —$(SO_2)R_{14}$, —$N(R_{14})_2$ or —O—(C1-C3 alkyl)-(CO)$OR_{14}$.

Further preferably, Q represents

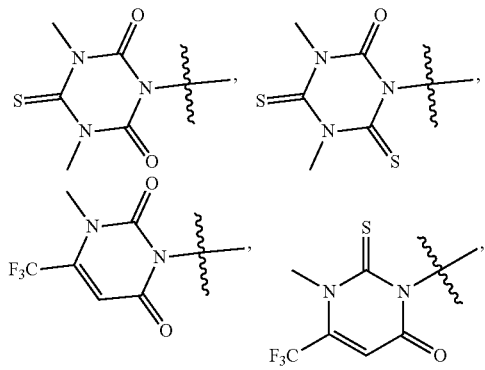

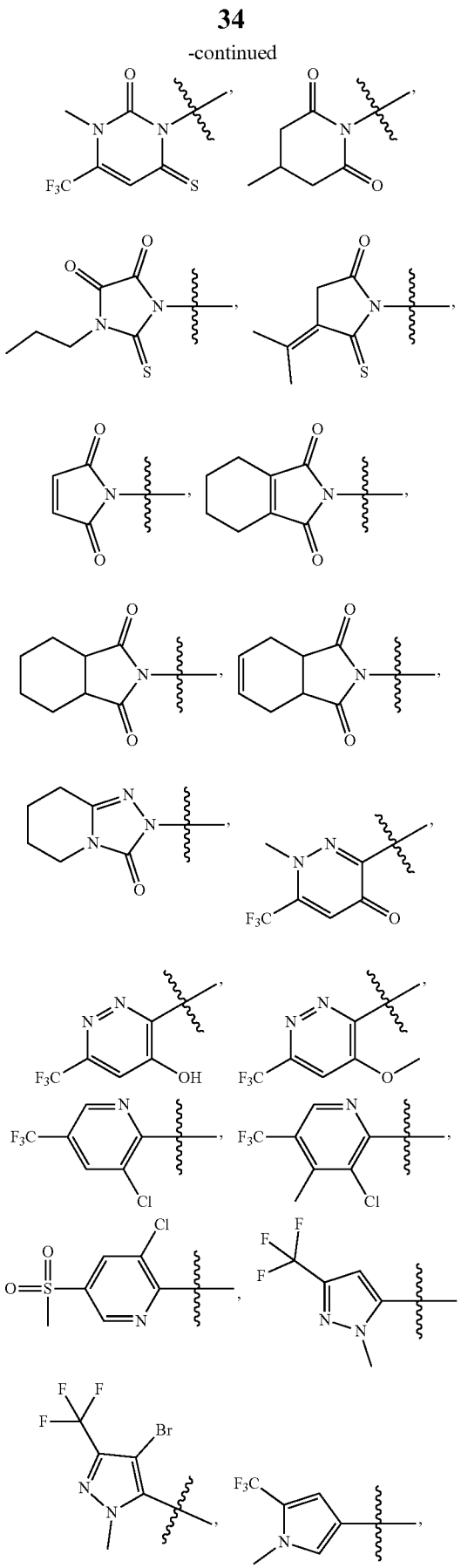

-continued

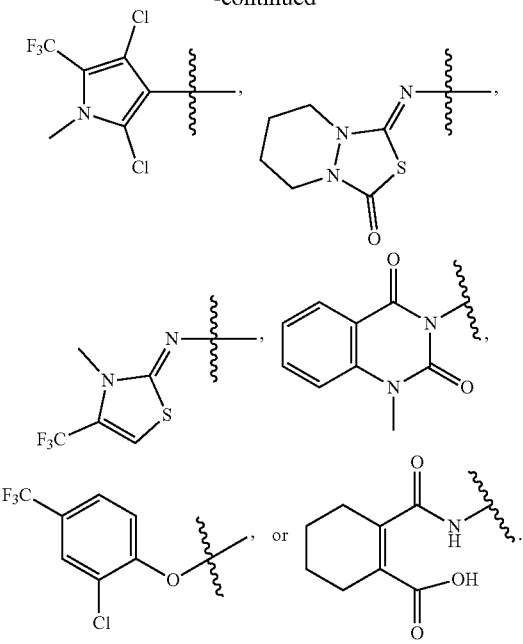

In the definition of the compound represented by the above Formula and all of the following structural formulas, the technical terms used, whether used alone or used in compound word, represent the following substituents: an alkyl having more than two carbon atoms may be linear or branched. For example, the alkyl in the compound word "-alkyl-(CO)OR$_{11}$" may be —CH$_2$—, —CH$_2$CH$_2$—, —CH(CH$_3$)—, —C(CH$_3$)$_2$—, and the like. The alkyl is, for example, C$_1$ alkyl: methyl; C$_2$ alkyl: ethyl; C$_3$ alkyl: propyl such as n-propyl or isopropyl; C$_4$ alkyl: butyl such as n-butyl, isobutyl, tert-butyl or 2-butyl; C$_5$ alkyl: pentyl such as n-pentyl; C$_6$ alkyl: hexyl such as n-hexyl, isohexyl and 1,3-dimethylbutyl. Similarly, the alkenyl is, for example, vinyl, allyl, 1-methylprop-2-en-1-yl, 2-methylprop-2-en-1-yl, but-2-en-1-yl, butyl-3-en-1-yl, 1-methylbut-3-en-1-yl and 1-methylbut-2-en-1-yl. The alkynyl is, for example, ethynyl, propargyl, but-2-yn-1-yl, but-3-yn-1-yl, 1-methylbut-3-yn-1-yl. A multiple bond may be placed at any position of each unsaturated group. The cycloalkyl is a carbocyclic saturated ring system having, for example, three to six carbon atoms, such as cyclopropyl, cyclobutyl, cyclopentyl or cyclohexyl. Similarly, the cycloalkenyl is monocycloalkenyl having, for example, three to six carbon ring members, such as cyclopropenyl, cyclobutenyl, cyclopentenyl, and cyclohexenyl, wherein double bond can be at any position. Halogen is fluorine, chlorine, bromine or iodine.

Unless otherwise specified, the "aryl" of the present invention includes, but is not limited to, phenyl, naphthyl

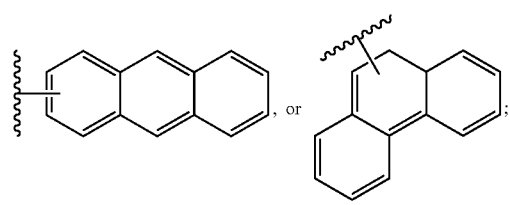

the "heterocyclyl" not only includes, but is not limited to, saturated or unsaturated non-aromatic cyclic group

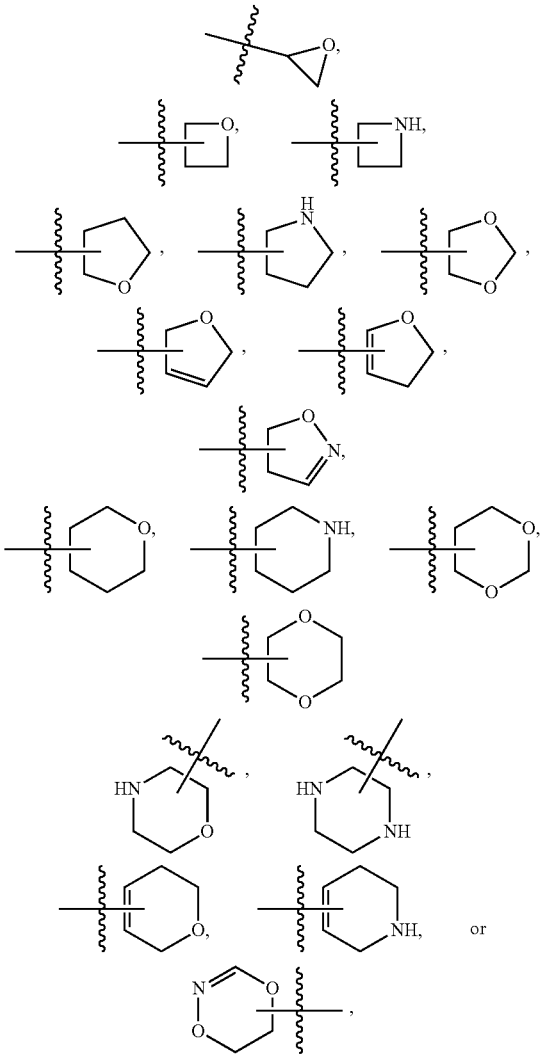

etc. but also includes, but is not limited to, "heteroaryl", which is an aromatic cyclic group having, for example, 3 to 6 ring atoms and which may also be fused with a benzo ring, and 1 to 4 (for example, 1, 2, 3 or 4) heteroatoms of the ring are selected from the group consisting of oxygen, nitrogen and sulfur. For example,

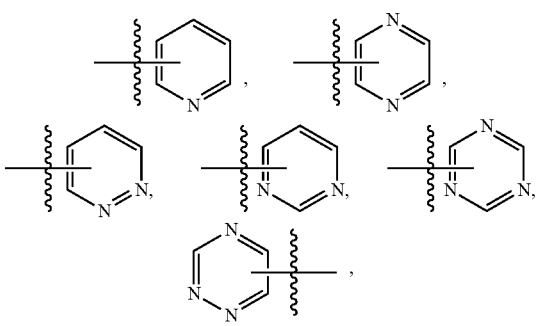

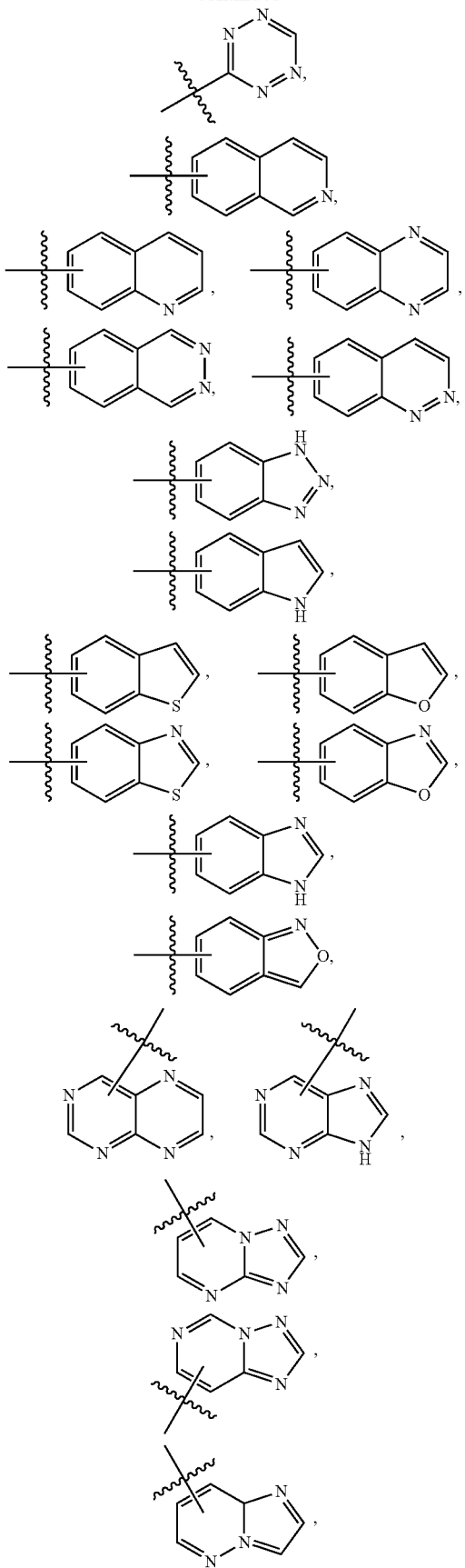
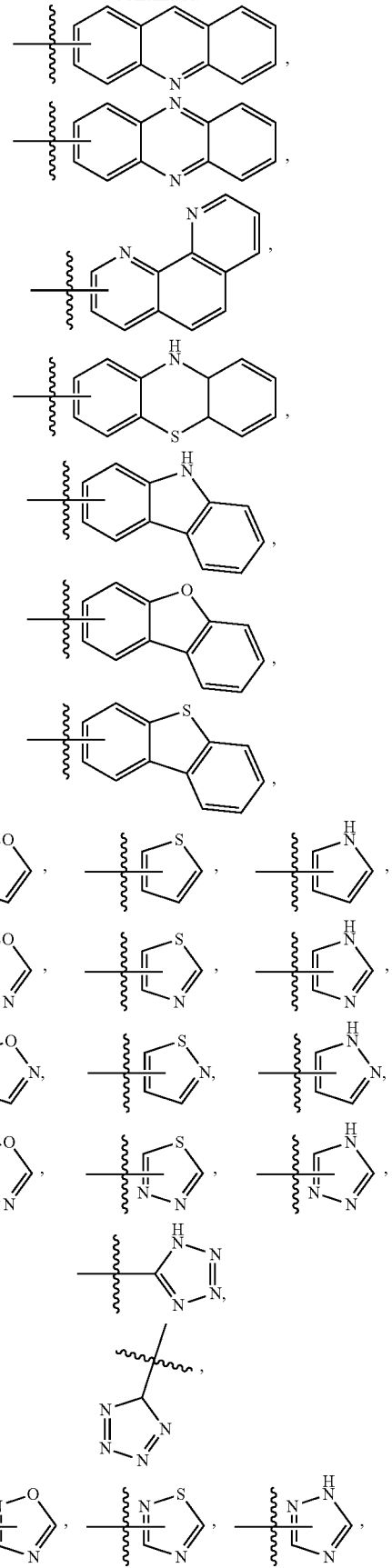

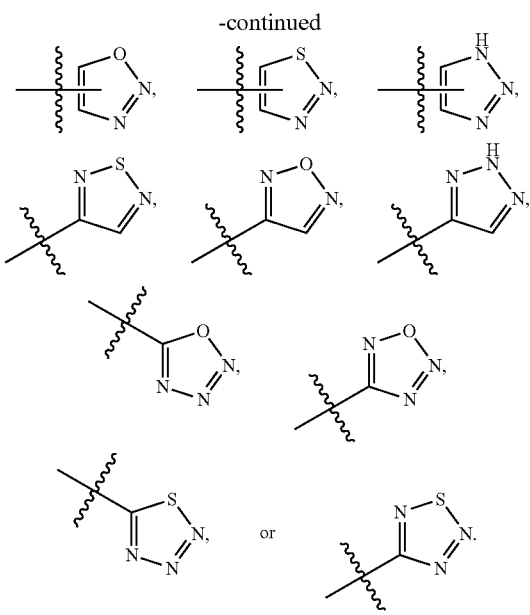

If a group is substituted by a group, which should be understood to mean that the group is substituted by one or more groups, which are same or different groups, selected from the mentioned groups. In addition, the same or different substitution characters contained in the same or different substituents are independently selected, and may be the same or different. This is also applicable to ring systems formed with different atoms and units. Meanwhile, the scope of the claims will exclude those compounds chemically unstable under standard conditions known to those skilled in the art.

In addition, unless specifically defined, the term "substituted by at least one group" herein refers to being substituted by 1, 2, 3, 4 or 5 groups; a group (including heterocyclyl, aryl, etc.) without being specified a linking site may be attached at any site, including a C or N site; if it is substituted, the substituent may be substituted at any site as long as it comply with the valence bond theory. For example, if the heteroaryl

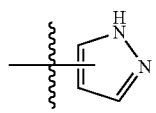

is substituted with one methyl, it can be

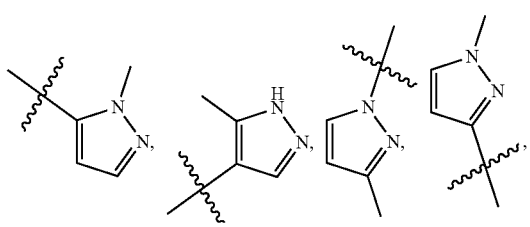

etc.

Depending on the property of substituents and the linkage manner thereof, the compound of Formula I and its deriva- tives may exist as a stereoisomer. The stereoisomer can be obtained from the mixtures obtained in the preparation by conventional separation methods, for example by chromatographic separation. The stereoisomer may also be prepared selectively by using stereoselective reactions and using optically active starting materials and/or auxiliaries. The present invention also relates to all stereoisomers and mixtures thereof which are included in general formula I but are not specifically defined.

The compound represented by general formula I of the present invention can be prepared by standard methods of organic chemistry, for example, a method for preparing the fused-ring substituted aromatic compound comprising the step:

converting a compound represented by general formula II

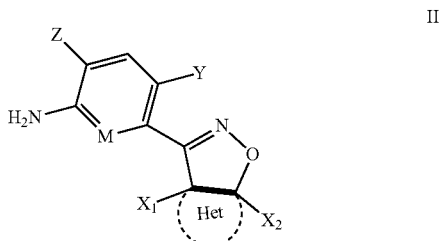

into a compound represented by general formula I; the method depends on the nature of the group Q. These methods are particularly described in U.S. Pat. No. 5,679,791, WO2012/041789, WO2019/101551, WO00/50409, CN105753853A and the like.

Alternatively, the compound represented by general formula I can be prepared by cyclization reaction of a compound represented by general formula IV and a compound represented by general formula V. Preferably, the reaction is carried out in the presence of a solvent and a base. The method in which the compound represented by general formula IV is involved is particularly described in patent WO1999/055693 and the like.

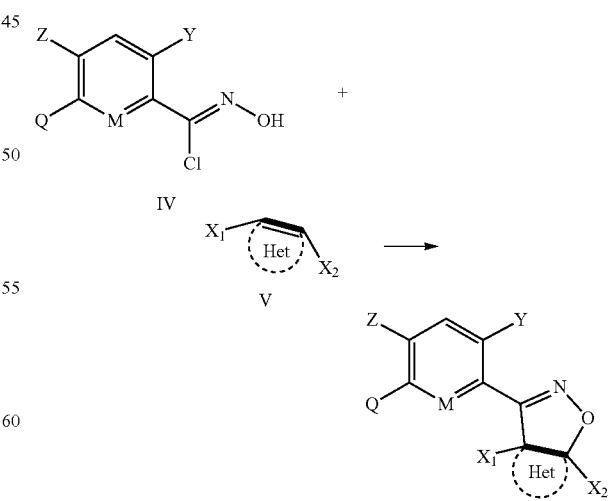

For example, when Q represents

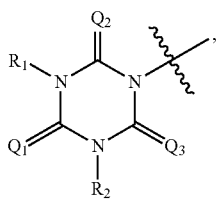

Q-1

(1) reacting a compound represented by general formula II with

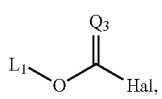

to obtain a compound represented by general formula II-1, and then cyclizing with a compound represented by general formula III-1, to obtain a compound represented by general formula I-1, the chemical reaction equation shown as follows:

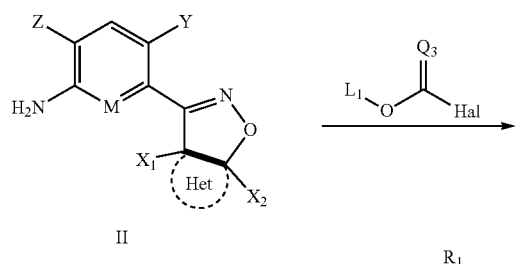

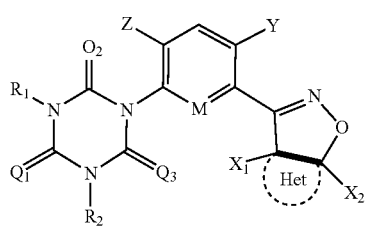

(2) reacting a compound represented by general formula II with

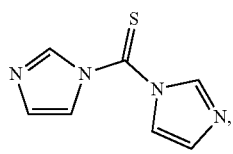

to obtain a compound represented by general formula II-2, and then reacting with a compound represented by general formula III-1 to obtain a compound represented by general formula I-2; the chemical reaction equation shown as follows:

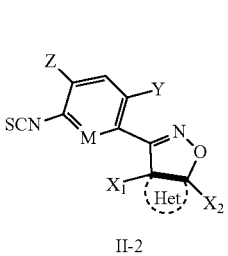

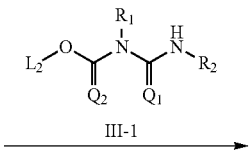

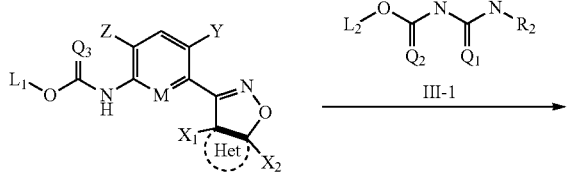

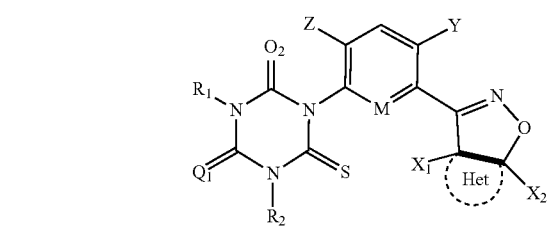

when Q represents

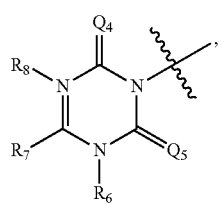

Q-2

(3) reacting a compound represented by general formula II with a compound represented by general formula III-2 to obtain a compound represented by general formula I-3; the chemical reaction equation shown as follows:

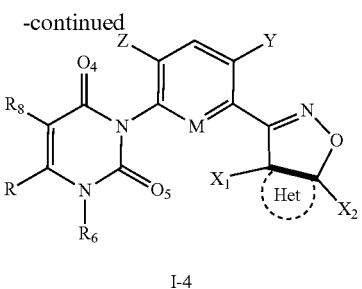

(5) reacting a compound represented by general formula II with

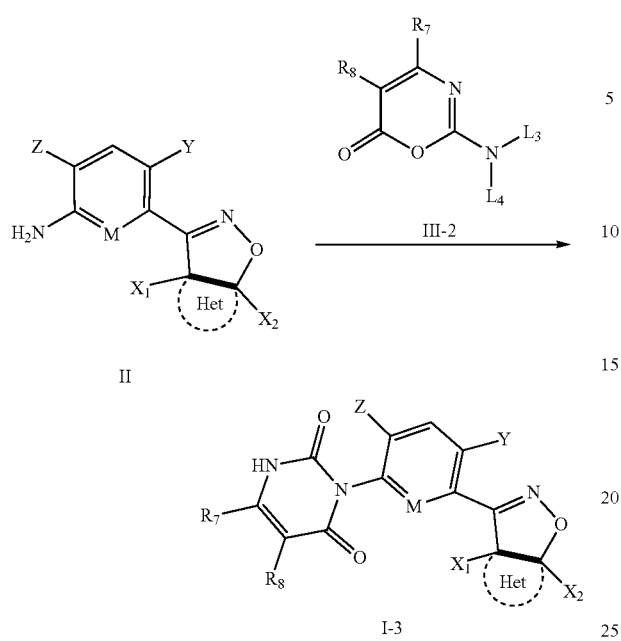

(4) reacting a compound represented by general formula II with

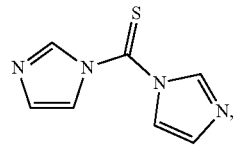

to obtain a compound represented by general formula II-3, and then cyclizing with a compound represented by general formula III-3, to obtain a compound represented by general formula I-4, the chemical reaction equation shown as follows:

to obtain a compound represented by general formula II-2, and then reacting with a compound represented by general formula III-4 to obtain a compound represented by general formula I-5; the chemical reaction equation shown as follows:

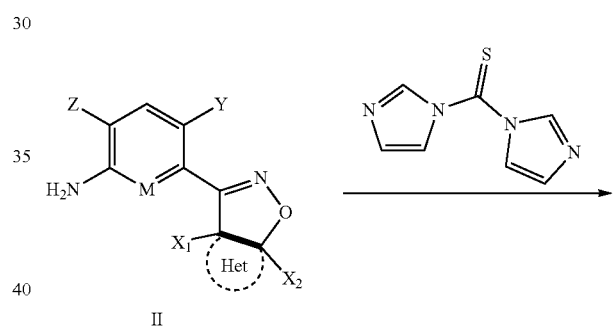

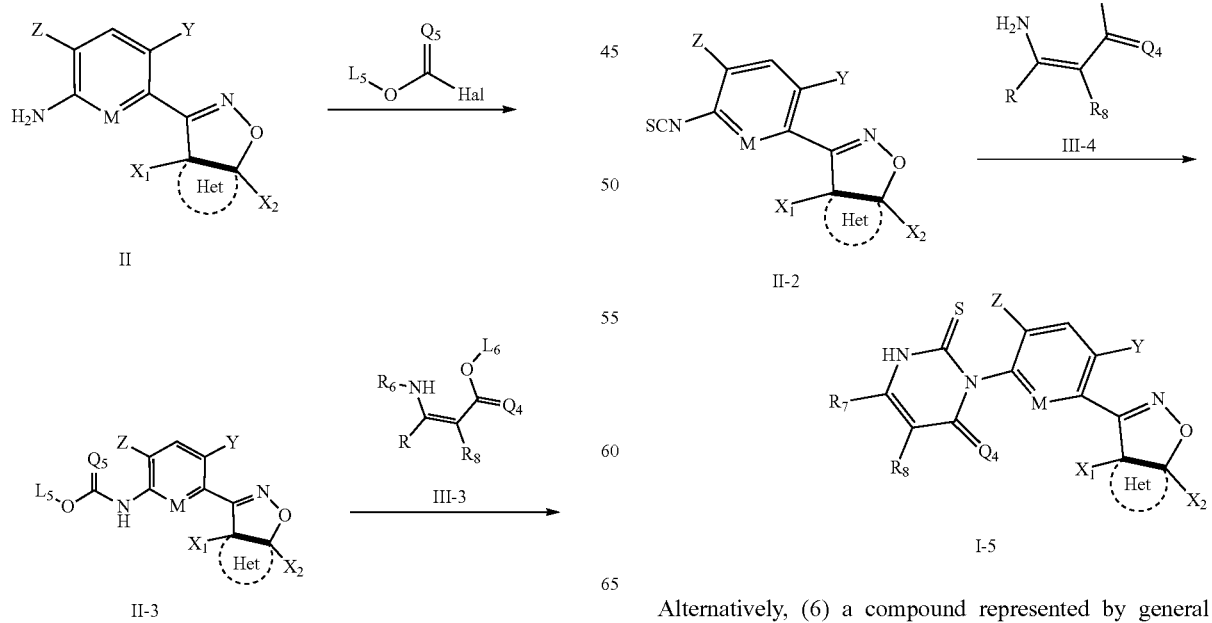

Alternatively, (6) a compound represented by general formula I-6 is subjected to substitution reaction with $R_6'$-Hal to obtain a compound represented by general formula 1-7; the chemical reaction equation shown as follows:

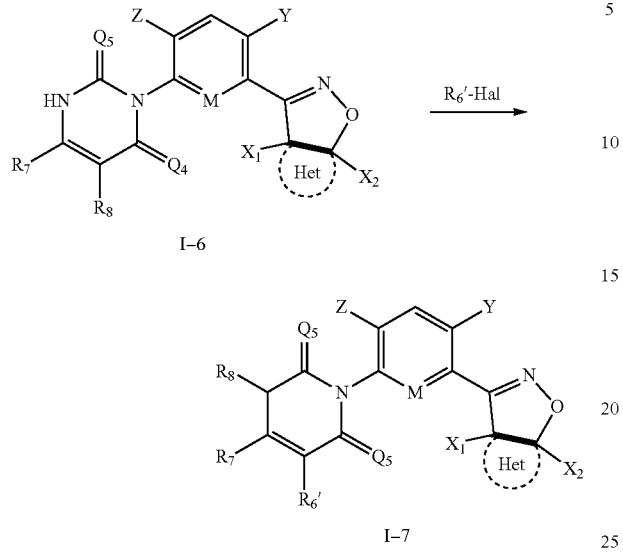

wherein, $L_1$, $L_2$, $L_3$, $L_4$, $L_5$, $L_6$ and $L_7$ each independently represent C1-C6 alkyl or aryl, preferably methyl, ethyl or phenyl; Hal independently represents halogen, preferably chlorine, iodine; $R_6'$ represents the groups except for H represented by $R_6$; other substituents $R_1$, $R_2$, $R_6$, $R_7$, $R_8$,

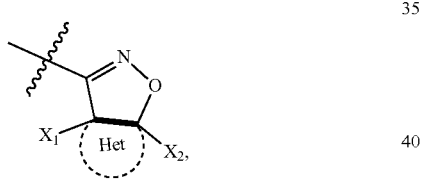

$Q_1$, $Q_2$, $Q_3$, $Q_4$, $Q_5$, Y, Z and M are as defined above.

Preferably, the first step in the step (1) and the first step in the step (4) are both carried out in the presence of a solvent.

Preferably, the second step in the step (1), the second step in the steps (2) and (4), and the steps (5) and (6) are all carried out in the presence of a base and a solvent.

Preferably, the step (3) is carried out in the presence of an acid.

The base is at least one selected from inorganic bases (such as $K_2CO_3$, $Na_2CO_3$, $Cs_2CO_3$, $NaHCO_3$, KF, CsF, KOAc, AcONa, $K_3PO_4$, t-BuONa, EtONa, NaOH, KOH, NaOMe and the like) or organic bases (such as pyrazole, triethylamine, DIEA and the like).

The solvent is at least one selected from DMF, DMA, methanol, ethanol, acetonitrile, dichloroethane, DMSO, Dioxane, dichloromethane, toluene or ethyl acetate.

The acid is selected from acetic acid, hydrochloric acid or sulfuric acid.

In addition, when at least one of the substituents $Q_1$, $Q_2$, $Q_3$ in Q

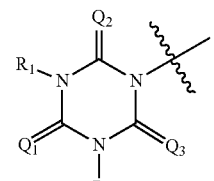

(       or

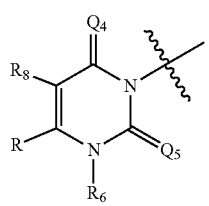

)

is S, or when at least one of $Q_4$ and $Q_5$ is S, it can also be prepared by using the corresponding compound wherein the Q represents

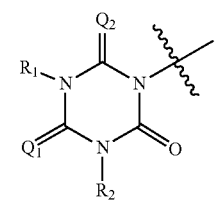

or

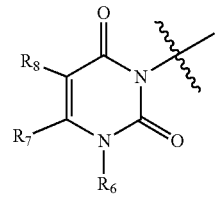

as raw compound through conventional sulfur substitution reaction in the presence of Lawson's reagent

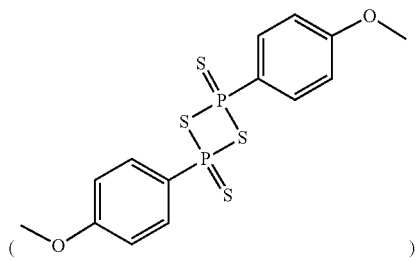

or phosphorus pentasulfide.

A herbicidal composition comprising a herbicidally effective dose of at least one of the fused-ring substituted aromatic compound; preferably, the herbicidal composition also comprises a preparation auxiliary.

A method for controlling a weed which includes applying a herbicidally effective dose of at least one of the fused-ring substituted aromatic compound or the herbicidal composition to a plant or a weed area.

Use of at least one of the fused-ring substituted aromatic compound or the herbicidal composition as above-described for controlling a weed, preferably, wherein the fused-ring substituted aromatic compound is used for preventing and/or controlling a weed in a useful crop, wherein the useful crop is a transgenic crop or a crop treated by gene editing technique.

The compounds of the formula I according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and *Sorghum*, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from amongst the annuals, and *Convolvulus, Cirsium, Rumex* and *Artemisia* in the case of the perennial weeds. The active compounds according to the invention also effect outstanding control of harmful plants which occur under the specific conditions of rice growing such as, for example, *Echinochloa, Sagittaria, Alisma, Eleocharis, Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera spica venti, Chenopodium album, Lamium purpureum, Polygonum convulvulus, Stellaria media, Veronica hederifolia, Veronica persica, Viola tricolor* and against *Amaranthus, Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula I according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula I can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of:

genetically engineered changes in crop plants in order to modify the starch synthesized in the plants (for example WO 92/11376, WO 92/14827, WO 91/19806), transgenic crop plants which are resistant to certain herbicides of the glufosinate-(cf., for example, EP-A 0 242 236, EP-A 0 242 246) or glyphosate-type (WO 92/00377), or of the sulfonylurea-type (EP-A 0 257 993, U.S. Pat. No. 5,013,659A), transgenic crop plants, for example cotton, having the ability to produce *Bacillus thuringiensis* toxins (Bt toxins) which impart resistance to certain pests to the plants (EP-A 0 142 924, EP-A 0 193 259), transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the above-mentioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula I. The compounds of the formula I can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil dispersions (OD), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflüchenaktive Äthylenoxidaddkte" [Surface-active ethylene oxide adducts], Wiss. Verlagagesell. Stuttgart 1976; Winnacker-Küchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of the formula I. In wettable powders the concentration of active compound is, for example, from about 10 to 99% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, the formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example World Herbicide New Product Technology Handbook, China Agricultural Science and Farming Techniques Press, 2010.9 and in the literature cited therein. For example the following active compounds may be mentioned as herbicides which can be combined with the compounds of the formula I (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, mogrton, dichlofluanid, naproanilide, diethatyl-ethyl, naptalam, flufenacet, EL-177, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC-C, orthosulfamuron, propyrisulfuron, metazosulfuron, acifluorfen, fomesafen, lactofen, fluoroglycofen, oxyfluorfen, chlornitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vernolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethyla mine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlornidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochloridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichlormid, halauxifen-methyl, DOW florpyrauxifen, UBH-509, D489, LS 82-556, KPP-300, NC-324, NC-330, KH-218, DPX-N8189, SC-0744, DOWC0535, DK-8910, V-53482, PP-600, MBH-001, KIH-9201, ET-751, KIH-6127 and KIH-2023.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula I required varies with the external conditions, such as temperature, humidity, the nature of the herbicide used and the like. It can vary within wide limits, for example between 0.001 and 1.0 kg a.i./ha or more of active substance, but it is preferably between 0.005 and 750 g a.i./ha, especially between 0.005 and 250 g a.i./ha.

Specific Mode for Carrying out the Invention

The following embodiments are used to illustrate the present invention in detail and should not be taken as any limit to the present invention. The scope of the invention would be explained through the Claims.

In view of economics and variety of a compound, we preferably synthesized several compounds, part of which are listed in the following Table 1. The structure and information of a certain compound are shown in Table 1. The compounds in Table 1 are listed for further explication of the present invention, other than any limit therefor. The subject of the present invention should not be interpreted by those skilled in the art as being limited to the following compounds.

TABLE 1

Structures and ¹H NMR data of compounds

| No. | M | [Het structure] | Y | Z | Q | ¹H NMR |
|-----|---|---|---|---|---|---|
| 1 | CH | cyclopentane-fused isoxazoline with -C(O)OH | Cl | F | dimethyl thioxo-triazinanedione | |
| 2 | CH | cyclopentane-fused isoxazoline with -C(O)OMe | Cl | F | dimethyl thioxo-triazinanedione | ¹H NMR (500 MHz, DMSO-d₆) δ 7.93-7.89 (m, 2H), 4.44 (d, J = 9.0 Hz, 1H), 3.75 (s, 3H), 3.63 (s, 6H), 2.23-2.09 (m, 2H), 1.98-1.82 (m, 2H), 1.68-1.63 (m, 1H), 1.54-1.44 (m, 1H) |
| 3 | CH | cyclopentane-fused isoxazoline with -C(O)OEt | Cl | F | dimethyl thioxo-triazinanedione | ¹H NMR (500 MHz, DMSO-d₆) δ 7.95 (d, J = 9.5 Hz, 1H), 7.91 (d, J = 7.5 Hz, 1H), 4.44-4.40 (m, 1H), 4.26-4.19 (m, 2H), 3.65 (s, 6H), 2.23-2.11 (m, 2H), 2.02-1.91 (m, 1H), 1.89-1.81 (m, 1H), 1.69-1.64 (m, 1H), 1.53-1.47 (m, 1H), 1.26 (t, J = 7.0 Hz, 3H). |
| 4 | CH | cyclopentane-fused isoxazoline with -C(O)OPr | Cl | F | dimethyl thioxo-triazinanedione | ¹H NMR (500 MHz, DMSO-d₆) δ 7.95 (d, J = 9.5 Hz, 1H), 7.90 (d, J = 7.5 Hz, 1H), 4.45 (d, J = 9.0 Hz, 1H), 4.18-4.11 (m, 2H), 3.65 (s, 6H), 2.22-2.11 (m, 2H), 2.01-1.84 (m, 2H), 1.69-1.62 (m, 3H), 1.54-1.46 (m, 1H), 0.92 (t, J = 7.5 Hz, 3H). |
| 5 | CH | cyclopentane-fused isoxazoline with -C(O)O-iPr | Cl | F | dimethyl thioxo-triazinanedione | |

TABLE 1-continued

Structures and ¹H NMR data of compounds

| No. | M | [structure] | Y | Z | Q | ¹H NMR |
|-----|---|-------------|---|---|---|--------|
| 6 | CH | butyl ester cyclopentane-fused isoxazoline | Cl | F | N,N'-dimethyl-thioxo-triazinedione | |
| 7 | CH | isobutyl ester cyclopentane-fused isoxazoline | Cl | F | N,N'-dimethyl-thioxo-triazinedione | |
| 8 | CH | tert-butyl ester cyclopentane-fused isoxazoline | Cl | F | N,N'-dimethyl-thioxo-triazinedione | |
| 9 | CH | oct-2-yl ester cyclopentane-fused isoxazoline | Cl | F | N,N'-dimethyl-thioxo-triazinedione | |
| 10 | CH | allyl ester cyclopentane-fused isoxazoline | Cl | F | N,N'-dimethyl-thioxo-triazinedione | ¹H NMR (500 MHz, DMSO-d₆) δ 7.95-7.90 (m, 2H), 6.01-5.94 (m, 1H), 5.36 (d, J = 10.5 Hz, 1H), 5.27 (d, J = 10.5 Hz, 1H), 4.77-4.65 (m, 2H), 4.47 (d, J = 9.0 Hz, 1H), 3.66-3.62 (s, 6H), 2.23-2.13 (m, 1H), 1.97-1.85 (m, 1H), 1.69-1.65 (m, 1H), 1.53-1.48 (m, 1H), 1.19 (t, J = 7.0 Hz, 2H). |

TABLE 1-continued

Structures and $^1$H NMR data of compounds

| No. | M | [structure] | Y | Z | Q | $^1$H NMR |
|---|---|---|---|---|---|---|
| 11 | CH | [2-methylallyl ester cyclopenta-isoxazole] | Cl | F | [dimethyl thioxo triazinanedione] | |
| 12 | CH | [but-3-enyl ester cyclopenta-isoxazole] | Cl | F | [dimethyl thioxo triazinanedione] | |
| 13 | CH | [prop-2-ynyl ester cyclopenta-isoxazole] | Cl | F | [dimethyl thioxo triazinanedione] | $^1$H NMR (500 MHz, DMSO-d$_6$) δ 7.95 (d, J = 9.5 Hz, 1H), 7.92 (d, J = 7.5 Hz, 1H), 4.87 (s, 2H), 4.46-4.42 (m, 1H), 3.67-3.62 (m, 7H), 2.25-2.12 (m, 2H), 2.01-1.92 (m, 1H), 1.90-1.85 (m, 1H), 1.70-1.65 (m, 1H), 1.55-1.47 (m, 1H). |
| 14 | CH | [but-3-ynyl ester cyclopenta-isoxazole] | Cl | F | [dimethyl thioxo triazinanedione] | |

TABLE 1-continued

Structures and $^1$H NMR data of compounds

| No. | M | (Het structure) | Y | Z | Q | $^1$H NMR |
|-----|---|---|---|---|---|---|
| 15 | CH | cyclopentane-fused isoxazoline with –C(=O)O–CH$_2$–C≡C–CH$_3$ ester | Cl | F | 1,3-dimethyl-6-thioxo-1,3,5-triazinane-2,4-dione (N-linked) | |
| 16 | CH | cyclopentane-fused isoxazoline with –C(=O)O–CH(CH$_3$)–C≡CH ester | Cl | F | 1,3-dimethyl-6-thioxo-1,3,5-triazinane-2,4-dione (N-linked) | |
| 17 | CH | cyclopentane-fused isoxazoline with –C(=O)O–cyclopropyl ester | Cl | F | 1,3-dimethyl-6-thioxo-1,3,5-triazinane-2,4-dione (N-linked) | |
| 18 | CH | cyclopentane-fused isoxazoline with –C(=O)O–CH$_2$–cyclopropyl ester | Cl | F | 1,3-dimethyl-6-thioxo-1,3,5-triazinane-2,4-dione (N-linked) | |
| 19 | CH | cyclopentane-fused isoxazoline with –C(=O)O–CH$_2$CH$_2$F ester | Cl | F | 1,3-dimethyl-6-thioxo-1,3,5-triazinane-2,4-dione (N-linked) | |

TABLE 1-continued

Structures and ¹H NMR data of compounds

| No. | M | (Het substructure) | Y | Z | Q | ¹H NMR |
|---|---|---|---|---|---|---|
| 20 | CH | cyclopentane-fused isoxazoline with CO₂CH₂CHF₂ ester | Cl | F | 1,3-dimethyl-2-thioxo-1,3,5-triazinane-4,6-dione (N-linked) | |
| 21 | CH | cyclopentane-fused isoxazoline with CO₂CH₂CF₃ ester | Cl | F | 1,3-dimethyl-2-thioxo-1,3,5-triazinane-4,6-dione (N-linked) | |
| 22 | CH | cyclopentane-fused isoxazoline with CO₂CH₂CH₂CH₂F ester | Cl | F | 1,3-dimethyl-2-thioxo-1,3,5-triazinane-4,6-dione (N-linked) | |
| 23 | CH | cyclopentane-fused isoxazoline with CO₂CH₂C(CH₃)F₂ ester | Cl | F | 1,3-dimethyl-2-thioxo-1,3,5-triazinane-4,6-dione (N-linked) | |
| 24 | CH | cyclopentane-fused isoxazoline with CO₂CH₂CH₂CF₃ ester | Cl | F | 1,3-dimethyl-2-thioxo-1,3,5-triazinane-4,6-dione (N-linked) | |

TABLE 1-continued

Structures and ¹H NMR data of compounds

| No. | M | | Y | Z | Q | ¹H NMR |
|---|---|---|---|---|---|---|
| 25 | CH | [3-chloropropyl ester of hexahydrocyclopenta[c]isoxazole-6a-carboxylate] | Cl | F | [1,3-dimethyl-6-thioxo-1,3,5-triazinane-2,4-dione, N-linked] | |
| 26 | CH | [3-chloroallyl ester of hexahydrocyclopenta[c]isoxazole-6a-carboxylate] | Cl | F | [1,3-dimethyl-6-thioxo-1,3,5-triazinane-2,4-dione, N-linked] | |
| 27 | CH | [cyanomethyl ester of hexahydrocyclopenta[c]isoxazole-6a-carboxylate] | Cl | F | [1,3-dimethyl-6-thioxo-1,3,5-triazinane-2,4-dione, N-linked] | |
| 28 | CH | [2-cyanoethyl ester of hexahydrocyclopenta[c]isoxazole-6a-carboxylate] | Cl | F | [1,3-dimethyl-4-thioxo-1,3,5-triazinane-2,6-dione, N-linked] | |
| 29 | CH | [3-(trimethylsilyl)prop-2-yn-1-yl ester of hexahydrocyclopenta[c]isoxazole-6a-carboxylate] | Cl | F | [1,3-dimethyl-6-thioxo-1,3,5-triazinane-2,4-dione, N-linked] | |

TABLE 1-continued
Structures and ¹H NMR data of compounds
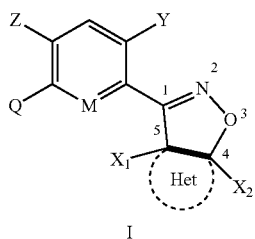
I
| No. | M | 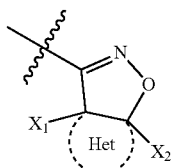 | Y | Z | Q | ¹H NMR |
|---|---|---|---|---|---|---|
| 30 | CH | | Cl | F | | |
| 31 | CH | | Cl | F | | |
| 32 | CH | | Cl | F | | |
| 33 | CH | | Cl | F | | |
| 34 | CH | | Cl | F | | |

TABLE 1-continued

Structures and $^1$H NMR data of compounds

| No. | M | (structure) | Y | Z | Q | $^1$H NMR |
|---|---|---|---|---|---|---|
| 35 | CH | | Cl | F | | |
| 36 | CH | | Cl | F | | |
| 37 | CH | | Cl | F | | |
| 38 | CH | | Cl | F | | |
| 39 | CH | | Cl | F | | |

TABLE 1-continued
Structures and ¹H NMR data of compounds
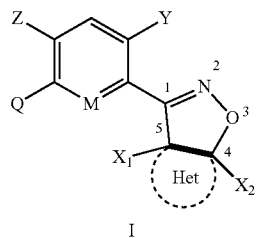
| No. | M | | Y | Z | Q | ¹H NMR |
|---|---|---|---|---|---|---|
| 40 | CH | | Cl | F | | |
| 41 | CH | | Cl | F | | |
| 42 | CH | | Cl | F | | |
| 43 | CH | | Cl | F | | |

TABLE 1-continued

Structures and ¹H NMR data of compounds

| No. | M | [Het group] | Y | Z | Q | ¹H NMR |
|-----|---|---|---|---|---|--------|
| 44 | CH | | Cl | F | | |
| 45 | CH | | Cl | F | | |
| 46 | CH | | Cl | F | | |
| 47 | CH | | Cl | F | | |

TABLE 1-continued

Structures and ¹H NMR data of compounds

| No. | M | Het | Y | Z | Q | ¹H NMR |
|---|---|---|---|---|---|---|
| 48 | CH | (bicyclic isoxazoline-cyclopentane with carboxylate ester linked via -O-CH(CH₃)-O-C(=O)-O-cyclohexyl) | Cl | F | (1,3-dimethyl-6-thioxo-1,3,5-triazinane-2,4-dione, N-linked) | |
| 49 | CH | (bicyclic isoxazoline-cyclopentane with carboxylate ester -C(=O)-O-CH₂-(tetrahydrofuran-2-yl)) | Cl | F | (1,3-dimethyl-6-thioxo-1,3,5-triazinane-2,4-dione, N-linked) | ¹H NMR (500 MHz, DMSO-d₆) δ 7.95 (d, J = 9.5 Hz, 1H), 7.91 (d, J = 7.5, Hz, 1H), 4.46 (d, J = 9.0 Hz, 1H), 4.23-4.04 (m, 3H), 3.77-3.72 (m, 1H), 3.69-3.66 (m, 1H), 3.65 (s, 6H), 2.23-2.12 (m, 2H), 1.96-1.92 (m, 2H), 1.89-1.78 (m, 3H), 1.69-1.59 (m, 2H), 1.55-1.47 (m, 1H). |
| 50 | CH | (bicyclic isoxazoline-cyclopentane with carboxylate ester -C(=O)-O-CH₂-(furan-2-yl)) | Cl | F | (1,3-dimethyl-6-thioxo-1,3,5-triazinane-2,4-dione, N-linked) | |

TABLE 1-continued

Structures and $^1$H NMR data of compounds

| No. | M | Het | Y | Z | Q | $^1$H NMR |
|-----|---|-----|---|---|---|-----------|
| 51 | CH | (bicyclic isoxazoline with cyclopentane fused, C(=O)O-CH$_2$-phenyl) | Cl | F | (dimethyl thioxo-triazine-dione) | $^1$H NMR (500 MHz, DMSO-d$_6$) δ 7.93 (d, J = 9.5 Hz, 1H), 7.89 (d, J = 7.5 Hz, 1H), 7.43-7.33 (m, 5H), 5.30-5.22 (m, 2H), 4.48-4.44 (m, 1H), 3.65 (s, 6H), 2.25-2.14 (m, 2H), 2.00-1.90 (m, 1H), 1.89-1.84 (m, 1H), 1.68-1.64 (m, 1H), 1.56-1.46 (m, 1H). |
| 52 | CH | (bicyclic isoxazoline with cyclopentane fused, C(=O)O-CH$_2$-(2-F-phenyl)) | Cl | F | (dimethyl thioxo-triazine-dione) | |
| 53 | CH | (bicyclic isoxazoline with cyclopentane fused, C(=O)O-CH$_2$-(4-F-phenyl)) | Cl | F | (dimethyl thioxo-triazine-dione) | |
| 54 | CH | (bicyclic isoxazoline with cyclopentane fused, C(=O)O-CH$_2$-(3-F-phenyl)) | Cl | F | (dimethyl thioxo-triazine-dione) | |

TABLE 1-continued

Structures and ¹H NMR data of compounds

| No. | M | (Het group) | Y | Z | Q | ¹H NMR |
|---|---|---|---|---|---|---|
| 55 | CH | 4-chlorobenzyl ester of cyclopentane-fused isoxazoline | Cl | F | 1,3-dimethyl-2-thioxo-1,3,5-triazinane-4,6-dione | |
| 56 | CH | 2,6-difluorobenzyl ester of cyclopentane-fused isoxazoline | Cl | F | 1,3-dimethyl-2-thioxo-1,3,5-triazinane-4,6-dione | |
| 57 | CH | 2,6-dichlorobenzyl ester of cyclopentane-fused isoxazoline | Cl | F | 1,3-dimethyl-2-thioxo-1,3,5-triazinane-4,6-dione | |
| 58 | CH | 2,4,6-trifluorobenzyl ester of cyclopentane-fused isoxazoline | Cl | F | 1,3-dimethyl-2-thioxo-1,3,5-triazinane-4,6-dione | |
| 59 | CH | 3-pyridylmethyl ester of cyclopentane-fused isoxazoline | Cl | F | 1,3-dimethyl-2-thioxo-1,3,5-triazinane-4,6-dione | |

TABLE 1-continued

Structures and ¹H NMR data of compounds

| No. | M | [Het group] | Y | Z | Q | ¹H NMR |
|-----|---|---|---|---|---|--------|
| 60 | CH | | Cl | F | | |
| 61 | CH | | Cl | F | | |
| 62 | CH | | Cl | F | | |
| 63 | CH | | Cl | F | | |

TABLE 1-continued

Structures and ¹H NMR data of compounds

| No. | M | [Het group] | Y | Z | Q | ¹H NMR |
|---|---|---|---|---|---|---|
| 64 | CH | | Cl | F | | |
| 65 | CH | | Cl | F | | |
| 66 | CH | | Cl | F | | ¹H NMR (500 MHz, DMSO-d₆) δ 7.96 (d, J = 9.5 Hz, 1H), 7.92 (d, J = 7.5 Hz, 1H), 4.54 (d, J = 9.0 Hz, 1H), 3.65 (s, 6H), 2.28-2.18 (m, 2H), 2.01-1.94 (m, 7H), 1.89-1.86 (m, 1H), 1.69-1.65 (m, 1H), 1.55-1.49 (m, 1H). |
| 67 | CH | | Cl | F | | |

TABLE 1-continued
Structures and ¹H NMR data of compounds
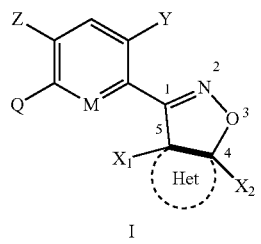
I
| No. | M | 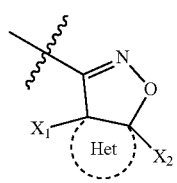 | Y | Z | Q | ¹H NMR |
|---|---|---|---|---|---|---|
| 68 | CH | 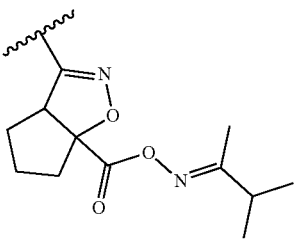 [SMILES: *C1=NOC2(C(=O)O/N=C(\C)C(C)C)CCCC12] | Cl | F | 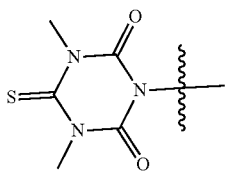 [SMILES: *n1c(=O)n(C)c(=S)n(C)c1=O] | |
| 69 | CH | | Cl | F | | |
| 70 | CH | 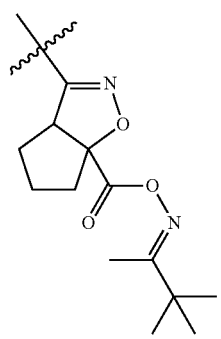 [SMILES: *C1=NOC2(C(=O)O/N=C(\C)C(C)(C)C)CCCC12] | Cl | F | | |
| 71 | CH | 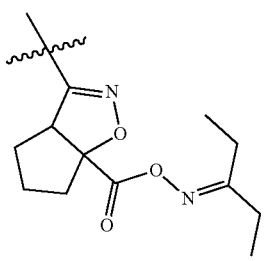 [SMILES: *C1=NOC2(C(=O)ON=C(CC)CC)CCCC12] | Cl | F | | |
| | | 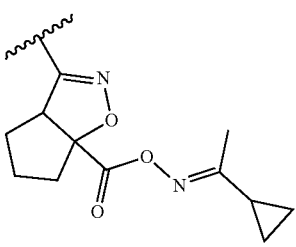 [SMILES: *C1=NOC2(C(=O)O/N=C(\C)C3CC3)CCCC12] | | | | |

TABLE 1-continued

Structures and $^1$H NMR data of compounds

| No. | M | (Het group) | Y | Z | Q | $^1$H NMR |
|---|---|---|---|---|---|---|
| 72 | CH | cyclopentane-fused isoxazoline with C(O)O-N=C(CH₃)CH₂F | Cl | F | 1,3-dimethyl-5-thioxo-1,3,5-triazinane-2,4-dione-N-yl | |
| 73 | CH | cyclopentane-fused isoxazoline with C(O)O-N=C(CH₃)CHF₂ | Cl | F | 1,3-dimethyl-5-thioxo-1,3,5-triazinane-2,4-dione-N-yl | |
| 74 | CH | cyclopentane-fused isoxazoline with C(O)O-N=C(CH₃)CF₃ | Cl | F | 1,3-dimethyl-5-thioxo-1,3,5-triazinane-2,4-dione-N-yl | |
| 75 | CH | cyclopentane-fused isoxazoline with C(O)O-N=C(CF₃)CF₃ | Cl | F | 1,3-dimethyl-5-thioxo-1,3,5-triazinane-2,4-dione-N-yl | |

TABLE 1-continued

Structures and ¹H NMR data of compounds

| No. | M | [structure] | Y | Z | Q | ¹H NMR |
|---|---|---|---|---|---|---|
| 76 | CH | cyclopentane-fused isoxazoline with -C(O)O-N=C(Cl)CH₃ | Cl | F | 1,3,5-triazine-2,4-dione-6-thione N,N-dimethyl | |
| 77 | CH | cyclopentane-fused isoxazoline with -C(O)O-N=C(OEt)CH₃ | Cl | F | 1,3,5-triazine-2,4-dione-6-thione N,N-dimethyl | |
| 78 | CH | cyclopentane-fused isoxazoline with -C(O)O-N=C(CH₂OMe)CH₃ | Cl | F | 1,3,5-triazine-2,4-dione-6-thione N,N-dimethyl | |
| 79 | CH | cyclopentane-fused isoxazoline with -C(O)O-N=C(CO₂Et)CH₃ | Cl | F | 1,3,5-triazine-2,4-dione-6-thione N,N-dimethyl | |

TABLE 1-continued

Structures and $^1$H NMR data of compounds

| No. | M | [Het group] | Y | Z | Q | $^1$H NMR |
|---|---|---|---|---|---|---|
| 80 | CH | cyclopenta-isoxazole with C(=O)-O-N=CH-phenyl | Cl | F | dimethyl-thioxo-dioxo-triazinane | |
| 81 | CH | cyclopenta-isoxazole with C(=O)-O-N=C(CH₃)-phenyl | Cl | F | dimethyl-thioxo-dioxo-triazinane | |
| 82 | CH | cyclopenta-isoxazole with C(=O)-O-N=C(phenyl)₂ | Cl | F | dimethyl-thioxo-dioxo-triazinane | |

TABLE 1-continued

Structures and $^1$H NMR data of compounds

| No. | M | | Y | Z | Q | $^1$H NMR |
|-----|---|---|---|---|---|-----------|
| 83 | CH | (cyclopenta-isoxazole with C(=O)O-N=CH-furan-2-yl) | Cl | F | N,N'-dimethyl-thioxo-triazinane-2,4-dione | |
| 84 | CH | (cyclopenta-isoxazole with C(=O)O-N=CH-(5-methylfuran-2-yl)) | Cl | F | N,N'-dimethyl-thioxo-triazinane-2,4-dione | |
| 85 | CH | (cyclopenta-isoxazole with C(=O)O-N=CH-(5-methylthiophen-2-yl)) | Cl | F | N,N'-dimethyl-thioxo-triazinane-2,4-dione | |
| 86 | CH | (cyclopenta-isoxazole with C(=O)O-N=cyclopentylidene) | Cl | F | N,N'-dimethyl-thioxo-triazinane-2,4-dione | |

TABLE 1-continued

Structures and $^1$H NMR data of compounds

| No. | M | | Y | Z | Q | $^1$H NMR |
|---|---|---|---|---|---|---|
| 87 | CH | (3-isoxazoline fused cyclopentane with C(O)O-CH2-O-N=C(CH3)2) | Cl | F | (dimethyl thioxo triazine-dione) | |
| 88 | CH | (3-isoxazoline fused cyclopentane with C(O)O-CH2CH2-O-N=C(CH3)2) | Cl | F | (dimethyl thioxo triazine-dione) | |
| 89 | CH | (3-isoxazoline fused cyclopentane with C(O)NH-S(O)2-CH3) | Cl | F | (dimethyl thioxo triazine-dione) | |
| 90 | CH | (3-isoxazoline fused cyclopentane with C(O)NH-S(O)2-CH2CH3) | Cl | F | (dimethyl thioxo triazine-dione) | |

TABLE 1-continued
Structures and $^1$H NMR data of compounds
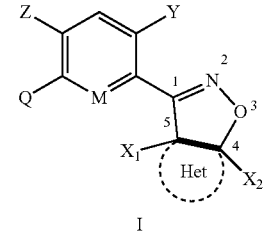
| No. | M | [structure] | Y | Z | Q | $^1$H NMR |
|---|---|---|---|---|---|---|
| 91 | CH | 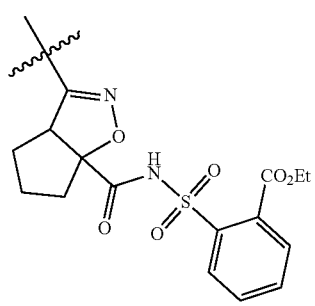 | Cl | F | 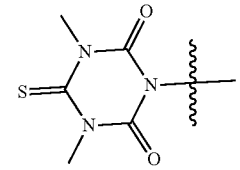 | |
| 92 | CH | 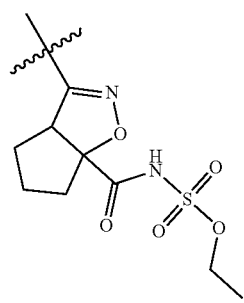 [SMILES: *C1=NOC2(C(=O)NS(=O)(=O)OCC)CCCC12] | Cl | F | 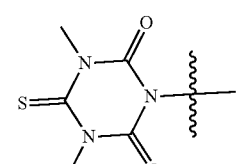 | |
| 93 | CH | 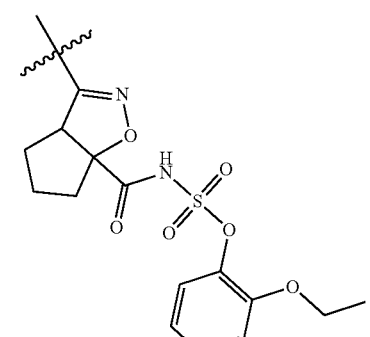 | Cl | F | 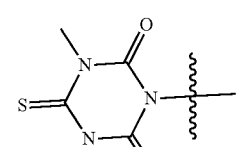 | |

TABLE 1-continued

Structures and ¹H NMR data of compounds

| No. | M | Het structure | Y | Z | Q | ¹H NMR |
|-----|-----|-----|-----|-----|-----|-----|
| 94 | CH | (3-isoxazoline fused cyclopentane with C(O)NHS(O)₂NH₂) | Cl | F | (1,3,5-triazine-2,4-dione-6-thione, N,N-dimethyl) | |
| 95 | CH | (3-isoxazoline fused cyclopentane with C(O)NHS(O)₂NHCH₃) | Cl | F | (1,3,5-triazine-2,4-dione-6-thione, N,N-dimethyl) | |
| 96 | CH | (3-isoxazoline fused cyclopentane with C(O)NHS(O)₂NH-iPr) | Cl | F | (1,3,5-triazine-2,4-dione-6-thione, N,N-dimethyl) | |
| 97 | CH | (3-isoxazoline fused cyclopentane with C(O)NHS(O)₂N(CH₃)₂) | Cl | F | (1,3,5-triazine-2,4-dione-6-thione, N,N-dimethyl) | |

TABLE 1-continued

Structures and $^1$H NMR data of compounds

| No. | M | [structure with X₁, Het, X₂] | Y | Z | Q | $^1$H NMR |
|-----|---|------|---|---|---|-----------|
| 98 | CH | | Cl | F | | |
| 99 | CH | | Cl | F | | |
| 100 | CH | | Cl | F | | |
| 101 | CH | | Cl | F | | |

TABLE 1-continued

Structures and ¹H NMR data of compounds

| No. | M | | Y | Z | Q | ¹H NMR |
|---|---|---|---|---|---|---|
| 102 | CH | (3a,6a-fused cyclopenta[c]isoxazole with 6a-C(O)NH-SO₂-pyrrolidine) | Cl | F | 1,3-dimethyl-4-thioxo-1,3,5-triazinane-2,6-dione-5-yl | |
| 103 | CH | (cyclopenta[c]isoxazole with 6a-C(O)NH₂) | Cl | F | 1,3-dimethyl-4-thioxo-1,3,5-triazinane-2,6-dione-5-yl | |
| 104 | CH | (cyclopenta[c]isoxazole with 6a-C(O)NHMe) | Cl | F | 1,3-dimethyl-4-thioxo-1,3,5-triazinane-2,6-dione-5-yl | |
| 105 | CH | (cyclopenta[c]isoxazole with 6a-C(O)NHEt) | Cl | F | 1,3-dimethyl-4-thioxo-1,3,5-triazinane-2,6-dione-5-yl | |
| 106 | CH | (cyclopenta[c]isoxazole with 6a-C(O)NH-iPr) | Cl | F | 1,3-dimethyl-4-thioxo-1,3,5-triazinane-2,6-dione-5-yl | |

TABLE 1-continued

Structures and ¹H NMR data of compounds

| No. | M | [Het group] | Y | Z | Q | ¹H NMR |
|-----|---|---|---|---|---|--------|
| 107 | CH | 3-(N,N-dimethylcarboxamide)-hexahydrocyclopenta[c]isoxazole | Cl | F | 1,3-dimethyl-5-thioxo-1,3,5-triazinane-2,4,6-trione linker | |
| 108 | CH | 3-(N-allylcarboxamide)-hexahydrocyclopenta[c]isoxazole | Cl | F | 1,3-dimethyl-5-thioxo-1,3,5-triazinane-2,4,6-trione linker | |
| 109 | CH | 3-(N-propargylcarboxamide)-hexahydrocyclopenta[c]isoxazole | Cl | F | 1,3-dimethyl-5-thioxo-1,3,5-triazinane-2,4,6-trione linker | |
| 110 | CH | 3-(N-methyl-N-propargylcarboxamide)-hexahydrocyclopenta[c]isoxazole | Cl | F | 1,3-dimethyl-5-thioxo-1,3,5-triazinane-2,4,6-trione linker | |
| 111 | CH | 3-(N-cyclopropylcarboxamide)-hexahydrocyclopenta[c]isoxazole | Cl | F | 1,3-dimethyl-5-thioxo-1,3,5-triazinane-2,4,6-trione linker | |

TABLE 1-continued
Structures and $^1$H NMR data of compounds
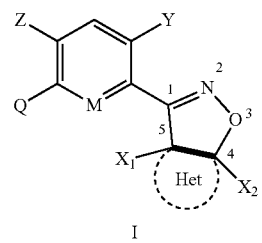
I
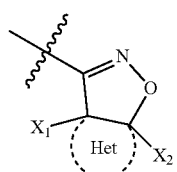
| No. | M | | Y | Z | Q | $^1$H NMR |
|---|---|---|---|---|---|---|
| 112 | CH | 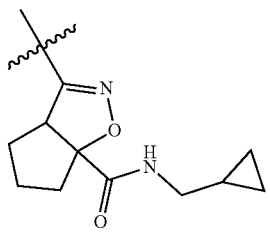 [SMILES: *C1=NOC2(C(=O)NCC3CC3)CCCC12] | Cl | F | 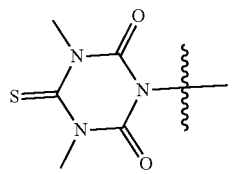 | |
| 113 | CH | 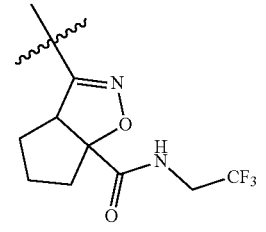 [SMILES: *C1=NOC2(C(=O)NCC(F)(F)F)CCCC12] | Cl | F | 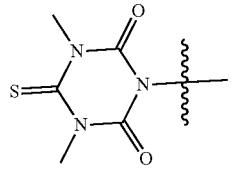 | |
| 114 | CH | 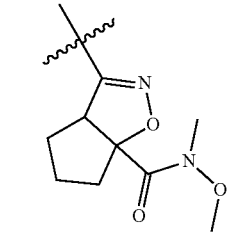 [SMILES: *C1=NOC2(C(=O)N(C)OC)CCCC12] | Cl | F | 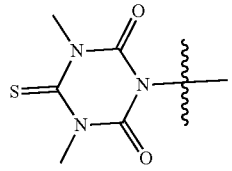 | |
| 115 | CH | 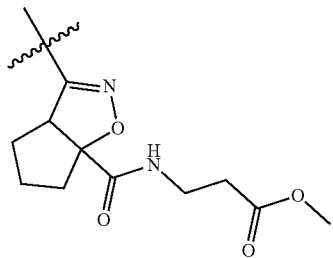 [SMILES: *C1=NOC2(C(=O)NCCC(=O)OC)CCCC12] | Cl | F | 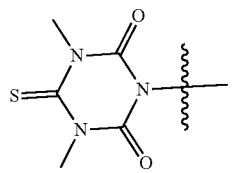 | |

TABLE 1-continued

Structures and $^1$H NMR data of compounds

| No. | M | (structure) | Y | Z | Q | $^1$H NMR |
|---|---|---|---|---|---|---|
| 116 | CH | | Cl | F | | |
| 117 | CH | | Cl | F | | |
| 118 | CH | | Cl | F | | |
| 119 | CH | | Cl | F | | |

TABLE 1-continued

Structures and ¹H NMR data of compounds

| No. | M | [structure] | Y | Z | Q | ¹H NMR |
|---|---|---|---|---|---|---|
| 120 | CH | [morpholine amide cyclopentane-fused isoxazoline] | Cl | F | [dimethyl thioxotriazinedione] | |
| 121 | CH | [dimethylpyrazole amide cyclopentane-fused isoxazoline] | Cl | F | [dimethyl thioxotriazinedione] | |
| 122 | CH | [S-ethyl thioester cyclopentane-fused isoxazoline] | Cl | F | [dimethyl thioxotriazinedione] | |
| 123 | CH | [S-benzyl thioester cyclopentane-fused isoxazoline] | Cl | F | [dimethyl thioxotriazinedione] | |
| 124 | CH | [O-ethyl thionoester cyclopentane-fused isoxazoline] | Cl | F | [dimethyl thioxotriazinedione] | |

TABLE 1-continued

Structures and $^1$H NMR data of compounds

| No. | M | [Het group] | Y | Z | Q | $^1$H NMR |
|---|---|---|---|---|---|---|
| 125 | CH | cyclopenta-fused isoxazoline with C(=S)SEt at 4-position | Cl | F | 1,3-dimethyl-6-thioxo-1,3,5-triazinane-2,4-dione-5-yl | |
| 126 | CH | cyclopenta-fused isoxazoline with F at 3a and C(O)OMe at 4-position | Cl | F | 1,3-dimethyl-6-thioxo-1,3,5-triazinane-2,4-dione-5-yl | |
| 127 | CH | cyclopenta-fused isoxazoline with F at 3a and C(O)OEt at 4-position | Cl | F | 1,3-dimethyl-6-thioxo-1,3,5-triazinane-2,4-dione-5-yl | |
| 128 | CH | cyclopenta-fused isoxazoline with F at 3a and C(O)OEt at 4-position | Cl | F | 1,3-dimethyl-6-thioxo-1,3,5-triazinane-2,4-dione-5-yl | |
| 129 | CH | cyclopenta-fused isoxazoline with Me at 3a and C(O)OMe at 4-position | Cl | F | 1,3-dimethyl-6-thioxo-1,3,5-triazinane-2,4-dione-5-yl | |

TABLE 1-continued

Structures and ¹H NMR data of compounds

| No. | M | | Y | Z | Q | ¹H NMR |
|-----|-----|-----|-----|-----|-----|-----|
| 130 | CH | (3a-methyl cyclopenta-isoxazoline with ethyl ester) | Cl | F | (dimethyl thioxo-triazinane-dione) | |
| 131 | CH | (3a-ethyl cyclopenta-isoxazoline with ethyl ester) | Cl | F | (dimethyl thioxo-triazinane-dione) | |
| 132 | CH | (3a-isopropyl cyclopenta-isoxazoline with ethyl ester) | Cl | F | (dimethyl thioxo-triazinane-dione) | |
| 133 | CH | (3a-vinyl cyclopenta-isoxazoline with ethyl ester) | Cl | F | (dimethyl thioxo-triazinane-dione) | |
| 134 | CH | (3a-propargyl cyclopenta-isoxazoline with ethyl ester) | Cl | F | (dimethyl thioxo-triazinane-dione) | |

TABLE 1-continued

Structures and $^1$H NMR data of compounds

| No. | M | Het | Y | Z | Q | $^1$H NMR |
|-----|---|-----|---|---|---|-----------|
| 135 | CH | cyclopropyl-spiro cyclopentane fused isoxazoline with ethyl ester | | Cl | F | 1,3-dimethyl-5-thioxo-1,3,5-triazinane-2,4-dione | |
| 136 | CH | cyclopropylmethyl cyclopentane fused isoxazoline with ethyl ester | | Cl | F | 1,3-dimethyl-5-thioxo-1,3,5-triazinane-2,4-dione | |
| 137 | CH | F$_3$C- cyclopentane fused isoxazoline with ethyl ester | | Cl | F | 1,3-dimethyl-5-thioxo-1,3,5-triazinane-2,4-dione | |
| 138 | CH | BrCH$_2$- cyclopentane fused isoxazoline with ethyl ester | | Cl | F | 1,3-dimethyl-5-thioxo-1,3,5-triazinane-2,4-dione | |
| 139 | CH | HO- cyclopentane fused isoxazoline with methyl ester | | Cl | F | 1,3-dimethyl-5-thioxo-1,3,5-triazinane-2,4-dione | |

TABLE 1-continued

Structures and ¹H NMR data of compounds

| No. | M | [Het group] | Y | Z | Q | ¹H NMR |
|---|---|---|---|---|---|---|
| 140 | CH | 3a-methoxy-hexahydrocyclopenta[c]isoxazole-6a-carboxylic acid methyl ester | Cl | F | 3,5-dimethyl-2,4-dioxo-6-thioxo-1,3,5-triazinan-1-yl | |
| 141 | CH | 3a-methoxy-hexahydrocyclopenta[c]isoxazole-6a-carboxylic acid ethyl ester | Cl | F | 3,5-dimethyl-2,4-dioxo-6-thioxo-1,3,5-triazinan-1-yl | |
| 142 | CH | 3a-ethoxy-hexahydrocyclopenta[c]isoxazole-6a-carboxylic acid ethyl ester | Cl | F | 3,5-dimethyl-2,4-dioxo-6-thioxo-1,3,5-triazinan-1-yl | |
| 143 | CH | 3a-(hydroxymethyl)-hexahydrocyclopenta[c]isoxazole-6a-carboxylic acid ethyl ester | Cl | F | 3,5-dimethyl-2,4-dioxo-6-thioxo-1,3,5-triazinan-1-yl | |
| 144 | CH | 3a-(methoxymethyl)-hexahydrocyclopenta[c]isoxazole-6a-carboxylic acid methyl ester | Cl | F | 3,5-dimethyl-2,4-dioxo-6-thioxo-1,3,5-triazinan-1-yl | |

TABLE 1-continued

Structures and ¹H NMR data of compounds

| No. | M | [Het/X₁/X₂ group] | Y | Z | Q | ¹H NMR |
|---|---|---|---|---|---|---|
| 145 | CH | (cyclopentane-fused isoxazoline with SMe and CO₂Et) | Cl | F | (1,3-dimethyl-2-thioxo-1,3,5-triazinane-4,6-dione-N-linked) | |
| 146 | CH | (cyclopentane-fused isoxazoline with NH₂ and CO₂Me) | Cl | F | (1,3-dimethyl-2-thioxo-1,3,5-triazinane-4,6-dione-N-linked) | |
| 147 | CH | (cyclopentane-fused isoxazoline with NHMe and CO₂Me) | Cl | F | (1,3-dimethyl-2-thioxo-1,3,5-triazinane-4,6-dione-N-linked) | |
| 148 | CH | (cyclopentane-fused isoxazoline with NMe₂ and CO₂Me) | Cl | F | (1,3-dimethyl-2-thioxo-1,3,5-triazinane-4,6-dione-N-linked) | |
| 149 | CH | (cyclopentane-fused isoxazoline with CN and CO₂Et) | Cl | F | (1,3-dimethyl-2-thioxo-1,3,5-triazinane-4,6-dione-N-linked) | |

TABLE 1-continued

Structures and ¹H NMR data of compounds

| No. | M | [X₁/Het/X₂ group] | Y | Z | Q | ¹H NMR |
|---|---|---|---|---|---|---|
| 150 | CH | cyclopentane-fused isoxazoline with CH₂CN and CO₂Et substituents | Cl | F | 1,3-dimethyl-2-thioxo-1,3,5-triazinane-4,6-dione | |
| 151 | CH | cyclopentane-fused isoxazoline with CHO and CO₂Et substituents | Cl | F | 1,3-dimethyl-2-thioxo-1,3,5-triazinane-4,6-dione | |
| 152 | CH | cyclopentane-fused isoxazoline with EtOOC and CO₂Et substituents | Cl | F | 1,3-dimethyl-2-thioxo-1,3,5-triazinane-4,6-dione | |
| 153 | CH | cyclopentane-fused isoxazoline with CH₂OCH₂CO₂Et and CO₂Et substituents | Cl | F | 1,3-dimethyl-2-thioxo-1,3,5-triazinane-4,6-dione | |
| 154 | CH | cyclopentane-fused isoxazoline with Ph and CO₂Me substituents | Cl | F | 1,3-dimethyl-2-thioxo-1,3,5-triazinane-4,6-dione | |

TABLE 1-continued

Structures and ¹H NMR data of compounds

| No. | M | [Het group structure] | Y | Z | Q | ¹H NMR |
|-----|---|---|---|---|---|--------|
| 155 | CH | 3a-(5-methylthiophen-2-yl)-hexahydrocyclopenta[c]isoxazole, methyl ester | Cl | F | 1,3-dimethyl-6-thioxo-1,3,5-triazinane-2,4-dione | |
| 156 | CH | 3a-benzyl-hexahydrocyclopenta[c]isoxazole, methyl ester | Cl | F | 1,3-dimethyl-6-thioxo-1,3,5-triazinane-2,4-dione | |
| 157 | CH | cyclobuta-isoxazole methyl ester | Cl | F | 1,3-dimethyl-6-thioxo-1,3,5-triazinane-2,4-dione | |
| 158 | CH | hexahydrobenzo[c]isoxazole methyl ester | Cl | F | 1,3-dimethyl-6-thioxo-1,3,5-triazinane-2,4-dione | |
| 159 | CH | 4-oxo-hexahydrocyclopenta[c]isoxazole methyl ester | Cl | F | 1,3-dimethyl-6-thioxo-1,3,5-triazinane-2,4-dione | |

TABLE 1-continued

Structures and ¹H NMR data of compounds

| No. | M | Het structure | Y | Z | Q | ¹H NMR |
|---|---|---|---|---|---|---|
| 160 | CH | 3a-(methoxycarbonyl)-tetrahydrofuro[3,4-d]isoxazole | Cl | F | 3,5-dimethyl-2-thioxo-1,3,5-triazinane-4,6-dione | ¹H NMR (500 MHz, Chloroform-d) δ 7.58 (d, J = 7.5 Hz, 1H), 7.45 (d, J = 9.0 Hz, 1H), 6.39 (s, 1H), 4.31-4.28 (m, 1H), 3.96-3.91 (m, 1H), 3.84 (s, 3H), 3.82 (s, 6H), 2.78-2.71 (m, 1H), 2.41-2.38 (m, 1H). |
| 161 | CH | 3a-(methoxycarbonyl)-dihydrofuro[3,4-d]isoxazole | Cl | F | 3,5-dimethyl-2-thioxo-1,3,5-triazinane-4,6-dione | |
| 162 | CH | 3a-(methoxycarbonyl)-tetrahydrothieno[3,4-d]isoxazole | Cl | F | 3,5-dimethyl-2-thioxo-1,3,5-triazinane-4,6-dione | ¹H NMR (500 MHz, DMSO-d₆) δ 7.94 (d, J = 9.5 Hz, 1H), 7.89 (d, J = 7.5 Hz, 1H), 4.95 (d, J = 7.0 Hz, 1H), 3.78 (s, 3H), 3.63 (s, 6H), 3.42-3.39 (m, 2H), 3.30-3.21 (m, 2H). |
| 163 | CH | 6a-(methoxycarbonyl)-cyclopenta-isoxazole | Cl | H | 3,5-dimethyl-2-thioxo-1,3,5-triazinane-4,6-dione | |
| 164 | CH | 6a-(methoxycarbonyl)-cyclopenta-isoxazole | Cl | Cl | 3,5-dimethyl-2-thioxo-1,3,5-triazinane-4,6-dione | |

TABLE 1-continued
Structures and ¹H NMR data of compounds
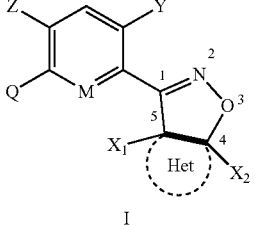
| No. | M | | Y | Z | Q | ¹H NMR |
|---|---|---|---|---|---|---|
| 165 | CH | 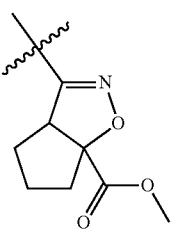 | Cl | OH | 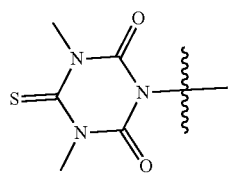 | |
| 166 | CH | 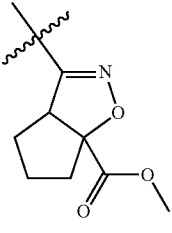 [SMILES: *C1=NOC2(C(=O)OC)CCCC12] | Br | F | 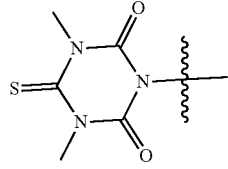 | |
| 167 | CH | 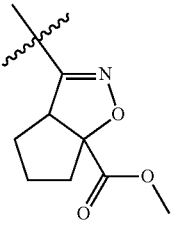 [SMILES: *C1=NOC2(C(=O)OC)CCCC12] | CF$_3$ | F | 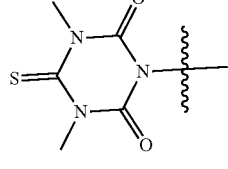 | |
| 168 | CH | 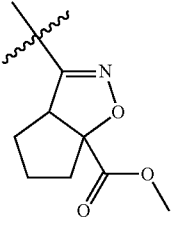 [SMILES: *C1=NOC2(C(=O)OC)CCCC12] | CN | F | 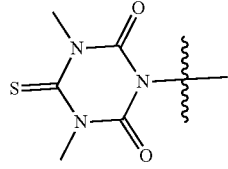 | |

TABLE 1-continued

Structures and ¹H NMR data of compounds

| No. | M | Het structure | Y | Z | Q | ¹H NMR |
|---|---|---|---|---|---|---|
| 169 | CH | cyclopentane-fused isoxazoline with methyl carboxylate | CN | H | 1,3-dimethyl-6-thioxo-1,3,5-triazinane-2,4-dione | |
| 170 | CH | cyclopentane-fused isoxazoline with methyl carboxylate | NO₂ | F | 1,3-dimethyl-6-thioxo-1,3,5-triazinane-2,4-dione | |
| 171 | CH | cyclopentane-fused isoxazoline with methyl carboxylate | NH₂ | F | 1,3-dimethyl-6-thioxo-1,3,5-triazinane-2,4-dione | |
| 172 | N | cyclopentane-fused isoxazoline with methyl carboxylate | Cl | F | 1,3-dimethyl-6-thioxo-1,3,5-triazinane-2,4-dione | |
| 173 | N | cyclopentane-fused isoxazoline with methyl carboxylate | Cl | H | 1,3-dimethyl-6-thioxo-1,3,5-triazinane-2,4-dione | |

TABLE 1-continued
Structures and ¹H NMR data of compounds
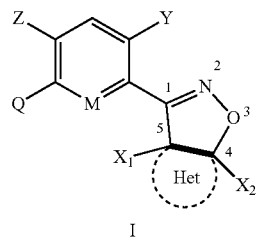
I
| No. | M | 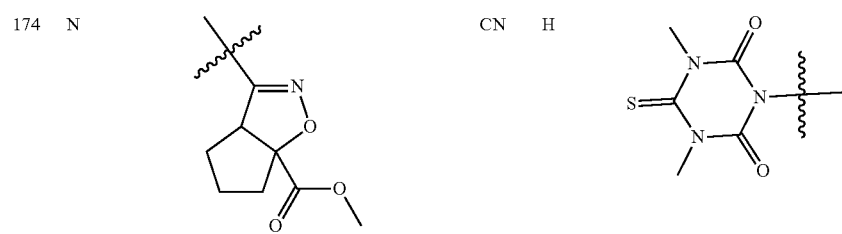 (X₁/Het/X₂) | Y | Z | Q | ¹H NMR |
|-----|-----|---|-----|----|---|--------|
| 174 | N | 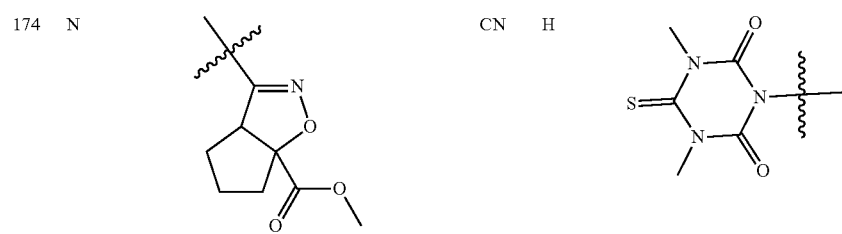 | CN | H | 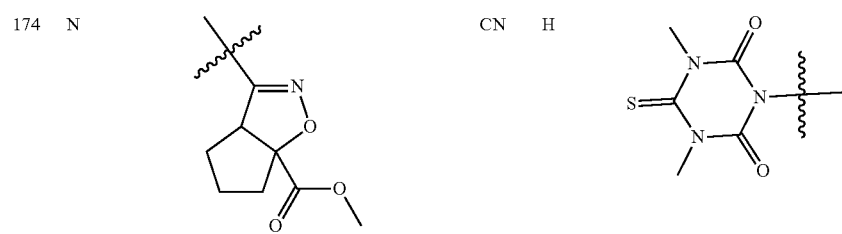 | |
| 175 | CH | 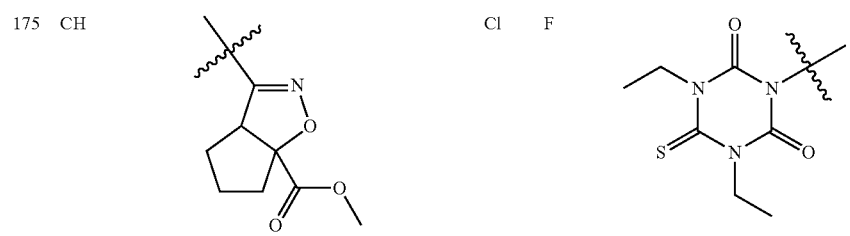 | Cl | F | 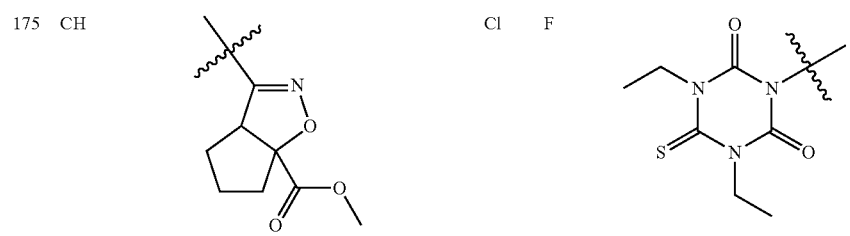 | |
| 176 | CH | 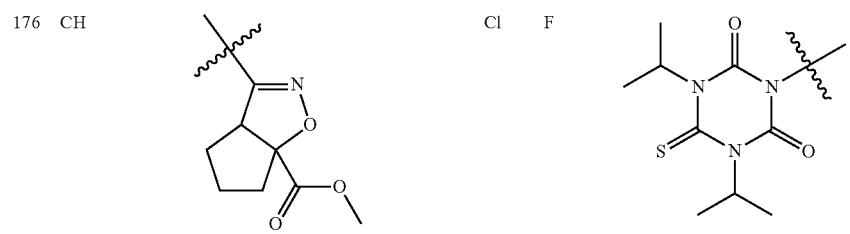 | Cl | F | 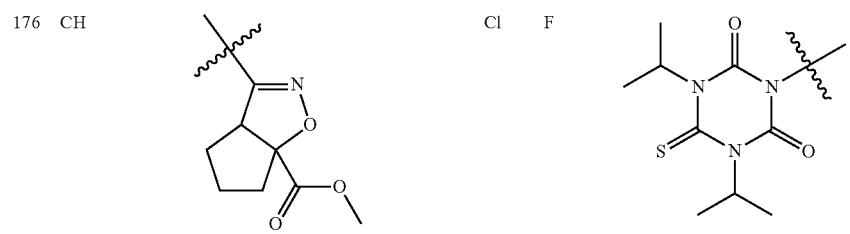 | |
| 177 | CH | 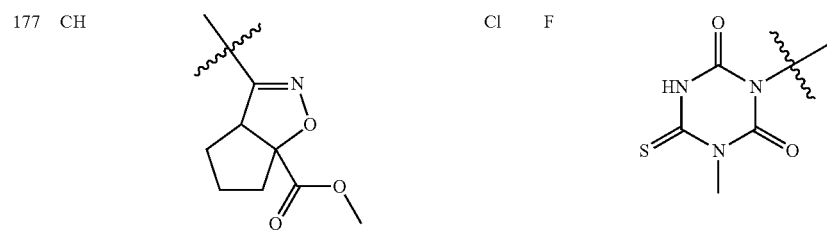 | Cl | F | 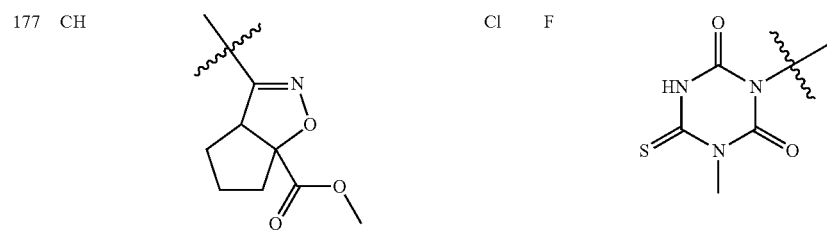 | |

TABLE 1-continued
Structures and ¹H NMR data of compounds
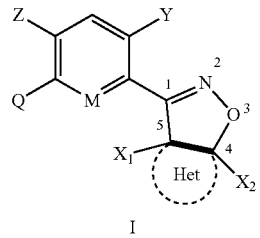
I
| No. | M | 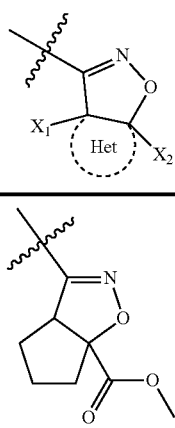 | Y | Z | Q | ¹H NMR |
|-----|-----|-----|-----|-----|-----|-----|
| 178 | CH | 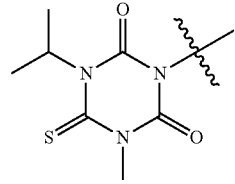 [SMILES: *n1c(=O)n(C)c(=S)n(C(C)C)c1=O] | Cl | F | 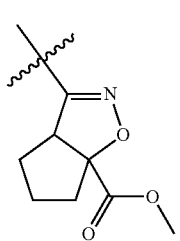 [SMILES: *C1=NOC2(C(=O)OC)CCCC12] | |
| 179 | CH | 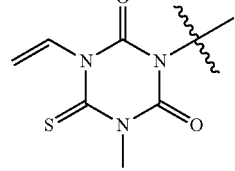 | Cl | F | 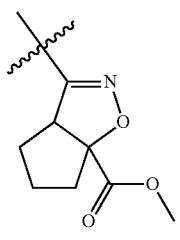 [SMILES: *C1=NOC2(C(=O)OC)CCCC12] | |
| 180 | CH | 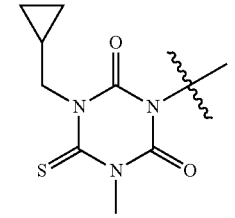 [SMILES: *n1c(=O)n(C)c(=S)n(CC2CC2)c1=O] | Cl | F | 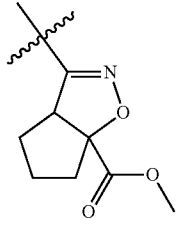 [SMILES: *C1=NOC2(C(=O)OC)CCCC12] | |
| 181 | CH | 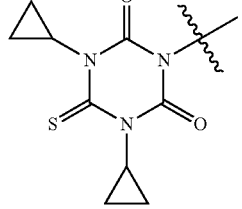 | Cl | F | 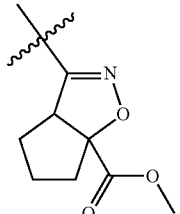 | |
| 182 | CH | | Cl | F | 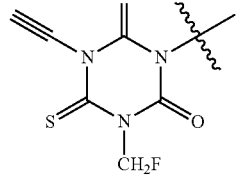 | |

TABLE 1-continued

Structures and ¹H NMR data of compounds

| No. | M | [Het substructure] | Y | Z | Q | ¹H NMR |
|---|---|---|---|---|---|---|
| 183 | CH | methyl hexahydrocyclopenta[c]isoxazole-6a-carboxylate | Cl | F | 1-amino-3-methyl-4-thioxo-1,3,5-triazinane-2,6-dione | |
| 184 | CH | methyl hexahydrocyclopenta[c]isoxazole-6a-carboxylate | Cl | F | 1-cyano-3-methyl-4-thioxo-1,3,5-triazinane-2,6-dione | |
| 185 | CH | methyl hexahydrocyclopenta[c]isoxazole-6a-carboxylate | Cl | F | 1-acetyl-3-methyl-4-thioxo-1,3,5-triazinane-2,6-dione | |
| 186 | CH | methyl hexahydrocyclopenta[c]isoxazole-6a-carboxylate | Cl | F | 1,3-dimethoxy-4-thioxo-1,3,5-triazinane-2,6-dione | |

TABLE 1-continued

Structures and $^1$H NMR data of compounds

| No. | M | | Y | Z | Q | $^1$H NMR |
|---|---|---|---|---|---|---|
| 187 | CH | [cyclopenta-fused isoxazoline with methyl ester] | Cl | F | [1,3,5-triazinane-2,4-dione with N-SMe and C=S, N-Me] | |
| 188 | CH | [cyclopenta-fused isoxazoline with methyl ester] | Cl | F | [1,3,5-triazinane with N-C(O)O-iPr, C=S, N-Me] | |
| 189 | CH | [cyclopenta-fused isoxazoline with methyl ester] | Cl | F | [1,3,5-triazinane with N-NHC(O)Me, C=S, N-Me] | |
| 190 | CH | [cyclopenta-fused isoxazoline with methyl ester] | Cl | F | [1,3,5-triazinane with N-C(O)NHMe, C=S, N-Me] | |
| 191 | CH | [cyclopenta-fused isoxazoline with methyl ester] | Cl | F | [1,3,5-triazinane with N-NHC(O)NH$_2$, C=S, N-Me] | |

TABLE 1-continued
Structures and ¹H NMR data of compounds
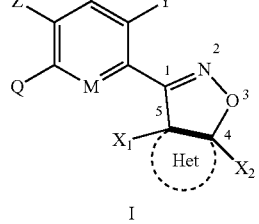
| No. | M | | Y | Z | Q | ¹H NMR |
|---|---|---|---|---|---|---|
| 192 | CH | 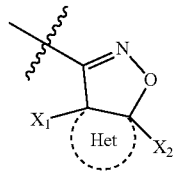 | Cl | F | 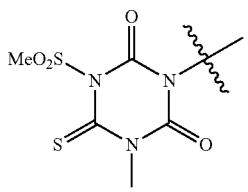 [SMILES: *n1c(=O)n(C)c(=S)n(S(C)(=O)=O)c1=O] | |
| 193 | CH | 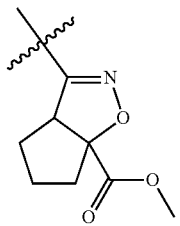 [SMILES: *C1=NOC2(C(=O)OC)CCCC12] | Cl | F | 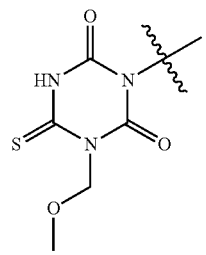 [SMILES: *n1c(=O)[nH]c(=S)n(COC)c1=O] | |
| 194 | CH | 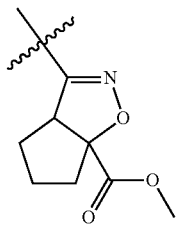 [SMILES: *C1=NOC2(C(=O)OC)CCCC12] | Cl | F | 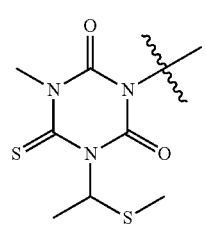 [SMILES: *n1c(=O)n(C)c(=S)n(C(C)SC)c1=O] | |
| 195 | CH | 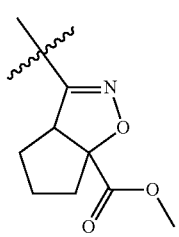 [SMILES: *C1=NOC2(C(=O)OC)CCCC12] | Cl | F | 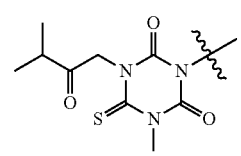 [SMILES: *n1c(=O)n(C)c(=S)n(CC(=O)C(C)C)c1=O] | |

TABLE 1-continued

Structures and $^1$H NMR data of compounds

| No. | M | Het structure | Y | Z | Q | $^1$H NMR |
|---|---|---|---|---|---|---|
| 196 | CH | methyl hexahydrocyclopenta[c]isoxazole-6a-carboxylate | Cl | F | 3-methyl-6-thioxo-1,3,5-triazinan-2,4-dione with N-CH₂COOH | |
| 197 | CH | methyl hexahydrocyclopenta[c]isoxazole-6a-carboxylate | Cl | F | 6-thioxo-1,3,5-triazinan-2,4-dione with N-CH₂C(O)OCH₃ | |
| 198 | CH | methyl hexahydrocyclopenta[c]isoxazole-6a-carboxylate | Cl | F | 3-methyl-6-thioxo-triazinanedione with N-CH(CH₃)OC(O)OEt | |
| 199 | CH | methyl hexahydrocyclopenta[c]isoxazole-6a-carboxylate | Cl | F | 3-methyl-6-thioxo-triazinanedione with N-CH₂N(CH₃)₂ | |

TABLE 1-continued

Structures and ¹H NMR data of compounds

| No. | M | [structure with X₁, Het, X₂] | Y | Z | Q | ¹H NMR |
|-----|---|---|---|---|---|--------|
| 200 | CH | cyclopentane-fused isoxazoline with CO₂Me | Cl | F | triazine-2,4-dione-6-thione with N-CH(CH₃)CN and N-CH₃ | |
| 201 | CH | cyclopentane-fused isoxazoline with CO₂Me | Cl | F | triazine-2,4-dione-6-thione with NH and N-Ph | |
| 202 | CH | cyclopentane-fused isoxazoline with CO₂Me | Cl | F | triazine-2,4-dione-6-thione with N-(3,4-dichlorophenyl) and N-CH₃ | |
| 203 | CH | cyclopentane-fused isoxazoline with CO₂Me | Cl | F | triazine-2,4-dione-6-thione with N-CH₃ and N-(1-methylpyrazol-3-yl) | |

TABLE 1-continued

Structures and $^1$H NMR data of compounds

| No. | M | | Y | Z | Q | $^1$H NMR |
|---|---|---|---|---|---|---|
| 204 | CH | [methyl hexahydrocyclopenta[c]isoxazole-6a-carboxylate] | Cl | F | [1-(tetrahydrofuran-3-yl)-3-methyl-6-thioxo-1,3,5-triazinane-2,4-dione] | |
| 205 | CH | [methyl hexahydrocyclopenta[c]isoxazole-6a-carboxylate] | Cl | F | [1-benzyl-3-methyl-6-thioxo-1,3,5-triazinane-2,4-dione] | |
| 206 | CH | [methyl hexahydrocyclopenta[c]isoxazole-6a-carboxylate] | Cl | F | [1-((5-methoxypyridin-3-yl)methyl)-3-methyl-6-thioxo-1,3,5-triazinane-2,4-dione] | |
| 207 | CH | [methyl hexahydrocyclopenta[c]isoxazole-6a-carboxylate] | Cl | F | [1-(furan-2-ylmethyl)-3-methyl-6-thioxo-1,3,5-triazinane-2,4-dione] | |
| 208 | CH | [methyl hexahydrocyclopenta[c]isoxazole-6a-carboxylate] | Cl | F | [1,3-dimethyl-1,3,5-triazinane-2,4,6-trione] | |

TABLE 1-continued
Structures and ¹H NMR data of compounds
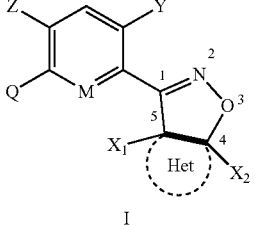
| No. | M | | Y | Z | Q | ¹H NMR |
|---|---|---|---|---|---|---|
| 209 | CH | 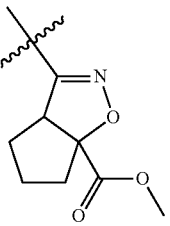 [SMILES: *C1=NOC2(C(=O)OC)CCCC12] | Cl | F | 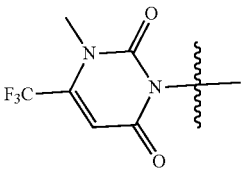 | ¹H NMR (500 MHz. DMSO-d$_6$) δ 7.93 (d, J = 9.5 Hz, 1H), 7.86 (d, J = 7.5, 1H). 6.65 (d, J = 4.0 Hz, 1H), 4.47 (t, J = 9.0 Hz, 1H), 3.77 (s, 3H), 3.44 (s, 3H), 2.25-2.16 (m, 2H), 2.01-1.78 (m, 2H), 1.70-1.62 (m, 1H), 1.55-1.45 (m, 1H) |
| 210 | CH | 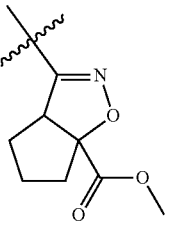 [SMILES: *C1=NOC2(C(=O)OC)CCCC12] | Br | F | 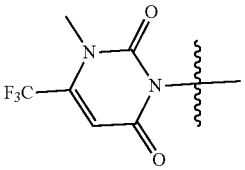 | 1H NMR (500 MHz, DMSO-d6) δ 8.03 (d, J = 9.0 Hz, 1H), 7.80-7.70 (m, 1H), 6.62 (s, 1H), 4.43-4.41 (m, 1H), 3.76 (s, 3H), 3.42 (s, 3H), 2.20-2.10 (m, 2H), 1.93-1.76 (m, 2H), 1.70-1.41 (m, 2H). |
| 211 | CH | 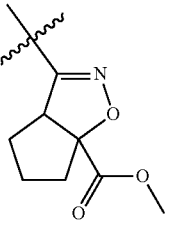 [SMILES: *C1=NOC2(C(=O)OC)CCCC12] | CF$_3$ | F | 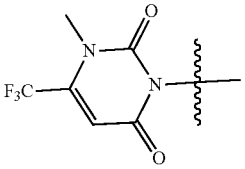 | 1H NMR (500 MHz, DMSO-d6) δ 8.12 (d, J = 10.0 Hz, 1H), 7.94 (d, J = 6.5 Hz, 1H), 6.66 (s, 1H), 4.29-4.27 (m, 1H), 3.75 (s, 3H), 3.44 (s, 3H), 2.21-2.10 (m, 2H), 1.91-1.83 (m, 2H), 1.74-1.62 (m, 1H), 1.59-1.40 (m, 1H). |
| 212 | CH | 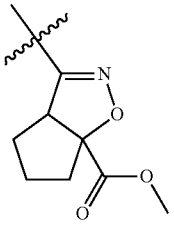 [SMILES: *C1=NOC2(C(=O)OC)CCCC12] | CN | F | 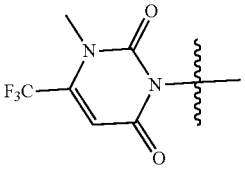 | 1H NMR (500 MHz, DMSO-d6) δ 8.29 (d, J = 9.0 Hz, 1H), 8.10-8.07 (m, 1H), 6.66 (s, 1H), 4.46 (t, J = 8.0 Hz, 1H), 3.74 (s, 3H), 3.43 (s, 3H), 2.24-2.12 (m, 2H), 2.05-2.01 (m, 1H), 1.90-1.71 (m, 2H), 1.52-1.47 (m, 1H). |

TABLE 1-continued

Structures and ¹H NMR data of compounds

| No. | M | | Y | Z | Q | ¹H NMR |
|---|---|---|---|---|---|---|
| 213 | CH | [3a-carboxy-hexahydrocyclopenta[c]isoxazole, –CO-OH at 6a] | Cl | F | N-methyl-6-(trifluoromethyl)uracil, N-linked | ¹H NMR (500 MHz, DMSO) δ 13.36 (s, 1H), 7.88 (d, J = 9.5 Hz, 1H), 7.83 (d, J = 7.0 Hz, 1H), 6.61 (d, J = 4.5 Hz, 1H), 4.39 (d, J = 9.0 Hz, 1H), 3.42 (s, 3H), 2.15-2.05 (m, 2H), 1.99-1.86 (m, 1H), 1.85-1.74 (m, 1H), 1.73-1.58 (m, 1H), 1.55-1.38 (m, 1H). |
| 214 | CH | [hexahydrocyclopenta[c]isoxazole, –CO-OMe at 6a] | Cl | F | N-methyl-6-(trifluoromethyl)uracil, N-linked | ¹H NMR (500 MHz, DMSO-d₆) δ 7.92 (d, J = 7.5 Hz, 1H), 7.86 (d, J = 9.0 Hz, 1H), 6.64 (s, 1H), 4.49-4.46 (m, 1H), 3.77 (s, 3H), 3.44 (s, 3H), 2.22-2.13 (m, 2H), 1.99-1.84 (m, 2H), 1.69-1.65 (m, 1H), 1.56-1.47 (m, 1H). |
| 215 | CH | [hexahydrocyclopenta[c]isoxazole, –CO-OEt at 6a] | Cl | F | N-methyl-6-(trifluoromethyl)uracil, N-linked | 1H NMR (500 MHz, DMSO) δ 7.91 (d, J = 9.5 Hz, 1H), 7.85 (d, J = 7.5 Hz, 1H), 6.64 (d, J = 4.5 Hz, 1H), 4.46 (d, J = 9.5 Hz, 1H), 4.23 (q, J = 7.0 Hz, 2H), 3.44 (s, 3H), 2.19-2.14 (m, 2H), 1.93-1.48 (m, 4H), 1.25 (t, J = 7.0 Hz, 3H). |
| 216 | CH | [hexahydrocyclopenta[c]isoxazole, –CO-OPr at 6a] | Cl | F | N-methyl-6-(trifluoromethyl)uracil, N-linked | 1H NMR (500 MHz, DMSO-d6) δ 7.97-7.79 (m, 2H), 6.64 (s, 1H), 4.47-4.45 (m, 1H), 4.15 (t, J = 7.0 Hz, 2H), 3.44 (s, 3H), 2.21-2.12 (m, 2H), 1.99-1.78 (m, 2H), 1.68-1.62 (m, 3H), 1.53-1.49 (m, 1H), 0.92 (t, J = 7.0 Hz, 3H). |
| 217 | CH | [hexahydrocyclopenta[c]isoxazole, –CO-OiPr at 6a, reversed attachment] | Cl | F | N-methyl-6-(trifluoromethyl)uracil, N-linked | ¹H NMR (500 MHz, Chloroform-d) δ 7.92 (d, J = 8.0 Hz, 1H), 7.88 (d, J = 7.5 Hz, 1H), 6.61 (s, 1H), 4.14-4.08 (m, 1H), 4.04 (s, 3H), 2.84-2.78 (m, 3H), 1.63-1.58 (m, 2H), 1.28-1.22 (m, 8H). |

TABLE 1-continued

Structures and ¹H NMR data of compounds

| No. | M | (Het group) | Y | Z | Q | ¹H NMR |
|-----|---|---|---|---|---|--------|
| 218 | CH | butyl ester cyclopentane-fused isoxazoline | Cl | F | N-methyl-6-(trifluoromethyl)pyrimidine-2,4-dione | |
| 219 | CH | isobutyl ester cyclopentane-fused isoxazoline | Cl | F | N-methyl-6-(trifluoromethyl)pyrimidine-2,4-dione | |
| 220 | CH | tert-butyl ester cyclopentane-fused isoxazoline | Cl | F | N-methyl-6-(trifluoromethyl)pyrimidine-2,4-dione | |
| 221 | CH | oct-2-yl ester cyclopentane-fused isoxazoline | Cl | F | N-methyl-6-(trifluoromethyl)pyrimidine-2,4-dione | |
| 222 | CH | allyl ester cyclopentane-fused isoxazoline | Cl | F | N-methyl-6-(trifluoromethyl)pyrimidine-2,4-dione | 1H NMR (500 MHz, DMSO-d6) δ 7.90 (d, J = 9.5 Hz, 1H), 7.83 (dd, J = 7.5, 2.0 Hz, 1H), 6.62 (s, 1H), 5.99-5.92 (m, 1H), 5.36-5.32 (m, 1H), 5.26-5.24 (m, 1H), 4.70-4.69 (m, 2H), 4.47-4.45 (m, 1H), 3.42 (s, 3H), 2.22-2.11 (m, 2H), 2.01-1.76 (m, 2H), 1.67-1.63 (m, 1H), 1.55-1.47 (m, 1H). |

TABLE 1-continued

Structures and ¹H NMR data of compounds

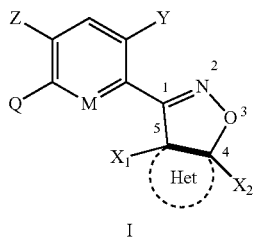

| No. | M | | Y | Z | Q | ¹H NMR |
|---|---|---|---|---|---|---|
| 223 | CH | methallyl ester cyclopentane-fused isoxazoline | Cl | F | N-methyl-6-(trifluoromethyl)uracil | |
| 224 | CH | but-3-enyl ester cyclopentane-fused isoxazoline | Cl | F | N-methyl-6-(trifluoromethyl)uracil | |
| 225 | CH | propargyl ester cyclopentane-fused isoxazoline | Cl | F | N-methyl-6-(trifluoromethyl)uracil | 1H NMR (500 MHz, DMSO-d6) δ 7.95-7.82 (m, 2H), 6.64 (s, 1H), 4.92-4.83 (m, 2H), 4.48-4.46 (m, 1H), 3.68-3.64 (m,1H), 3.44 (s, 3H), 2.24-2.12 (m, 2H), 1.99-1.79 (m, 2H), 1.74-1.43 (m, 2H). |
| 226 | CH | but-3-ynyl ester cyclopentane-fused isoxazoline | Cl | F | N-methyl-6-(trifluoromethyl)uracil | |

TABLE 1-continued

Structures and ¹H NMR data of compounds

| No. | M | [structure with X₁/Het/X₂] | Y | Z | Q | ¹H NMR |
|-----|---|---|---|---|---|--------|
| 227 | CH | [cyclopentane-fused isoxazoline with C(=O)O-CH₂-C≡C-CH₃ ester] | Cl | F | [N-methyl-6-(trifluoromethyl)pyrimidine-2,4-dione] | |
| 228 | CH | [cyclopentane-fused isoxazoline with C(=O)O-CH(CH₃)-C≡CH ester] | Cl | F | [N-methyl-6-(trifluoromethyl)pyrimidine-2,4-dione] | |
| 229 | CH | [cyclopentane-fused isoxazoline with cyclopropyl ester, reversed orientation] | Cl | F | [N-methyl-6-(trifluoromethyl)pyrimidine-2,4-dione] | |
| 230 | CH | [cyclopentane-fused isoxazoline with C(=O)O-CH₂-cyclopropyl ester] | Cl | F | [N-methyl-6-(trifluoromethyl)pyrimidine-2,4-dione] | |
| 231 | CH | [cyclopentane-fused isoxazoline with C(=O)O-CH₂-CH₂-F ester] | Cl | F | [N-methyl-6-(trifluoromethyl)pyrimidine-2,4-dione] | ¹H NMR (500 MHz, DMSO-$d_6$) δ 7.92 (d, J = 9.0 Hz, 1H), 7.85 (d, J = 7.5 Hz, 1H), 6.64 (s, 1H), 4.73 (t, J = 4.0 Hz, 1H), 4.64 (t, J = 4.0 Hz, 1H), 4.54-4.45 (m, 2H), 4.42 (t, J = 4.0 Hz, 1H), 3.44 (s, 3H), 2.25-2.15 (m, 1H), 2.12-2.00 (m, 1H), 1.99-1.86 (m, 1H), 1.70-1.66 (m, 1H), 1.56-1.50 (m, 1H), 1.34-1.21 (m, 1H). |

TABLE 1-continued

Structures and ¹H NMR data of compounds

| No. | M | [Het structure] | Y | Z | Q | ¹H NMR |
|-----|---|---|---|---|---|--------|
| 232 | CH | cyclopentane-fused isoxazoline with C(=O)O-CH₂CHF₂ ester | Cl | F | N-methyl-6-(trifluoromethyl)pyrimidine-2,4-dione | |
| 233 | CH | cyclopentane-fused isoxazoline with CF₃CH₂-O-C(=O) ester | Cl | F | N-methyl-6-(trifluoromethyl)pyrimidine-2,4-dione | |
| 234 | CH | cyclopentane-fused isoxazoline with C(=O)O-CH₂CH₂CH₂F ester | Cl | F | N-methyl-6-(trifluoromethyl)pyrimidine-2,4-dione | |
| 235 | CH | cyclopentane-fused isoxazoline with C(=O)O-CH₂C(CH₃)F₂ ester | Cl | F | N-methyl-6-(trifluoromethyl)pyrimidine-2,4-dione | |
| 236 | CH | cyclopentane-fused isoxazoline with C(=O)O-CH₂CH₂CF₃ ester | Cl | F | N-methyl-6-(trifluoromethyl)pyrimidine-2,4-dione | |

TABLE 1-continued

Structures and ¹H NMR data of compounds

| No. | M | [structure] | Y | Z | Q | ¹H NMR |
|---|---|---|---|---|---|---|
| 237 | CH | cyclopentane-fused isoxazoline with -C(=O)O-CH₂CH₂CH₂-Cl ester | Cl | F | N-methyl-6-(trifluoromethyl)pyrimidine-2,4(1H,3H)-dione linked via N | |
| 238 | CH | cyclopentane-fused isoxazoline with -C(=O)O-CH₂-CH=CH-Cl ester | Cl | F | N-methyl-6-(trifluoromethyl)pyrimidine-2,4(1H,3H)-dione linked via N | |
| 239 | CH | cyclopentane-fused isoxazoline with -C(=O)O-CH₂-CN ester | Cl | F | N-methyl-6-(trifluoromethyl)pyrimidine-2,4(1H,3H)-dione linked via N | |
| 240 | CH | cyclopentane-fused isoxazoline with -C(=O)O-CH₂CH₂-CN ester | Cl | F | N-methyl-6-(trifluoromethyl)pyrimidine-2,4(1H,3H)-dione linked via N | |
| 241 | CH | cyclopentane-fused isoxazoline with -C(=O)O-CH₂-C≡C-TMS ester | Cl | F | N-methyl-6-(trifluoromethyl)pyrimidine-2,4(1H,3H)-dione linked via N | |

TABLE 1-continued

Structures and ¹H NMR data of compounds

| No. | M | (Het structure) | Y | Z | Q | ¹H NMR |
|-----|---|-----------------|---|---|---|--------|
| 242 | CH | | Cl | F | | |
| 243 | CH | | Cl | F | | |
| 244 | CH | | Cl | F | | |
| 245 | CH | | Cl | F | | ¹H NMR (500 MHz, DMSO-d₆) δ 7.92 (d, J = 9.0 Hz, 1H), 7.84 (d, J = 7.5 Hz, 1H), 6.63 (s, 1H), 4.47 (t, J = 9.0 Hz, 1H), 4.31 (d, J = 5.0 Hz, 2H), 3.59 (t, J = 5.0 Hz, 2H), 3.44 (s, 3H), 3.29 (s, 3H), 2.25-2.12 (m, 1H), 2.09 (s, 2H), 1.89-1.77 (m, 1H), 1.72-1.60 (m, 1H), 1.58-1.42 (m, 1H). |
| 246 | CH | | Cl | F | | |

TABLE 1-continued

Structures and ¹H NMR data of compounds

| No. | M | (structure) | Y | Z | Q | ¹H NMR |
|---|---|---|---|---|---|---|
| 247 | CH | | Cl | F | | |
| 248 | CH | | Cl | F | | |
| 249 | CH | | Cl | F | | |
| 250 | CH | | Cl | F | | |
| 251 | CH | | Cl | F | | |

TABLE 1-continued
Structures and ¹H NMR data of compounds
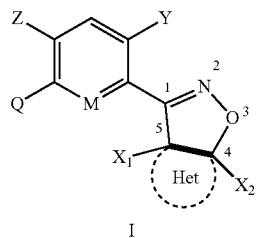
| No. | M | | Y | Z | Q | ¹H NMR |
|---|---|---|---|---|---|---|
| 252 | CH | | Cl | F | | |
| 253 | CH | | Cl | F | | |
| 254 | CH | | Cl | F | | |
| 255 | CH | | Cl | F | | |

TABLE 1-continued

Structures and ¹H NMR data of compounds

| No. | M | | Y | Z | Q | ¹H NMR |
|-----|---|---|---|---|---|--------|
| 256 | CH | | Cl | F | | |
| 257 | CH | | Cl | F | | |
| 258 | CH | | Cl | F | | |
| 259 | CH | | Cl | F | | |

TABLE 1-continued
Structures and ¹H NMR data of compounds
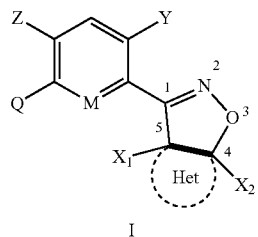
I
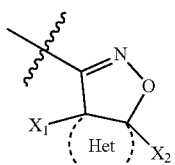
| No. | M | | Y | Z | Q | ¹H NMR |
|---|---|---|---|---|---|---|
| 260 | CH | 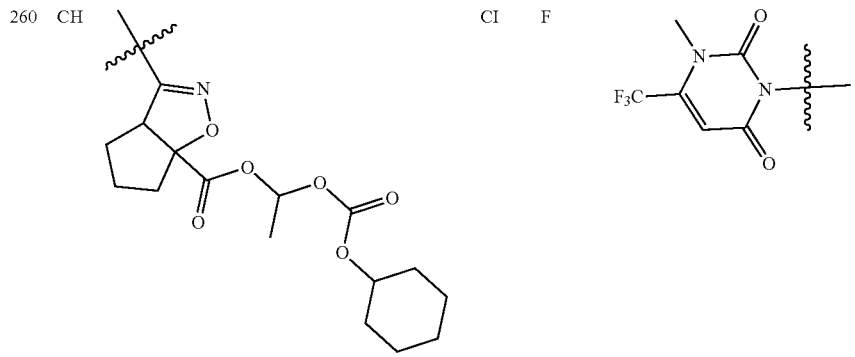 | Cl | F | | |
| 261 | CH | 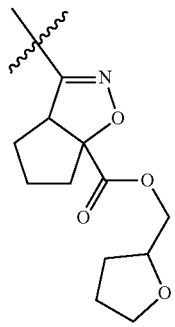 [SMILES: *C1=NOC2(C(=O)OCC3CCCO3)CCCC12] | Cl | F | 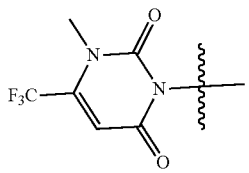 | ¹H NMR (500 MHz, DMSO-d$_6$) δ 7.92 (d, J = 9.5 Hz, 1H), 7.85 (d, J = 7.5 Hz, 1H), 6.64 (d, J = 5.0 Hz, 1H), 4.48-4.46 (m, 1H), 4.20-4.08 (m, 2H), 3.75-3.65 (m, 3H), 3.44 (s, 3H), 2.20-2.09 (m, 3H), 2.03-1.72 (m, 4H), 1.66-1.43 (m, 2H), 1.31-1.13 (m, 1H). |
| 262 | CH | 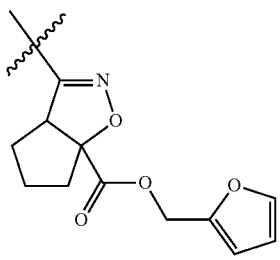 [SMILES: *C1=NOC2(C(=O)OCc3ccco3)CCCC12] | Cl | F | 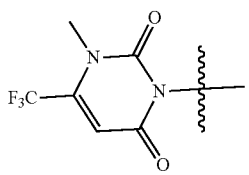 | |

TABLE 1-continued

Structures and ¹H NMR data of compounds

| No. | M | (X₁/Het/X₂ group) | Y | Z | Q | ¹H NMR |
|---|---|---|---|---|---|---|
| 263 | CH | cyclopentane-fused isoxazoline with benzyl ester | Cl | F | 1-methyl-6-(trifluoromethyl)-2,4-dioxopyrimidin-3-yl | |
| 264 | CH | cyclopentane-fused isoxazoline with 2-fluorobenzyl ester | Cl | F | 1-methyl-6-(trifluoromethyl)-2,4-dioxopyrimidin-3-yl | 1H NMR (500 MHz, DMSO) δ 7.97-7.89 (m, 2H), 7.50-7.46 (m, 2H), 7.35-7.25 (m, 2H), 6.65 (d, J = 4.5 Hz, 1H), 5.33 (q, J = 12.5 Hz, 2H), 4.46 (d, J = 9.0 Hz, 1H), 3.44 (s, 3H), 2.24-2.12 (m, 2H), 1.97-1.48 (m, 4H). |
| 265 | CH | cyclopentane-fused isoxazoline with 4-fluorobenzyl ester | Cl | F | 1-methyl-6-(trifluoromethyl)-2,4-dioxopyrimidin-3-yl | |
| 266 | CH | cyclopentane-fused isoxazoline with 3-fluorobenzyl ester | Cl | F | 1-methyl-6-(trifluoromethyl)-2,4-dioxopyrimidin-3-yl | |

TABLE 1-continued

Structures and ¹H NMR data of compounds

| No. | M | | Y | Z | Q | ¹H NMR |
|---|---|---|---|---|---|---|
| 267 | CH | 4-chlorobenzyl ester of cyclopenta-fused isoxazoline | Cl | F | N-methyl-6-(trifluoromethyl)pyrimidine-2,4-dione | |
| 268 | CH | 2,6-difluorobenzyl ester of cyclopenta-fused isoxazoline | Cl | F | N-methyl-6-(trifluoromethyl)pyrimidine-2,4-dione | |
| 269 | CH | 2,6-dichlorobenzyl ester of cyclopenta-fused isoxazoline | Cl | F | N-methyl-6-(trifluoromethyl)pyrimidine-2,4-dione | |
| 270 | CH | 2,4,6-trifluorobenzyl ester of cyclopenta-fused isoxazoline | Cl | F | N-methyl-6-(trifluoromethyl)pyrimidine-2,4-dione | |
| 271 | CH | pyridin-3-ylmethyl ester of cyclopenta-fused isoxazoline | Cl | F | N-methyl-6-(trifluoromethyl)pyrimidine-2,4-dione | |

TABLE 1-continued
Structures and ¹H NMR data of compounds
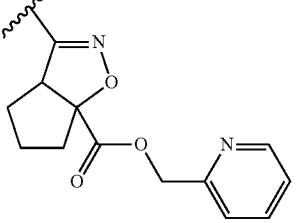
I
| No. | M |  | Y | Z | Q | ¹H NMR |
|---|---|---|---|---|---|---|
| 272 | CH | 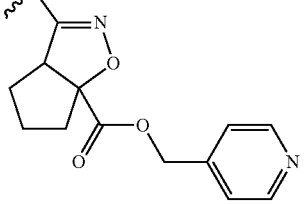 | Cl | F | 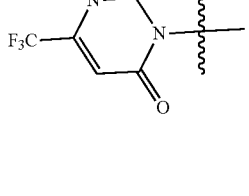 | |
| 273 | CH | 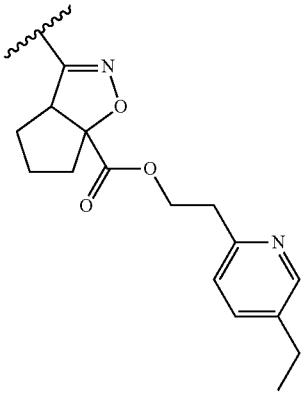 [SMILES: *C1=NOC2(C(=O)OCCc3ccc(CC)cn3)CCCC12] | Cl | F | | |
| 274 | CH | 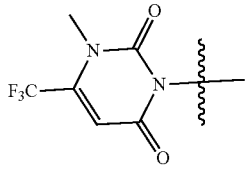 | Cl | F | 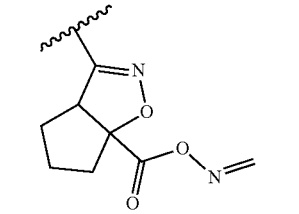 [SMILES: *C1=NOC2(C(=O)ON=C)CCCC12] | |
| 275 | CH | 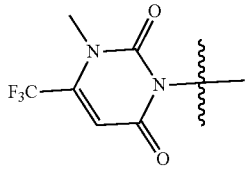 | Cl | F | | |

TABLE 1-continued

Structures and ¹H NMR data of compounds

| No. | M | (structure) | Y | Z | Q | ¹H NMR |
|---|---|---|---|---|---|---|
| 276 | CH | | Cl | F | | |
| 277 | CH | | Cl | F | | |
| 278 | CH | | Cl | F | | ¹H NMR (500 MHz, DMSO) δ 7.92 (d, J = 9.5 Hz, 1H), 7.87 (d, J = 7.0 Hz, 1H), 6.64 (d, J = 5.0 Hz, 1H), 4.56 (d, J = 9.0 Hz, 1H), 3.44 (s, 3H), 2.34-2.15 (m, 2H), 2.02-1.98 (m, 6H), 1.98-1.91 (m, 1H), 1.90-1.85 (m, 1H), 1.74-1.63 (m, 1H), 1.60-1.50 (m, 1H). |
| 279 | CH | | Cl | F | | |

TABLE 1-continued

Structures and ¹H NMR data of compounds

| No. | M | | Y | Z | Q | ¹H NMR |
|---|---|---|---|---|---|---|
| 280 | CH | 3-(oxime ester with isopropyl ketone) cyclopentane-fused isoxazoline | Cl | F | 1-methyl-6-(trifluoromethyl)-2,4-dioxopyrimidin-3-yl | |
| 281 | CH | 3-(oxime ester with tert-butyl methyl ketone) cyclopentane-fused isoxazoline | Cl | F | 1-methyl-6-(trifluoromethyl)-2,4-dioxopyrimidin-3-yl | |
| 282 | CH | 3-(oxime ester with diethyl ketone) cyclopentane-fused isoxazoline | Cl | F | 1-methyl-6-(trifluoromethyl)-2,4-dioxopyrimidin-3-yl | |
| 283 | CH | 3-(oxime ester with cyclopropyl methyl ketone) cyclopentane-fused isoxazoline | Cl | F | 1-methyl-6-(trifluoromethyl)-2,4-dioxopyrimidin-3-yl | |

TABLE 1-continued
Structures and $^1$H NMR data of compounds
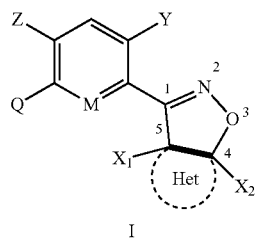
| No. | M | 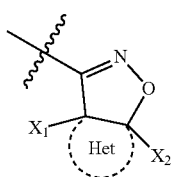 | Y | Z | Q | $^1$H NMR |
|---|---|---|---|---|---|---|
| 284 | CH | 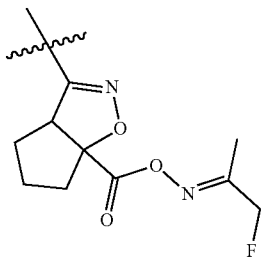 [SMILES: *C1=NOC2(C(=O)O/N=C(\C)CF)CCCC12] | Cl | F | 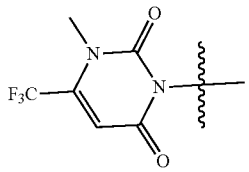 | |
| 285 | CH | | Cl | F | | |
| 286 | CH | | Cl | F | | |
| 287 | CH | | Cl | F | | |

TABLE 1-continued

Structures and ¹H NMR data of compounds

| No. | M | [Het/X₁/X₂ structure] | Y | Z | Q | ¹H NMR |
|---|---|---|---|---|---|---|
| 288 | CH | cyclopentane-fused isoxazoline with –C(O)O–N=C(Cl)CH₃ | Cl | F | 1-methyl-6-(trifluoromethyl)-2,4-dioxopyrimidin-3-yl | |
| 289 | CH | cyclopentane-fused isoxazoline with –C(O)O–N=C(OEt)CH₃ | Cl | F | 1-methyl-6-(trifluoromethyl)-2,4-dioxopyrimidin-3-yl | |
| 290 | CH | cyclopentane-fused isoxazoline with –C(O)O–N=C(CH₂OMe)CH₃ | Cl | F | 1-methyl-6-(trifluoromethyl)-2,4-dioxopyrimidin-3-yl | |
| 291 | CH | cyclopentane-fused isoxazoline with –C(O)O–N=C(CO₂Et)CH₃ | Cl | F | 1-methyl-6-(trifluoromethyl)-2,4-dioxopyrimidin-3-yl | |

TABLE 1-continued
Structures and $^1$H NMR data of compounds
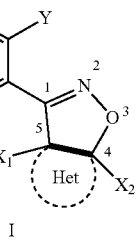
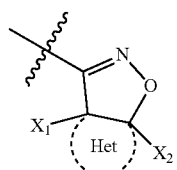
| No. | M | | Y | Z | Q | $^1$H NMR |
|---|---|---|---|---|---|---|
| 292 | CH | | Cl | F | | |
| 293 | CH | | Cl | F | | |
| 294 | CH | | Cl | F | | |

TABLE 1-continued
Structures and ¹H NMR data of compounds
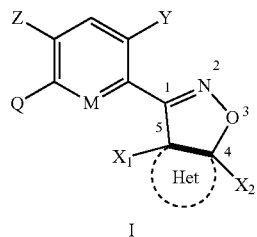
I
| No. | M | 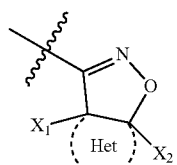 | Y | Z | Q | ¹H NMR |
|---|---|---|---|---|---|---|
| 295 | CH | | Cl | F | | |
| 296 | CH | | Cl | F | | |
| 297 | CH | | Cl | F | | |
| 298 | CH | | Cl | F | | |

TABLE 1-continued

Structures and ¹H NMR data of compounds

| No. | M | [Het group] | Y | Z | Q | ¹H NMR |
|---|---|---|---|---|---|---|
| 299 | CH | bicyclic isoxazoline-cyclopentane with C(=O)O-CH₂-O-N=C(CH₃)₂ substituent | Cl | F | N-methyl-6-(trifluoromethyl)pyrimidine-2,4-dione (N-linked) | |
| 300 | CH | bicyclic isoxazoline-cyclopentane with C(=O)O-CH₂CH₂-O-N=C(CH₃)₂ substituent | Cl | F | N-methyl-6-(trifluoromethyl)pyrimidine-2,4-dione (N-linked) | |
| 301 | CH | bicyclic isoxazoline-cyclopentane with C(=O)NH-S(=O)₂-CH₃ substituent | Cl | F | N-methyl-6-(trifluoromethyl)pyrimidine-2,4-dione (N-linked) | |
| 302 | CH | bicyclic isoxazoline-cyclopentane with C(=O)NH-S(=O)₂-CH₂CH₃ substituent | Cl | F | N-methyl-6-(trifluoromethyl)pyrimidine-2,4-dione (N-linked) | |

TABLE 1-continued
Structures and ¹H NMR data of compounds
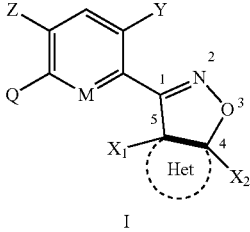
| No. | M | | Y | Z | Q | ¹H NMR |
|---|---|---|---|---|---|---|
| 303 | CH |  | Cl | F |  | |
| 304 | CH | 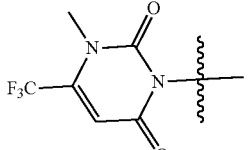 | Cl | F |  | |
| 305 | CH |  | Cl | F | 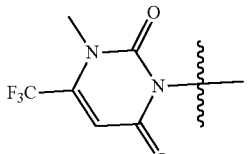 | |

TABLE 1-continued

Structures and ¹H NMR data of compounds

| No. | M | Het structure | Y | Z | Q | ¹H NMR |
|---|---|---|---|---|---|---|
| 306 | CH | cyclopentane-fused isoxazoline with C(O)NHS(O)₂NH₂ | Cl | F | 1-methyl-6-(trifluoromethyl)-2,4-dioxopyrimidin-3-yl | |
| 307 | CH | cyclopentane-fused isoxazoline with C(O)NHS(O)₂NHCH₃ | Cl | F | 1-methyl-6-(trifluoromethyl)-2,4-dioxopyrimidin-3-yl | |
| 308 | CH | cyclopentane-fused isoxazoline with C(O)NHS(O)₂NH-iPr | Cl | F | 1-methyl-6-(trifluoromethyl)-2,4-dioxopyrimidin-3-yl | |
| 309 | CH | cyclopentane-fused isoxazoline with C(O)NHS(O)₂N(CH₃)₂ | Cl | F | 1-methyl-6-(trifluoromethyl)-2,4-dioxopyrimidin-3-yl | |

TABLE 1-continued

Structures and ¹H NMR data of compounds

| No. | M | [Het group] | Y | Z | Q | ¹H NMR |
|-----|---|---|---|---|---|--------|
| 310 | CH | cyclopentane-fused isoxazoline with -C(O)NH-S(O)₂-N(CH₃)(iPr) | Cl | F | 3-methyl-6-(trifluoromethyl)-2,4-dioxopyrimidin-1-yl | |
| 311 | CH | cyclopentane-fused isoxazoline with -C(O)-N(CH₃)-S(O)₂-N(CH₃)(iPr) | Cl | F | 3-methyl-6-(trifluoromethyl)-2,4-dioxopyrimidin-1-yl | |
| 312 | CH | cyclopentane-fused isoxazoline with -C(O)NH-S(O)₂-N(CH₃)(OCH₃) | Cl | F | 3-methyl-6-(trifluoromethyl)-2,4-dioxopyrimidin-1-yl | |
| 313 | CH | cyclopentane-fused isoxazoline with -C(O)NH-S(O)₂-N(CH₃)-S(O)₂CH₃ | Cl | F | 3-methyl-6-(trifluoromethyl)-2,4-dioxopyrimidin-1-yl | |

TABLE 1-continued
Structures and $^1$H NMR data of compounds
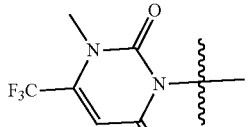
| No. | M | (Het structure) | Y | Z | Q | $^1$H NMR |
|---|---|---|---|---|---|---|
| 314 | CH | 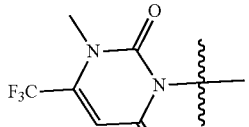 | Cl | F | 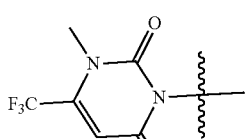 | |
| 315 | CH | 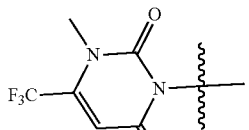 | Cl | F | | |
| 316 | CH | | Cl | F | | |
| 317 | CH | | Cl | F | | |
| 318 | CH | 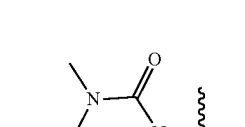 | Cl | F | | |

TABLE 1-continued

Structures and ¹H NMR data of compounds

| No. | M | (Het structure) | Y | Z | Q | ¹H NMR |
|-----|---|---|---|---|---|---|
| 319 | CH | | Cl | F | | |
| 320 | CH | | Cl | F | | |
| 321 | CH | | Cl | F | | |
| 322 | CH | | Cl | F | | |
| 323 | CH | | Cl | F | | |

TABLE 1-continued
Structures and ¹H NMR data of compounds
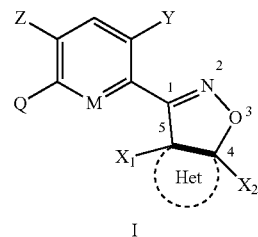
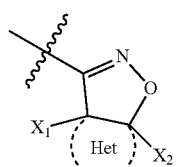
| No. | M | | Y | Z | Q | ¹H NMR |
|---|---|---|---|---|---|---|
| 324 | CH | | Cl | F | | |
| 325 | CH | | Cl | F | | |
| 326 | CH | | Cl | F | | |
| 327 | CH | | Cl | F | | |

TABLE 1-continued
Structures and ¹H NMR data of compounds
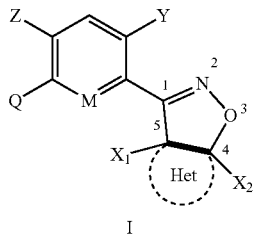
I
| No. | M | 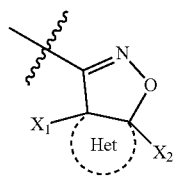 | Y | Z | Q | ¹H NMR |
|---|---|---|---|---|---|---|
| 328 | CH | 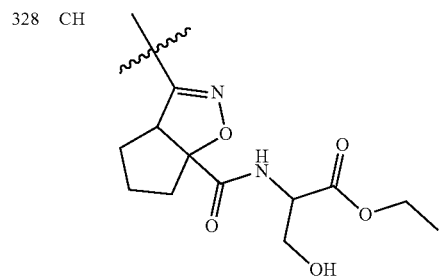 | Cl | F | 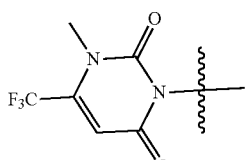 | |
| 329 | CH | 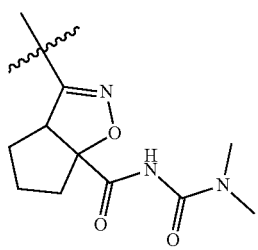 [SMILES: *C1=NOC2(C(=O)NC(=O)N(C)C)CCCC12] | Cl | F | 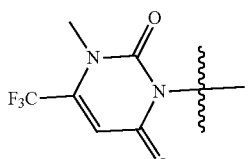 | |
| 330 | CH | 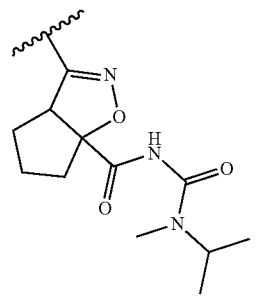 [SMILES: *C1=NOC2(C(=O)NC(=O)N(C)C(C)C)CCCC12] | Cl | F | 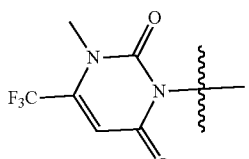 | |
| 331 | CH | 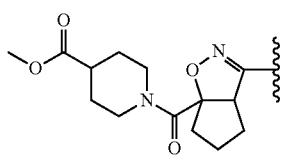 [SMILES: *C1=NOC2(C(=O)N3CCC(C(=O)OC)CC3)CCCC12] | Cl | F | 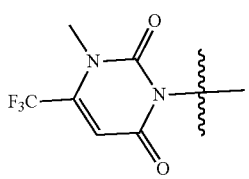 [SMILES: *n1c(=O)cc(C(F)(F)F)n(C)c1=O] | |

TABLE 1-continued
Structures and ¹H NMR data of compounds
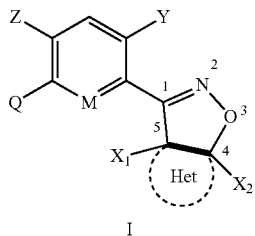
| No. | M | 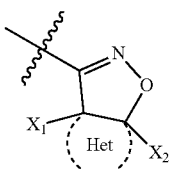 | Y | Z | Q | ¹H NMR |
|---|---|---|---|---|---|---|
| 332 | CH | | Cl | F | | |
| 333 | CH | | Cl | F | | ¹H NMR (500 MHz, DMSO) δ 7.91 (d, J = 9.5 Hz, 1H), 7.85 (d, J = 5.5 Hz, 1H), 6.63 (d, J = 3.0 Hz, 1H), 6.25 (s, 1H), 4.80 (d, J = 8.5 Hz, 1H), 3.44 (s, 3H), 2.52 (s, 3H), 2.50-2.38 (m, 2H), 2.25-2.10 (m, 4H), 1.98-1.88 (m, 1H), 1.74-1.65 (m, 1H), 1.64-1.53 (m, 1H). |
| 334 | CH | | Cl | F | | ¹H NMR (500 MHz, DMSO-d₆) δ 7.92 (d, J = 9.0 Hz, 1H), 7.83 (d, J = 7.5 Hz, 1H), 6.63 (s, 1H), 4.88 (t, J = 9.0 Hz, 1H), 3.47 (t, J = 8.0 Hz, 2H), 3.44 (s, 3H), 2.24-2.15 (m, 1H), 2.13-2.04 (m, 1H), 2.00-1.82 (m, 2H), 1.73-1.45 (m, 2H), 1.16 (t, J = 8.0 Hz, 3H). |
| 335 | CH | | Cl | F | | |
| 336 | CH | | Cl | F | | |

TABLE 1-continued

Structures and ¹H NMR data of compounds

| No. | M | | Y | Z | Q | ¹H NMR |
|---|---|---|---|---|---|---|
| 337 | CH | (3-ethylthiothiocarbonyl hexahydrocyclopenta[c]isoxazole) | Cl | F | 1-methyl-6-(trifluoromethyl)pyrimidine-2,4-dione | |
| 338 | CH | (3a-fluoro, 6a-methoxycarbonyl hexahydrocyclopenta[c]isoxazole) | Cl | F | 1-methyl-6-(trifluoromethyl)pyrimidine-2,4-dione | |
| 339 | CH | (3a-fluoro, 6a-ethoxycarbonyl hexahydrocyclopenta[c]isoxazole) | Cl | F | 1-methyl-6-(trifluoromethyl)pyrimidine-2,4-dione | |
| 340 | CH | (3a-chloro, 6a-ethoxycarbonyl hexahydrocyclopenta[c]isoxazole) | Cl | F | 1-methyl-6-(trifluoromethyl)pyrimidine-2,4-dione | |
| 341 | CH | (3a-methyl, 6a-methoxycarbonyl hexahydrocyclopenta[c]isoxazole) | Cl | F | 1-methyl-6-(trifluoromethyl)pyrimidine-2,4-dione | ¹H NMR (500 MHz, DMSO-d₆) δ 7.79 (d, J = 8.5 Hz, 1H), 7.18 (d, J = 7.5 Hz, 1H), 6.58 (s, 1H), 3.95 (s, 3H), 3.76 (s, 3H), 2.43-2.37 (m, 2H), 1.76-1.66 (m, 3H), 1.24-1.09 (m, 4H). |

TABLE 1-continued

Structures and ¹H NMR data of compounds

| No. | M | [Het group] | Y | Z | Q | ¹H NMR |
|-----|---|---|---|---|---|---|
| 342 | CH | 3a-methyl-hexahydrocyclopenta[c]isoxazole-6a-carboxylic acid ethyl ester | Cl | F | 1-methyl-6-(trifluoromethyl)pyrimidine-2,4-dione | |
| 343 | CH | 3a-ethyl-hexahydrocyclopenta[c]isoxazole-6a-carboxylic acid ethyl ester | Cl | F | 1-methyl-6-(trifluoromethyl)pyrimidine-2,4-dione | |
| 344 | CH | 3a-isopropyl-hexahydrocyclopenta[c]isoxazole-6a-carboxylic acid ethyl ester | Cl | F | 1-methyl-6-(trifluoromethyl)pyrimidine-2,4-dione | |
| 345 | CH | 3a-vinyl-hexahydrocyclopenta[c]isoxazole-6a-carboxylic acid ethyl ester | Cl | F | 1-methyl-6-(trifluoromethyl)pyrimidine-2,4-dione | |
| 346 | CH | 3a-propargyl-hexahydrocyclopenta[c]isoxazole-6a-carboxylic acid ethyl ester | Cl | F | 1-methyl-6-(trifluoromethyl)pyrimidine-2,4-dione | |

TABLE 1-continued

Structures and $^1$H NMR data of compounds

| No. | M | [Het group] | Y | Z | Q | $^1$H NMR |
|---|---|---|---|---|---|---|
| 347 | CH | cyclopentane-fused isoxazoline with cyclopropyl at X₁ and ethyl ester at X₂ | Cl | F | N-methyl-6-(trifluoromethyl)pyrimidine-2,4-dione | |
| 348 | CH | cyclopentane-fused isoxazoline with cyclopropylmethyl at X₁ and ethyl ester at X₂ | Cl | F | N-methyl-6-(trifluoromethyl)pyrimidine-2,4-dione | |
| 349 | CH | cyclopentane-fused isoxazoline with CF₃ at X₁ and ethyl ester at X₂ | Cl | F | N-methyl-6-(trifluoromethyl)pyrimidine-2,4-dione | |
| 350 | CH | cyclopentane-fused isoxazoline with BrCH₂ at X₁ and ethyl ester at X₂ | Cl | F | N-methyl-6-(trifluoromethyl)pyrimidine-2,4-dione | |
| 351 | CH | cyclopentane-fused isoxazoline with HO at X₁ and methyl ester at X₂ | Cl | F | N-methyl-6-(trifluoromethyl)pyrimidine-2,4-dione | 1H NMR (500 MHz, DMSO) δ 7.91 (d, J = 8.5 Hz, 1H), 7.52 (d, J = 8.5 Hz, 1H), 6.62 (s, 1H), 3.44 (s, 3H), 3.34 (s, 3H), 2.38-1.90 (m, 4H), 1.73-1.28 (m, 2H). |

TABLE 1-continued

Structures and ¹H NMR data of compounds

| No. | M | [Het substructure] | Y | Z | Q | ¹H NMR |
|-----|---|---|---|---|---|--------|
| 352 | CH | 3a-methoxy-cyclopentane-fused isoxazoline with 7a-CO₂Me | Cl | F | N-methyl-6-(trifluoromethyl)pyrimidine-2,4-dione | |
| 353 | CH | 3a-methoxy-cyclopentane-fused isoxazoline with 7a-CO₂Et | Cl | F | N-methyl-6-(trifluoromethyl)pyrimidine-2,4-dione | |
| 354 | CH | 3a-ethoxy-cyclopentane-fused isoxazoline with 7a-CO₂Et | Cl | F | N-methyl-6-(trifluoromethyl)pyrimidine-2,4-dione | |
| 355 | CH | 3a-(hydroxymethyl)-cyclopentane-fused isoxazoline with 7a-CO₂Et | Cl | F | N-methyl-6-(trifluoromethyl)pyrimidine-2,4-dione | |
| 356 | CH | 3a-(methoxymethyl)-cyclopentane-fused isoxazoline with 7a-CO₂Me | Cl | F | N-methyl-6-(trifluoromethyl)pyrimidine-2,4-dione | |

TABLE 1-continued

Structures and ¹H NMR data of compounds

| No. | M | | Y | Z | Q | ¹H NMR |
|-----|---|---|---|---|---|--------|
| 357 | CH | 3a-(methylthio)-7a-(ethoxycarbonyl)-hexahydrocyclopenta[c]isoxazole | Cl | F | 3-methyl-6-(trifluoromethyl)-2,4-dioxo-pyrimidin-1-yl | |
| 358 | CH | 3a-amino-7a-(methoxycarbonyl)-hexahydrocyclopenta[c]isoxazole | Cl | F | 3-methyl-6-(trifluoromethyl)-2,4-dioxo-pyrimidin-1-yl | |
| 359 | CH | 3a-(methylamino)-7a-(methoxycarbonyl)-hexahydrocyclopenta[c]isoxazole | Cl | F | 3-methyl-6-(trifluoromethyl)-2,4-dioxo-pyrimidin-1-yl | |
| 360 | CH | 3a-(dimethylamino)-7a-(methoxycarbonyl)-hexahydrocyclopenta[c]isoxazole | Cl | F | 3-methyl-6-(trifluoromethyl)-2,4-dioxo-pyrimidin-1-yl | |
| 361 | CH | 3a-cyano-7a-(ethoxycarbonyl)-hexahydrocyclopenta[c]isoxazole | Cl | F | 3-methyl-6-(trifluoromethyl)-2,4-dioxo-pyrimidin-1-yl | |

TABLE 1-continued

Structures and $^1$H NMR data of compounds

| No. | M | [Het substructure] | Y | Z | Q | $^1$H NMR |
|---|---|---|---|---|---|---|
| 362 | CH | (NC-CH2 substituted bicyclic isoxazoline with ethyl ester) | Cl | F | (N-methyl, N'-linked, 6-CF3 pyrimidine-2,4-dione) | |
| 363 | CH | (CHO substituted bicyclic isoxazoline with ethyl ester) | Cl | F | (N-methyl, N'-linked, 6-CF3 pyrimidine-2,4-dione) | |
| 364 | CH | (EtOOC substituted bicyclic isoxazoline with ethyl ester) | Cl | F | (N-methyl, N'-linked, 6-CF3 pyrimidine-2,4-dione) | |
| 365 | CH | (EtOOC-CH2-O-CH2 substituted bicyclic isoxazoline with ethyl ester) | Cl | F | (N-methyl, N'-linked, 6-CF3 pyrimidine-2,4-dione) | |
| 366 | CH | (Ph substituted bicyclic isoxazoline with methyl ester) | Cl | F | (N-methyl, N'-linked, 6-CF3 pyrimidine-2,4-dione) | |

TABLE 1-continued

Structures and ¹H NMR data of compounds

| No. | M | Het group | Y | Z | Q | ¹H NMR |
|---|---|---|---|---|---|---|
| 367 | CH | 5-methylthiophene-substituted cyclopentane-fused isoxazoline with methyl ester | Cl | F | 3-methyl-6-(trifluoromethyl)-2,4-dioxopyrimidin-1-yl | |
| 368 | CH | benzyl-substituted cyclopentane-fused isoxazoline with methyl ester | Cl | F | 3-methyl-6-(trifluoromethyl)-2,4-dioxopyrimidin-1-yl | |
| 369 | CH | cyclobutane-fused isoxazoline with methyl ester | Cl | F | 3-methyl-6-(trifluoromethyl)-2,4-dioxopyrimidin-1-yl | |
| 370 | CH | cyclohexane-fused isoxazoline with methyl ester | Cl | F | 3-methyl-6-(trifluoromethyl)-2,4-dioxopyrimidin-1-yl | 1H NMR (500 MHz, DMSO) δ 7.91 (d, J = 8.5 Hz, 1H), 7.52 (d, J = 8.5 Hz, 1H), 6.62 (s, 1H), 3.44 (s, 3H), 3.34 (s, 3H), 2.38-1.90 (m, 3H), 1.73-1.28 (m, 6H). |
| 371 | CH | 4-oxocyclopentane-fused isoxazoline with methyl ester | Cl | F | 3-methyl-6-(trifluoromethyl)-2,4-dioxopyrimidin-1-yl | |

TABLE 1-continued
Structures and ¹H NMR data of compounds
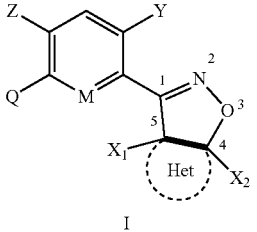
| No. | M | | Y | Z | Q | ¹H NMR |
|---|---|---|---|---|---|---|
| 372 | CH | 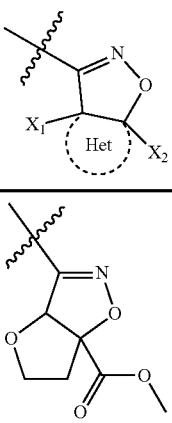 | Cl | F | 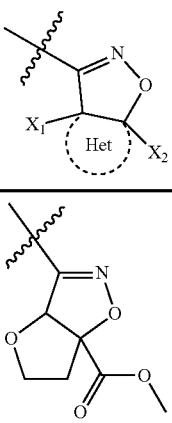 | 1H NMR (500 MHz, Chloroform-d) δ 7.48 (d, J = 7.5 Hz, 1H), 7.40 (d, J = 9.0 Hz, 1H), 6.36 (s, 1H), 6.33 (s, 1H), 4.26-4.23 (m, 1H), 3.92-3.86 (m, 1H), 3.79 (s, 3H), 3.56 (s, 3H), 2.74-2.67 (m, 1H), 2.36-2.33 (m, 1H). |
| 373 | CH | 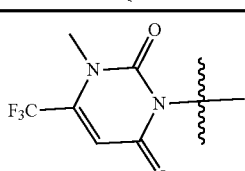 | Cl | F | 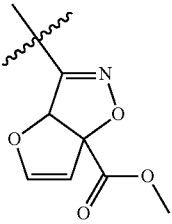 | |
| 374 | CH | 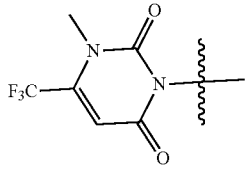 | Cl | F | 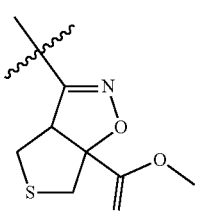 | ¹H NMR (500 MHz, DMSO-d₆) δ 7.94 (d, J = 9.5 Hz, 1H), 7.85 (d, J = 8.0 Hz, 1H), 6.64 (s, 1H), 4.94-4.96 (m, 1H), 3.80 (s, 3H), 3.43-3.41 (m, 5H), 3.34-3.33 (m, 1H), 3.27-3.23 (m, 1H). |
| 375 | CH | 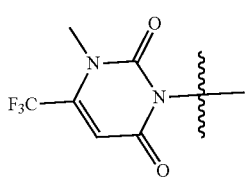 | Cl | F | 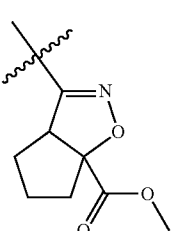 | |
| 376 | CH | 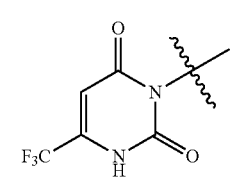 [SMILES: *n1c(=O)cc(C(F)(F)F)[nH]c1=O] | Cl | F | 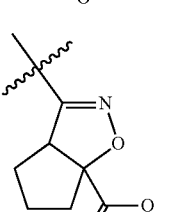 | |

TABLE 1-continued

Structures and ¹H NMR data of compounds

| No. | M | | Y | Z | Q | ¹H NMR |
|---|---|---|---|---|---|---|
| 377 | CH | | Cl | F | | |
| 378 | CH | | Cl | F | | |
| 379 | CH | | Cl | F | | |
| 380 | CH | | Cl | F | | |
| 381 | CH | | Cl | F | | |

TABLE 1-continued

Structures and ¹H NMR data of compounds

| No. | M | [Het structure] | Y | Z | Q | ¹H NMR |
|-----|---|---|---|---|---|--------|
| 382 | CH | cyclopentane-fused isoxazoline with methyl ester | Cl | F | 1-methyl-3-(attachment)-6-trifluoromethyl-5-chloro-pyrimidine-2,4-dione | |
| 383 | CH | cyclopentane-fused isoxazoline with ethyl ester and F | Cl | F | 1,3-dimethyl-2-thioxo-1,3,5-triazinane-4,6-dione (attached at N5) | |
| 384 | CH | cyclopentane-fused isoxazoline with ethyl ester and OH | Cl | F | 1,3-dimethyl-2-thioxo-1,3,5-triazinane-4,6-dione (attached at N5) | |
| 385 | CH | cyclopentane-fused isoxazoline with ethyl ester and =O | Cl | F | 1,3-dimethyl-2-thioxo-1,3,5-triazinane-4,6-dione (attached at N5) | |
| 386 | CH | tetrahydrofuran-fused isoxazoline with methyl ester | Cl | F | 1,3-dimethyl-2-thioxo-1,3,5-triazinane-4,6-dione (attached at N5) | |

TABLE 1-continued

Structures and $^1$H NMR data of compounds

| No. | M | (Het structure) | Y | Z | Q | $^1$H NMR |
|---|---|---|---|---|---|---|
| 387 | CH | furanone-fused isoxazoline with COOEt | Cl | F | dimethyl-thioxo-triazinedione | |
| 388 | CH | sulfone-fused isoxazoline with COOEt | Cl | F | dimethyl-thioxo-triazinedione | |
| 389 | CH | cyclopentane-fused isoxazoline with COOEt | Cl | F | dimethyl-thioxo-triazinedione | |
| 390 | CH | cyclopentane-fused isoxazoline with COOEt | Cl | F | dimethyl-thioxo-triazinedione | |
| 391 | CH | cyclohexane-fused isoxazoline with COOH | Cl | F | dimethyl-thioxo-triazinedione | |

TABLE 1-continued
Structures and $^1$H NMR data of compounds
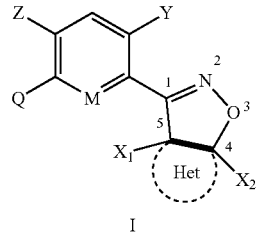
I
| No. | M | 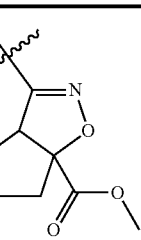 | Y | Z | Q | $^1$H NMR |
|-----|---|---|---|---|---|---|
| 392 | CH | 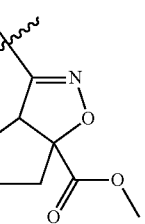 | Cl | F | 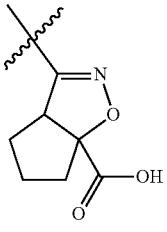 [SMILES: *C1=NOC2(C(=O)O)CCCC12] | |
| 393 | CH | | Cl | F | | |
| 394 | CH | | Cl | F | | |
| 395 | CH | | Cl | F | | 1H NMR (500 MHz, DMSO-d6) δ 7.95-7.85 (m, 2H), 4.46-4.42 (m, 1H), 4.15 (s, 3H), 3.77 (s, 3H), 3.64 (s, 3H), 2.22-2.12 (m, 2H), 1.98-1.93 (m, 1H), 2.00-1.89 (m, 1H), 1.68-1.62 (m, 1H), 1.53-1.44 (m, 1H). |
| 396 | CH | | Br | F | | |

TABLE 1-continued
Structures and ¹H NMR data of compounds
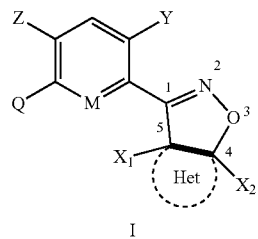
I
| No. | M | 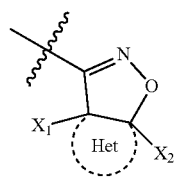 | Y | Z | Q | ¹H NMR |
|---|---|---|---|---|---|---|
| 397 | CH | 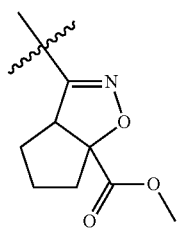 [SMILES: *C1=NOC2(C(=O)OC)CCCC12] | CF3 | F | 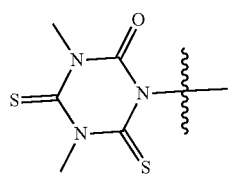 | |
| 398 | CH | 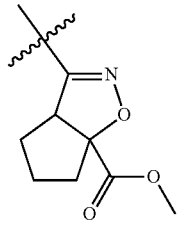 [SMILES: *C1=NOC2(C(=O)OC)CCCC12] | CN | F | 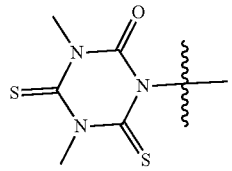 | |
| 399 | CH | 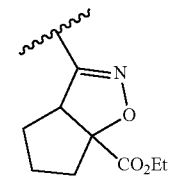 [SMILES: *C1=NOC2(C(=O)OCC)CCCC12] | Cl | F | 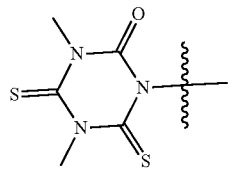 | |
| 400 | CH | 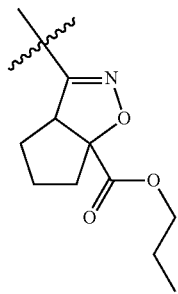 [SMILES: *C1=NOC2(C(=O)OCCC)CCCC12] | Cl | F | 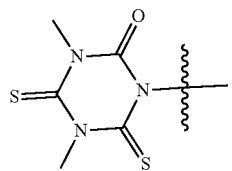 | |

TABLE 1-continued
Structures and ¹H NMR data of compounds
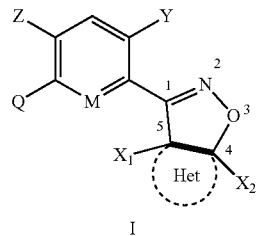
I
| No. | M | 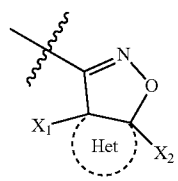 | Y | Z | Q | ¹H NMR |
|---|---|---|---|---|---|---|
| 401 | CH | 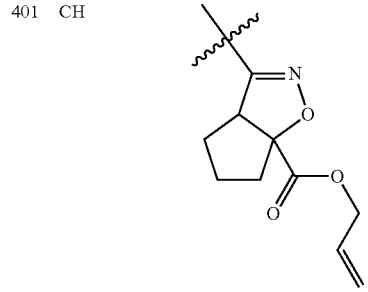 | Cl | F | 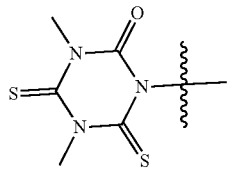 | |
| 402 | CH | | Cl | F | 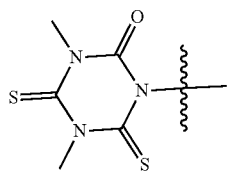 | |
| 403 | CH | | Cl | F | 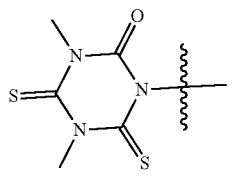 | |

TABLE 1-continued

Structures and ¹H NMR data of compounds

| No. | M | (structure) | Y | Z | Q | ¹H NMR |
|---|---|---|---|---|---|---|
| 404 | CH | | Cl | F | | |
| 405 | CH | | Cl | F | | |
| 406 | CH | | Cl | F | | |
| 407 | CH | | Cl | F | | |

TABLE 1-continued

Structures and ¹H NMR data of compounds

| No. | M | | Y | Z | Q | ¹H NMR |
|---|---|---|---|---|---|---|
| 408 | CH | (isoxazoline with HO and cyclopentane fused, methyl ester) | Cl | F | (1,3,5-triazinane-2-one-4,6-dithione, N,N-dimethyl) | |
| 409 | CH | (isoxazoline with MeO and cyclopentane fused, methyl ester) | Cl | F | (1,3,5-triazinane-2-one-4,6-dithione, N,N-dimethyl) | |
| 410 | CH | (isoxazoline with H₂N and cyclopentane fused, methyl ester) | Cl | F | (1,3,5-triazinane-2-one-4,6-dithione, N,N-dimethyl) | |
| 411 | CH | (isoxazoline with cyclobutane fused, methyl ester) | Cl | F | (1,3,5-triazinane-2-one-4,6-dithione, N,N-dimethyl) | |
| 412 | CH | (isoxazoline with cyclohexane fused, methyl ester) | Cl | F | (1,3,5-triazinane-2-one-4,6-dithione, N,N-dimethyl) | |

TABLE 1-continued

Structures and ¹H NMR data of compounds

| No. | M | [Het group] | Y | Z | Q | ¹H NMR |
|-----|---|---|---|---|---|---|
| 413 | CH | 4-oxo-hexahydrocyclopenta[c]isoxazole-6a-carboxylic acid methyl ester | Cl | F | 1,3-dimethyl-4,6-dithioxo-1,3,5-triazinan-2-one (N-linked) | |
| 414 | CH | hexahydrofuro[3,4-c]isoxazole-6a-carboxylic acid methyl ester | Cl | F | 1,3-dimethyl-4,6-dithioxo-1,3,5-triazinan-2-one (N-linked) | |
| 415 | CH | 3a,6a-dihydrofuro[3,4-c]isoxazole-6a-carboxylic acid methyl ester | Cl | F | 1,3-dimethyl-4,6-dithioxo-1,3,5-triazinan-2-one (N-linked) | |
| 416 | CH | hexahydrothieno[3,4-c]isoxazole-6a-carboxylic acid methyl ester | Cl | F | 1,3-dimethyl-4,6-dithioxo-1,3,5-triazinan-2-one (N-linked) | |
| 417 | N | hexahydrocyclopenta[c]isoxazole-6a-carboxylic acid methyl ester | Br | F | 1,3-dimethyl-4,6-dithioxo-1,3,5-triazinan-2-one (N-linked) | |

TABLE 1-continued

Structures and ¹H NMR data of compounds

| No. | M | | Y | Z | Q | ¹H NMR |
|---|---|---|---|---|---|---|
| 418 | N | | CF₃ | F | | |
| 419 | N | | CN | F | | |
| 420 | N | | Cl | F | | |
| 421 | N | | Br | F | | |
| 422 | N | | CF₃ | F | | |

TABLE 1-continued

Structures and ¹H NMR data of compounds

| No. | M | (Het group) | Y | Z | Q | ¹H NMR |
|---|---|---|---|---|---|---|
| 423 | N | cyclopentane-fused isoxazoline with methyl ester | CN | F | 1,3-dimethyl-2,4-dithioxo-1,3,5-triazinan-5-yl | |
| 424 | CH | cyclopentane-fused isoxazoline with 2-chloroethyl ester | Cl | F | 3-methyl-6-(trifluoromethyl)-2,4-dioxo-3,4-dihydropyrimidin-1(2H)-yl | ¹H NMR (500 MHz, Chloroform-d) δ 7.92 (d, J = 8.0 Hz, 1H), 7.88 (d, J = 7.5 Hz, 1H), 6.61 (s, 1H), 4.36-4.32 (m, 2H), 4.04-3.92 (m, 2H), 4.04 (s, 3H), 2.84-2.78 (m, 1H), 2.14-2.02 (m, 2H), 1.93-1.78 (m, 2H), 1.58-1.42 (m, 2H). |
| 425 | CH | cyclopentane-fused isoxazoline with ethoxymethyl ester | Cl | F | 3-methyl-6-(trifluoromethyl)-2,4-dioxo-3,4-dihydropyrimidin-1(2H)-yl | 1H NMR (500 MHz, DMSO-d6) δ 7.92 (d, J = 9.5 Hz, 1H), 7.85 (d, J = 7.5 Hz, 1H), 6.64 (s, 1H), 5.43-5.36 (m, 2H), 4.49 (t, J = 9.0 Hz, 1H), 3.69 (q, J = 7.0 Hz, 2H), 3.44 (s, 3H), 2.23-2.14 (m, 2H), 2.00-1.82 (m, 2H), 1.73-1.45 (m, 2H), 1.19-1.14 (m, 3H). |
| 426 | CH | cyclopentane-fused isoxazoline with phenyl ester | Cl | F | 3-methyl-6-(trifluoromethyl)-2,4-dioxo-3,4-dihydropyrimidin-1(2H)-yl | 1H NMR (500 MHz, DMSO) δ 7.97-7.89 (m, 2H), 7.50-7.46 (m, 2H), 7.35-7.25 (m, 3H), 6.65 (d, J = 4.5 Hz, 1H), 4.71 (d, J = 9.0 Hz, 1H), 3.45 (s, 3H), 2.38-2.34 (m, 2H), 2.04-1.58 (m, 4H). |

TABLE 1-continued

Structures and ¹H NMR data of compounds

| No. | M | | Y | Z | Q | ¹H NMR |
|---|---|---|---|---|---|---|
| 427 | CH | | Cl | F | | ¹H NMR (500 MHz, DMSO) δ 7.91 (d, J = 9.5 Hz, 1H), 7.85 (d, J = 7.5 Hz, 1H), 6.63 (d, J = 4.0 Hz, 1H), 4.78-4.72 (m, 1H), 3.78-2.68 (m, 1H), 3.68-3.60 (m, 1H), 3.44 (s, 3H), 3.42-3.37 (m, 2H), 2.51-2.47 (m, 1H), 2.40-2.33 (m, 1H), 2.10-2.00 (m, 1H), 1.98-1.86 (m, 2H), 1.88-1.76 (m, 3H), 1.70-1.60 (m, 1H), 1.58-1.43 (m, 1H). |
| 428 | CH | | Cl | F | | |
| 429 | CH | | Cl | F | | |
| 430 | CH | | Cl | F | | |

TABLE 1-continued

Structures and $^1$H NMR data of compounds

| No. | M | [Het group] | Y | Z | Q | $^1$H NMR |
|---|---|---|---|---|---|---|
| 431 | CH | (isoxazoline fused with cyclic sulfate, COOEt) | Cl | F | (N-methyl-6-CF$_3$-pyrimidine-2,4-dione) | |
| 432 | CH | (isoxazoline fused with cyclopentene, COOEt) | Cl | F | (N-methyl-6-CF$_3$-pyrimidine-2,4-dione) | |
| 433 | CH | (isoxazoline fused with cyclopentene, COOEt) | Cl | F | (N-methyl-6-CF$_3$-pyrimidine-2,4-dione) | 1H NMR (500 MHz, DMSO) δ 7.93 (d, J = 9.5 Hz, 1H), 7.86 (d, J = 7.5 Hz, 1H), 6.63 (s, 1H), 6.31 (d, J = 5.0 Hz, 1H), 5.84 (d, J = 5.0 Hz, 1H), 4.80-4.75 (m, 1H), 4.25 (q, J = 7.0 Hz, 2H), 3.44 (s, 3H), 2.92-2.88 (m, 1H), 2.36-2.30 (m, 1H), 1.27 (t, J = 7.0 Hz, 3H). |
| 434 | CH | (isoxazoline fused with cyclohexane, COOH) | Cl | F | (N-methyl-6-CF$_3$-pyrimidine-2,4-dione) | 1H NMR (500 MHz, DMSO) δ 12.63 (s, 1H), 7.91 (d, J = 8.5 Hz, 1H), 7.52 (d, J = 8.5 Hz, 1H), 6.62 (s, 1H), 3.43 (m, 3H), 2.37-1.91 (m, 3H), 1.74-1.26 (m, 6H). |
| 435 | CH | (isoxazoline fused with cycloheptane, COOMe) | Cl | F | (N-methyl-6-CF$_3$-pyrimidine-2,4-dione) | $^1$H NMR (500 MHz, DMSO-d$_6$) δ 7.28 (d, J = 8.5 Hz, 1H), 7.22 (d, J = 7.5 Hz, 1H), 6.26 (s, 1H), 3.44 (s, 3H), 3.34 (s, 3H), 3.28-3.18 (m, 1H), 2.38-1.90 (m, 4H), 1.73-1.28 (m, 6H). |

TABLE 1-continued

Structures and ¹H NMR data of compounds

| No. | M | Het structure | Y | Z | Q | ¹H NMR |
|---|---|---|---|---|---|---|
| 436 | CH | cyclooctane-fused isoxazoline with CO₂Me | Cl | F | N-methyl-6-(trifluoromethyl)pyrimidine-2,4-dione | ¹H NMR (500 MHz, DMSO-d₆) δ 7.68 (d, J = 8.5 Hz, 1H), 7.53 (d, J = 7.5 Hz, 1H), 6.26 (s, 1H), 3.44 (s, 3H), 3.34 (s, 3H), 3.28-3.18 (m, 1H), 2.38-1.90 (m, 4H), 1.73-1.28 (m, 8H). |
| 437 | CH | tetrahydropyran-fused isoxazoline with CO₂Me | Cl | F | N-methyl-6-(trifluoromethyl)pyrimidine-2,4-dione | |
| 438 | CH | tetrahydropyran-fused isoxazoline with CO₂Me | Cl | F | N-methyl-6-(trifluoromethyl)pyrimidine-2,4-dione | 1H NMR (500 MHz, Chloroform-d) δ 7.92 (d, J = 8.0 Hz, 1H), 7.84 (d, J = 7.5 Hz, 1H), 6.64 (s, 1H), 4.30 (s, 2H), 4.08 (s, 3H), 3.94 (s, 3H), 3.69-3.58 (m, 2H), 2.84 (m, 1H), 2.47-2.41 (m, 2H). |
| 439 | CH | tetrahydropyran-fused isoxazoline with CO₂Me | Cl | F | N-methyl-6-(trifluoromethyl)pyrimidine-2,4-dione | |
| 440 | CH | cyclopentane-fused isoxazoline with CO₂Me | Cl | Cl | N-methyl-6-(trifluoromethyl)pyrimidine-2,4-dione | ¹H NMR (500 MHz, DMSO-d₆) δ 8.06 (s, 1H), 7.87 (s, 1H), 8.64 (d, J = 3.5 Hz, 1H), 4.46 (d, J = 9.0 Hz, 1H), 3.75 (s, 3H), 3.43 (s, 3H), 2.19-2.10 (m, 2H), 1.96-1.89 (m, 1H), 1.86-1.81 (m, 1H), 1.67-1.63 (m, 1H), 1.53-1.44 (m, 1H). |

TABLE 1-continued

Structures and ¹H NMR data of compounds

| No. | M | [Het group] | Y | Z | Q | ¹H NMR |
|---|---|---|---|---|---|---|
| 441 | CH | F-substituted cyclopentane-fused isoxazoline with CO₂Me | Cl | F | N-methyl-6-(trifluoromethyl)pyrimidine-2,4-dione | 1H NMR (500 MHz, DMSO-d6) δ 7.93-7.86 (m, 2H), 6.62 (d, J = 5.0 Hz, 1H), 5.50-5.31 (m, 1H), 3.81 (s, 3H), 3.44 (s, 3H), 2.27-1.97 (m, 3H), 1.45-1.04 (m, 2H). |
| 442 | CH | Cl-substituted cyclopentane-fused isoxazoline with CO₂Me | Cl | F | N-methyl-6-(trifluoromethyl)pyrimidine-2,4-dione | |
| 443 | CH | methyl-substituted cyclopentane-fused isoxazoline with CO₂Me | Cl | F | N-methyl-6-(trifluoromethyl)pyrimidine-2,4-dione | ¹H NMR (500 MHz, DMSO-d₆) δ 7.92 (dd, J = 9.5 Hz, 1H), 7.86 (d, J = 7.5 Hz, 1H), 6.64 (d, J = 5.0 Hz, 1H), 4.09-4.08 (m, 1H), 3.78 (s, 3H), 3.44 (s, 3H), 2.17-1.97 (m, 3H), 1.79-1.77 (m, 1H), 1.56-1.55 (m, 1H), 1.00 (d, J = 7.0 Hz, 3H). |
| 444 | CH | HO-substituted cyclopentane-fused isoxazoline with CO₂Me | Cl | F | N-methyl-6-(trifluoromethyl)pyrimidine-2,4-dione | ¹H NMR (500 MHz, DMSO-d₆) δ 7.95 (d, J = 9.5 Hz, 1H), 7.84 (d, J = 7.5 Hz, 1H), 6.65 (d, J = 5.0 Hz, 1H), 5.30-5.29 (m, 1H), 4.08-4.01 (m, 2H), 3.82 (s, 3H), 3.44 (s, 3H), 2.21-2.17 (m, 2H), 1.80-1.79 (m, 1H), 1.68-1.63 (m, 1H). |
| 445 | CH | MeO-substituted cyclopentane-fused isoxazoline with CO₂Me | Cl | F | N-methyl-6-(trifluoromethyl)pyrimidine-2,4-dione | |

TABLE 1-continued

Structures and $^1$H NMR data of compounds

| No. | M | (Het structure) | Y | Z | Q | $^1$H NMR |
|---|---|---|---|---|---|---|
| 446 | CH | S-substituted cyclopentane-fused isoxazoline with SMe and CO₂Me | Cl | F | N-methyl-6-(trifluoromethyl)uracil-N-yl | |
| 447 | CH | cyclopentane-fused isoxazoline with CN and CO₂Me | Cl | F | N-methyl-6-(trifluoromethyl)uracil-N-yl | |
| 448 | CH | cyclopentane-fused isoxazoline with NH₂ and CO₂Me | Cl | F | N-methyl-6-(trifluoromethyl)uracil-N-yl | |
| 449 | CH | cyclopentane-fused isoxazoline with NMe₂ and CO₂Me | Cl | F | N-methyl-6-(trifluoromethyl)uracil-N-yl | |
| 450 | CH | cyclopentane-fused isoxazoline with =N-OMe and CO₂Me | Cl | F | N-methyl-6-(trifluoromethyl)uracil-N-yl | |

TABLE 1-continued
Structures and $^1$H NMR data of compounds
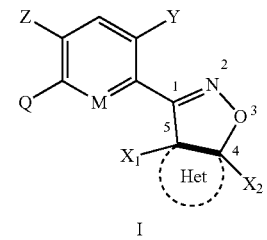
I
| No. | M | 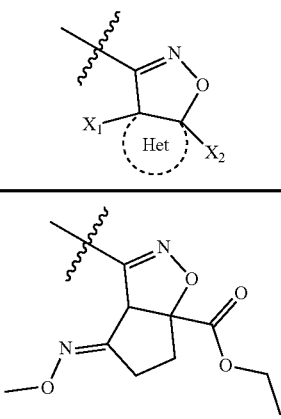 | Y | Z | Q | $^1$H NMR |
|---|---|---|---|---|---|---|
| 451 | CH | 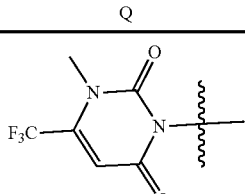 | Cl | F | 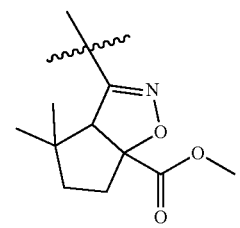 | $^1$H NMR (500 MHz, DMSO) δ 7.92 (d, J = 9.5 Hz, 1H), 7.87 (d, J = 6.0 Hz, 1H), 6.63 (d, J = 4.0 Hz, 1H), 4.62 (s, 1H), 4.25-4.15 (m, 2H), 3.76 (s, 3H), 3.42 (s, 3H), 2.70-2.60 (m, 1H), 2.43-2.34 (m, 1H), 2.20-2.15 (m, 1H), 1.84 (s, 1H), 1.21 (t, J = 7.1 Hz, 3H). |
| 452 | CH | 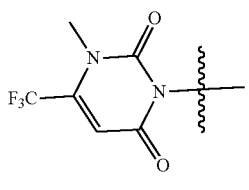 | Cl | F | 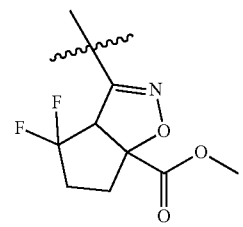 [SMILES: *C1=NOC2(C(=O)OC)CCC(F)C12] | |
| 453 | CH | 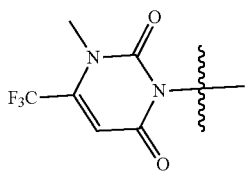 | Cl | F | 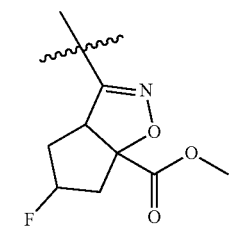 | |
| 454 | CH | 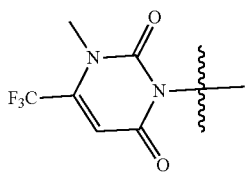 | Cl | F | 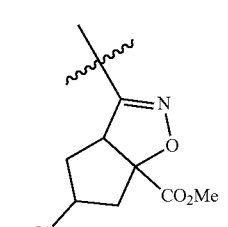 | |
| 455 | CH | 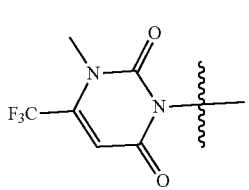 | Cl | F | | |

TABLE 1-continued

Structures and ¹H NMR data of compounds

| No. | M | [Het structure] | Y | Z | Q | ¹H NMR |
|---|---|---|---|---|---|---|
| 456 | CH | cyclopentane-fused isoxazoline with methyl and CO₂Me | Cl | F | N-methyl-6-(trifluoromethyl)pyrimidine-2,4-dione | ¹H NMR (500 MHz, DMSO-d₆) δ 7.91 (d, J = 8.0 Hz, 1H), 7.87 (d, J = 7.5 Hz, 1H), 6.68 (s, 1H), 4.06 (s, 3H), 3.77 (s, 3H), 3.33-3.27 (m, 1H), 2.32-2.22 (m, 1H), 1.71-1.54 (m, 3H), 1.13-0.92 (m, 4H). |
| 457 | CH | cyclopentane-fused isoxazoline with CF₃ and CO₂Me | Cl | F | N-methyl-6-(trifluoromethyl)pyrimidine-2,4-dione | |
| 458 | CH | cyclopentane-fused isoxazoline with HO and CO₂Me | Cl | F | N-methyl-6-(trifluoromethyl)pyrimidine-2,4-dione | |
| 459 | CH | cyclopentane-fused isoxazoline with OMe and CO₂Me | Cl | F | N-methyl-6-(trifluoromethyl)pyrimidine-2,4-dione | |

TABLE 1-continued

Structures and ¹H NMR data of compounds

| No. | M | (structure) | Y | Z | Q | ¹H NMR |
|---|---|---|---|---|---|---|
| 460 | CH | 3-isoxazoline fused cyclopentane with SMe and CO₂Me | Cl | F | N-methyl-6-(trifluoromethyl)pyrimidine-2,4-dione | |
| 461 | CH | 3-isoxazoline fused cyclopentane with NC and CO₂Me | Cl | F | N-methyl-6-(trifluoromethyl)pyrimidine-2,4-dione | |
| 462 | CH | 3-isoxazoline fused cyclopentane with H₂N and CO₂Me | Cl | F | N-methyl-6-(trifluoromethyl)pyrimidine-2,4-dione | |
| 463 | CH | 3-isoxazoline fused cyclopentane with NMe₂ and CO₂Me | Cl | F | N-methyl-6-(trifluoromethyl)pyrimidine-2,4-dione | |

TABLE 1-continued

Structures and ¹H NMR data of compounds

| No. | M | [Het group] | Y | Z | Q | ¹H NMR |
|---|---|---|---|---|---|---|
| 464 | CH | bicyclic isoxazoline with cyclopentane fused, bearing CO₂Me and CH₂CO₂Me substituents | Cl | F | N-methyl-6-(trifluoromethyl)pyrimidine-2,4(1H,3H)-dione linked via N | 1H NMR (500 MHz, DMSO) δ 7.90 (d, J = 8.0 Hz, 1H), 7.53 (d, J = 8.0 Hz, 1H), 6.63 (s, 1H), 3.63 (m, 3H), 3.39 (s, 3H), 3.34 (s, 3H), 2.45-2.12 (m, 5H), 1.99-1.93 (m, 1H). |
| 465 | CH | bicyclic isoxazoline with cyclopentane fused, bearing CO₂Me and S(O)Me substituents | Cl | F | N-methyl-6-(trifluoromethyl)pyrimidine-2,4(1H,3H)-dione linked via N | |
| 466 | CH | bicyclic isoxazoline with cyclopentane fused, bearing CO₂Me and S(O)₂Me substituents | Cl | F | N-methyl-6-(trifluoromethyl)pyrimidine-2,4(1H,3H)-dione linked via N | |
| 467 | CH | bicyclic isoxazoline with cyclopentanone fused, bearing CO₂Me substituent | Cl | F | N-methyl-6-(trifluoromethyl)pyrimidine-2,4(1H,3H)-dione linked via N | |

TABLE 1-continued

Structures and $^1$H NMR data of compounds

| No. | M | [Het substituent] | Y | Z | Q | $^1$H NMR |
|---|---|---|---|---|---|---|
| 468 | CH | 3-oxa-2-aza bicyclic with =N-OMe and CO$_2$Me | Cl | F | 1-methyl-6-(CF$_3$)-pyrimidine-2,4-dione | |
| 469 | CH | gem-dimethyl cyclopentane-fused isoxazoline with CO$_2$Me | Cl | F | 1-methyl-6-(CF$_3$)-pyrimidine-2,4-dione | |
| 470 | CH | gem-difluoro cyclopentane-fused isoxazoline with CO$_2$Me | Cl | F | 1-methyl-6-(CF$_3$)-pyrimidine-2,4-dione | |
| 471 | CH | mono-fluoro cyclopentane-fused isoxazoline with CO$_2$Me | Cl | F | 1-methyl-6-(CF$_3$)-pyrimidine-2,4-dione | |

TABLE 1-continued

Structures and $^1$H NMR data of compounds

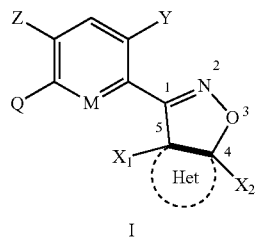

I

| No. | M | 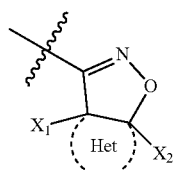 | Y | Z | Q | $^1$H NMR |
|---|---|---|---|---|---|---|
| 472 | CH | ethyl ester with F on cyclopentane fused isoxazoline | Cl | F | N-methyl-6-(trifluoromethyl)pyrimidine-2,4-dione | 1H NMR (500 MHz, DMSO) δ 7.95 (d, J = 9.5 Hz, 1H), 7.93 (d, J = 7.5 Hz, 1H), 6.65 (s, 1H), 4.35-4.28 (m, 2H), 4.16-4.12 (m, 1H), 3.45 (s, 3H), 3.29-3.15 (m, 1H), 2.26-2.14 (m, 2H), 1.82-1.70 (m, 2H), 1.28 (t, J = 7.0 Hz, 3H). |
| 473 | CH | CO$_2$Me with Cl on cyclopentane fused isoxazoline | Cl | F | N-methyl-6-(trifluoromethyl)pyrimidine-2,4-dione | |
| 474 | CH | ethyl ester with Br on cyclopentane fused isoxazoline | Cl | F | N-methyl-6-(trifluoromethyl)pyrimidine-2,4-dione | 1H NMR (500 MHz, DMSO-d6) δ 7.96-7.92 (m, 2H), 6.65 (s, 1H), 4.87-4.84 (m, 1H), 4.73-4.70 (m, 1H), 4.29 (q, J = 7.0 Hz, 2H), 3.45 (s, 3H), 2.47-2.28 (m, 1H), 2.23-2.09 (m, 2H), 1.75-1.69 (m, 1H), 1.29 (t, J = 7.0 Hz, 3H). |
| 475 | CH | 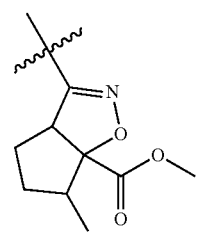 [SMILES: *C1=NOC2(C(=O)OC)C(C)CCC12] | Cl | F | 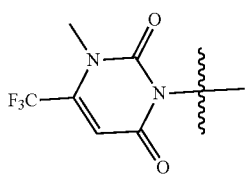 | |

TABLE 1-continued

Structures and ¹H NMR data of compounds

| No. | M | [Het substructure] | Y | Z | Q | ¹H NMR |
|---|---|---|---|---|---|---|
| 476 | CH | cyclopentane-fused isoxazoline with CO₂Et and methyl | Cl | F | 1-methyl-6-(CF₃)-pyrimidine-2,4-dione | ¹H NMR (500 MHz, DMSO-d₆) δ 7.91 (d, J = 9.5 Hz, 1H), 7.88-7.82 (m, 1H), 6.63 (d, J = 5.0 Hz, 1H), 4.55-4.44 (m, 1H), 4.31-4.18 (m, 2H), 3.44 (s, 3H), 2.50-2.46 (m, 2H), 1.98-1.76 (m, 1H), 1.61-1.55 (m, 2H), 1.30-1.23 (m, 3H), 1.10-0.94 (m, 3H). |
| 477 | CH | cyclopentane-fused isoxazoline with CO₂Et and ethyl | Cl | F | 1-methyl-6-(CF₃)-pyrimidine-2,4-dione | ¹H NMR (500 MHz, DMSO-d₆) δ 8.05-7.77 (m, 2H), 6.63 (s, 1H), 4.52-4.38 (m, 1H), 4.30-4.16 (m, 2H), 3.44 (s, 3H), 2.44-1.34 (m, 7H), 1.30-1.32 (m, 3H), 0.96-0.88 (m, 3H). |
| 478 | CH | cyclopentane-fused isoxazoline with CO₂Me and CF₃ | Cl | F | 1-methyl-6-(CF₃)-pyrimidine-2,4-dione | |
| 479 | CH | cyclopentane-fused isoxazoline with CO₂Me and OH | Cl | F | 1-methyl-6-(CF₃)-pyrimidine-2,4-dione | |

TABLE 1-continued

Structures and $^1$H NMR data of compounds

| No. | M | Het structure | Y | Z | Q | $^1$H NMR |
|---|---|---|---|---|---|---|
| 480 | CH | (3-ethoxycarbonyl-3-hydroxy cyclopenta-fused isoxazoline) | Cl | F | 1-methyl-6-(trifluoromethyl)-2,4-dioxopyrimidin-3-yl | 1H NMR (500 MHz, DMSO) δ 7.92 (d, J = 9.5 Hz, 1H), 7.87 (d, J = 7.5 Hz, 1H), 6.63 (s, 1H), 5.55 (s, 1H), 4.62 4.53 (m, 1H), 4.25-4.18 (m, 2H), 3.44 (s, 3H), 2.30-2.20 (m, 1H), 1.78-1.63 (m, 2H), 1.61-1.53 (m, 2H), 1.27 (t, J = 7.0 Hz, 3H) |
| 481 | CH | (methoxycarbonyl-methoxy cyclopenta-fused isoxazoline) | Cl | F | 1-methyl-6-(trifluoromethyl)-2,4-dioxopyrimidin-3-yl | |
| 482 | CH | (methoxycarbonyl-methylthio cyclopenta-fused isoxazoline) | Cl | F | 1-methyl-6-(trifluoromethyl)-2,4-dioxopyrimidin-3-yl | |
| 483 | CH | (methoxycarbonyl-methylsulfinyl cyclopenta-fused isoxazoline) | Cl | F | 1-methyl-6-(trifluoromethyl)-2,4-dioxopyrimidin-3-yl | |

TABLE 1-continued
Structures and ¹H NMR data of compounds
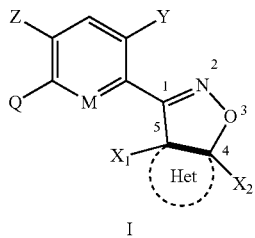
I
| No. | M | 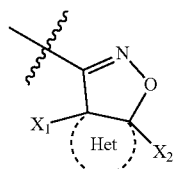 | Y | Z | Q | ¹H NMR |
|---|---|---|---|---|---|---|
| 484 | CH | 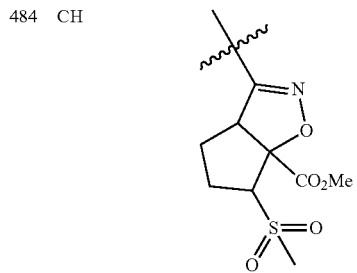 | Cl | F | 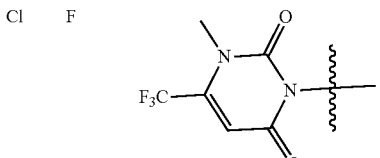 | |
| 485 | CH | 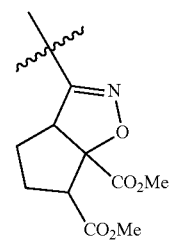 [SMILES: *C1=NOC2(C(=O)OC)C(C(=O)OC)CCC12] | Cl | F | 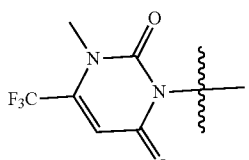 | |
| 486 | CH | 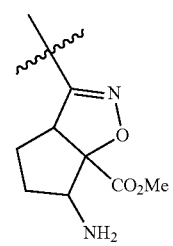 [SMILES: *C1=NOC2(C(=O)OC)C(N)CCC12] | Cl | F | 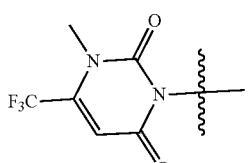 | |
| 487 | CH | 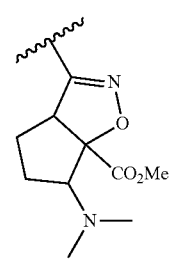 [SMILES: *C1=NOC2(C(=O)OC)C1CCC2N(C)C] | Cl | F | 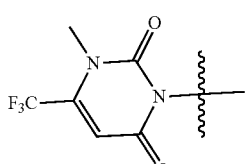 | |

TABLE 1-continued

Structures and ¹H NMR data of compounds

| No. | M | [Het structure] | Y | Z | Q | ¹H NMR |
|---|---|---|---|---|---|---|
| 488 | CH | cyclopentane-fused isoxazoline with CO₂Me and CN substituents | Cl | F | N-methyl-6-(trifluoromethyl)pyrimidine-2,4-dione | |
| 489 | CH | cyclopentane-fused isoxazoline with CO₂Me and ketone | Cl | F | N-methyl-6-(trifluoromethyl)pyrimidine-2,4-dione | |
| 490 | CH | cyclopentane-fused isoxazoline with CO₂Et and ketone | Cl | F | N-methyl-6-(trifluoromethyl)pyrimidine-2,4-dione | 1H NMR (500 MHz, DMSO) δ 7.92 (d, J = 9.5 Hz, 1H), 7.87 (d, J = 7.5 Hz, 1H), 6.63 (s, 1H), 4.97-4.86 (m, 1H), 4.23 (q, J = 7.0 Hz, 2H), 3.43 (s, 3H), 2.70-2.58 (m, 1H), 2.48-2.40 (m, 1H), 2.36-2.30 (m, 1H), 1.96-1.90 (m, 1H), 1.22 (t, J = 7.0 Hz, 3H). |
| 491 | CH | cyclopentane-fused isoxazoline with CO₂Et and N-OH oxime | Cl | F | N-methyl-6-(trifluoromethyl)pyrimidine-2,4-dione | ¹H NMR (500 MHz, DMSO) δ 11.50 (s, 1H), 7.92 (d, J = 9.5 Hz, 1H), 7.89 (d, J = 7.5 Hz, 1H), 6.62 (s, 1H), 4.66 (d, J = 8.5 Hz, 1H), 4.24-4.15 (m, 2H), 3.42 (s, 3H), 2.85-2.78 (m, 1H), 2.30-2.20 (m, 2H), 1.88-1.82 (m, 1H), 1.22 (t, J = 7.0 Hz, 3H). |

TABLE 1-continued

Structures and ¹H NMR data of compounds

| No. | M | Het | Y | Z | Q | ¹H NMR |
|---|---|---|---|---|---|---|
| 492 | CH | (cyclopentane-fused isoxazoline with CO₂Me and =N-OMe) | Cl | F | 1-methyl-6-(trifluoromethyl)-2,4-dioxopyrimidin-3-yl | |
| 493 | CH | (cyclopentane-fused isoxazoline with CO₂Et and =N-OMe) | Cl | F | 1-methyl-6-(trifluoromethyl)-2,4-dioxopyrimidin-3-yl | 1H NMR (500 MHz, DMSO-d6) δ 7.94 (d, J = 9.5 Hz, 1H), 7.91 (d, J = 7.5 Hz, 1H), 6.64 (d, J = 3.0 Hz, 1H), 4.26 (q, J = 7.0 Hz, 2H), 3.86 (s, 3H), 3.44 (s, 3H), 2.86-2.77 (m, 1H), 2.41-2.17 (m, 2H), 1.88 (t, J = 11.5 Hz, 2H), 1.25 (t, J = 7.0 Hz, 3H). |
| 494 | CH | (cyclopentane-fused isoxazoline with CO₂Me and gem-dimethyl) | Cl | F | 1-methyl-6-(trifluoromethyl)-2,4-dioxopyrimidin-3-yl | |
| 495 | CH | (cyclopentane-fused isoxazoline with CO₂Me and gem-difluoro) | Cl | F | 1-methyl-6-(trifluoromethyl)-2,4-dioxopyrimidin-3-yl | |

TABLE 1-continued
Structures and $^1$H NMR data of compounds
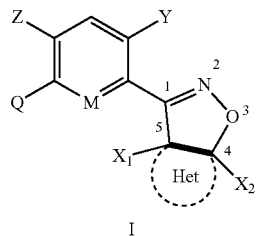
I
| No. | M | | Y | Z | Q | $^1$H NMR |
|---|---|---|---|---|---|---|
| 496 | CH | 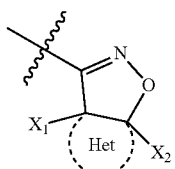 | Cl | F | | |
| 497 | CH | 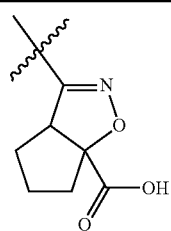 | Cl | F | | 1H NMR (500 MHz, DMSO-d6) δ 8.16 (d, J = 8.0 Hz, 1H), 8.09 (d, J = 9.0 Hz, 1H), 6.99 (s, 1H), 4.49-4.46 (m, 1H), 3.77 (s, 3H), 2.19 (s, 3H), 2.33-2.23 (m, 2H), 1.99-1.88 (m, 2H), 1.77-1.71 (m, 1H), 1.55-1.46 (m, 1H). |
| 498 | CH | 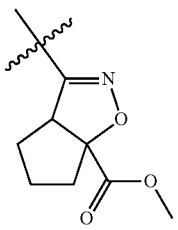 | Cl | F | | 1H NMR (500 MHz, DMSO-d6) δ 7.93-7.82 (m, 2H), 7.13 (s, 1H), 4.46 (t, J = 10.0 Hz, 1H), 3.77 (s, 3H), 3.44 (s, 3H), 2.21-2.14 (m, 2H), 1.98-1.80 (m, 2H), 1.69-1.59 (m, 1H), 1.51-1.47 (m, 1H). |
| 499 | CH | 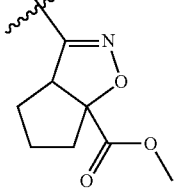 | Br | F | | |
| 500 | CH | 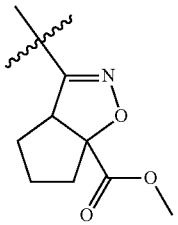 [SMILES: *C1=NOC2(C(=O)OC)CCCC12] | CF3 | F | | |

TABLE 1-continued

Structures and ¹H NMR data of compounds

| No. | M | | Y | Z | Q | ¹H NMR |
|---|---|---|---|---|---|---|
| 501 | CH | (isoxazoline fused cyclopentane with CO₂Me) | CN | F | N-methyl-6-(trifluoromethyl)-4-thioxopyrimidin-2(1H)-one linkage | |
| 502 | CH | (isoxazoline fused cyclopentane with CO₂Me) | Cl | F | N-methyl-6-(trifluoromethyl)-2,4-dithioxopyrimidine linkage | |
| 503 | CH | (isoxazoline fused cyclopentane with CO₂Et) | Cl | F | N-methyl-6-(trifluoromethyl)-4-thioxopyrimidin-2(1H)-one linkage | |
| 504 | CH | (isoxazoline fused cyclopentane with CO₂nPr) | Cl | F | N-methyl-6-(trifluoromethyl)-4-thioxopyrimidin-2(1H)-one linkage | |

TABLE 1-continued
Structures and ¹H NMR data of compounds
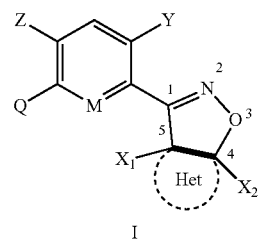
I
| No. | M | 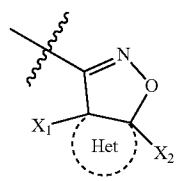 | Y | Z | Q | ¹H NMR |
|---|---|---|---|---|---|---|
| 505 | CH | 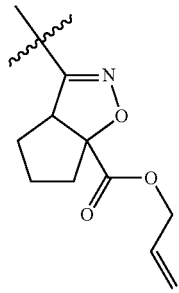 [SMILES: *C1=NOC2(C(=O)OCC=C)CCCC12] | Cl | F | 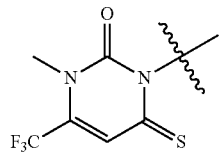 | |
| 506 | CH | 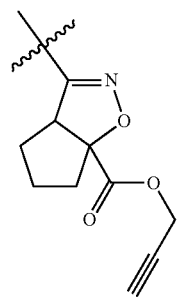 [SMILES: *C1=NOC2(C(=O)OCC#C)CCCC12] | Cl | F | 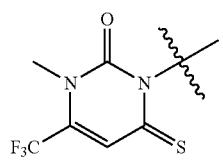 [SMILES: *n1c(=S)cc(C(F)(F)F)n(C)c1=O] | |
| 507 | CH | 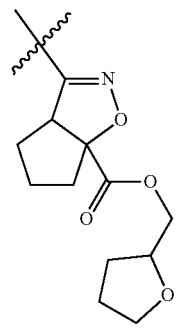 [SMILES: *C1=NOC2(C(=O)OCC3CCCO3)CCCC12] | Cl | F | 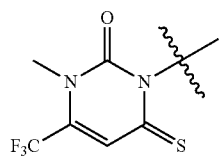 | |

TABLE 1-continued
Structures and $^1$H NMR data of compounds
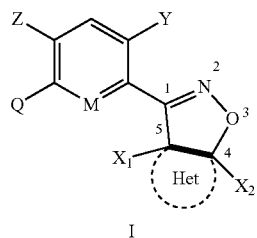
I
| No. | M | 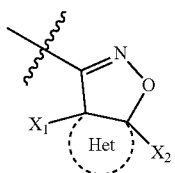 | Y | Z | Q | $^1$H NMR |
|---|---|---|---|---|---|---|
| 508 | CH | 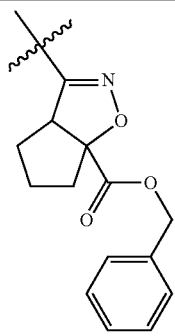 [SMILES: *C1=NOC2(C(=O)OCc3ccccc3)CCCC12] | Cl | F | 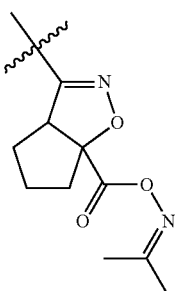 | |
| 509 | CH | 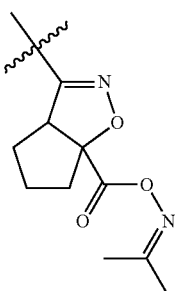 | Cl | F | 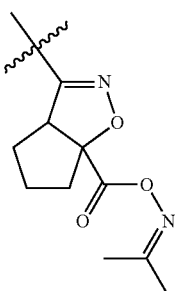 | |
| 510 | CH | 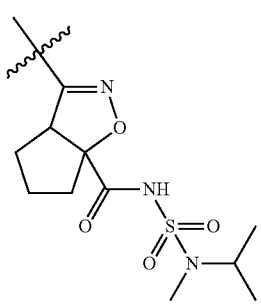 [SMILES: *C1=NOC2(C(=O)NS(=O)(=O)N(C)C(C)C)CCCC12] | Cl | F | 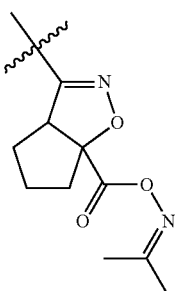 | |
| 511 | CH | 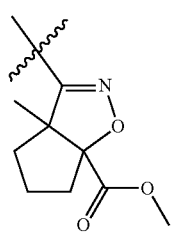 [SMILES: *C1=NOC2(C(=O)OC)CCCC12C] | Cl | F | 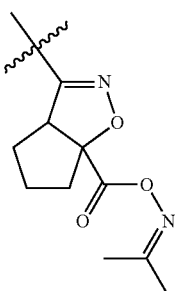 | |

TABLE 1-continued

Structures and ¹H NMR data of compounds

| No. | M | (structure) | Y | Z | Q | ¹H NMR |
|---|---|---|---|---|---|---|
| 512 | CH | (cyclopentane-fused isoxazoline with HO and CO₂Me) | Cl | F | (N-methyl-N'-CF₃ thiouracil) | |
| 513 | CH | (cyclopentane-fused isoxazoline with OMe and CO₂Me) | Cl | F | (N-methyl-N'-CF₃ thiouracil) | |
| 514 | CH | (cyclopentane-fused isoxazoline with H₂N and CO₂Me) | Cl | F | (N-methyl-N'-CF₃ thiouracil) | |
| 515 | CH | (cyclobutane-fused isoxazoline with CO₂Me) | Cl | F | (N-methyl-N'-CF₃ thiouracil) | |
| 516 | CH | (cyclohexane-fused isoxazoline with CO₂Me) | Cl | F | (N-methyl-N'-CF₃ thiouracil) | |

TABLE 1-continued

Structures and ¹H NMR data of compounds

| No. | M | | Y | Z | Q | ¹H NMR |
|---|---|---|---|---|---|---|
| 517 | CH | | Cl | F | | |
| 518 | CH | | Cl | F | | |
| 519 | CH | | Cl | F | | |
| 520 | CH | | Cl | F | | |
| 521 | N | | Cl | F | | ¹H NMR (500 MHz, DMSO) δ 8.62 (d, J = 8.5 Hz, 1H), 6.66 (s, 1H), 4.39 (d, J = 8.5 Hz, 1H), 3.74 (s, 3H), 3.45 (s, 3H), 2.25-2.12 (m, 2H), 1.99-1.89 (m, 1H), 1.88-1.80 (m, 2H), 1.51-1.46 (m, 1H). |

TABLE 1-continued

Structures and ¹H NMR data of compounds

| No. | M | | Y | Z | Q | ¹H NMR |
|---|---|---|---|---|---|---|
| 522 | N | | Br | F | | |
| 523 | N | | CF₃ | F | | |
| 524 | N | | CN | F | | |
| 525 | N | | Cl | F | | |
| 526 | N | | Br | F | | |

TABLE 1-continued
Structures and $^1$H NMR data of compounds
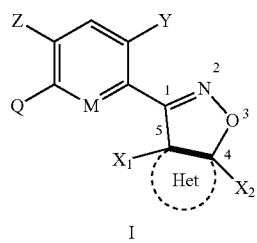
I
| No. | M | 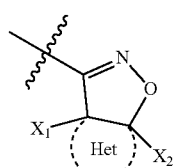 | Y | Z | Q | $^1$H NMR |
|---|---|---|---|---|---|---|
| 527 | N | 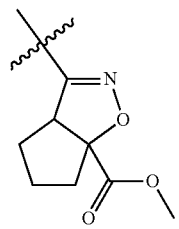 [SMILES: *C1=NOC2(C(=O)OC)CCCC12] | CF$_3$ | F | | |
| 528 | N | | CN | F | | |
| 529 | N | 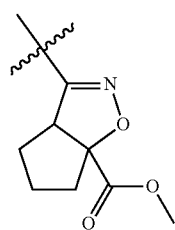 [SMILES: *C1=NOC2(C(=O)OC)CCCC12] | Cl | F | | |
| 530 | CH | 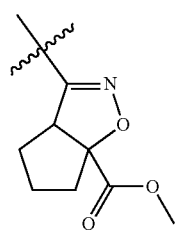 [SMILES: *C1=NOC2(C(=O)OC)CCCC12] | Cl | F | 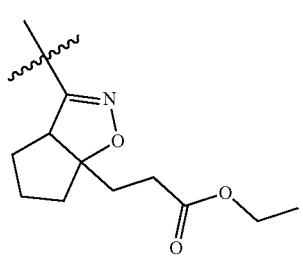 [SMILES: *C1=NOC2(CCC(=O)OCC)CCCC12] | 1H NMR (500 MHz, DMSO-d6) δ 7.91 (d, J = 9.5 Hz, 1H), 7.84 (d, J = 7.5 Hz, 1H), 4.10-4.04 (m, 2H), 3.89 (s, 1H), 3.65 (s, 6H), 2.49-2.38 (m, 2H), 2.12-2.01 (m, 4H), 1.84-1.79 (m, 1H), 1.75-1.68 (m, 2H), 1.58-1.54 (m, 1H), 1.20 (t, J = 7.0 Hz, 3H). |

TABLE 1-continued

Structures and ¹H NMR data of compounds

| No. | M | (structure) | Y | Z | Q | ¹H NMR |
|---|---|---|---|---|---|---|
| 531 | CH | | Cl | F | | |
| 532 | CH | | Cl | F | | |
| 533 | CH | | Cl | F | | 1H NMR (500 MHz, DMSO-d6) δ 7.89 (d, J = 9.5 Hz, 1H), 7.78 (d, J = 7.5 Hz, 1H), 6.63 (s, 1H), 4.08 (q, J = 7.0 Hz, 2H), 3.90 (s, 1H), 3.44 (s, 3H), 2.50-2.38 (m, 2H), 2.12-2.01 (m, 3H), 1.84-1.77 (m, 1H), 1.74-1.68 (m, 2H), 1.58-1.54 (m, 1H), 1.48-1.41 (m, 1H), 1.20 (t, J = 7.0 Hz, 3H). |
| 534 | CH | | Cl | F | | 1H NMR (500 MHz, DMSO) δ 7.93 (d, J = 9.5 Hz, 1H), 7.86 (d, J = 7.5 Hz, 1H), 6.63 (s, 1H), 6.21 (d, J = 5.0 Hz, 1H), 5.94 (d, J = 5.0 Hz, 1H), 4.80-4.75 (m, 1H), 4.25 (q, J = 7.0 Hz, 2H), 3.44 (s, 3H), 2.92-2.88 (m, 1H), 2.36-2.30 (m, 1H), 1.27 (t, J = 7.0 Hz, 3H). |
| 535 | CH | | Cl | F | | |

TABLE 1-continued
Structures and ¹H NMR data of compounds
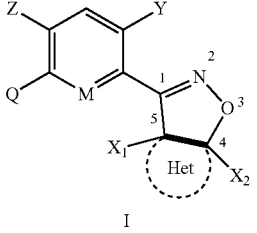
| No. | M | 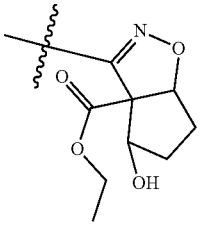 [SMILES: *C1=NOC2CCC(O)C12C(=O)OCC] | Y | Z | Q | ¹H NMR |
|---|---|---|---|---|---|---|
| 536 | CH | 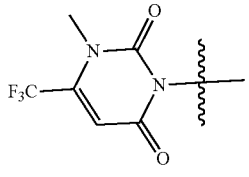 | Cl | F | 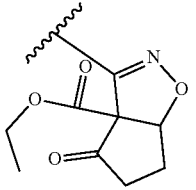 [SMILES: *C1=NOC2CCC(=O)C12C(=O)OCC] | 1H NMR (500 MHz, DMSO) δ 7.91 (d, J = 9.5 Hz, 1H), 7.85 (d, J = 7.5 Hz, 1H), 6.64 (s, 1H), 5.43 (s, 1H), 4.48-4.40 (m, 1H), 4.27-4.17 (m, 2H), 3.44 (s, 3H), 2.68-2.60 (m, 1H), 1.95-1.75 (m, 2H), 1.55-1.49 (m, 2H), 1.26 (t, J = 7.0 Hz, 3H). |
| 537 | CH | 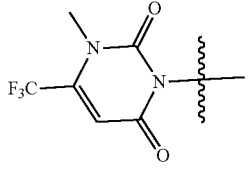 | Cl | F | 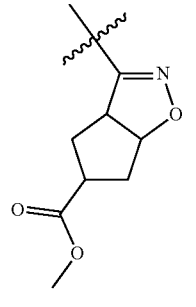 [SMILES: *C1=NOC2CC(C(=O)OC)CC12] | 1H NMR (500 MHz, DMSO) δ 7.92 (d, J = 9.5 Hz, 1H), 7.87 (d, J = 7.5 Hz, 1H), 6.66 (s, 1H), 4.96-4.90 (m, 1H), 4.28-4.20 (m, 2H), 3.45 (s, 3H), 2.68-2.60 (m, 1H), 2.49-2.39 (m, 1H), 2.39-2.30 (m, 1H), 1.99-1.88 (m, 1H), 1.23 (t, J = 7.0 Hz, 3H). |
| 538 | CH | 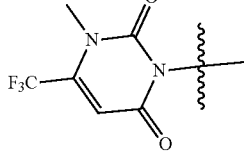 | Cl | F | 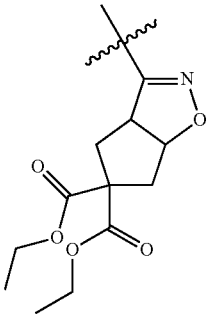 [SMILES: *C1=NOC2CC(C(=O)OCC)(C(=O)OCC)CC12] | |
| 539 | CH | 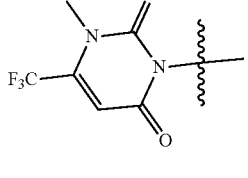 | Cl | F | 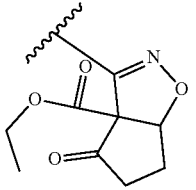 [SMILES: *C1=NOC2CCC(=O)C12C(=O)OCC] | 1H NMR (500 MHz, DMSO) δ 7.92 (d, J = 9.5 Hz, 1H), 7.87 (d, J = 7.5 Hz, 1H), 6.36 (s, 1H), 4.25-4.18 (m, 4H), 3.44 (s, 3H), 3.66-3.60 (m, 1H), 2.56-2.50 (m, 2H), 2.36-2.30 (m, 1H), 2.30-2.20 (m, 2H), 1.23 (t, J = 7.0 Hz, 6H). |

TABLE 1-continued

Structures and ¹H NMR data of compounds

| No. | M | Het | Y | Z | Q | ¹H NMR |
|---|---|---|---|---|---|---|
| 540 | CH | (cyclooctane-fused isoxazoline with methyl ester) | Cl | F | N-methyl-6-(trifluoromethyl)pyrimidine-2,4-dione | ¹H NMR (500 MHz, DMSO-d₆) δ 7.68 (d, J = 8.5 Hz, 1H), 7.53 (d, J = 7.5 Hz, 1H), 6.26 (s, 1H), 3.64 (s, 3H), 3.24 (s, 3H), 3.38-3.31 (m, 1H), 2.38-1.90 (m, 4H), 1.73-1.28 (m, 8H). |
| 541 | CH | (cyclopentane-fused isoxazoline with methyl ester) | Cl | F | maleimide | ¹H NMR (500 MHz, DMSO) δ 7.92 (d, J = 9.5 Hz, 1H), 7.85 (d, J = 7.5 Hz, 1H), 7.33 (s, 2H), 4.49 (d, J = 9.0 Hz, 1H), 3.77 (s, 3H), 2.17-2.15 (m, 2H), 1.96-1.79 (m, 2H), 1.69-1.67 (m, 1H), 1.60-1.46 (m, 1H). |
| 542 | CH | (cyclopentane-fused isoxazoline with methyl ester) | Cl | F | 4,5,6,7-tetrahydroisoindole-1,3-dione | ¹H NMR (500 MHz, DMSO-d₆) δ 7.90 (d, J = 9.5 Hz, 1H), 7.80 (d, J = 7.5 Hz, 1H), 4.50-4.47 (m, 1H), 3.77 (s, 3H), 2.40-2.36 (m, 4H), 2.22-2.10 (m, 2H), 1.96-1.82 (m, 2H), 1.78-1.74 (m, 4H), 1.71-1.44 (m, 2H). |
| 543 | CH | (cyclopentane-fused isoxazoline with methyl ester) | Cl | F | 5-fluoroisoindoline-1,3-dione | |
| 544 | CH | (cyclopentane-fused isoxazoline with methyl ester) | Cl | F | 3-(propan-2-ylidene)-4-methylpyrrolidine-2,5-dione | ¹H NMR (500 MHz, DMSO) δ 7.90 (d, J = 9.5 Hz, 1H), 7.79 (d, J = 7.5 Hz, 1H), 4.49 (d, J = 9.0 Hz, 1H), 3.78 (s, 3H), 3.55-3.53 (m, 2H), 2.32 (s, 3H), 2.17-2.15 (m, 2H), 1.93-1.90 (m, 4H), 1.87-1.79 (m, 1H), 1.69-1.65 (m, 1H), 1.59-1.48 (m, 1H). |

TABLE 1-continued
Structures and $^1$H NMR data of compounds
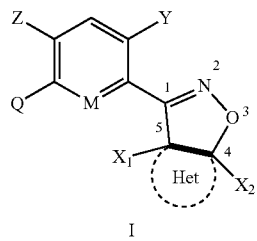
I
| No. | M | 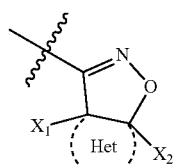 | Y | Z | Q | $^1$H NMR |
|---|---|---|---|---|---|---|
| 545 | CH | 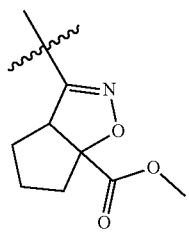 [SMILES: *C1=NOC2(C(=O)OC)CCCC12] | | Cl | F | 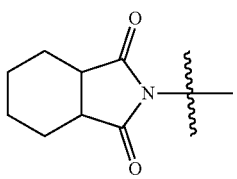 [SMILES: *N1C(=O)C2CCCCC2C1=O] | $^1$H NMR (500 MHz, DMSO-d$_6$) δ 7.91 (d, J = 9.5 Hz, 1H), 7.79 (d, J = 7.5 Hz, 1H), 4.54-4.51 (m, 1H), 3.78 (s, 3H), 2.22-2.12 (m, 2H), 2.00-1.62 (m, 8H), 1.61-1.24 (m, 6H). |
| 546 | CH | 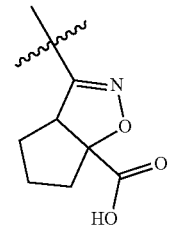 [SMILES: *C1=NOC2(C(=O)O)CCCC12] | | Cl | F | 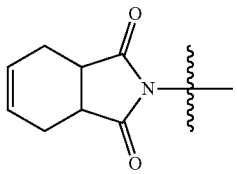 [SMILES: *N1C(=O)C2CC=CCC2C1=O] | $^1$H NMR (500 MHz, DMSO) δ 12.03 (s, 1H), 7.88 (d, J = 9.0 Hz, 1H), 7.72 (d, J = 7.0 Hz, 1H), 5.97 (s, 2H), 4.50-4.40 (m, 1H), 3.36-3.21 (m, 2H), 2.50-2.46 (m, 2H), 2.35-2.30 (m, 2H), 2.20-2.10 (m, 2H), 1.94-1.77 (m, 2H), 1.68-1.62 (m, 1H), 1.55-1.50 (m, 1H). |
| 547 | CH | 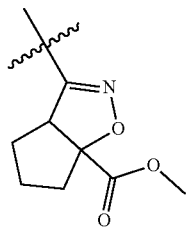 [SMILES: *C1=NOC2(C(=O)OC)CCCC12] | | Cl | F | 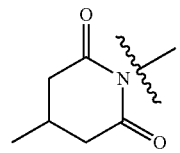 | $^1$H NMR (500 MHz, DMSO) δ 7.82 (d, J = 8.5 Hz, 1H), 7.70 (d, 8.0 Hz, 1H), 4.54-4.45 (m, 1H), 3.77 (s, 3H), 2.88-2.82 (m, 2H), 2.69-2.55 (m, 2H), 2.45-2.30 (m, 1H), 2.25-2.10 (m, 2H), 1.97-1.80 (m, 2H), 1.68-1.60 (m, 1H), 1.58-1.50 (m, 1H), 1.15-1.05 (m, 3H). |
| 548 | CH | 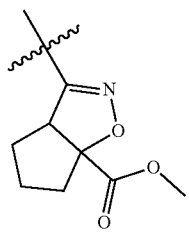 [SMILES: *C1=NOC2(C(=O)OC)CCCC12] | | Cl | F | 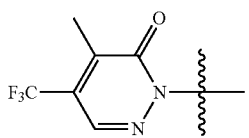 | |

TABLE 1-continued
Structures and ¹H NMR data of compounds
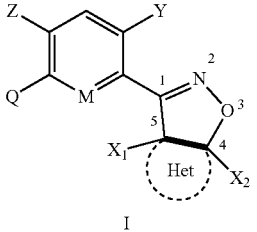
| No. | M | 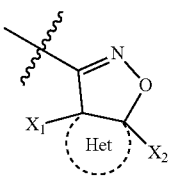 | Y | Z | Q | ¹H NMR |
|---|---|---|---|---|---|---|
| 549 | CH | 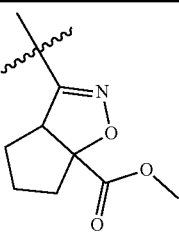 | Cl | F | 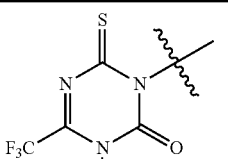 | |
| 550 | CH | 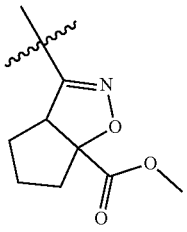 [SMILES: *C1=NOC2(C(=O)OC)CCCC12] | Cl | F | 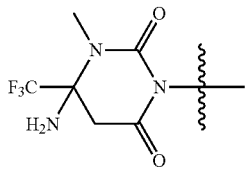 [SMILES: *N1C(=O)CC(N)(C(F)(F)F)N(C)C1=O] | |
| 551 | CH | 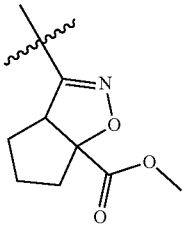 [SMILES: *C1=NOC2(C(=O)OC)CCCC12] | Cl | F | 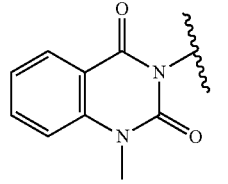 [SMILES: *n1c(=O)c2ccccc2n(C)c1=O] | ¹H NMR (500 MHz, DMSO) δ 8.16-8.05 (m, 1H), 7.95-7.85 (m, 3H), 7.57 (d, J = 8.5 Hz, 1H), 7.38 (t, J = 7.5 Hz, 1H), 4.46 (d, J = 9.0 Hz, 1H), 3.75 (s, 3H), 3.57 (d, J = 2.0 Hz, 3H), 2.22-2.08 (m, 2H), 1.96-1.87 (m, 1H), 1.88-1.81 (m, 1H), 1.70-1.62 (m, 1H), 1.55-1.45 (m, 1H). |
| 552 | CH | 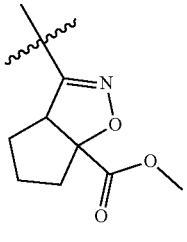 [SMILES: *C1=NOC2(C(=O)OC)CCCC12] | Cl | F | 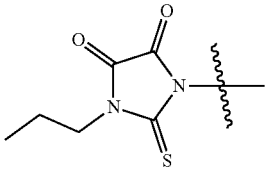 [SMILES: *N1C(=O)C(=O)N(CCC)C1=S] | ¹H NMR (500 MHz, DMSO) δ 7.98 (d, J = 9.5 Hz, 1H), 7.84 (s, 1H), 4.48-4.40 (m, 1H), 3.94-3.82 (m, 2H), 3.77 (s, 3H), 2.27-2.08 (m, 2H), 1.90-1.88 (m, 2H), 1.71-1.65 (m, 3H), 1.56-1.43 (m, 2H), 0.96-0.90 (, m, 3H). |
| 553 | CH | 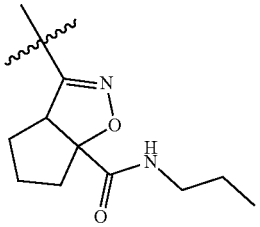 [SMILES: *C1=NOC2(C(=O)NCCC)CCCC12] | Cl | F | 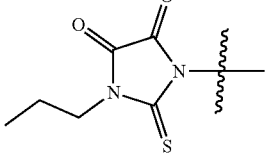 | ¹H NMR (500 MHz, DMSO) δ 8.24 (s, 1H), 7.97 (d, J = 9.5 Hz, 1H), 7.84 (d, J = 7.5 Hz, 1H), 4.28 (d, J = 8.5 Hz, 1H), 3.95-3.79 (m, 2H), 3.17-3.05 (m, 2H), 2.21-2.07 (m, 2H), 1.88-1.85 (m, 2H), 1.69-1.67 (m, 3H), 1.57-1.42 (m, 3H), 0.98-0.93 (m, 3H), 0.83 (t, J = 7.5 Hz, 3H). |

TABLE 1-continued

Structures and ¹H NMR data of compounds

| No. | M | Het | Y | Z | Q | ¹H NMR |
|---|---|---|---|---|---|---|
| 554 | CH | | Cl | F | | |
| 555 | CH | | Cl | F | | |
| 556 | CH | | Cl | F | | |
| 557 | CH | | Cl | F | | |

TABLE 1-continued
Structures and ¹H NMR data of compounds
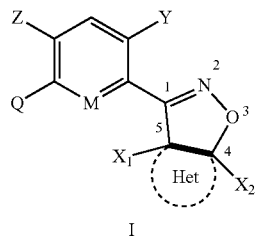
I
| No. | M | 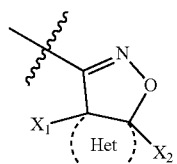 | Y | Z | Q | ¹H NMR |
|---|---|---|---|---|---|---|
| 558 | CH | 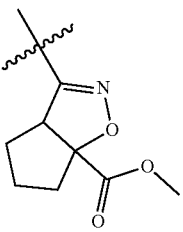 [SMILES: *C1=NOC2(C(=O)OC)CCCC12] | Cl | F | 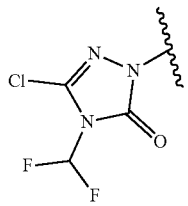 [SMILES: *n1nc(Cl)n(C(F)F)c1=O] | |
| 559 | CH | 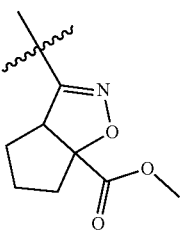 [SMILES: *C1=NOC2(C(=O)OC)CCCC12] | Cl | F | 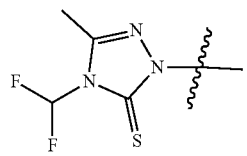 | |
| 560 | CH | 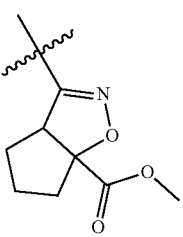 [SMILES: *C1=NOC2(C(=O)OC)CCCC12] | Cl | F | 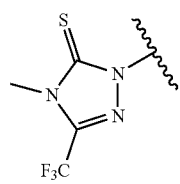 [SMILES: *n1nc(C(F)(F)F)n(C)c1=S] | |
| 561 | CH | | Cl | F | 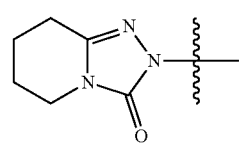 [SMILES: *n1nc2n(c1=O)CCCC2] | 1H NMR (500 MHz, DMSO-d6) δ 7.85 (d, J = 10.0 Hz, 1H), 7.81 (d, J = 7.5 Hz, 1H), 4.53-4.51 (m, 1H), 3.75 (s, 3H), 3.55 (t, J = 6.0 Hz, 2H), 2.68 (t, J = 6.5 Hz, 2H), 2.24-1.98 (m, 4H), 1.93-1.71 (m, 4H), 1.68-1.48 (m, 2H). |

TABLE 1-continued
Structures and ¹H NMR data of compounds
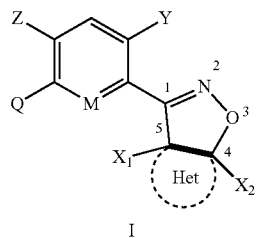
| No. | M | | Y | Z | Q | ¹H NMR |
|---|---|---|---|---|---|---|
| 562 | CH | | Cl | F | | |
| 563 | CH | | Cl | N | | |
| 564 | CH | | Cl | F | | |
| 565 | CH | | Cl | F | | |

TABLE 1-continued
Structures and $^1$H NMR data of compounds
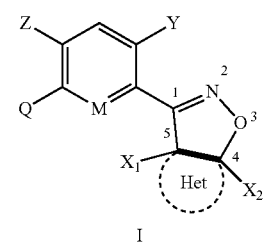
| No. | M | | Y | Z | Q | $^1$H NMR |
|---|---|---|---|---|---|---|
| 566 | CH | 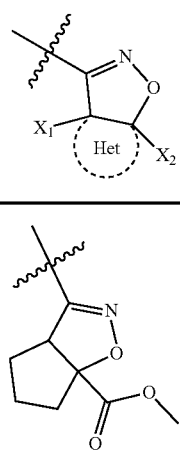 | Cl | F | 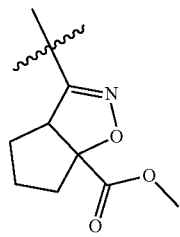 [SMILES: *C1=NOC2(C(=O)OC)CCCC12] | |
| 567 | CH | 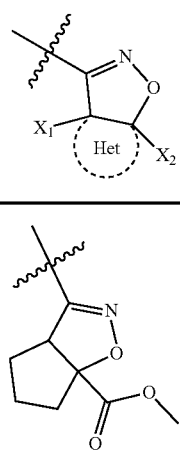 | Cl | F | 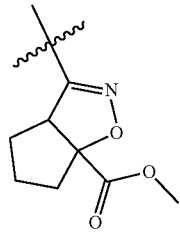 [SMILES: *C1=NOC2(C(=O)OC)CCCC12] | |
| 568 | CH | 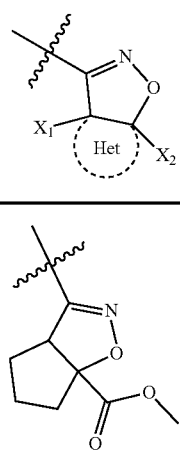 | Cl | F | 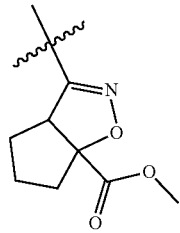 [SMILES: *C1=NOC2(C(=O)OC)CCCC12] | |
| 569 | CH | 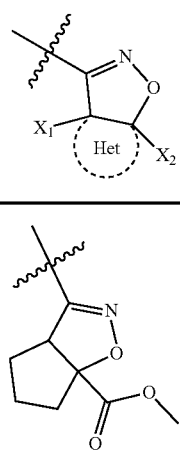 | Cl | F |  | |

TABLE 1-continued
Structures and ¹H NMR data of compounds
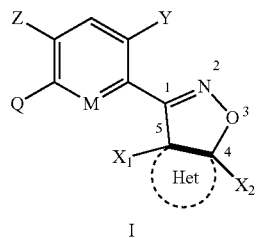
| No. | M | | Y | Z | Q | ¹H NMR |
|---|---|---|---|---|---|---|
| 570 | CH | | Cl | F | | |
| 571 | CH | | Cl | F | | |
| 572 | CH | | Cl | F | | |
| 573 | CH | | Cl | F | | |

TABLE 1-continued
Structures and ¹H NMR data of compounds
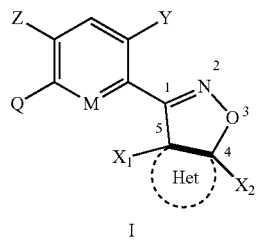
I
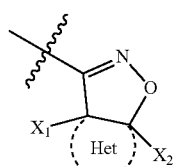
| No. | M | | Y | Z | Q | ¹H NMR |
|---|---|---|---|---|---|---|
| 574 | CH | 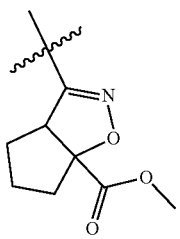 [SMILES: *C1=NOC2(C(=O)OC)CCCC12] | Cl | F | ![Q574](methyl-trifluoromethyl-thiazolyl-imino) | 1H NMR (500 MHz, DMSO-d6) δ 7.67 (d, J = 10.0 Hz, 1H), 7.41 (d, J = 8.5 Hz, 1H), 7.38 (s, 1H), 3.76 (s, 3H), 3.50 (s, 3H), 2.20-2.11 (m, 2H), 1.95-1.87 (m, 1H), 1.86-1.79 (m, 1H), 1.72-1.65 (m, 1H), 1.58-1.47 (m, 2H). |
| 575 | CH | 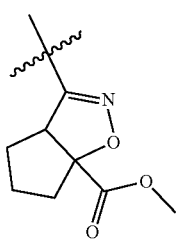 [SMILES: *C1=NOC2(C(=O)OC)CCCC12] | Cl | F | ![Q575] | ¹H NMR (500 MHz, DMSO-d₆) δ 8.05-7.78 (m, 2H), 4.52-4.47 (m, 1H), 4.10-4.06 (m, 1H), 3.95-3.81 (m, 1H), 3.80-3.77 (m, 4H), 3.60-3.58 (m, 1H), 2.23-2.12 (m, 2H), 2.04-1.77 (m, 6H), 1.70-1.67 (m, 1H), 1.55-1.49 (m, 1H). |
| 576 | CH | 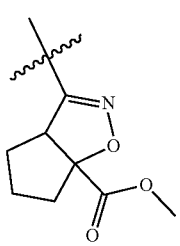 [SMILES: *C1=NOC2(C(=O)OC)CCCC12] | Cl | F | ![Q576] | |
| 577 | CH | 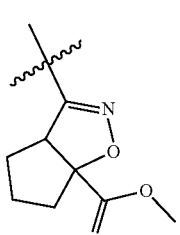 | Cl | F | ![Q577] | ¹H NMR (500 MHz, DMSO) δ 7.98 (s, 1H), 7.81 (d, J = 7.5 Hz, 1H), 7.78 (d, J = 9.5 Hz, 1H), 4.32 (d, J = 8.5 Hz, 1H), 4.04 (s, 3H), 2.10-2.04 (m, 1H), 1.98-1.92 (m, 1H), 1.78-1.72 (m, 1H), 1.72-1.63 (m, 1H), 1.62-1.52 (m, 1H), 1.45-1.30 (m, 1H). |

TABLE 1-continued

Structures and ¹H NMR data of compounds

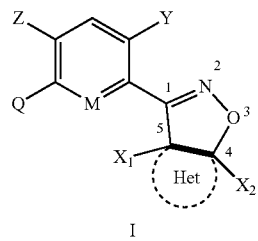

| No. | M | (Het group) | Y | Z | Q | ¹H NMR |
|---|---|---|---|---|---|---|
| 578 | CH | cyclopentane-fused isoxazoline with CO₂Me | Cl | F | pyridazine with CF₃ and OMe | ¹H NMR (500 MHz, DMSO) δ 8.01 (s, 1H), 7.95 (d, J = 7.0 Hz, 1H), 7.87 (d, J = 9.5 Hz, 1H), 4.56 (d, J = 9.0 Hz, 1H), 4.07 (s, 3H), 3.76 (s, 3H), 2.25-2.12 (m, 2H), 1.95-1.88 (m, 1H), 1.88-1.80 (m, 1H), 1.75-1.68 (m, 1H), 1.59-1.52 (m, 1H). |
| 579 | CH | cyclopentane-fused isoxazoline with CO₂Me | Cl | F | N-methyl pyridazinone with CF₃ | ¹H NMR (500 MHz, DMSO) δ 8.21 (s, 1H), 7.98 (d, J = 7.0 Hz, 1H), 7.85 (d, J = 9.5 Hz, 1H), 4.56 (d, J = 9.0 Hz, 1H), 4.07 (s, 3H), 2.76 (s, 3H), 2.25-2.12 (m, 2H), 1.95-1.88 (m, 1H), 1.88-1.80 (m, 1H), 1.75-1.68 (m, 1H), 1.59-1.52 (m, 1H). |
| 580 | CH | cyclopentane-fused isoxazoline with CO₂Me | Cl | F | N-methyl dihydropyridinedione with CF₃ | |
| 581 | CH | cyclopentane-fused isoxazoline with CO₂Me | Cl | F | N-methyl pyridinone with CF₃ | |

TABLE 1-continued
Structures and ¹H NMR data of compounds
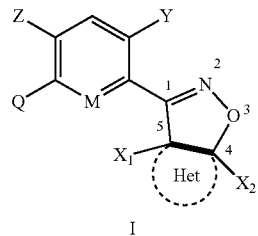
I
| No. | M | 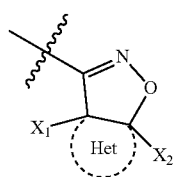 | Y | Z | Q | ¹H NMR |
|---|---|---|---|---|---|---|
| 582 | CH | 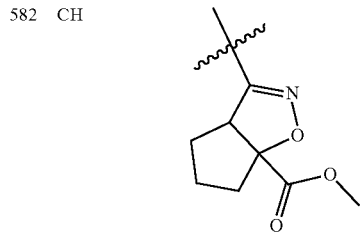 | Cl | F | 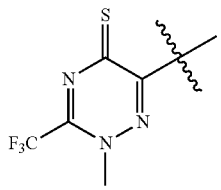 [SMILES: *c1nn(C)c(C(F)(F)F)nc1=S] | |
| 583 | CH | 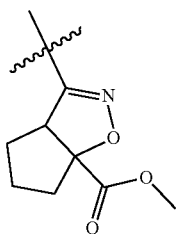 [SMILES: *C1=NOC2(C(=O)OC)CCCC12] | Cl | F | 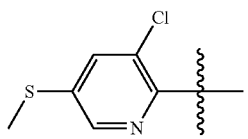 [SMILES: *c1ncc(SC)cc1Cl] | |
| 584 | CH | 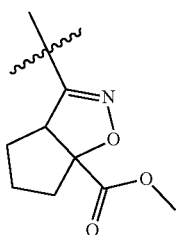 [SMILES: *C1=NOC2(C(=O)OC)CCCC12] | Cl | F | 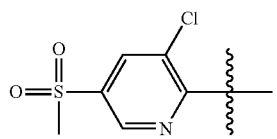 [SMILES: *c1ncc(S(C)(=O)=O)cc1Cl] | ¹H NMR (500 MHz, DMSO-d₆) δ 9.14 (d, J = 2.0 Hz, 1H), 8.66 (d, J = 2.0 Hz, 1H), 7.91-7.85 (m, 2H), 4.60-4.456 (m, 1H), 3.74 (s, 3H), 3.46 (s, 3H), 2.22-2.04 (m, 3H), 1.97-1.81 (m, 1H), 1.71-1.67 (m, 1H), 1.58-1.50 (m, 1H). |
| 585 | CH | 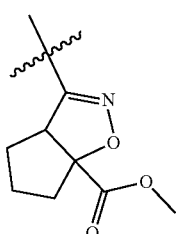 | Cl | F | 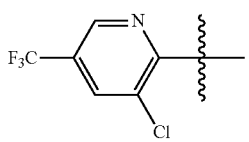 [SMILES: *c1ncc(C(F)(F)F)cc1Cl] | ¹H NMR (500 MHz, DMSO-d₆) δ 9.14 (s, 1H), 8.73 (s, 1H), 7.90 (dd, J = 8.5, 5.5 Hz, 2H), 4.56-4.53 (m, 1H), 3.77 (s, 3H), 2.17-2.11 (m, 2H), 1.99-1.76 (m, 2H), 1.77-1.44 (m, 2H). |

TABLE 1-continued
Structures and ¹H NMR data of compounds
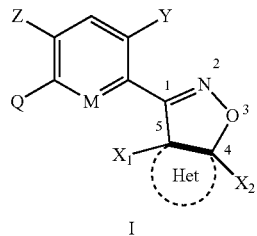
I
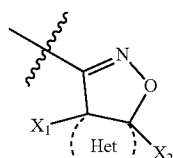
| No. | M | | Y | Z | Q | ¹H NMR |
|---|---|---|---|---|---|---|
| 586 | CH | 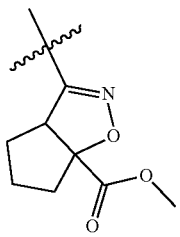 [SMILES: *C1=NOC2(C(=O)OC)CCCC12] | Cl | F | 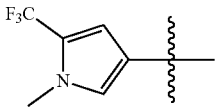 [SMILES: *c1cc(C(F)(F)F)n(C)c1] | ¹H NMR (500 MHz, DMSO-d₆) δ 8.96 (s, 1H), 7.86-7.84 (m, 2H), 4.53-4.54 (m, 1H), 3.74 (s, 3H), 2.59 (s, 3H), 2.14-2.12 (m, 2H), 1.96-1.75 (m, 2H), 1.72-1.44 (m, 2H). |
| 587 | CH | 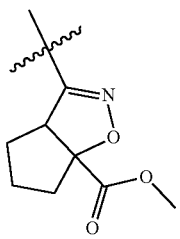 [SMILES: *C1=NOC2(C(=O)OC)CCCC12] | Cl | F | 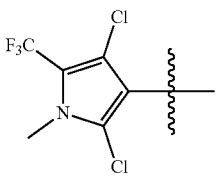 | |
| 588 | CH | 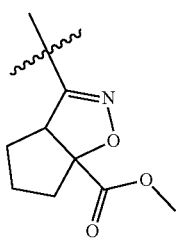 [SMILES: *C1=NOC2(C(=O)OC)CCCC12] | Cl | F | 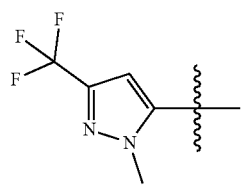 [SMILES: *c1cc(C(F)(F)F)nn1C] | ¹H NMR (500 MHz, DMSO) δ 7.91 (d, J = 4.5 Hz, 1H), 7.89 (d, J = 7.0 Hz, 1H), 4.52 (d, J = 9.0 Hz, 1H), 3.75 (s, 3H), 3.11 (s, 3H), 2.21-2.10 (m, 2H), 1.88-1.82 (m, 2H), 1.75-1.68 (m, 1H), 1.56-1.52 (m, 1H) |
| 589 | CH | 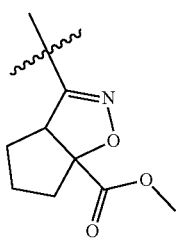 [SMILES: *C1=NOC2(C(=O)OC)CCCC12] | Cl | F | | ¹H NMR (500 MHz, DMSO) δ 7.95-7.88 (m, 2H), 7.05 (s, 1H), 4.58 (d, J = 8.5 Hz, 1H), 3.87 (s, 3H), 3.77 (s, 3H), 2.21-2.15 (m, 2H), 1.94-1.80 (m, 2H), 1.78-1.72 (m, 1H), 1.62-1.56 (m, 1H) |

TABLE 1-continued

Structures and ¹H NMR data of compounds

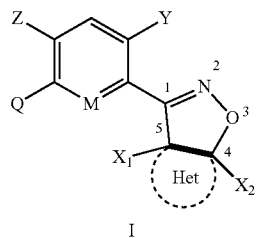

| No. | M | | Y | Z | Q | ¹H NMR |
|---|---|---|---|---|---|---|
| 590 | CH | (methyl hexahydrocyclopenta[c]isoxazole-carboxylate) | Cl | F | 4-Br-3-CF₃-1-methylpyrazol-5-yl | ¹H NMR (500 MHz, DMSO) δ 7.96-7.89 (m, 2H), 4.59 (d, J = 8.5 Hz, 1H), 3.87 (s, 3H), 3.77 (s, 3H), 2.22-2.15 (m, 2H), 1.96-1.80 (m, 2H), 1.78-1.71 (m, 1H), 1.64-1.58 (m, 1H) |
| 591 | CH | (methyl hexahydrocyclopenta[c]isoxazole-carboxylate) | Cl | F | 4-Cl-5-CHF₂-1-methylpyrazol-3-yl | |
| 592 | CH | (methyl hexahydrocyclopenta[c]isoxazole-carboxylate) | Cl | F | 4-Br-5-CF₃-1-methylpyrazol-3-yl | |
| 593 | CH | (methyl hexahydrocyclopenta[c]isoxazole-carboxylate) | Cl | F | 4-Cl-5-OiPr-1-methylpyrazol-3-yl | |

TABLE 1-continued
Structures and ¹H NMR data of compounds
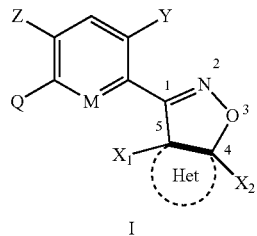
I
| No. | M | 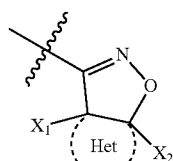 | Y | Z | Q | ¹H NMR |
|---|---|---|---|---|---|---|
| 594 | CH | 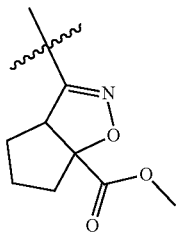 [SMILES: *C1=NOC2(C(=O)OC)CCCC12] | Cl | F | 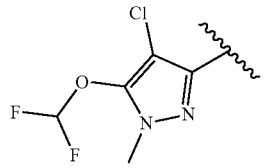 [SMILES: *c1nn(C)c(OC(F)F)c1Cl] | |
| 595 | CH | 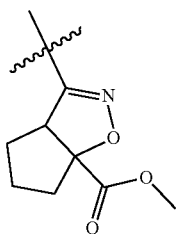 [SMILES: *C1=NOC2(C(=O)OC)CCCC12] | Cl | F | 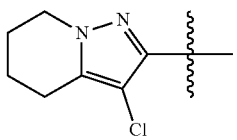 [SMILES: *c1nn2c(c1Cl)CCCC2] | |
| 596 | CH | 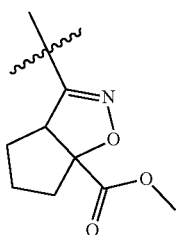 [SMILES: *C1=NOC2(C(=O)OC)CCCC12] | Cl | F | 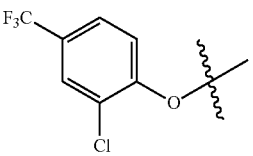 [SMILES: *Oc1ccc(C(F)(F)F)cc1Cl] | ¹H NMR (500 MHz, DMSO) δ 8.10 (s, 1H), 7.97 (d, J = 9.5 Hz, 1H), 7.73 (d, J = 7.5 Hz, 1H), 7.49-7.43 (m, 1H), 7.22 (d, J = 8.5 Hz, 1H), 4.35 (d, J = 8.5 Hz, 1H), 3.43 (s, 3H), 2.10-2.05 (m, 1H), 1.98-1.90 (m, 1H), 1.82-1.75 (m, 1H), 1.73-1.65 (m, 1H), 1.66-1.55 (m, 1H), 1.45-1.35 (m, 1H). |
| 597 | CH | 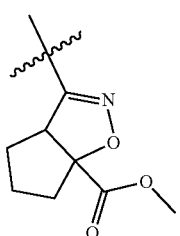 | Cl | F | 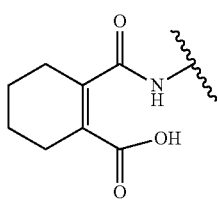 [SMILES: *NC(=O)C1=C(C(=O)O)CCCC1] | ¹H NMR (500 MHz, DMSO) δ 7.32 (d, J = 11.0 Hz, 1H), 6.96 (d, J = 9.0 Hz, 1H), 4.45 (d, J = 9.0 Hz, 1H), 3.77 (s, 3H), 2.37-2.32 (m, 2H), 2.21-2.11 (m, 3H), 1.95-1.81 (m, 3H), 1.80-1.75 (m, 2H), 1.72-1.60 (m, 2H), 1.55-1.42 (m, 2H). |

TABLE 1-continued

Structures and $^1$H NMR data of compounds

| No. | M | | Y | Z | Q | $^1$H NMR |
|---|---|---|---|---|---|---|
| 598 | CH | | Cl | F | 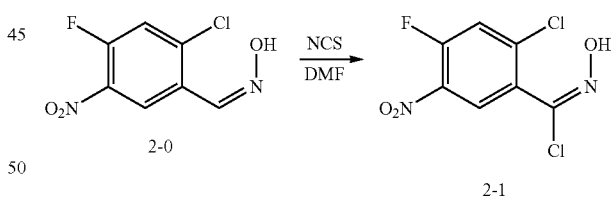 | |

The method for preparing the compound of the invention will be explained in detail in the following program and embodiment. The material is commercial available or prepared through known method reported in the literature or shown in the route. Those skilled in the art should understand that the compound of the invention can also be synthesized by other synthetic route. Although the detailed material and reaction condition in the synthetic route have been explicated in the following text, it is still easy to be replaced by other similar material and condition. Isomer of the compound, for example, that produced with the variation of the preparation method of the present invention is included in the scope of the present invention. In addition, the following preparation method can be further modified according to the disclosures of the present invention by using common chemical method known to those skilled in the art, for example, protection of suitable group in the process of the reaction, etc.

The following method of application can be used to improve further understanding of the preparation method of the present invention. The specific material, class and condition have been determined to be further explication of the present invention, not to be any limit of the reasonable scope thereof. Reagents of the following synthetic compound showed in the table can either be purchased from the market or easily prepared by those skilled in the art.

Examples of representative compounds are as follows, the synthesis methods of other compounds are similar, and will not be described in detail here.

1. Synthesis of Compound 2

(1) Compound 2-0 (20 g, 91.5 mmol, 1.0 eq) was added to 150 ml of DMF, and then NCS (13.4 g, 100.7 mmol, 1.1 eq) was slowly added to the reaction solution at 35° C. After the addition was completed, the reaction solution was stirred at 35° C. for 1.5 hours. The raw materials were almost completely reacted, as detected by LCMS. The reaction solution was poured into 100 ml of HCl (1 M) and then extracted with dichloromethane. The organic phase was washed with saturated brine (100 ml×3), and then concentrated to obtain a crude product of Compound 2-1 (26 g, crude product) (yellow oil). The crude product was used in the next step without further purification.

(2) Compound 2-1 (1 g) and Et$_3$N (600 mg, 6.0 mmol, 1.5 eq) were added to 10 ml of DCM, and then Compound a (605 mg, 4.8 mmol, 1.2 eq) was added to the reaction solution at 0° C. The reaction solution was slowly heated to 2° C., and reacted for 16 hours. A product was detected by LCMS. 10 ml of water was added to the reaction solution, and then the reaction solution was extracted with dichloromethane (10 ml×3). The organic phase was dried with anhydrous sodium sulfate and then concentrated. The resulting crude product was isolated and purified by column chromatography to obtain Compound 2-2 (400 mg, 1.2 mmol, yield: 30%).

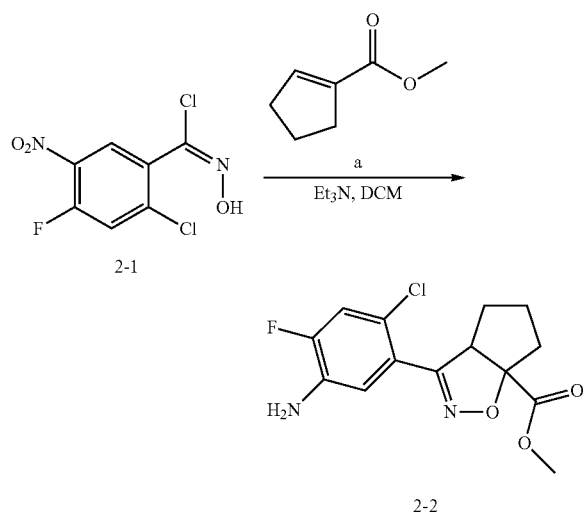

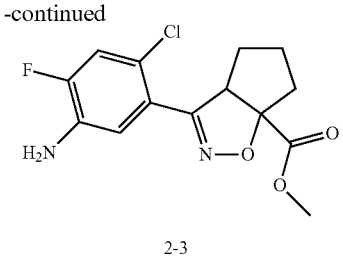

(4) Compound 2-3 (0.3 g, 0.96 mmol, 1.0 eq) and Compound b (165 mg, 1.06 mmol, 1.1 eq) were dissolved in 5 ml of dioxane. The reaction solution was heated at 110° C. for 30 minutes. It was detected by LCMS that the reaction of raw materials was basically completed, and the principal peak of LCMS chromatogram belonged to the product. The reaction solution was concentrated by removing the solvent. The resulting crude product was isolated by column chromatography to obtain Compound 2-4 (0.4 g, 0.92 mmol, yield: 96%).

(3) Compound 2-2 (400 mg, 1.2 mmol, 1.0 eq), Fe powder (202 mg, 3.6 mmol, 3 eq), NH₄Cl (127 mg, 2.4 mmol, 2 eq) and water (1 ml) were added to 5 ml of EtOH in sequence. Then, the reaction solution was reacted at 80° C. for 2 hours. It was detected by LCMS that the peaks of raw materials in LCMS chromatogram disappeared, and the principal peak in the chromatogram belonged to the product. After cooling down, the reaction solution was filtered with celite and then concentrated by removing ethanol. Water (10 ml) was added to the reaction solution. The reaction solution was extracted with ethyl acetate and then concentrated to obtain a black crude product. The crude product was isolated and purified by column chromatography to obtain Compound 2-3 (300 mg, 0.96 mmol, yield: 80%).

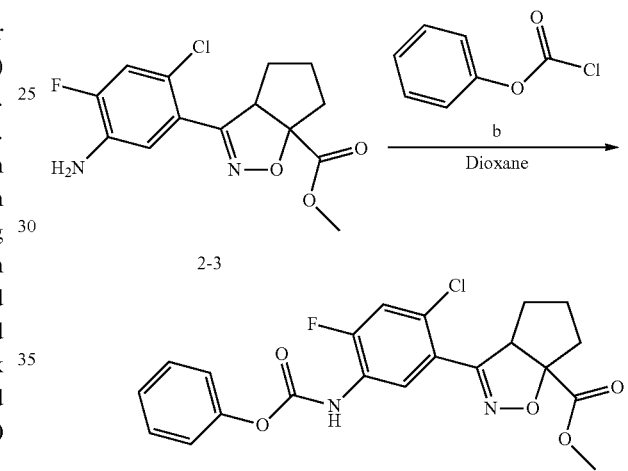

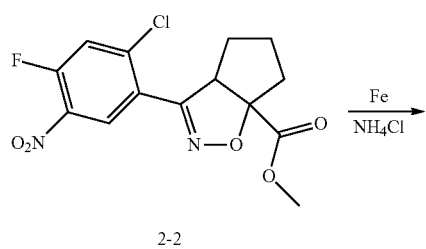

(5) Compound c (217 mg, 0.97 mmol, 1.05 eq) and AcONa (38 mg, 0.46 mmol, 0.5 eq) were added to 3 ml of DMF, and then Compound 2-4 (0.4 g, 0.92 mmol, 1.0 eq) was slowly added to the reaction solution at 60° C., followed by reacting at 60° for 10 minutes. A product was detected by LCMS. Water (10 ml) was added to the reaction solution, and then the reaction solution was extracted with ethyl acetate. The organic phase was washed with saturated brine (20 ml×1), and then concentrated. The resulting crude product was isolated by column chromatography to obtain Compound 2 (0.3 g, 0.64 mmol, yield: 70%).

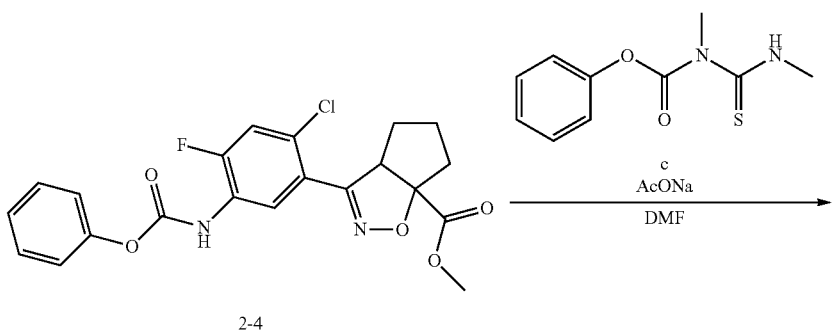

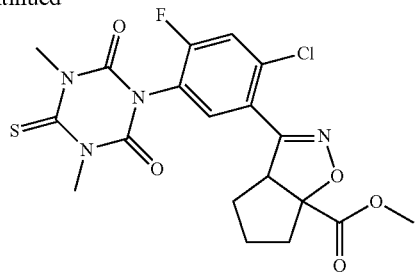

2. Synthesis of Compound 49

In a 50 ml eggplant-shaped bottle, Compound 2 (1.0 eq, 100 mg) was dissolved in Compound 49-1 (5V), to which was added tetraisopropyl titanate (20% mol). The reaction solution was reacted at 80° C. for 1-2 hours. It was detected by LCMS that the peaks of raw materials in LCMS chromatogram disappeared, and the principal peak in the chromatogram belonged to the product. The reaction solution was directly mixed with silica gel. The crude product was isolated and purified by column chromatography to obtain Compound 49 (31 mg, yield: 22%) (light yellow solid).

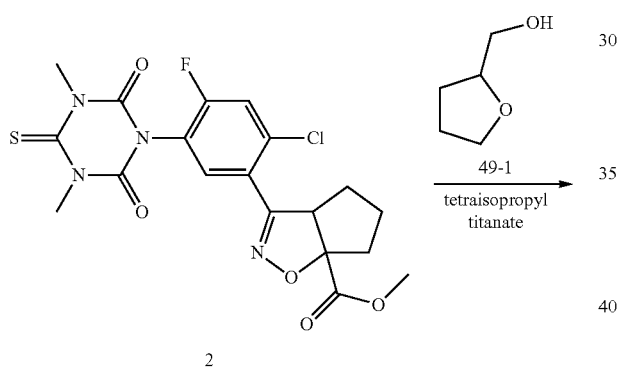

3. Synthesis of Compound 209

(1) Compound 2-3 (1.0 eq) and raw material Compound 210-7 (1.0 eq) were added to 10V of acetic acid. The reaction solution was reacted at 125° C. for 1 hour, followed by rotary evaporation to remove the carboxylic acid. The obtained product was used in the next step without further purification.

(2) Compound 209-1 (1.0 eq), methyl iodide (4.0 eq) and $K_2CO_3$ (2.0 eq) were added to 5V of DMF in sequence. Then, the reaction solution was reacted at 25-30° for 16 hours, and the reaction was completed as detected by LCMS. Water was added to the reaction solution, and then the reaction solution was extracted with ethyl acetate. The organic phase was washed with saturated brine, and then isolated by column chromatography to obtain Compound 209 (yield: 30%).

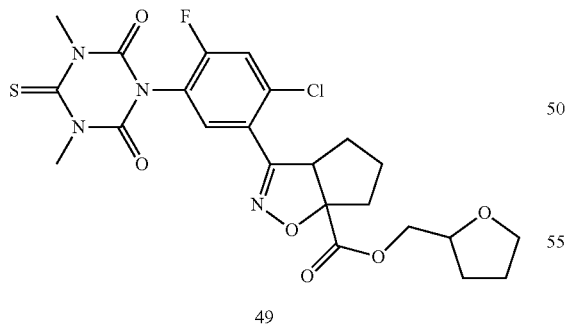

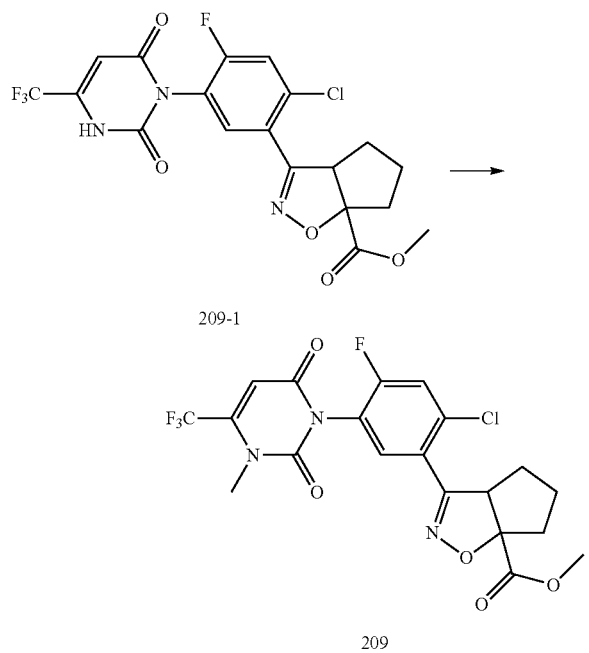

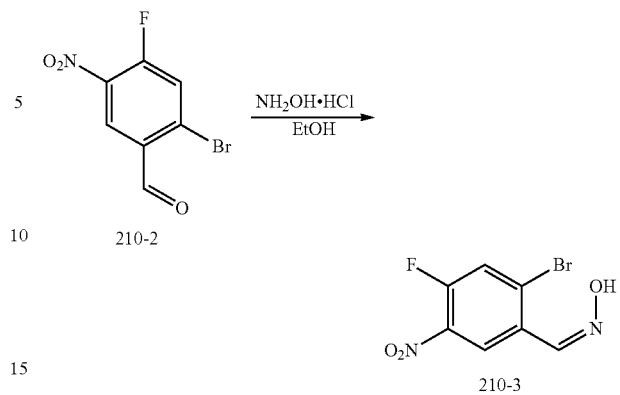

4. Synthesis of compounds 210 and 212

(1) At 0° C., fuming nitric acid (18.62 g, 0.296 mol, 3 eq) was added gradually to concentrated sulfuric acid (87 g, 0.887 mol, 9 eq). After the addition was completed, at 0° C., Compound 210-1 (20 g, 98.52 mmol, 1 eq) was added to the above solution in batches. Then, the reaction solution was reacted at 0° C. for 8 hours. As detected by LCMS, a small amount of raw materials was remained, and one new principle peak emerged. The reaction solution was slowly added to a mixture of ice and water, and extracted with ethyl acetate. The organic phase was washed with saturated sodium bicarbonate until weakly alkaline, dried over anhydrous sodium sulfate, concentrated, and then Compound 210-2 was isolated by column chromatography (16 g, yield: 65%).

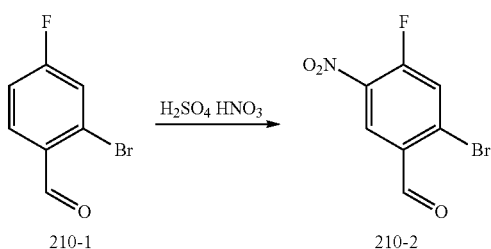

(2) Compound 210-2 (16 g, 64.5 mmol, 1.0 eq) was added to 160 ml of EtOH, and then an aqueous solution (20 ml) containing NH₂OH·HCl (4.93 g, 70.97 mmol, 1.1 eq) was added dropwise to the reaction solution at 0° C. After the addition was completed, the reaction solution was stirred at 0° for 3 hours. It was detected by LCMS that the raw materials almost used up, and a new principle peak emerged in LCMS chromatogram. The reaction solution was concentrated to remove most of the ethanol and then poured into 100 ml of water, to precipitate out a solid. After filtration, the filter cake was washed with water and dried to obtain Compound 210-3 (15 g, yield: 88%).

(3) Compound 210-3 (10 g, 38.02 mmol, 1.0 eq) was added to 150 ml of DMF, and then NCS (5.58 g, 41.82 mmol, 1.1 eq) was slowly added to the reaction solution at 35° C. After the addition was completed, the reaction solution was stirred at 35° C. for 2 hours. The reaction of raw materials was basically completed as detected by LCMS. The reaction solution was poured into 100 ml of water, and extracted with dichloromethane. The organic phase was washed with saturated brine (100 ml×3), and then concentrated to obtain a crude product of Compound 210-4 (11 g, yield: 97%). The crude product was used in the next step without further purification.

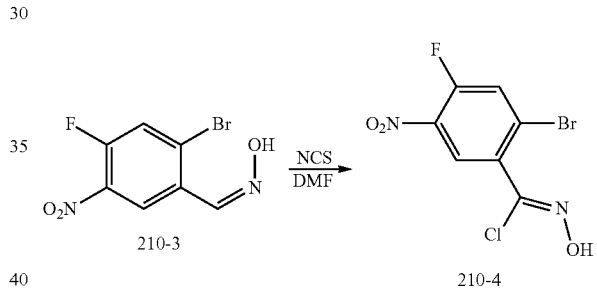

(4) Compound 210-4 (11 g, 36.98 mmol, 1.0 eq) and Et₃N (5.61 g, 55.47 mmol, 1.5 eq) were added to 200 ml of DCM, and then Compound a (5.13 g, 40.68 mmol, 1.1 eq) was added to the reaction solution at 0². The reaction solution was reacted at 0° C. for 1 hour, and then slowly warmed to room temperature, and reacted at room temperature overnight. A product was formed as detected by LCMS. 100 ml of water was added to the reaction solution, and then the reaction solution was extracted with dichloromethane (100 ml×3). The organic phase was dried over anhydrous sodium sulfate, and then concentrated. The resulting crude product was purified by column chromatography to obtain Compound 210-5 (4.7 g, yield: 32%).

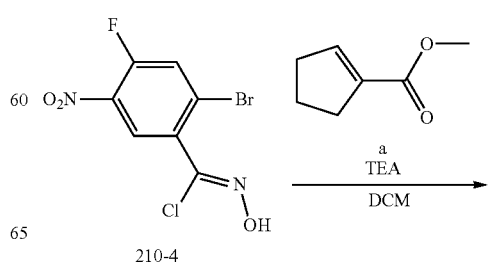

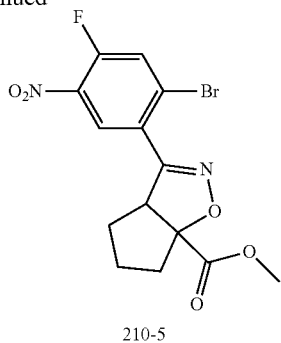

210-5

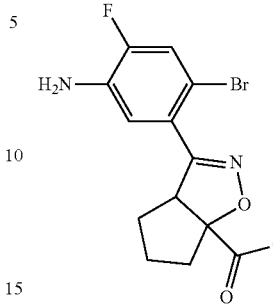

210-6

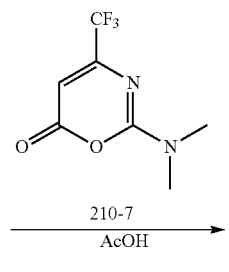

210-7

(5) Compound 210-5 (4.7 g, 12.14 mmol, 1.0 eq), Fe powder (2.03 g, 36.42 mmol, 3 eq), NH$_4$CN (1.95 g, 36.42 mmol, 3 eq) and water (50 ml) were added to 200 ml of EtOH in sequence. Then, the reaction solution was reacted at 80° C. for 1 hour. It was detected by LCMS that the raw materials were used up, and the principal peak in LCMS chromatogram belonged to the product. The reaction solution was filtered with celite and then concentrated to remove ethanol. Water (100 ml) was added to the reaction solution, and then the reaction solution was extracted with ethyl acetate. The organic phase was concentrated to obtain Compound 210-6 (4.2 g, yield: 96%).

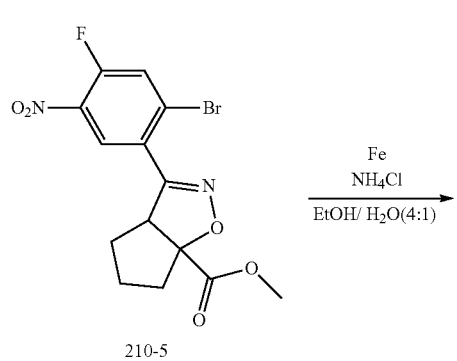

210-5

210-6

(6) Compound 210-6 (4.25 g, 11.9 mmol, 1.0 eq), and Compound 210-7 (2.48 g, 11.9 mmol, 1.0 eq) were added to 50 ml of acetic acid. The reaction solution was reacted at 125° C. for 0.5-1 hour. It was detected by LCMS that the reaction of raw materials was basically completed, and the principal peak of LCMS chromatogram belonged to the product. The reaction solution was concentrated to remove the solvent to obtain a crude product of Compound 210-8 (9 g).

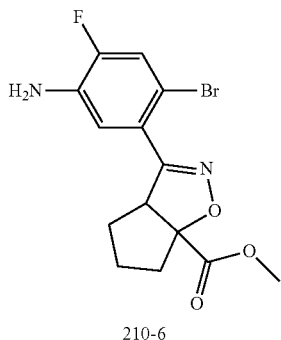

210-8

(7) Compound 210-8 (9 g, 17.30 mmol, 1.0 eq) and K$_2$CO$_3$ (7.17 g, 51.9 mmol, 3 eq) were added to 100 ml of DMF in sequence, to which was added dropwise methyl iodide (7.37 g, 51.9 mmol, 3 eq) at room temperature. Then, the reaction solution was reacted at 35° C. for 3 hours. The molecular weight of the product was determined by LCMS, and the peaks of raw materials in LCMS chromatogram almost disappeared. The reaction solution was extracted with ethyl acetate and water. The organic phase was washed three times with saturated aqueous solution of sodium chloride, dried and concentrated, and purified by column chromatography to obtain Compound 210 (2 g, red solid).

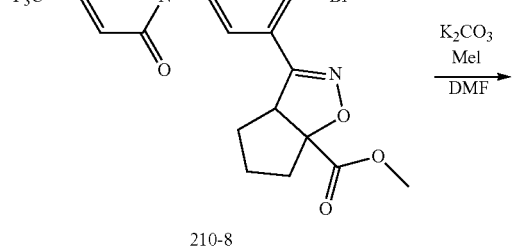

210-8

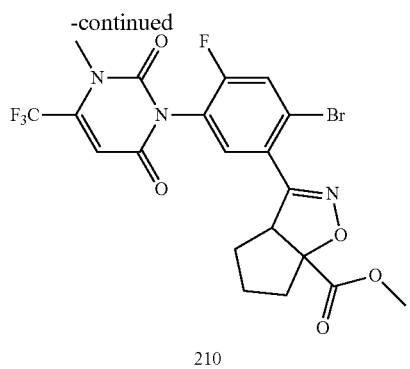

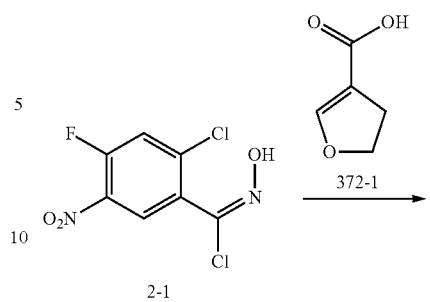

(8) 10 ml of DMF, Compound 210 (0.5 g, 0.3935 mmol, 1.0 eq), CuCN (167.6 mg, 1.87 mmol, 2 eq) were added to a microwave tube containing 20 ml of DMF in sequence, and, under the protection of $N_2$, the reaction was carried out with microwave at 150° C. for 1 hour. The reaction of raw materials was basically completed as detected by LCMS, and the principle peaks in LCMS chromatogram belonged to the product. The reaction solution was extracted with ethyl acetate and water. The organic phase was washed three times with saturated aqueous solution of sodium chloride, dried and concentrated, and purified by column chromatography to obtain Compound 212 (0.1 g, yield: 22%).

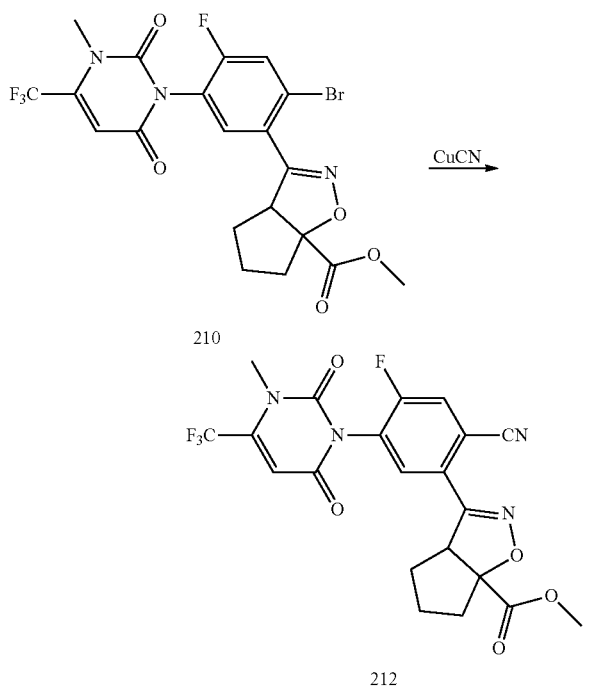

5. Synthesis of Compound 372

(1) Compound 2-1 (1.0 eq) and dichloromethane as a solvent (10 V) were charged in a 50 ml bottle, to which was added dropwise triethylamine (1.5 eq), and then added with Compound 372-1 (1.1 eq) in condition of ice-water bath. The above solution was warmed to room temperature, and reacted with stirring overnight. After the reaction was completed, the reaction solution was washed with water. The organic phase was collected, mixed with silica gel and sent for separation (DCM:MeOH), to obtain Compound 372-2, yield: 42%.

(2) Compound 372-2 (1.0 eq) obtained in the previous step, dichloromethane as a solvent (5V) and DMF (10% mol) at a catalytic amount were charged in a 50 ml bottle, to which was added dropwise thionyl chloride (2.0 eq) in condition of water bath. After the addition was completed, the reaction solution was warmed to reflux for 2 h. After the reaction was completed, the solvent and excess thionyl chloride were removed under reduced pressure. The residue was dissolved in dichloromethane (5V), to which was added dropwise methanol (10.0 eq), followed by warming to reflux. After the reaction was completed, the solvent and methanol were removed under reduced pressure. The residue was dissolved in ethyl acetate, and washed with brine. The organic phase was collected, mixed with silica gel and sent for separation, to obtain Compound 372-3, (yield: 85%).

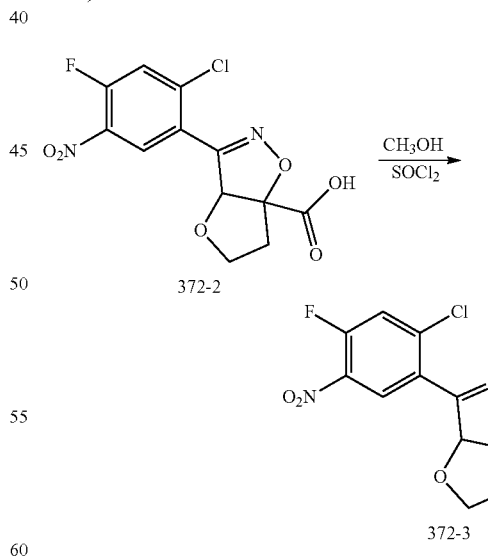

(3) The Compound 372-3 obtained in the previous step, ethanol and water (5:1) as a solvent, Fe powder (3.0 eq), and ammonium chloride (2.0 eq) were charged in a 50 ml bottle. The reaction solution was warmed to 80° C. and reacted with stirring for 1 h. After the reaction was completed, the reaction solution was filtered with celite, and the filtrate was collected and concentrated by rotary evaporation. The residue was dissolved in ethyl acetate, and washed with brine. The organic phase was collected, dried and concentrated by rotary evaporation, to obtain Compound 372-4, (yield: 40%).

was added to the reaction solution for dilution, and then the reaction solution was extracted with ethyl acetate. The organic phase was washed with saturated brine, collected, mixed with silica gel and sent for separation, to obtain Compound 372, (yield: 32%).

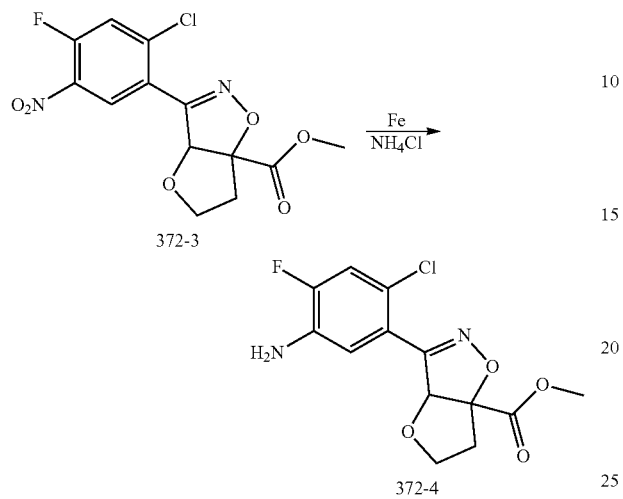

(4) Compound 372-4 obtained in the previous step, acetic acid (10V) as a solvent, and cyclic lactone Compound 210-7 (1.1 eq) were charged in a 50 ml bottle. The above solution was warmed to 125° C. to carry out reaction for 0.5 hours. After the reaction was completed, the solvent was removed by rotary evaporation under reduced pressure, and the residue was dissolved in DMF and put aside for later use.

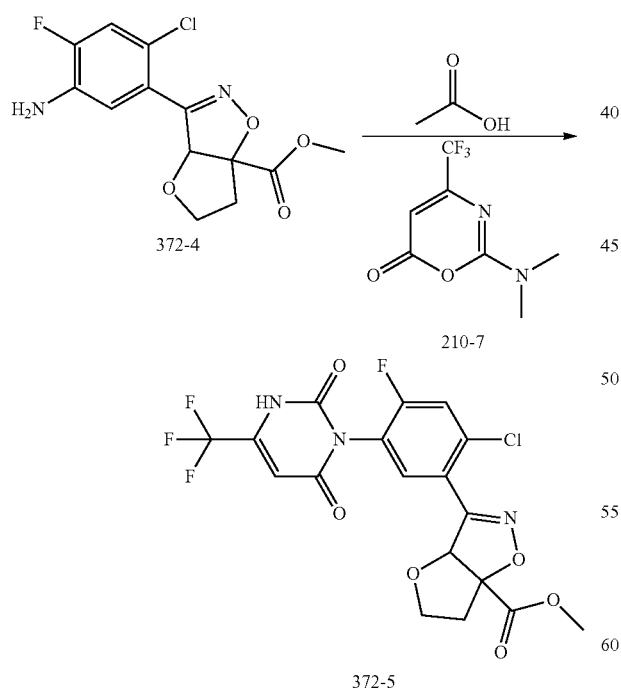

(5) Methyl iodide (3.0 eq) and anhydrous potassium carbonate (5.0 eq) were directly added in the reaction bottle of the previous step. Then, the reaction solution was reacted at 30° overnight. After the reaction was completed, water

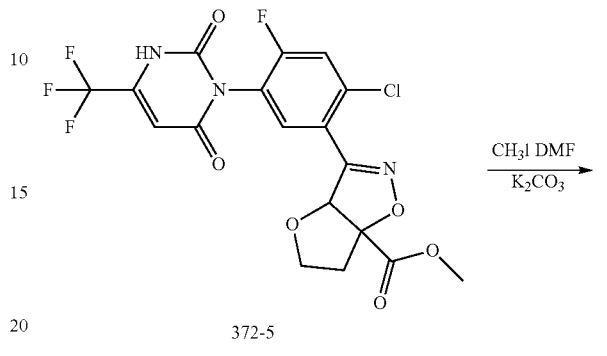

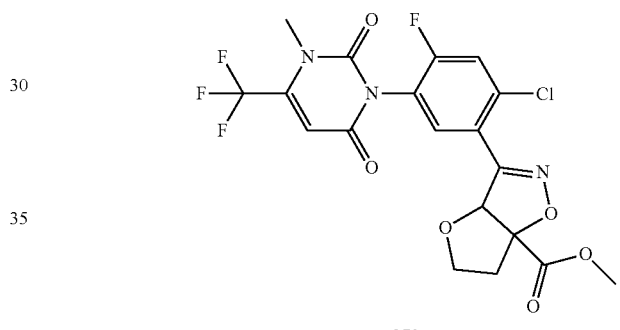

6. Synthesis of Compound 521

With a reference to the method in steps (2) and (3) of Item 4 described in the above, Compound 521-1 was prepared from

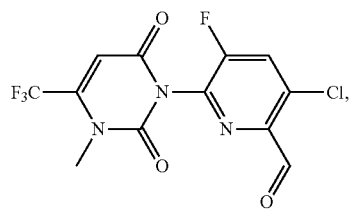 [SMILES: Cn1c(C(F)(F)F)cc(=O)n(-c2nc(C=O)c(Cl)cc2F)c1=O]

and then Compound 521-1 (0.4 g, 1 mmol, 1.0 eq), Compound a (0.126 g, 1 mmol, 1.0 eq) and TEA (0.202 g, 2 mmol, 2.0 eq) were added to 10 ml of DCM. Thereafter, the above solution was reacted at room temperature with stirring for 2 hours. The completion of the reaction was detected by LCMS. The reaction solution was concentrated, and purified by column chromatography to obtain Compound 521 (0.245 g, yield: 50%) (white oil).

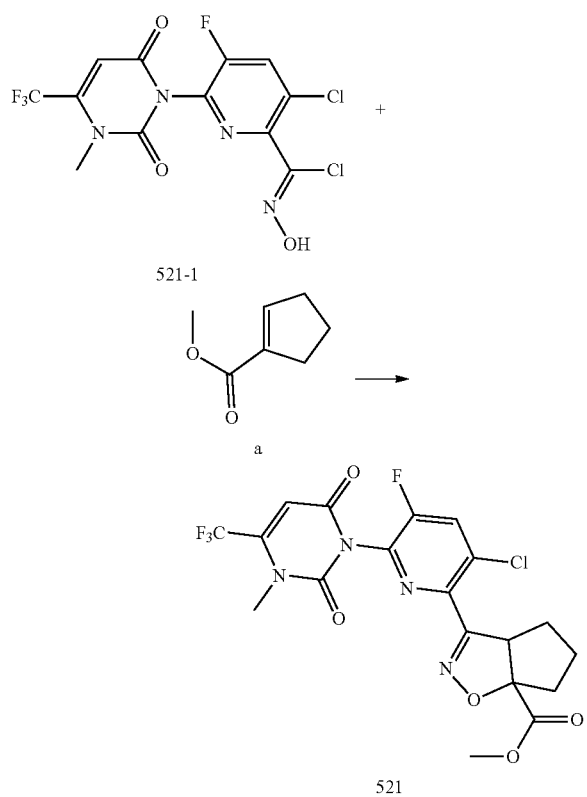

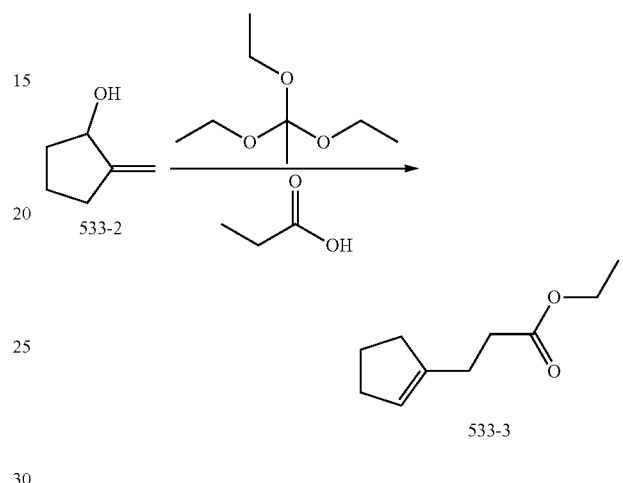

7. Synthesis of Compound 533

(1) Trimethylsulfur iodide (4 eq) and THF as a solvent (10 V) were charged to a 100 ml three-necked flask, the temperature was reduced to −20° C., and then, under the protection of nitrogen, n-butyl lithium (3.3 eq) was added dropwise. After the addition was completed, the reaction solution was stirred under thermal insulation condition for 30 min, to which was then added dropwise a solution of 1,2-epoxycyclopentane (Compound 533-1) in THF. After the addition was completed, the reaction solution was slowly warmed to room temperature within 1 h, and stirred at room temperature for 2 h. After the reaction was completed, the reaction solution was quenched with water and then extracted with ethyl ether. The organic phase was collected, washed with brine, dried over anhydrous magnesium sulfate, filtered, and concentrated to about 10 ml remaining, and put aside for later use.

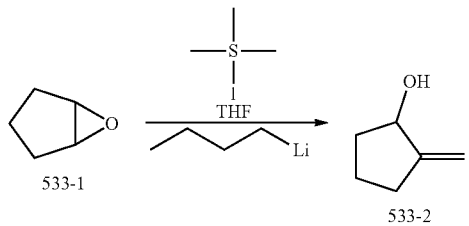

(2) Triethyl orthoacetate (5.38 eq) and propionic acid (0.26 eq) were charged in the flask of the previous step, followed by warming to 145° C. The reaction solution was reacted under open condition to evaporate the ethanol produced. After the ethanol was removed, the reaction solution was kept at 145° and reacted with stirring for 1 h. After the reaction was completed, the reaction solution was cooled to room temperature, diluted by adding ethyl ether, and then reacted with 1M $KHSO_4$ (30 ml) with stirring overnight. The organic phase was isolated, and the aqueous phase was extracted with ethyl ether. The organic phases were combined, washed with saturated sodium bicarbonate, collected, dried over anhydrous sodium sulfate and rotary-evaporated, to obtain Compound 533-3. The obtained product was used in the next step without further purification.

(3) Compound 2-1 (1.0 eq) and dichloromethane as a solvent (5 V) were charged in a 50 ml bottle. In condition of ice-water bath, triethylamine (2 eq) and then 533-3 (1.2 eq) were added dropwise. The above solution was warmed to room temperature, and reacted with stirring overnight. After the reaction was completed, the reaction solution was washed with water. The organic phase was collected, mixed with silica gel and sent for separation, to obtain Compound 533-4.

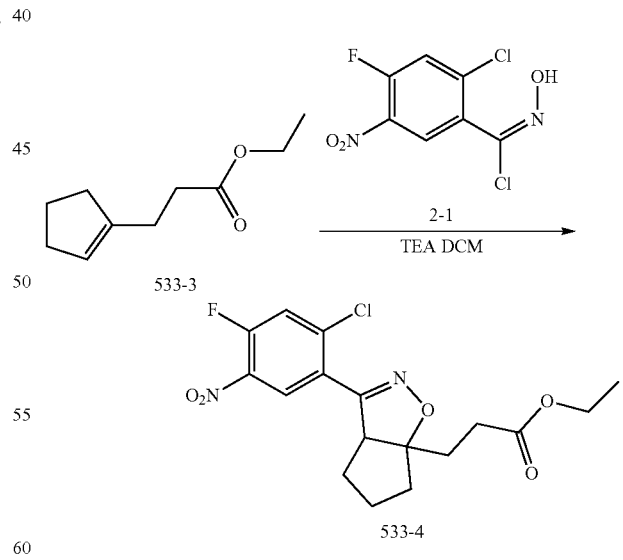

(4) Compound 533-4 (1.0 eq) obtained in the previous step, a mixed solvent of ethanol and water (5:1), Fe powder (3 eq) and ammonium chloride (2 eq) were charged in a 50 ml bottle. The above solution was warmed to 80° and reacted with stirring for 1 h. After the reaction was completed, the reaction solution was filtered with celite, and the filtrate was collected and rotary-evaporated. The residue was dissolved with ethyl acetate, and washed with brine. The organic phase was collected, dried and rotary-evaporated, to obtain Compound 533-5.

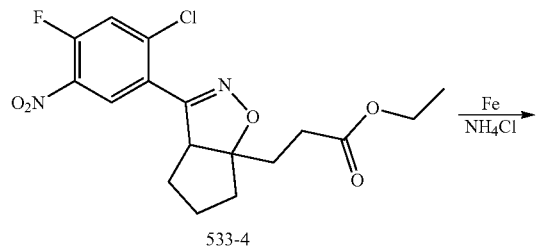

(5) Compound 533-5 (1.0 eq) obtained in the previous step, acetic acid as a solvent (10 V) and Compound 210-7 (1.1 eq) were charged in a 50 ml bottle. The above solution was warmed to 125° C. to carry out reaction for 0.5 hours. After the reaction was completed, the reaction solution was rotary-evaporated under reduced pressure to remove the solvent. The residue was dissolved in DMF and put aside for later use.

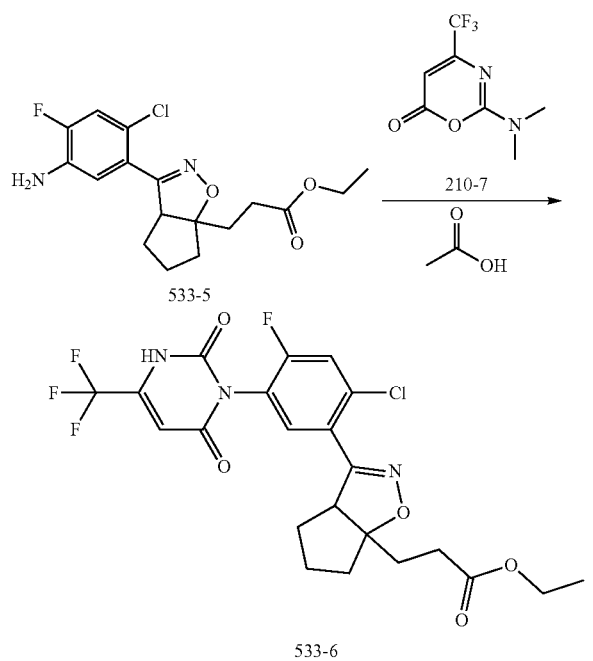

(6) Methyl iodide (3.0 eq) and anhydrous potassium carbonate (5 eq) were directly added in the flask of the previous step. Then, the reaction solution was reacted at 30° C. overnight. After the reaction was completed, the reaction solution was added with water for dilution and extracted with ethyl acetate. The organic phase was washed with saturated brine, collected, mixed with silica gel and sent for separation, to obtain Compound 533.

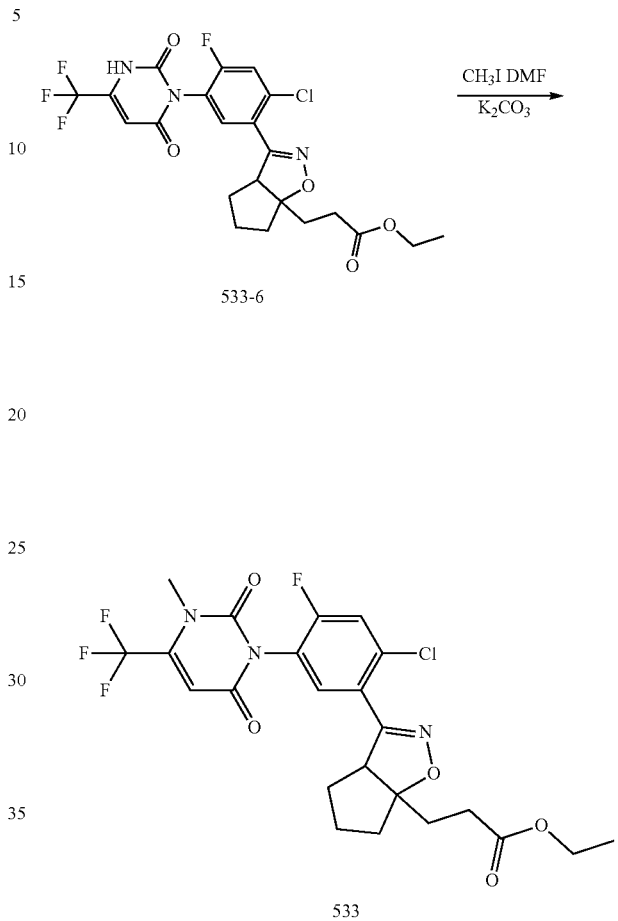

8. Synthesis of Compounds 541 and 544

(1) Compounds 2-3 and 541-1 (2.0 eq) were added to 20 ml of acetic acid. The reaction solution was reacted at 125° C. for 15 hours. It was detected by LCMS that the reaction of raw materials was basically completed, and the principal peak in LCMS chromatogram belonged to the product. The reaction solution was concentrated to remove the solvent. The resulting crude product was separated by column chromatography to obtain Compound 541 (yield: 54%).

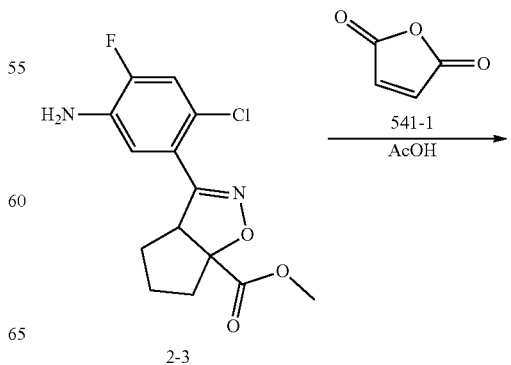

-continued

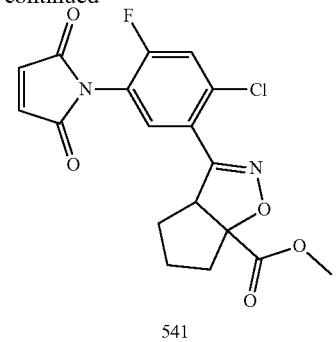
541

(2) Compound 541, nitroisopropane (1.5 eq) and TEA (1.5 eq) were added to 20 ml of DCM. Then, the above solution was reacted at room temperature for 10 minutes. It was detected by LCMS that the peaks of raw materials in LCMS chromatogram disappeared. The resulting crude product was directly mixed with silica gel, and purified by column chromatography to obtain Compound 544 (yellow solid), yield 56%.

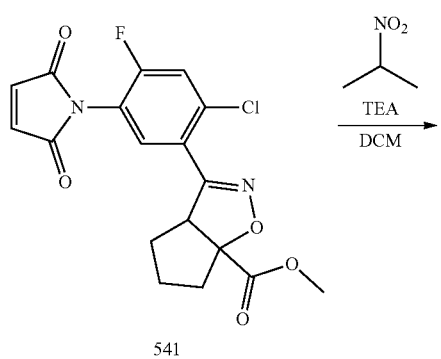
541

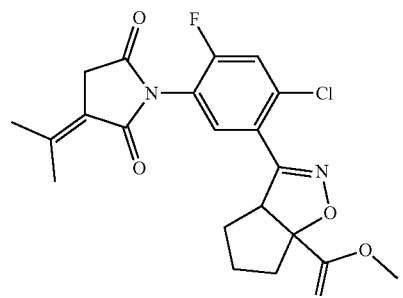
544

9. Synthesis of Compound 545

Compound 2-3 (1.0 eq), Compound 545-1 (2.0 eq) and glacial acetic acid were charged in a single-necked flask. The reaction solution was warmed to 125°, and stirred for 3 hours. It was detected by LCMS that the reaction of raw materials was basically completed. The reaction solution was rotary-evaporated to remove the solvent. The residue was dissolved with ethyl acetate, mixed with silica gel, and purified by column chromatography to obtain Compound 545 (yield 62%).

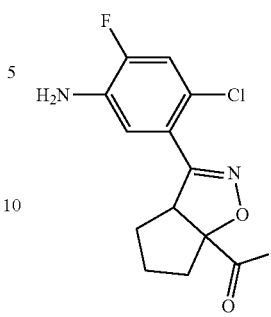 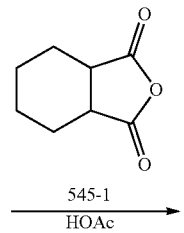
2-3

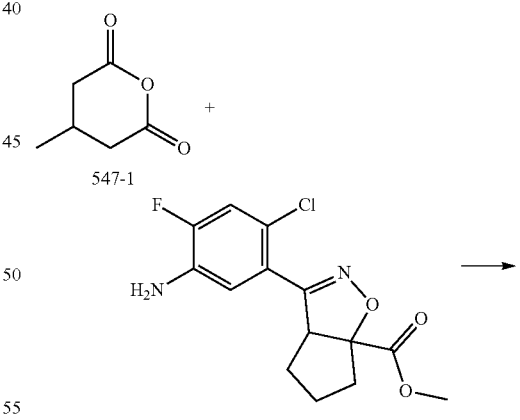
545

10. Synthesis of Compound 547

Compound 547-1 (0.128 g, 1 mmol, 1.0 eq) and Compound 2-3 (0.312 g, 1 mmol, 1.0 eq) were added to 10 ml of acetic acid. Then, the reaction solution was stirred at 120° C. for 12 hours. The completion of the reaction was detected by LCMS. The reaction solution was concentrated, and purified by column chromatography to obtain Compound 547. (0.11 g, yield: 26%) (white oil).

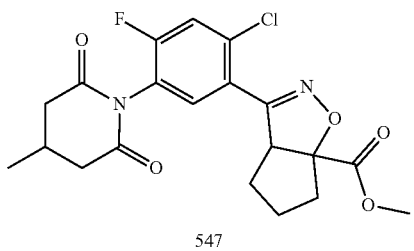
547-1

2-3

547

11. Synthesis of Compound 551

Compound 2-3 (0.312 g, 1 mmol, 1.0 eq), Compound 551-1 (0.165 g, 1 mmol, 1.0 eq), TEA (0.202 g, 2 mmol, 2.0 eq) and CDI (0.162 g, 1 mmol, 1.0 eq) were added to 10 ml of acetonitrile. Then, the reaction solution was stirred at 60° for 1 hour. The completion of the reaction was detected by LCMS. The reaction solution was concentrated, and purified by column chromatography to obtain Compound 551, 0.11 g (26% yield) (white solid).

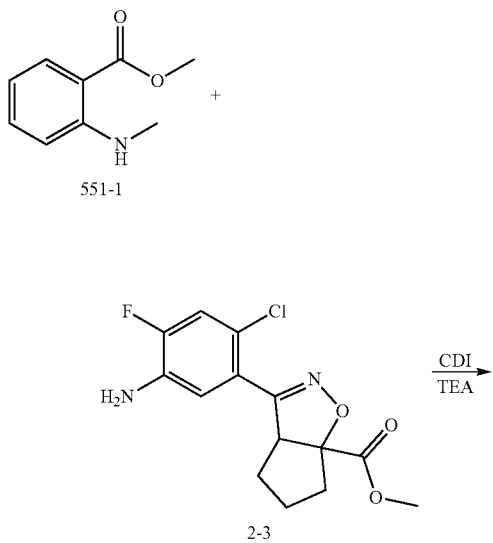

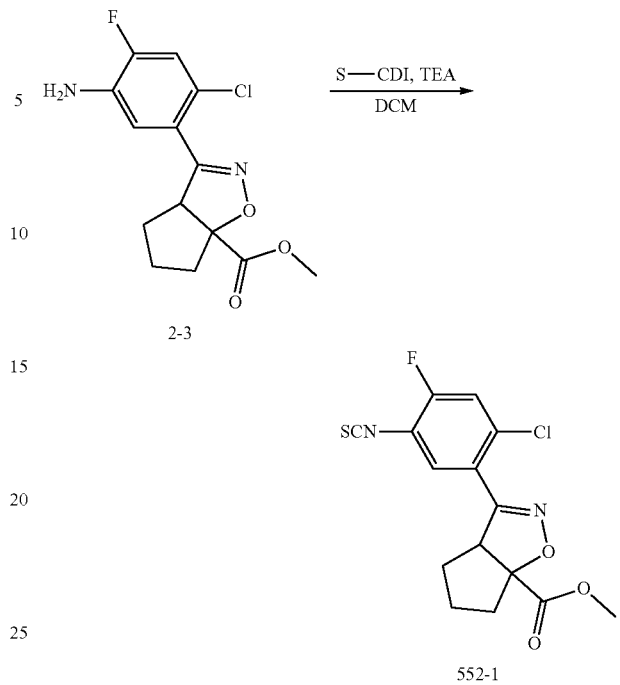

(2) Compound 552-1, Et$_3$N (3 eq) and propylamine (3 eq) were added to 20 ml of DCM. Then, the above solution was reacted at room temperature for 3 hours. It was detected by LCMS that the peaks of raw materials in LCMS chromatogram disappeared. The resulting crude product was directly mixed with silica gel, and purified by column chromatography to obtain Compound 552-2 (yellow solid); yield: 52%.

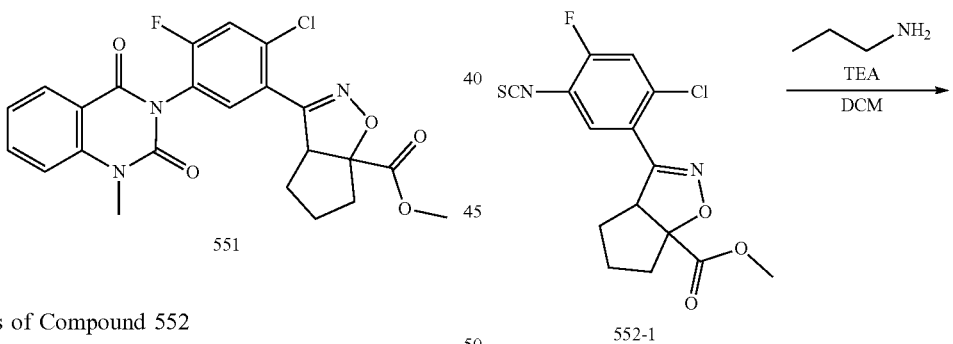

12. Synthesis of Compound 552

(1) Compound 2-3 (260 mg), Et$_3$N (3 eq) and S-CDI

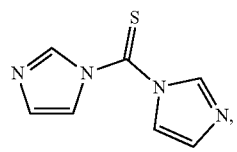 [SMILES: S=C(n1ccnc1)n1ccnc1]

3.0 eq) were added to 20 ml of DCM. Then, the reaction solution was reacted at room temperature overnight. It was detected by LCMS that the peaks of raw materials in LCMS chromatogram disappeared. The resulting crude product was directly mixed with silica gel, and purified by column chromatography to obtain Compound 552-1 (yield: 65%) (yellow solid).

(3) Compound 552-2, potassium carbonate (3 eq) and oxalyl chloride (1.1 eq) were added to 20 ml of DMF. The above solution was first reacted in condition of ice bath for half an hour, and then warmed to 50° C. to continue the reaction for 1 hour. It was detected by LCMS that the peaks of raw materials in LCMS chromatogram disappeared. The reaction solution was washed with water, and extracted with ethyl acetate. The organic phase was mixed with silica gel, and purified by column chromatography to obtain Compound 552 (yellow solid); yield: 38%.

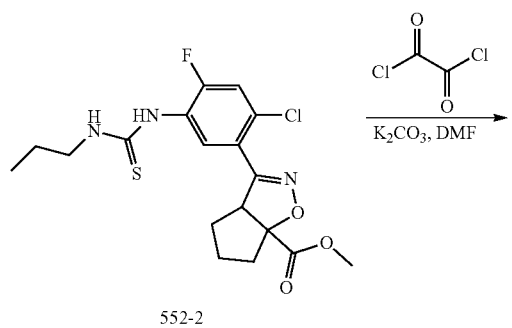

552-2

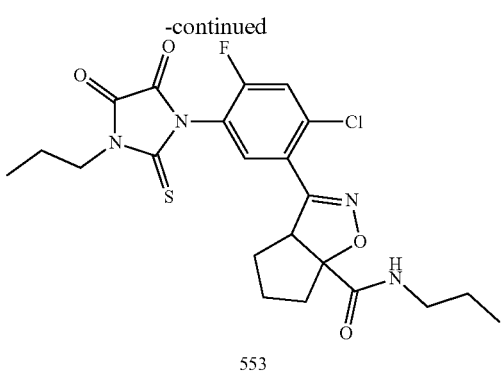

553

14. Synthesis of Compound 561

(1) Activated carbon powder (0.25 g) was added to Compound 561-2 (3.10 ml, 25.7 mmol) with stirring at −20° C. (cooled in a dry ice/isopropanol bath) in nitrogen-protection condition. Compound 561-1 (2.55 g, 25.7 mmol) was dissolved in ethyl acetate (25 ml), and slowly added dropwise to the reaction system, while keeping the temperature below 0° C. The reaction solution was reacted at room temperature overnight. It was detected by TLC (potassium permanganate for color developing) that the reaction of raw materials was almost completed. The reaction solution was filtered to remove a precipitate and activated carbon, and the filter cake was washed with ethyl acetate. The filtrate was dried under vacuum at 40° C. to obtain crude product of Compound 561-3 (1.8 g). Compound 561-3 was yellow turbid oil.

552

13. Synthesis of Compound 553

Compound 552 and propylamine (10 eq) were added to 20 ml of DCM. Then, the above solution was reacted at room temperature for 3 hours. It was detected by LCMS that the peaks of raw materials in LCMS chromatogram disappeared. The resulting crude product was directly mixed with silica gel, and purified by column chromatography to obtain Compound 553 (yellow solid): yield: 72%.

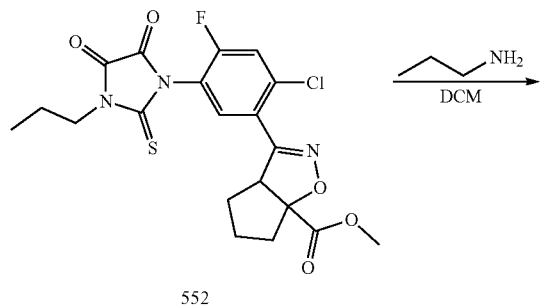

552

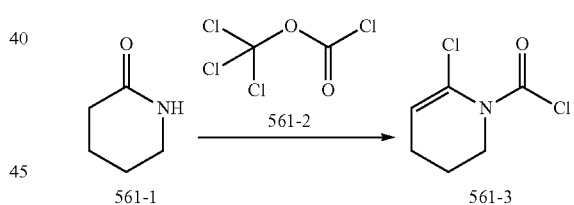

561-1      561-3

(2) Compound 2-3 (1.5 g, 4.8 mmol) was dissolved in concentrated hydrochloric acid (15 ml). The solution was cooled to −5° C., to which was slowly added dropwise an aqueous solution of NaNO₂ (397 mg, 5.76 mmol), followed by reacting at ~5° C. for 1 hour. Stannous chloride (2.27 g, 11.99 mmol) was dissolved in concentrated hydrochloric acid (5 ml), and slowly added dropwise to the reaction system, followed by reacting at 0° C. for 1-2 hours. It was detected by LCMS that the reaction of raw materials was almost completed, and a product was formed in an amount of ~75%, 10 g of celite was added to the reaction system with vigorous stirring. The pH of the reaction system was adjusted to about 8-9 with 10% NaOH aqueous solution at 0° C., followed by extraction twice with dichloromethane. The organic phase was dried and then concentrated, to obtain crude product of Compound 561-4 (1.2 g).

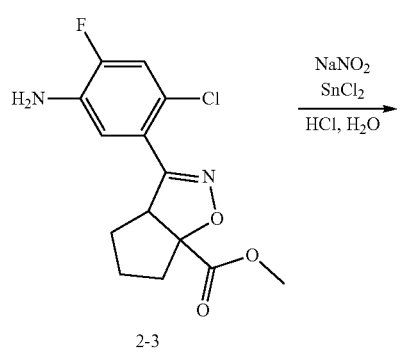

2-3

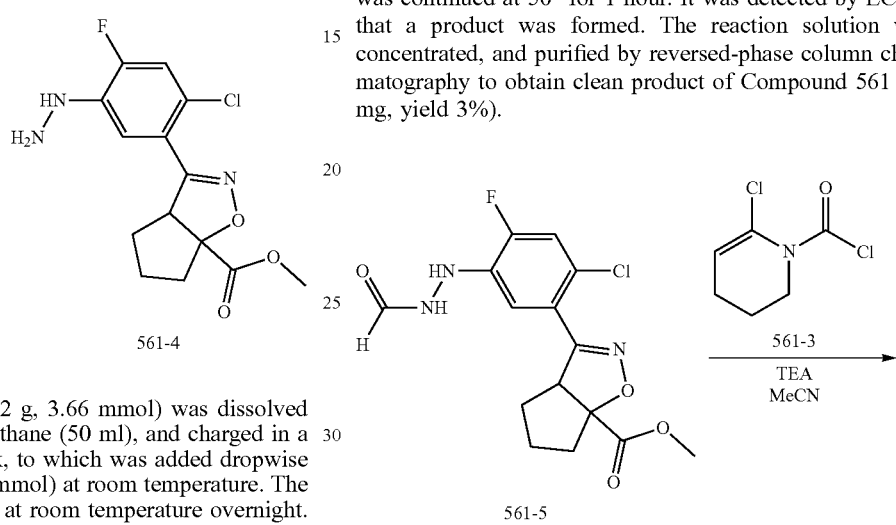

(4) Compound 561-5 (0.75 g, 2.11 mmol) was dissolved with anhydrous acetonitrile (30 ml), and charged in a 100 mL single-necked flask. The solution was cooled to 0° C., to which was added dropwise a solution of Compound 561-3 (417 mg, 2.32 mmol) in acetonitrile (10 ml). While keeping the temperature below 10° C., triethylamine (87 mg, 2.16 mmol) was added dropwise. The above solution was reacted at 0° C. for 30 min, and then warmed to 50° C. to continue the reaction for 6-7 hours. It was detected by LCMS that the reaction of raw materials was completed, and an intermediate state was formed. 6N HCl (3.16 ml, 18.97 mmol) was added dropwise to the reaction system, and then the reaction was continued at 50° for 1 hour. It was detected by LCMS that a product was formed. The reaction solution was concentrated, and purified by reversed-phase column chromatography to obtain clean product of Compound 561 (27 mg, yield 3%).

(3) Compound 561-4 (1.2 g, 3.66 mmol) was dissolved with anhydrous dichloromethane (50 ml), and charged in a 100 mL single-necked flask, to which was added dropwise formic acid (185 mg, 4.03 mmol) at room temperature. The above solution was reacted at room temperature overnight. It was detected by LCMS that the reaction of raw materials was completed, and the principal peak of LCMS chromatogram belonged to the product. The reaction solution was concentrated at 40° C. to obtain crude product of Compound 561-5 (0.8 g).

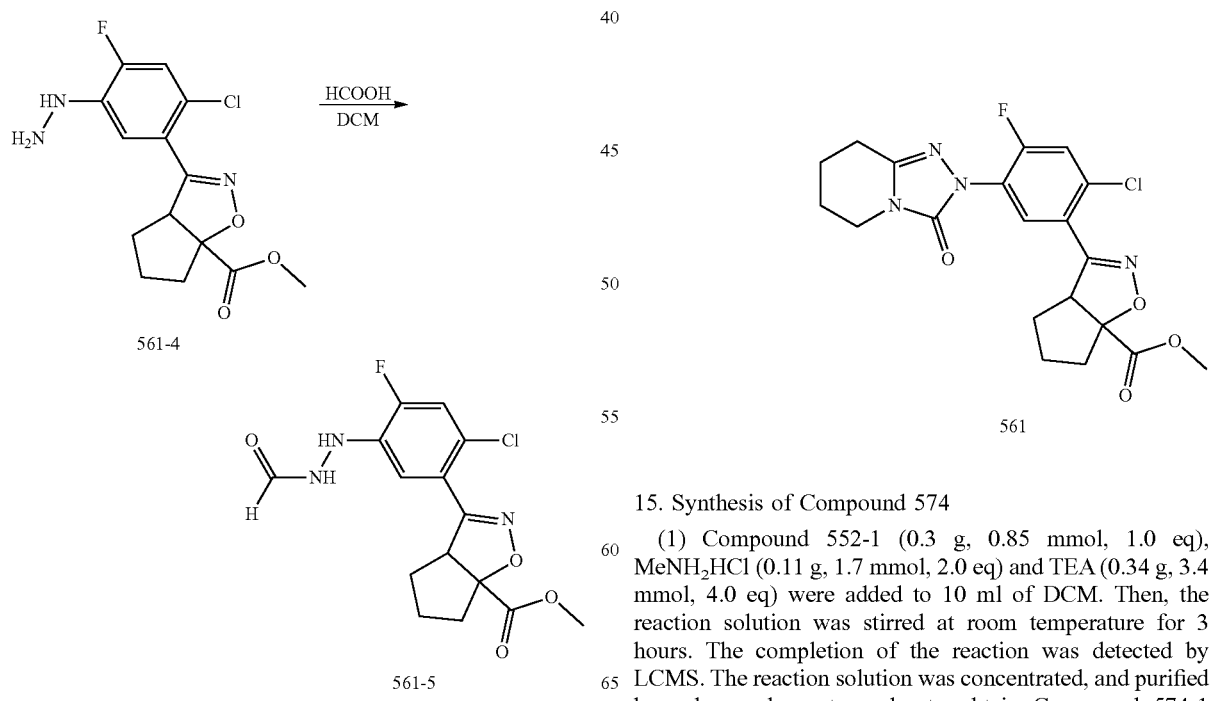

15. Synthesis of Compound 574

(1) Compound 552-1 (0.3 g, 0.85 mmol, 1.0 eq), MeNH₂HCl (0.11 g, 1.7 mmol, 2.0 eq) and TEA (0.34 g, 3.4 mmol, 4.0 eq) were added to 10 ml of DCM. Then, the reaction solution was stirred at room temperature for 3 hours. The completion of the reaction was detected by LCMS. The reaction solution was concentrated, and purified by column chromatography to obtain Compound 574-1 (0.25 g, yield: 76%) (white oil).

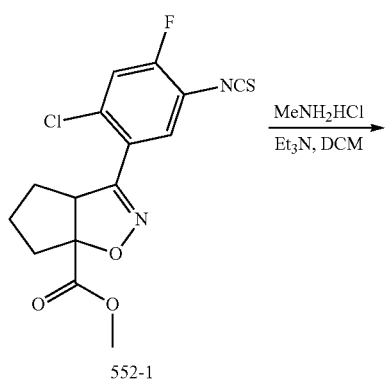

552-1

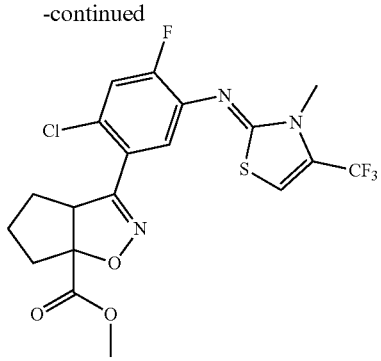

574

16. Synthesis of Compound 575

Compound 552-1 (1.0 eq) and hexahydropyridazine hydrochloride (1.1 eq) and triethylamine (3.0 eq) were dissolved in DCM (10 V), followed by reacting at room temperature for 1 hour. After the In-Process Control was completed, CDI (1.5 eq) was added. The reaction solution was warmed to 45° C. to continue the reaction overnight, and there was a product formed during the In-Process Control. The resulting crude product was mixed with silica gel, and purified by column chromatography to obtain Compound 575 (yield 38%).

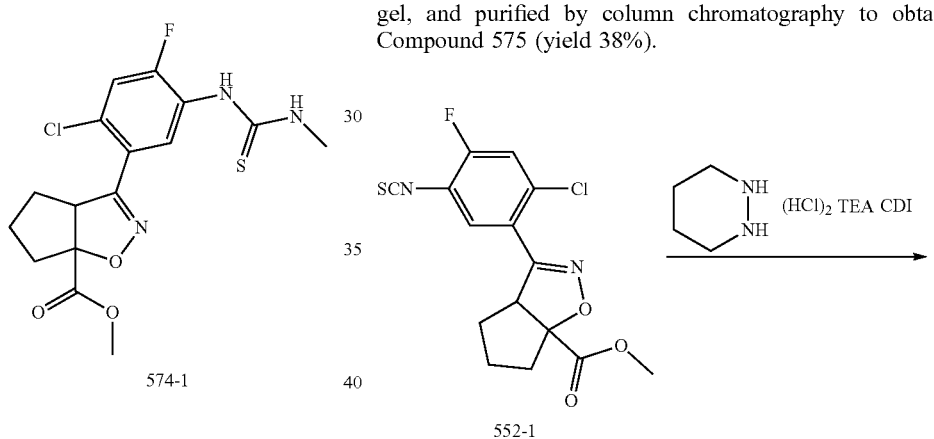

574-1

552-1

575

(2) Compound 574-1 (0.25 g, 0.65 mmol, 1.0 eq), Compound 574-2 (0.14 g, 0.71 mmol, 1.1 eq) and TEA (0.08 g, 0.78 mmol, 1.2 eq) were added to 10 ml of toluene. Then, the reaction solution was stirred at 100° C. for 8 hours. The completion of the reaction was detected by LCMS. The reaction solution was concentrated, and purified by column chromatography to obtain Compound 574 (0.03 g, yield: 10%) (white solid).

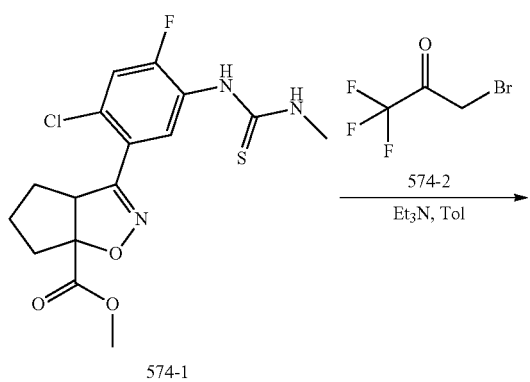

574-1

17. Synthesis of Compounds 577, 578 and 579

(1) Compound 2-3 (0.312 g, mmol, 1.0 eq) and NaNO$_2$ (0.14 g, 2 mmol, 2.0 eq) were added to 10 ml of HBr aqueous solution, and CuBr (0.284 g, 2 mmol, 2.0 eq) was added at 0° C. Then, the reaction solution was stirred at room temperature for 2 hours. The completion of the reaction was detected by LCMS. The reaction solution was concentrated, and extracted with ethyl acetate. The organic phase was washed with saturated brine, evaporated to dryness, and purified by column chromatography, to obtain Compound 578-1 as an intermediate (0.3 g, yield: 85%) (yellow solid).

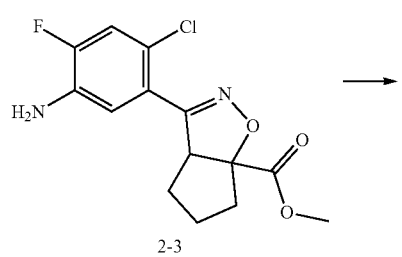

2-3

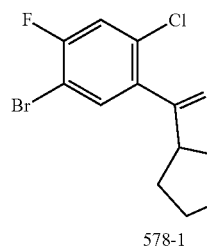

578-1

(2) Compound 578-1 (0.376 g, 1 mmol, 1.0 eq), Compound 578-2 (0.254 g, 1 mmol, 1.0 eq) and KOAc (0.2 g, 2 mmol, 2.0 eq) were added to 10 ml of dioxane, and Pd(dppf)Cl$_2$ (0.1 g, 0.1 mmol, 0.1 eq) was added in nitrogen-protection condition. Then, the reaction solution was stirred at 80° C. for 12 hours. The completion of the reaction was detected by LCMS. The reaction solution was concentrated, and purified by column chromatography to obtain Compound 578-3 as an intermediate (0.17 g, yield: 50%) (white oil).

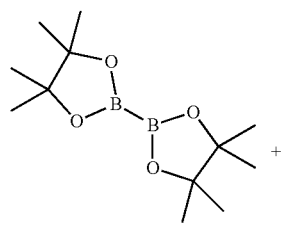

578-2

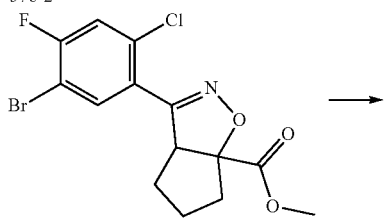

578-1

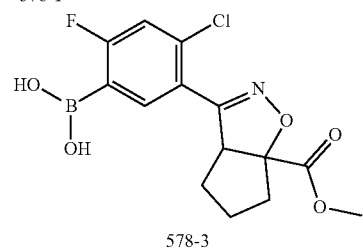

578-3

(3) Compound 578-4 was dissolved in dioxane which has a volume 12 times of Compound 578-4, to which was slowly added dropwise sodium methoxide solution (1.5 eq, 30%), followed by warming to 100° C. and reacting for 16 hours. After the In-Process Control was completed, the reaction solution was cooled, and filtered under vacuum. The solid was dissolved with 1M hydrochloric acid solution. The liquid phase was concentrated and then dissolved with 1M hydrochloric acid solution. The two solutions were combined, and extracted with ethyl acetate until the aqueous phase had no product. The organic phase was concentrated to obtain a solid, which was then beated and purified with petroleum ether ethyl acetate=10:1, filtered, and dried to obtain Compound 578-5.

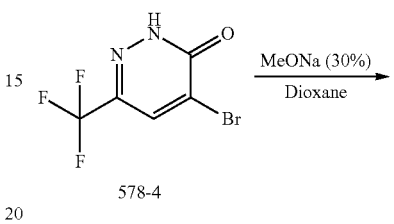

578-4

578-5

(4) Compound 578-5 was added to DCE which has a volume 10 times of Compound 578-5, to which were then added phosphorus oxychloride (3.0 eq) and a catalytic amount of DMF (5%), followed by warming to 100° and reacting for 16 hours. After the In-Process Control, the reaction solution was cooled, and concentrated to remove excess phosphorus oxychloride. After the addition of water to quench the reaction, the pH of the reaction solution was adjusted to 8-9 with potassium carbonate. The reaction solution was extracted with dichloromethane. The organic phase was concentrated, mixed with silica gel, and purified by column chromatography to obtain Compound 578-6.

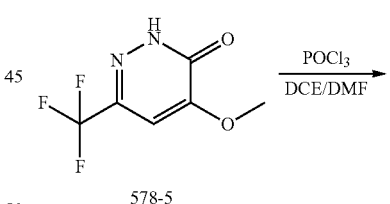

578-5

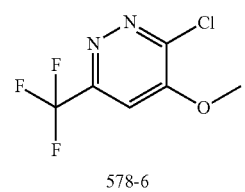

578-6

(5) Water (1 ml), Compound 578-6 (0.212 g, 1 mmol, 1.0 eq), Compound 578-3 (0.341 g, 1 mmol, 1.0 eq) and Cs$_2$CO$_3$ (0.652 g, 2 mmol, 2.0 eq) were added to 10 ml of dioxane, and Pd(dppf)Cl$_2$ (0.1 g, 0.1 mmol, 0.1 eq) was added in nitrogen-protection condition. Then, the reaction solution was stirred at 100° C. for 12 hours. The completion of the reaction was detected by LCMS. The reaction solution was concentrated, and purified by column chromatography to obtain Compound 578 (0.24 g, yield: 50%) (white oil).

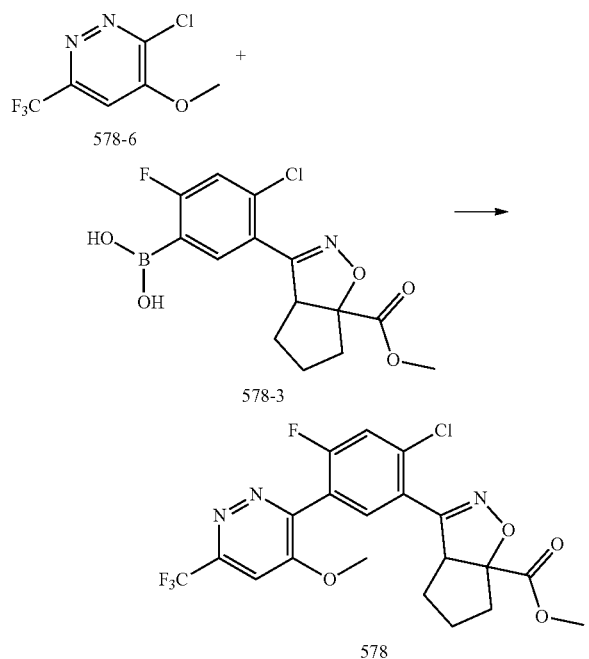

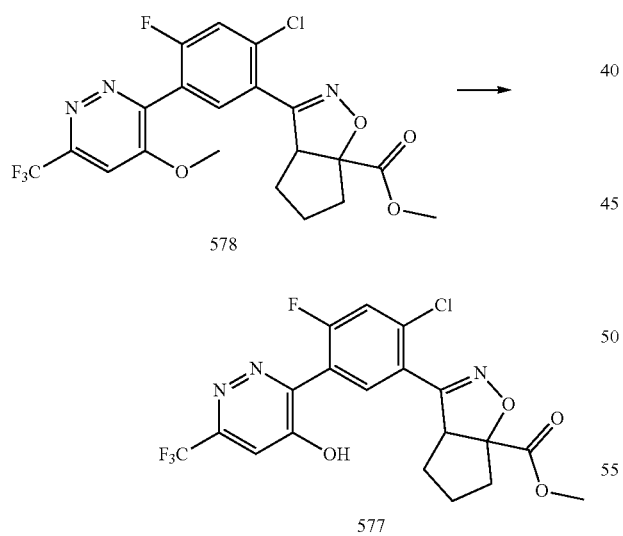

(6) Compound 578 (0.473 g, 1 mmol, 1.0 eq) and KOAc (0.2 g, 2 mmol, 2.0 eq) were added to 10 ml of DMSO. Then, the reaction solution was stirred at 12° C. for 2 hours. LCMS test showed the completion of the reaction. The reaction solution was concentrated, and purified by column chromatography to obtain compound 577 (0.23, g51% yield) (white oil).

(7) Compound 577 (0.459 g, 1 mmol, 1.0 eq), K₂CO₃ (0.276 g, 2 mmol, 2.0 eq), IME (0.286 g, 2 mmol, 2.0 eq) were added to 10 ml of DMF. Then, the reaction solution was stirred at room temperature for 2 hours. The completion of the reaction was detected by LCMS. The reaction solution was concentrated, and purified by column chromatography to obtain Compound 579 (0.12 g, yield: 25%) (white oil).

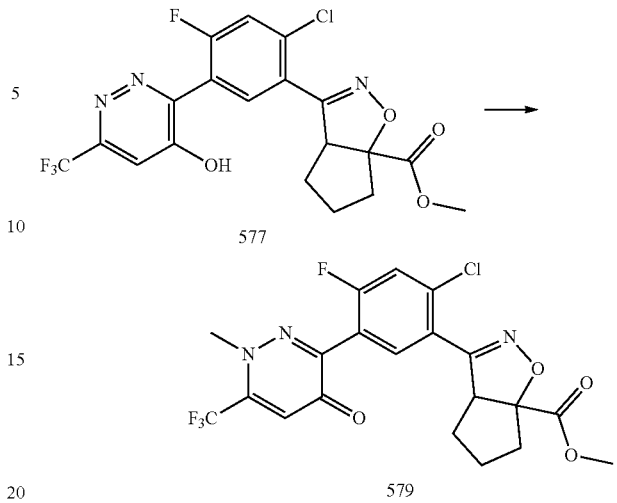

18. Synthesis of Compounds 587 and 588

(1) Compound 587-1 (0.1 g, 1 mmol, 1.0 eq), Compound 578-1 (0.376 g, 1 mmol, 1.0 eq) and TEA (0.202 g, 2 mmol, 2.0 eq) were added to 10 ml of dioxane. Pd(pph₃)₄ (0.1 g, 0.1 mmol, 0.1 eq) and CuI (0.019 g, 0.1 mmol, 0.1 eq) were added in nitrogen-protection condition. Then, the reaction solution was stirred at 100° C. for 12 hours. The completion of the reaction was detected by LCMS. The reaction solution was concentrated, and purified by column chromatography to obtain product 0.19 g (yield: 49%) (yellow solid).

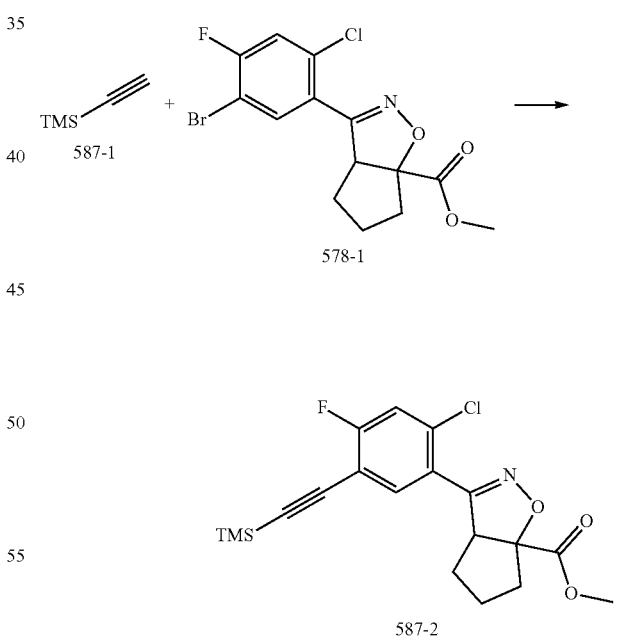

(2) Compound 587-2 (0.394 g, 1 mmol, 1.0 eq) and K₂CO₃ (0.138 g, 1 mmol, 1.0 eq) were added to 10 ml of THF. Then, the reaction solution was stirred at room temperature for 2 hours. The completion of the reaction was detected by LCMS. The reaction solution was concentrated, and purified by column chromatography to obtain product 0.2 g (yield: 62%) (white oil).

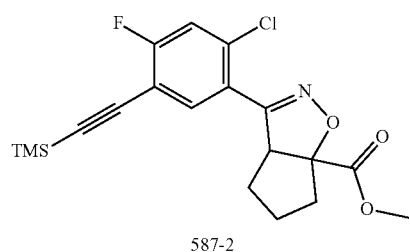

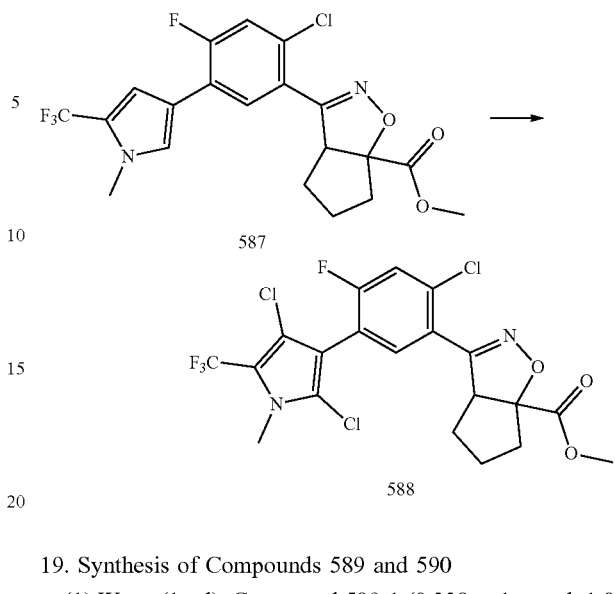

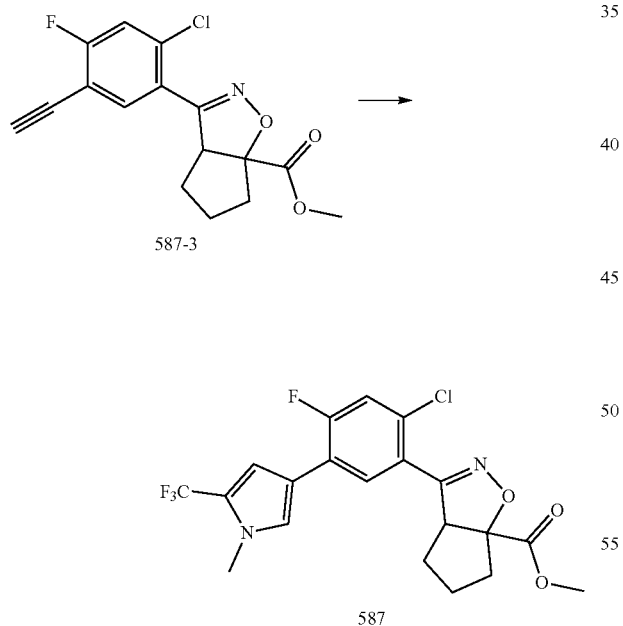

(3) Compound 587-3 (0.321 g, 1 mmol, 1.0 eq), Sarcosine (0.2 g, 2 mmol, 2.0 eq) and (CF$_3$CO)$_2$O (0.218 g, 1 mmol, 1.0 eq) were added to 10 ml of Ac$_2$O. Then, the reaction solution was stirred at 120° C. for 12 hours. The completion of the reaction was detected by LCMS. The reaction solution was concentrated, and purified by column chromatography to obtain product 0.22 g (yield: 51%) (white oil).

(4) Compound 587 (0.44 g, 1 mmol, 1.0 eq) and NCS (0.27 g, 2 mmol, 2.0 eq) were added to 10 ml of DMF. Then, the reaction solution was stirred at 60° C. for 2 hours. The completion of the reaction was detected by LCMS. The reaction solution was concentrated, and purified by column chromatography to obtain product 0.1 g (yield: 20%) (white oil).

19. Synthesis of Compounds 589 and 590

(1) Water (1 ml), Compound 589-1 (0.228 g, 1 mmol, 1.0 eq), Compound 578-3 (0.341 g, 1 mmol, 1.0 eq) and Cs$_2$CO$_3$ (0.652 g, 2 mmol, 2.0 eq) were added to 10 ml of dioxane, and Pd(dppf)Cl$_2$ (0.1 g, 0.1 mmol, 0.1 eq) was added in nitrogen-protection condition. Then, the reaction solution was stirred at 100° C. for 12 hours. The completion of the reaction was detected by LCMS. The reaction solution was concentrated, and purified by column chromatography to obtain product 0.11 g (yield: 25%) (white solid).

(2) Compound 589 (0.44 g, 1 mmol, 1.0 eq) and NBS (0.178 g, 1 mmol, 1.0 eq) were added to 10 ml of DMF. Then, the reaction solution was stirred at 80° C. for 12 hours. The completion of the reaction was detected by LCMS. The reaction solution was concentrated, and purified by column chromatography to obtain product 0.1 g (yield: 19%) (white solid).

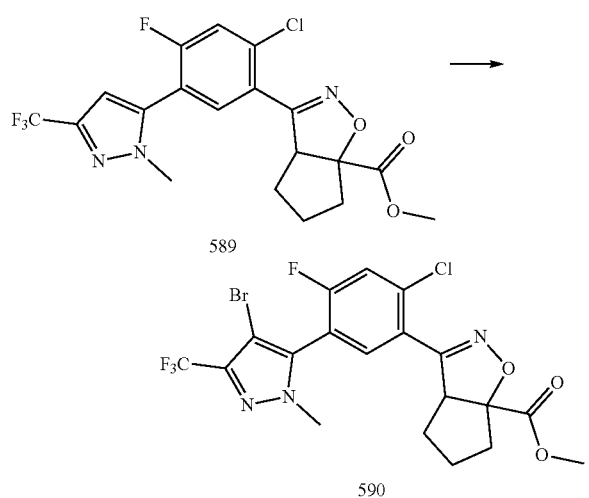

20. Synthesis of Compound 596

Compound 596-1 (0.196 g, 1 mmol, 1.0 eq), Compound 578-1 (0.375 g, 1 mmol, 1.0 eq), $K_2CO_3$ (0.276 g, 2 mmol, 2.0 eq) and $Cu_2O$ (0.028 g, 0.2 mmol, 0.2 eq) were added to 10 ml of DMF. Then, the reaction solution was stirred at 140° for 2 hours. The completion of the reaction was detected by LCMS. The reaction solution was concentrated, and purified by column chromatography to obtain Compound 596 (0.1 g, yield: 21%) (white oil).

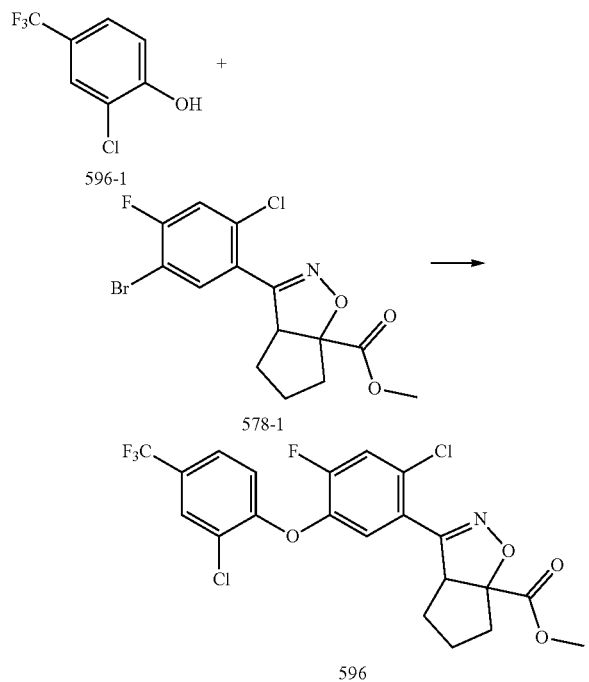

Biological Activity Evaluation:

The activity level criteria for plant damage (i.e., growth control rate) are as follows:

Level 5: growth control rate is above 85%;
Level 4: growth control rate is greater than or equal to 60% and less than 85%;
Level 3: growth control rate is greater than or equal to 40% and less than 60%;
Level 2: growth control rate is greater than or equal to 20% and less than 40%;
Level 1: growth control rate is greater than or equal to 5% and less than 20%;
Level 0: growth control rate is less than 5%.

The above growth control rates are fresh weight control rates.

Experiment on weeding effect in post-emergence stage:

Monocotyledonous and dicotyledonous weed seeds (*Descurainia sophia, Capsella bursa-pastoris, Abutilon theophrasti, Galium aparine, Stellaria media, Lithospermum arvense, Rorippa indica, Alopecurus aequalis, Alopecurus japonicus, Eleusine indica, Beckmannia syzigachne, Sclerochloa dura, Phleum paniculatum, Veronica didyma Tenore, Bromus japonicus, Aegilops tauschii, Phalaris arundinacea, Amaranthus retrojlexus, Chenopodiaceae, Commelina communis, Sonchus arvensis, convolvulus arvensis, Cirsium setosum, Solanum nigrum, Acalypha australis, Digitaria sanguinalis, Echinochloa crusgalli, Setaria viridis, Setaria glauca, Leptochloa chinensis, Monochoria vaginalis, Sagittaria trifolia, Scirpus juncoides, Cyperus rotundus, Cyperus iria, Cyperus difformis, Fimbristylis, Portulaca oleracea, Xanthium sibiricum, Pharbitis nil, Conyza japonica*, etc.) and major crop seeds (wheat, corn, rice, soybean, cotton, oilseed rape, millet, sorghum, potato, sesame, ricinus, etc.) were placed in plastic pots filled with soil, then covered with 0.5-2 cm of soil, allowed to grow in a good greenhouse environment. After 2 weeks of sowing, the test plants were treated in the 2-3 leaf stage. The tested compounds of the present invention were respectively dissolved in acetone, then added with Tween 80 and 1.5 liter/ha of emulsifiable concentrate of methyl oleate as synergist, diluted with a certain amount of water to obtain a solution with a certain concentration, and sprayed with a spray tower onto the plants. After the application, the plants were cultured for 3 weeks in the greenhouse, and then the experimental results of the weeding were counted. The doses of the used compounds were 500, 250, 125, 60, 15, 7.5 g a.i./ha, and the averages were obtained by repeating for three times. Representative data are listed in Table 2-3.

TABLE 2

Results on weeding effect in post-emergence stage

| Compound No. | *Alopecurus japonicus* | *Beckmannia syzigachne* | *Conyza japonica* | *Capsella bursa-pastoris* | Dose (g a.i./ha) |
|---|---|---|---|---|---|
| 2 | 5 | 5 | 5 | 5 | 15 |
| 3 | 5 | 5 | 4 | 5 | 15 |
| 4 | 5 | 5 | 4 | 5 | 15 |
| 10 | 5 | 5 | 4 | 5 | 15 |
| 13 | 5 | 5 | 4 | 5 | 15 |
| 49 | 4 | 5 | 4 | 5 | 15 |
| 51 | 4 | 4 | 4 | 5 | 15 |
| 66 | 5 | 4 | 4 | 5 | 15 |
| 209 | 5 | 5 | 5 | 5 | 15 |
| 210 | 5 | 5 | 5 | 5 | 15 |
| 211 | N | N | 5 | 5 | 15 |
| 212 | N | N | 5 | 5 | 15 |
| 213 | 5 | 5 | 4 | 5 | 15 |
| 214 | 5 | 5 | 5 | 5 | 15 |
| 215 | 5 | 5 | 4 | 5 | 15 |
| 216 | 5 | 5 | 4 | 5 | 15 |
| 217 | 5 | 5 | 4 | 5 | 15 |
| 222 | 5 | 5 | 4 | 5 | 15 |
| 225 | 5 | 5 | 4 | 5 | 15 |
| 231 | 5 | 5 | 4 | 5 | 15 |
| 245 | 5 | 5 | 4 | 5 | 15 |
| 261 | 5 | 5 | 4 | 5 | 15 |
| 264 | N | N | 4 | 5 | 15 |

TABLE 2-continued

Results on weeding effect in post-emergence stage

| Compound No. | Alopecurus japonicus | Beckmannia syzigachne | Conyza japonica | Capsella bursa-pastoris | Dose (g a.i./ha) |
|---|---|---|---|---|---|
| 278 | 5 | 5 | 4 | 5 | 15 |
| 333 | 4 | 4 | 4 | 4 | 15 |
| 334 | N | N | 4 | 5 | 15 |
| 351 | N | N | 4 | N | 15 |
| 370 | N | N | N | 5 | 125 |
| 372 | 4 | 4 | 4 | 5 | 125 |
| 374 | N | N | 5 | 5 | 125 |
| 395 | N | N | N | 5 | 125 |
| 424 | 5 | 5 | 5 | 5 | 15 |
| 425 | 5 | 5 | 4 | 5 | 15 |
| 426 | 5 | 4 | 4 | 5 | 15 |
| 427 | 5 | 4 | 4 | 5 | 15 |
| 435 | N | N | N | 5 | 15 |
| 440 | N | N | N | 5 | 15 |
| 441 | 4 | 4 | 4 | 5 | 15 |
| 443 | 5 | 5 | 4 | 5 | 15 |
| 444 | 4 | N | N | 5 | 15 |
| 451 | 4 | 4 | 4 | 5 | 15 |
| 456 | N | N | 4 | 5 | 15 |
| 464 | 5 | N | N | 5 | 15 |
| 472 | N | N | 4 | 5 | 15 |
| 474 | 4 | 4 | 4 | 5 | 15 |
| 476 | 5 | 5 | 4 | 5 | 15 |
| 477 | 5 | 4 | 4 | 5 | 15 |
| 491 | N | N | N | 5 | 15 |
| 497 | N | N | N | 5 | 15 |
| 498 | 5 | 5 | 4 | 5 | 15 |
| 521 | 5 | 5 | 4 | 5 | 15 |
| 530 | 5 | 4 | 4 | 5 | 125 |
| 533 | 5 | 5 | 5 | 5 | 125 |
| 534 | N | N | 4 | 5 | 15 |
| 542 | 5 | 4 | 4 | 4 | 15 |
| 544 | N | N | N | 5 | 125 |
| 545 | N | N | N | 5 | 125 |
| 546 | N | N | N | 5 | 125 |
| 547 | N | N | N | 5 | 125 |
| 551 | N | N | N | 5 | 125 |
| 552 | N | N | N | 5 | 125 |
| 553 | N | N | N | 5 | 15 |
| 561 | N | N | N | 5 | 125 |
| 574 | N | N | 5 | 5 | 15 |
| 575 | 4 | N | 4 | 5 | 15 |
| 577 | N | N | 5 | 5 | 125 |
| 578 | 5 | N | 4 | 5 | 15 |
| 579 | 4 | N | N | 5 | 15 |
| 584 | N | N | 5 | 5 | 125 |
| 585 | 5 | 5 | 4 | 5 | 15 |
| 586 | N | N | 5 | 5 | 125 |
| 587 | N | N | N | 5 | 125 |
| 588 | N | N | N | 5 | 125 |
| 589 | N | N | N | 5 | 125 |
| 590 | N | N | N | 5 | 125 |
| 597 | N | N | 4 | 5 | 15 |

Note:
N represents no data.

TABLE 3

Control test results on weeding effect in post-emergence stage

| Compound No. | Setaria viridis | Digitaria sanguinalis | Eleusine indica | Conyza japonica | Rorippa indica | Dose (g a.i./ha) |
|---|---|---|---|---|---|---|
| 3 | 4 | 4 | 4 | 3 | 5 | 7.5 |
| Control compound A | 2 | 2 | 3 | 2 | 2 | 7.5 |
| 209 | 5 | 5 | 5 | 4 | 5 | 7.5 |
| Control compound B | 3 | 2 | 3 | 2 | 2 | 7.5 |

Note:
Control compound A:

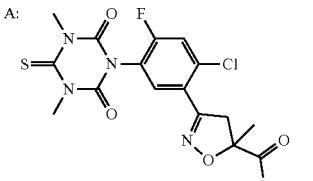

Control compound B:

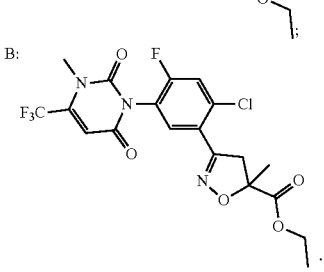

Experiment on weed effect in pre-emergence stage:

Seeds of monocotyledonous and dicotyledonous weeds and main crops (e.g. wheat, corn, rice, soybean, cotton, oilseed rape, millet and sorghum) were put into a plastic pot loaded with soil and covered with 0.5-2 cm soil. The test compounds of the present invention was dissolved with acetone, then added with tween 80, diluted by a certain amount of water to reach a certain concentration, and sprayed immediately after sowing. The obtained seeds were incubated for 4 weeks in the greenhouse after spraying and the test results were observed. It was observed that the herbicide mostly had excellent effect at the application rate of 250 g a.i./ha, especially to weeds such as *Echinochloa crusgalli*, *Digitaria sanguinalis* and *Abutilon theophrasti*, etc. And many compounds had good selectivity for corn, wheat, rice, and soybean, etc.

It is indicated from the experiment of main weeds in wheat and rice fields that the compound of the present invention generally have good weed control efficacy. Above all, it is noted that the compound of the invention have extremely high activity to broad-leaved weeds and cyperaceae weeds, which are resistant to ALS inhibitor, like *Sagittaria trifolia*, *Scirpus juncoides*, *Cyperus difformis*, *Descurainia sophia*, *Capsella bursa-pastoris*, *Lithospermum arvense*, *Galium aparine*, and *Cyperus rotundus*, etc., and have excellent commercial value.

Transplanted rice safety evaluation and weed control effect evaluation in rice field:

Rice field soil was loaded into a 1/1,000,000 ha pot. The seeds of *Echinochloa crusgalli*, *Scirpus juncoides*, and *Bidens tripartita L.* were sowed and gently covered with soil, then left to stand still in greenhouse in the state of 0.5-1 cm of water storage. The tuber of *Sagittaria trifolia* was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Echinochloa crusgalli*, *Scirpus juncoides*, and *Bidens tripartita L*. reached 0.5 leaf stage and *Sagittaria trifolia* reached the time point of primary leaf stage.

In addition, the rice field soil that loaded into the 1/1,000,000 ha pot was leveled to keep water storage at 3-4 cm depth. The 3 leaf stage rice (japonica rice) was transplanted at 3 cm of transplanting depth the next day. The compound of the present invention was treated by the same way after 5 days of transplantation.

The fertility condition of *Echinochloa crusgalli*, *Scirpus juncoides*, *Bidens tripartita L*., and *Sagittaria trifolia* 14 days after the treatment of the compound of the invention and the fertility condition of rice 21 days after the treatment of the compound of the invention respectively with the naked eye. Evaluate the weed control effect with the above activity standard level. Many compounds show excellent activity and selectivity.

Note: The seeds of *Echinochloa crusgalli*, *Scirpus juncoides*, and *Bidens tripartita L*., and *Sagittaria trifolia* were collected from Heilongjiang Province of China. The tests indicated that the weeds were resistant to the common doses of Pyrazosulfuron-ethyl.

At the same time, it is found after several tests that the compounds and compositions of the present invention have good selectivity to many gramineae grasses such as zoysia japonica, bermuda grass, tall fescue, bluegrass, ryegrass and seashore paspalum etc, and are able to control many important grass weeds and broad-leaved weeds. The compounds also show excellent selectivity and commercial value in the tests on sugarcane, soybean, cotton, oil sunflower, potato, orchards and vegetables in different herbicide application methods.

What is claimed is:

1. A fused-ring substituted aromatic compound, represented by general formula I:

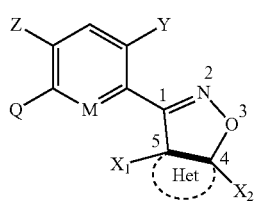

I wherein,
Q represents

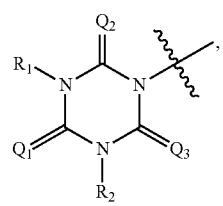

Q-1

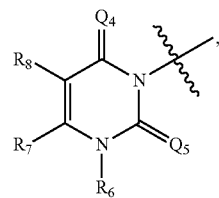

Q-2

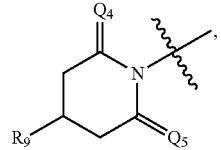

Q-3

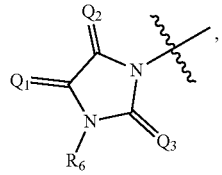

Q-4

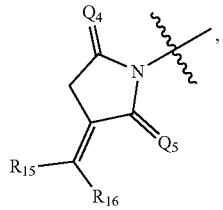

Q-5

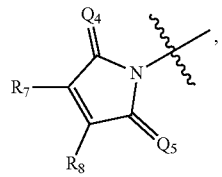

Q-6

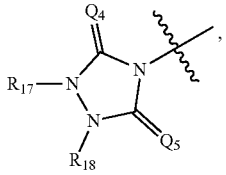

Q-7

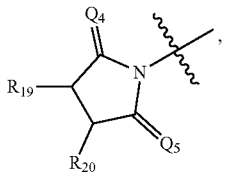

Q-8

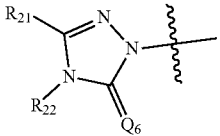

Q-9

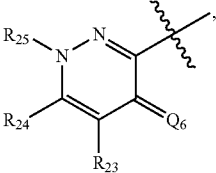

Q-10

Q-11 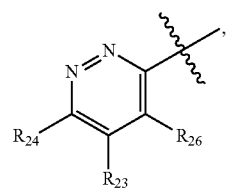
Q-12 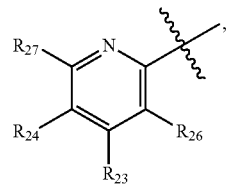
Q-13 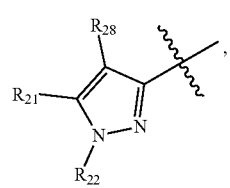
Q-14 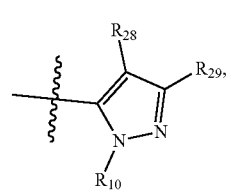
Q-15 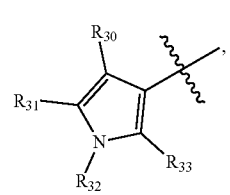
Q-16 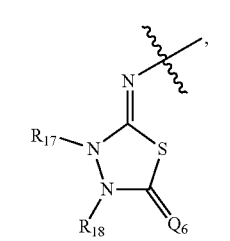
Q-17 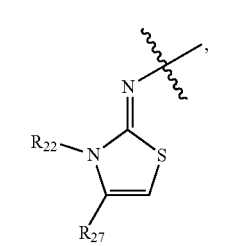
Q-18 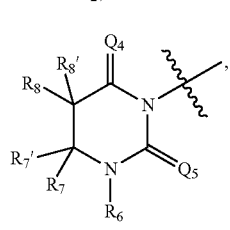
Q-19 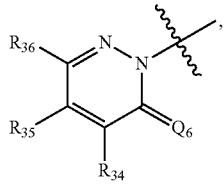
Q-20 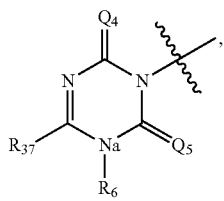
Q-21 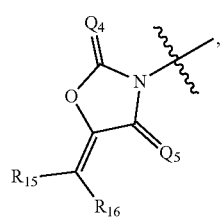
Q-22 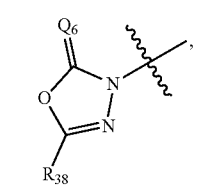
Q-23 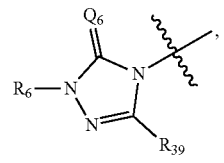
Q-24 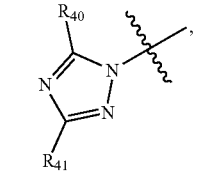
Q-25 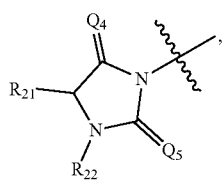
Q-26 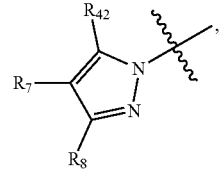

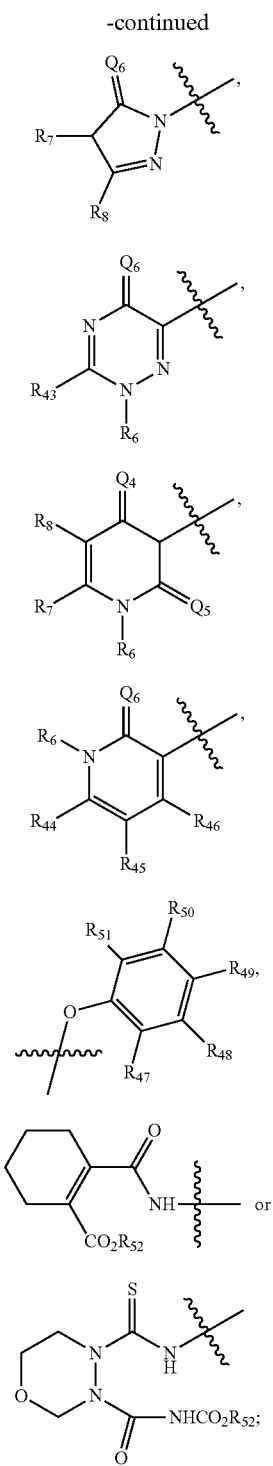

Y represents halogen, haloalkyl, cyano, nitro or amino;
Z represents H, halogen or hydroxy;
M represents CH or N;
$Q_1$, $Q_2$, $Q_3$, $Q_4$, $Q_5$, $Q_6$ each independently represent O or S;
Het represents a cyclic structure that shares two carbon atoms at 4- and 5-positions with isoxazoline ring to form a fused ring; the cyclic structure is 3-8 member saturated or unsaturated carbocyclyl or saturated or unsaturated heterocyclyl containing 1, 2 or 3 heteroatoms selected from O, S, N, NH, CO, $SO_2$ or C=N—O—$R_{14}$; except for the 4- and 5-positions that are respectively substituted by $X_2$ or $X_1$, other positions on the Het are each independently unsubstituted or substituted by at least one group selected from halogen, cyano, nitro, alkyl, alkenyl, alkynyl, cycloalkyl, haloalkyl, haloalkenyl, haloalkynyl, halo cycloalkyl, alkyl-substituted cycloalkyl, —$OR_{14}$, —$SR_{14}$, —$SOR_{14}$, —(CO)$OR_{14}$, —($SO_2$)$R_{14}$, —N($R_{14}$)$_2$ or —O—(CO)$OR_{14}$;

$X_1$, $X_2$ each independently represent H, halogen, nitro, cyano, thiocyano, hydroxy, mercapto, sulfo, formyl, haloformyl, azido, alkyl, alkenyl, alkynyl, cycloalkyl, cycloalkylalkyl, cycloalkenyl, cycloalkenylalkyl, —PO(OR')$_2$, —OR", —(CO)R", —SR", —(SO)R", —($SO_2$)R", —Si(R")$_3$, —O(CO)R", —O—($SO_2$)R", —S(CO)R", —($SO_2$)OR", —O(CO)OR", —(CO)(CO)OR", —CR'=N—OH, —CR'=N—O—R", heterocyclyl, heterocyclylalkyl, aryl, arylalkyl, amino, aminoalkyl, amino carbonyl alkyl, amino carbonyloxy alkyl, amino thio carbonyloxy alkyl, amino sulfonyl or amino sulfonyloxy alkyl, wherein, the groups "alkyl", "alkenyl" and "alkynyl" are each independently unsubstituted or substituted by at least one group selected from halogen, cyano, hydroxy, mercapto, carboxyl, —OR", —(CO)R", —SR", —($SO_2$)R", —O(CO)H, —O(CO)R", —O—($SO_2$)R", —(CO)OR", —O(CO)OR", —O(CO)(CO)OH, —O(CO)(CO)OR", —O-alkyl-(CO)OH or —O—alkyl-(CO)OR", the groups "cycloalkyl", "cycloalkylalkyl", "cycloalkenyl", "cycloalkenylalkyl", "heterocyclyl", "heterocyclylalkyl", "aryl" and "arylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —$OR_{14}$, —$SR_{14}$, —(CO)$OR_{14}$, —($SO_2$)$R_{14}$, —N($R_{14}$)$_2$ or —O-alkyl-(CO)$OR_{14}$, or two adjacent carbon atoms on the ring together with unsubstituted or halogen-substituted —$OCH_2CH_2$— or —$OCH_2O$— form a fused ring, the groups "amino", "aminoalkyl", "amino carbonyl alkyl", "amino carbonyloxy alkyl", "amino thio carbonyloxy alkyl", "amino sulfonyl" and "amino sulfonyloxy alkyl" are each independently unsubstituted or substituted by one or two groups selected from —$R_1$, —$OR_{11}$, —(CO)$R_{11}$, —(CO)$OR_{11}$, -alkyl-(CO)$OR_{11}$, —($SO_2$)$R_{11}$, —($SO_2$)$OR_{11}$, -alkyl-($SO_2$)$R_{11}$, —(CO)N($R_{12}$)$_2$ or —($SO_2$)N($R_{12}$)$_2$;

R' independently represents H, halogen, alkoxy, alkoxyalkyl, alkyl, alkenyl, alkynyl, cycloalkyl, cycloalkylalkyl, cycloalkenyl, cycloalkenylalkyl, aryl, arylalkyl, heterocyclyl or heterocyclylalkyl; wherein, the groups "alkyl", "alkenyl" and "alkynyl" are each independently unsubstituted or substituted by halogen; the groups "cycloalkyl", "cycloalkylalkyl", "cycloalkenyl", "cycloalkenylalkyl", "aryl", "arylalkyl", "heterocyclyl" and "heterocyclylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —$OR_{14}$, —$SR_{14}$, —$(CO)OR_{14}$, —$(SO_2)R_{14}$, —$N(R_{14})_2$ or —O-alkyl-$(CO)OR_{14}$, or two adjacent carbon atoms on the ring together with unsubstituted or halogen-substituted —$OCH_2CH_2$— or —$OCH_2O$— form a fused ring;

R" independently represents alkyl, alkenyl, alkynyl, cycloalkyl, cycloalkylalkyl, cycloalkenyl, cycloalkenylalkyl, aryl, arylalkyl, arylalkenyl, heterocyclyl, heterocyclylalkyl or heterocyclylalkenyl; wherein, the groups "alkyl", "alkenyl" and "alkynyl" are each independently unsubstituted or substituted by at least one group selected from halogen, cyano, trialkylsilyl, —$OR_{13}$, —$SR_{13}$, —$O(CO)R_{13}$, —$(CO)R_{13}$, —$(CO)OR_{13}$ or —$O(CO)OR_{11}$; the groups "cycloalkyl", "cycloalkylalkyl", "cycloalkenyl", "cycloalkenylalkyl", "aryl", "arylalkyl", "arylalkenyl", "heterocyclyl", "heterocyclylalkyl" and "heterocyclylalkenyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —$OR_{14}$, —$SR_{14}$, —$(CO)OR_{14}$, —$(SO_2)R_{14}$, —$N(R_{14})_2$ or —O-alkyl-$(CO)OR_{14}$, or two adjacent carbon atoms on the ring together with unsubstituted or halogen-substituted —$OCH_2CH_2$— or —$OCH_2O$— form a fused ring;

$W_1$ represents O, S, NH or N-alkyl;

$W_2$ represents $OW_3$, $SW_3$ or $N(W_3)_2$;

$W_3$ independently represents H, alkyl, alkenyl, alkynyl, cycloalkyl, cycloalkenyl, heterocyclyl, aryl,

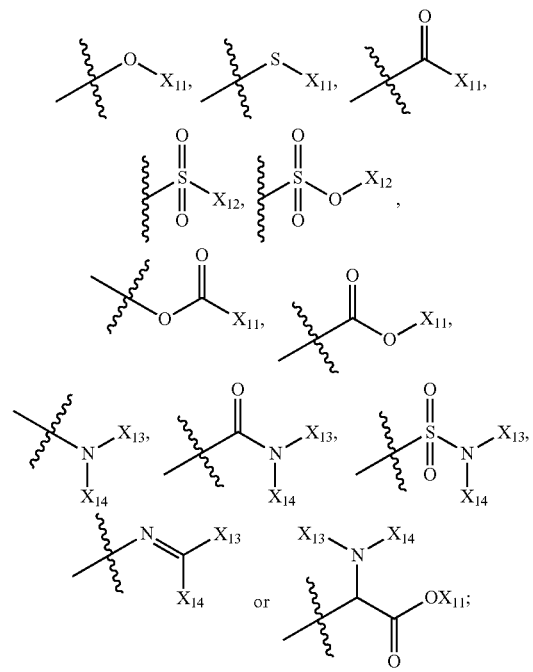

wherein, the groups "alkyl", "alkenyl" and "alkynyl" are each independently unsubstituted or substituted by at least one group selected from halogen, cyano, nitro, cycloalkyl, trialkylsilyl, cycloalkenyl, heterocyclyl, aryl,

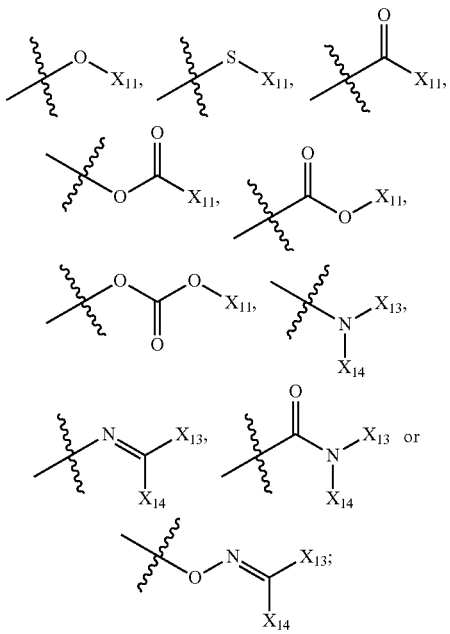

the groups "cycloalkyl", "cycloalkenyl", "heterocyclyl" and "aryl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —$OR_{14}$, —$SR_{14}$, —$(CO)OR_{14}$, —$(SO_2)R_{14}$, —$N(R_{14})_2$ or —O-alkyl-$(CO)OR_{14}$, or two adjacent carbon atoms on the ring together with unsubstituted or halogen-substituted —$OCH_2CH_2$— or —$OCH_2O$— form a fused ring;

or $N(W_3)_2$ represents unsubstituted or substituted heterocyclyl with nitrogen atom at 1-position;

$X_{11}$ independently represents H, alkyl, alkenyl, alkynyl, cycloalkyl, cycloalkylalkyl, cycloalkenyl, cycloalkenylalkyl, heterocyclyl, heterocyclylalkyl, aryl or arylalkyl; wherein, the groups "cycloalkyl", "cycloalkylalkyl", "cycloalkenyl", "cycloalkenylalkyl", "heterocyclyl", "heterocyclylalkyl", "aryl" and "arylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —$OR_{14}$, —$SR_{14}$, —$(CO)OR_{14}$, —$(SO_2)R_{14}$, —$N(R_{14})_2$ or —O-alkyl-$(CO)OR_{14}$, or two adjacent carbon atoms on the ring together with unsubstituted or halogen-substituted —$OCH_2CH_2$— or —$OCH_2O$— form a fused ring;

$X_{12}$ independently represents alkyl, alkenyl, alkynyl, cycloalkyl, cycloalkylalkyl, cycloalkenyl, cycloalkenylalkyl, heterocyclyl, heterocyclylalkyl, aryl or arylalkyl;

wherein, the groups "cycloalkyl", "cycloalkylalkyl", "cycloalkenyl", "cycloalkenylalkyl", "heterocyclyl", "heterocyclylalkyl", "aryl" and "arylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —$OR_{14}$, —$SR_{14}$, —$(CO)OR_{14}$, —$(SO_2)R_{14}$, —$N(R_{14})_2$ or —O-alkyl-$(CO)OR_{14}$, or two adjacent carbon atoms on the ring together with unsubstituted or halogen-substituted —$OCH_2CH_2$— or —$OCH_2O$— form a fused ring;

$X_{13}$, $X_{14}$ each independently represent H, halogen, cyano, alkoxy, alkoxyalkyl, alkyl carbonyl, alkoxy carbonyl, alkyl sulfonyl, alkyl, alkenyl, alkynyl, cycloalkyl, cycloalkylalkyl, cycloalkenyl, cycloalkenylalkyl, aryl, arylalkyl, heterocyclyl or heterocyclylalkyl, or the group $CX_{13}X_{14}$, taken together, forms unsubstituted or substituted cyclic structure, or the group $NX_{13}X_{14}$, taken together, forms unsubstituted or substituted heterocyclyl with nitrogen atom at 1-position; wherein, the groups "alkyl", "alkenyl" and "alkynyl" are each independently unsubstituted or substituted by halogen; the groups "cycloalkyl", "cycloalkylalkyl", "cycloalkenyl", "cycloalkenylalkyl", "aryl", "arylalkyl", "heterocyclyl" and "heterocyclylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —$OR_{14}$, —$SR_{14}$, —$(CO)OR_{14}$, —$(SO_2)R_{14}$, —$N(R_{14})_2$ or —O-alkyl-$(CO)OR_{14}$, or two adjacent carbon atoms on the ring together with unsubstituted or halogen-substituted —$OCH_2CH_2$— or —$OCH_2O$— form a fused ring;

$R_1$, $R_2$, $R_6$, $R_{10}$, $R_{17}$, $R_{18}$, $R_{22}$, $R_{25}$, $R_{32}$ each independently represent H, cyano, alkyl, alkenyl, alkynyl, formylalkyl, cyanoalkyl, amino, aminoalkyl, amino carbonyl, amino carbonyl alkyl, amino sulfonyl, cycloalkyl, cycloalkylalkyl, cycloalkenyl, cycloalkenylalkyl, heterocyclyl, heterocyclylalkyl, aryl, arylalkyl, $R_4R_5N$—(CO)—$NR_3$—,

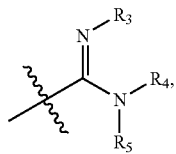

$R_3$—$S(O)_m$-(alkyl)$_n$-, $R_3$—O-(alkyl)$_n$-, $R_3$—(CO)-(alkyl)$_n$-, $R_3$—O-(alkyl)$_n$-(CO)—, $R_3$—(CO)—O-(alkyl)$_n$-, $R_3$—S—(CO)-(alkyl)$_n$-, $R_3$—O—(CO)-alkyl- or $R_3$—O—(CO)—O-alkyl-, wherein, the groups "alkyl", "alkenyl" and "alkynyl" are each independently unsubstituted or substituted by halogen, the groups "amino", "aminoalkyl", "amino carbonyl", "amino carbonyl alkyl" and "amino sulfonyl" are each independently unsubstituted or substituted by one or two groups selected from —$R_{11}$, —$OR_{11}$, —$(CO)R_{11}$, —$(CO)OR_{11}$, -alkyl-$(CO)OR_{11}$, —$(SO_2)R_{11}$, —$(SO_2)OR_{11}$, -alkyl-$(SO_2)R_{11}$, —$(CO)N(R_{12})_2$ or —$(SO_2)N(R_{12})_2$, the groups "cycloalkyl", "cycloalkylalkyl", "cycloalkenyl", "cycloalkenylalkyl", "heterocyclyl", "heterocyclylalkyl", "aryl" and "arylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —$OR_{14}$, —$SR_{14}$, —$(CO)OR_{14}$, —$(SO_2)R_{14}$, —$N(R_{14})_2$ or —O-alkyl-$(CO)OR_{14}$, or two adjacent carbon atoms on the ring together with unsubstituted or halogen-substituted —$OCH_2CH_2$— or —$OCH_2O$— form a fused ring;

or $R_{17}$, $R_{18}$, taken together, forms —$CH_2CH_2CH_2CH_2$— or —$CH_2CH_2OCH_2$— that is unsubstituted or substituted by at least one group selected from halogen, alkyl or haloalkyl;

$R_3$, $R_4$, $R_5$ each independently represent H, alkyl, alkenyl, alkynyl, cycloalkyl, cycloalkylalkyl, cycloalkenyl, cycloalkenylalkyl, heterocyclyl, heterocyclylalkyl, aryl or arylalkyl; wherein, the groups "alkyl", "alkenyl" and "alkynyl" are each independently unsubstituted or substituted by halogen; the groups "cycloalkyl", "cycloalkylalkyl", "cycloalkenyl", "cycloalkenylalkyl", "heterocyclyl", "heterocyclylalkyl", "aryl" and "arylalkyl" are each independently unsubstituted or substituted by at least one group selected from oxo, halogen, cyano, nitro, alkyl, alkenyl, alkynyl, cycloalkyl, haloalkyl, haloalkenyl, haloalkynyl, halo cycloalkyl, alkyl-substituted cycloalkyl, —$OR_{14}$, —$SR_{14}$, —$(CO)OR_{14}$, —$(SO_2)R_{14}$, —$N(R_{14})_2$ or —O-alkyl-$(CO)OR_{14}$, or two adjacent carbon atoms on the ring together with unsubstituted or halogen-substituted —$OCH_2CH_2$— or —$OCH_2O$— form a fused ring;

$R_7$, $R_8$, $R_7'$, $R_8'$, $R_9$, $R_1$, $R_{20}$, $R_{21}$, $R_{23}$, $R_{24}$, $R_{25}$, $R_{27}$, $R_{28}$, $R_{29}$, $R_{30}$, $R_{31}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, $R_{45}$, $R_{46}$, $R_{47}$, $R_{48}$, $R_{49}$, $R_{50}$, $R_{51}$ each independently represent H, halogen, hydroxy, mercapto, formyl, hydroxyalkyl, nitro, cyano, alkyl, alkenyl, alkynyl, cycloalkyl, cycloalkylalkyl, cycloalkenyl, cycloalkenylalkyl, —$OR_{11}$, —$SR_{11}$, —$(SO)R_{11}$, —$(SO_2)R_{11}$, —$(SO_2)OR_{11}$, —$O(SO_2)R_{11}$, —$N(R_{12})_2$, phenyl or benzyl, wherein, the groups "alkyl", "alkenyl", "alkynyl", "cycloalkyl", "cycloalkylalkyl", "cycloalkenyl" and "cycloalkenylalkyl" are each independently unsubstituted or substituted by halogen; the groups "phenyl" and "benzyl" are each independently unsubstituted or substituted by at least one group selected from halogen, cyano, nitro, alkyl, haloalkyl, alkoxy carbonyl, alkylthio, alkyl sulfonyl, alkoxy or haloalkoxy;

or $R_7$, $R_8$, taken together, form —$CH_2CH_2CH_2CH_2$— or —CH═CH—CH═CH— that is unsubstituted or substituted by at least one group selected from halogen, alkyl or haloalkyl;

or $R_{19}$, $R_{20}$, taken together, form —$CH_2CH_2CH_2CH_2$— or —$CH_2CH$═$CHCH_2$— that is unsubstituted or substituted by at least one group selected from halogen, alkyl or haloalkyl;

or $R_{21}$, $R_{22}$, taken together, form —$CH_2CH_2CH_2$—, —$CH_2OCH_2CH_2$— or —$CH_2CH_2CH_2CH_2$— that is unsubstituted or substituted by at least one group selected from halogen, alkyl or haloalkyl;

$R_{11}$ independently represents alkyl, alkenyl, alkynyl, cycloalkyl, cycloalkylalkyl, cycloalkenyl, cycloalkenylalkyl, phenyl or benzyl; wherein, the groups "alkyl", "alkenyl" and "alkynyl" are each independently unsubstituted or substituted by halogen; the groups "phenyl" and "benzyl" are each independently unsubstituted or substituted by at least one group selected from halogen, cyano, nitro, alkyl, haloalkyl, alkoxy carbonyl, alkylthio, alkyl sulfonyl, alkoxy or haloalkoxy;

$R_{12}$ independently represents H, alkyl, alkenyl, alkynyl, alkoxy, alkyl sulfonyl, cycloalkyl, cycloalkylalkyl, cycloalkenyl or cycloalkenylalkyl, or the group N($R_{12}$)$_2$ in —(CO)N($R_{12}$)$_2$ or —(SO$_2$)N($R_{12}$)$_2$ independently represents unsubstituted or substituted heterocyclyl with nitrogen atom at 1-position;

$R_{13}$ independently represents alkyl, alkenyl, alkynyl, cycloalkyl, phenyl or phenyl substituted by at least one group selected from: halogen, cyano, nitro, alkyl, haloalkyl, alkoxy, haloalkoxy, alkoxy carbonyl, alkylthio, alkyl sulfonyl or phenoxy substituted by at least one group selected from halogen, cyano, nitro, alkyl, haloalkyl, alkoxy or haloalkoxy;

$R_{14}$ independently represents H, alkyl, haloalkyl, phenyl or phenyl substituted by at least one group selected from halogen, cyano, nitro, alkyl, haloalkyl, alkoxy carbonyl, alkylthio, alkyl sulfonyl, alkoxy or haloalkoxy;

$R_{15}$, $R_1$%, $R_{52}$ each independently represent H, halogen, alkyl, alkenyl, alkynyl, cycloalkyl, cycloalkylalkyl, cycloalkenyl or cycloalkenylalkyl, wherein, the groups "alkyl", "alkenyl", "alkynyl", "cycloalkyl", "cycloalkylalkyl", "cycloalkenyl" and "cycloalkenylalkyl" are each independently unsubstituted or substituted by halogen;

m represents 0, 1 or 2; n independently represents 0 or 1.

2. The fused-ring substituted aromatic compound according to claim 1, which is characterized in that, Y represents halogen, halo C1-C8 alkyl, cyano, nitro or amino;

Het represents a cyclic structure that shares two carbon atoms at 4- and 5-positions with isoxazoline ring to form a fused ring; the cyclic structure is 3-8 member saturated or unsaturated carbocyclyl or saturated or unsaturated heterocyclyl containing 1, 2 or 3 heteroatoms selected from O, S, N, NH, CO, SO$_2$ or C=N—O—$R_{14}$; except for the 4- and 5-positions that are respectively substituted by $X_2$ or $X_1$, other positions on the Het are each independently unsubstituted or substituted by at least one group selected from halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —O$R_{14}$, —S$R_{14}$, —SO$R_{14}$, —(CO)O$R_{14}$, —(SO$_2$)$R_{14}$, —N($R_{14}$)$_2$ or —O—(CO)O$R_{14}$;

$X_1$, $X_2$ each independently represent H, halogen, nitro, cyano, thiocyano, hydroxy, mercapto, sulfo, formyl, haloformyl, azido, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, —PO(OR')$_2$, —OR", —(CO)R", —SR", —(SO)R", —(SO$_2$)R", —Si(R")$_3$, —(CO)R", —O—(SO$_2$)R", —S(CO)R", —(SO$_2$)OR", —O(CO)OR", —(CO)(CO)OR",

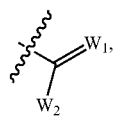

—CR'=N—OH, —CR'=N—O—R", heterocyclyl, heterocyclyl C1-C8 alkyl, aryl, aryl C1-C8 alkyl, amino, amino C1-C8 alkyl, amino carbonyl C1-C8 alkyl, amino carbonyloxy C1-C8 alkyl, amino thio carbonyloxy C1-C8 alkyl, amino sulfonyl or amino sulfonyloxy C1-C8 alkyl, wherein, the groups "C1-C8 alkyl", "C2-C8 alkenyl" and "C2-C8 alkynyl" are each independently unsubstituted or substituted by at least one group selected from halogen, cyano, hydroxy, mercapto, carboxyl, —OR", —(CO)R", —SR", —(SO$_2$)R", —O(CO)H, —O(CO)R", —O—(SO$_2$)R", —(CO)OR", —O(CO)OR", —O(CO)(CO)OH, —O(CO)(CO)OR", —O—(C1-C8 alkyl)-(CO)OH or —O—(C1-C8 alkyl)-(CO)OR", the groups "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" and "aryl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —O$R_{14}$, —S$R_{14}$, —(CO)O$R_{14}$, —(SO$_2$)$R_{14}$, —N($R_{14}$)$_2$ or —O—(C1-C8 alkyl)-(CO)O$R_{14}$, or two adjacent carbon atoms on the ring together with unsubstituted or halogen-substituted —OCH$_2$CH$_2$— or —OCH$_2$O— form a fused ring, the groups "amino", "amino C1-C8 alkyl", "amino carbonyl C1-C8 alkyl", "amino carbonyloxy C1-C8 alkyl", "amino thio carbonyloxy C1-C8 alkyl", "amino sulfonyl" and "amino sulfonyloxy C1-C8 alkyl" are each independently unsubstituted or substituted by one or two groups selected from —$R_{11}$, —O$R_{11}$, —(CO)$R_{11}$, —(CO)O$R_{11}$, —(C1-C8 alkyl)-(CO)O$R_{11}$, —(SO$_2$)$R_{11}$, —(SO$_2$)O$R_{11}$, —(C1-C8 alkyl)-(SO$_2$)$R_{11}$, —(CO)N($R_{12}$)$_2$ or —(SO$_2$)N($R_{12}$)$_2$;

R' independently represents H, halogen, C1-C8 alkoxy, C1-C8 alkoxy C1-C8 alkyl, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, heterocyclyl or heterocyclyl C1-C8 alkyl, wherein, the groups "C1-C8 alkyl", "C2-C8 alkenyl" and "C2-C8 alkynyl" are each independently unsubstituted or substituted by halogen; the groups "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "heterocyclyl" and "heterocyclyl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —O$R_{14}$, —S$R_{14}$, —(CO)O$R_{14}$, —(SO$_2$)$R_{14}$, —N($R_{14}$)$_2$ or —O—(C1-C8 alkyl)-(CO)O$R_{14}$, or two adjacent carbon atoms on the ring together with unsubstituted or halogen-substituted —OCH$_2$CH$_2$— or —OCH$_2$O— form a fused ring;

R" independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, aryl C2-C8 alkenyl, heterocyclyl, heterocyclyl C1-C8 alkyl or heterocyclyl C2-C8 alkenyl; wherein, the groups "C1-C8 alkyl", "C2-C8 alkenyl" and "C2-C8 alkynyl" are each independently unsubstituted or substituted by at least one group selected from halogen, cyano, tri C1-C8 alkylsilyl, —O$R_{13}$, —S$R_{13}$, —O(CO)$R_{13}$, —(CO)$R_{13}$, —(CO)O$R_{13}$ or —O(CO)O$R_{13}$; the groups "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "aryl C2-C8 alkenyl", "heterocyclyl", "heterocyclyl C1-C8 alkyl" and "heterocyclyl C2-C8 alkenyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —OR$_{14}$, —SR$_{14}$, —(CO)OR$_{14}$, —(SO$_2$)R$_{14}$, —N(R$_{14}$)$_2$ or —O—(C1-C8 alkyl)-(CO)OR$_{14}$, or two adjacent carbon atoms on the ring together with unsubstituted or halogen-substituted —OCH$_2$CH$_2$— or —OCH$_2$O— form a fused ring;

W$_1$ represents O, S, NH or N—(C1-C8 alkyl);

W$_3$ independently represents H, C1-C8 alkyl, C2-C8 alkenyl, C2-C8 alkynyl, C3-C8 cycloalkyl, C3-C8 cycloalkenyl, heterocyclyl, aryl,

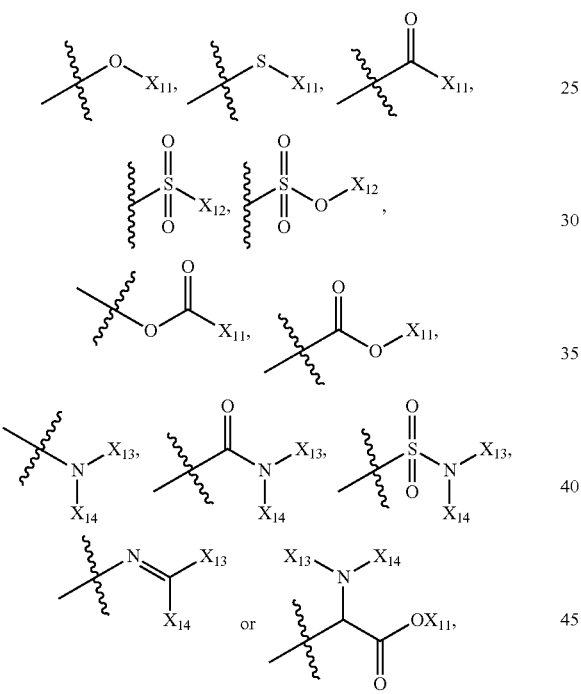

wherein, the groups "C1-C8 alkyl", "C2-C8 alkenyl" and "C2-C8 alkynyl" are each independently unsubstituted or substituted by at least one group selected from halogen, cyano, nitro, C3-C8 cycloalkyl, tri C1-C8 alkylsilyl, C3-C8 cycloalkenyl, heterocyclyl, aryl,

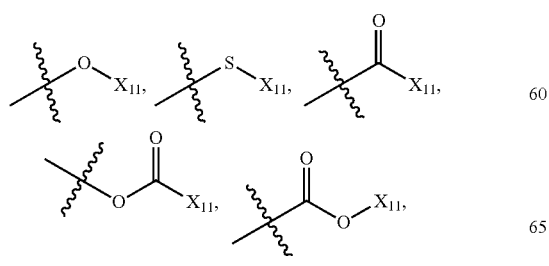

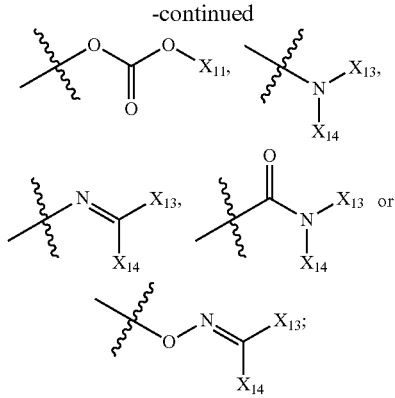

the groups "C3-C8 cycloalkyl", "C3-C8 cycloalkenyl", "heterocyclyl" and "aryl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —OR$_{14}$, —SR$_{14}$, —(CO)OR$_{14}$, —(SO$_2$)R$_{14}$, —N(R$_{14}$)$_2$ or —O—(C1-C8 alkyl)-(CO)OR$_{14}$, or two adjacent carbon atoms on the ring together with unsubstituted or halogen-substituted —OCH$_2$CH$_2$— or —OCH$_2$O— form a fused ring;

or N(W$_3$)$_2$ represents

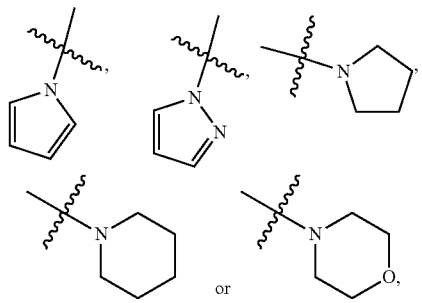

which is unsubstituted or substituted by at least one group selected from oxo, C1-C8 alkyl or C1-C8 alkoxy carbonyl;

X$_{11}$ independently represents H, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocyclyl C1-C8 alkyl, aryl or aryl C1-C8 alkyl; wherein, the groups "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" and "aryl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —OR$_{14}$, —SR$_{14}$, —(CO)OR$_{14}$, —(SO$_2$)R$_{14}$, —N(R$_{14}$)$_2$ or —O—(C1-C8 alkyl)-(CO)OR$_{14}$, or two adjacent carbon atoms on the ring together with unsubstituted or halogen-substituted —OCH$_2$CH$_2$— or —OCH$_2$O— form a fused ring;

$X_{12}$ independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocyclyl C1-C8 alkyl, aryl or aryl C1-C8 alkyl; wherein, the groups "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" and "aryl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —$OR_{14}$, —$SR_{14}$, —(CO)$OR_{14}$, —($SO_2$)$R_{14}$, —$N(R_{14})_2$ or —O—(C1-C8 alkyl)-(CO)$OR_{14}$, or two adjacent carbon atoms on the ring together with unsubstituted or halogen-substituted —$OCH_2CH_2$— or —$OCH_2O$— form a fused ring;

$X_{13}$, $X_{14}$ each independently represent H, halogen, cyano, C1-C8 alkoxy, C1-C8 alkoxy C1-C8 alkyl, C1-C8 alkyl carbonyl, C1-C8 alkoxy carbonyl, C1-C8 alkyl sulfonyl, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, heterocyclyl or heterocyclyl C1-C8 alkyl, or the group $CX_{13}X_{14}$, taken together, forms 5-8 membered carbocyclyl or oxygen-, sulfur- or nitrogen-containing heterocyclyl, or the group $NX_{13}X_1$, taken together, forms

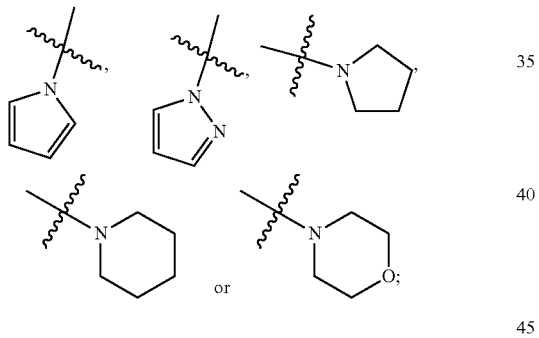

wherein, the groups "C1-C8 alkyl", "C2-C8 alkenyl" and "C2-C8 alkynyl" are each independently unsubstituted or substituted by halogen; the groups "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "heterocyclyl" and "heterocyclyl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —$OR_{14}$, —$SR_{14}$, —(CO)$OR_{14}$, —($SO_2$)$R_{14}$, —$N(R_{14})_2$ or —O—(C1-C8 alkyl)-(CO)$OR_{14}$, or two adjacent carbon atoms on the ring together with unsubstituted or halogen-substituted —$OCH_2CH_2$— or —$OCH_2O$— form a fused ring; the groups "5~8 membered carbocyclyl or oxygen-, sulfur- or nitrogen-containing heterocyclyl" are unsubstituted or substituted by at least one group selected from C1-C8 alkyl, C1-C8 alkoxy carbonyl or benzyl, or together with aryl or heterocyclyl form a fused ring; the groups

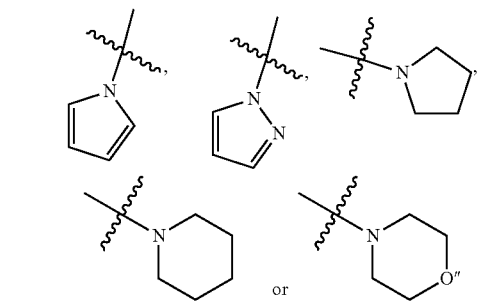

are unsubstituted or substituted by at least one group selected from oxo, C1-C8 alkyl or C1-C8 alkoxy carbonyl;

$R_1$, $R_2$, $R_6$, $R_{10}$, $R_{17}$, $R_{18}$, $R_{22}$, $R_{25}$, $R_{32}$ each independently represent H, cyano, C1-C8 alkyl, C2-C8 alkenyl, C2-C8 alkynyl, formyl C1-C8 alkyl, cyano C1-C8 alkyl, amino, amino C1-C8 alkyl, amino carbonyl, amino carbonyl C1-C8 alkyl, amino sulfonyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocyclyl C1-C8 alkyl, aryl, aryl C1-C8 alkyl, $R_4R_5N$—(CO)—$NR_3$—,

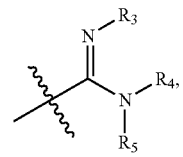

$R_3$—S(O)$_m$—(C1-C8 alkyl)$_n$-, $R_3$—O—(C1-C8 alkyl)$_n$-, $R_3$—(CO)—(C1-C8 alkyl)$_n$-, $R_3$—O—(C1-C8 alkyl)$_n$-(CO)—, $R_3$—(CO)—O—(C1-C8 alkyl)$_n$-, $R_3$—S—(CO)—(C1-C8 alkyl)$_n$-, $R_3$—O—(CO)—(C1-C8 alkyl)- or $R_3$—O—(CO)—O—(C1-C8 alkyl)-, wherein, the groups "C1-C8 alkyl", "C2-C8 alkenyl" and "C2-C8 alkynyl" are each independently unsubstituted or substituted by halogen, the groups "amino", "amino C1-C8 alkyl", "amino carbonyl", "amino carbonyl C1-C8 alkyl" and "amino sulfonyl" are each independently unsubstituted or substituted by one or two groups selected from —$R_{11}$, —$OR_{11}$, —(CO)$R_{11}$, —(CO)$OR_{11}$, —(C1-C8 alkyl)-(CO)$OR_{11}$, —($SO_2$)$R_{11}$, —($SO_2$)$OR_{11}$, —(C1-C8 alkyl)-($SO_2$)$R_{11}$, —(CO)$N(R_{12})_2$ or —($SO_2$)$N(R_{12})_2$, the groups "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" and "aryl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —$OR_{14}$, —$SR_{14}$, —(CO)$OR_{14}$, —($SO_2$)$R_{14}$, —$N(R_{14})_2$ or —O—(C1-C8 alkyl)-(CO)$OR_{14}$, or two adjacent carbon atoms on the ring together with unsubstituted or halogen-substituted —$OCH_2CH_2$— or —$OCH_2O$— form a fused ring;

or R$_{17}$, R$_{18}$, taken together, form —CH$_2$CH$_2$CH$_2$CH$_2$— or —CH$_2$CH$_2$OCH$_2$— that is unsubstituted or substituted by at least one group selected from halogen, C1-C8 alkyl or halo C1-C8 alkyl;

R$_3$, R$_4$, R$_5$ each independently represent H, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocyclyl C1-C8 alkyl, aryl or aryl C1-C8 alkyl, wherein, the groups "C1-C8 alkyl", "C2-C8 alkenyl" and "C2-C8 alkynyl" are each independently unsubstituted or substituted by halogen, the groups "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" and "aryl C1-C8 alkyl" are each independently unsubstituted or substituted by at least one group selected from oxo, halogen, cyano, nitro, C1-C8 alkyl, C2-C8 alkenyl, C2-C8 alkynyl, C3-C8 cycloalkyl, halo C1-C8 alkyl, halo C2-C8 alkenyl, halo C2-C8 alkynyl, halo C3-C8 cycloalkyl, C1-C8 alkyl-substituted C3-C8 cycloalkyl, —OR$_{14}$, —SR$_{14}$, —(CO)OR$_{14}$, —(SO$_2$)R$_{14}$, —N(R$_{14}$)$_2$ or —O—(C1-C8 alkyl)-(CO)OR$_{14}$, or two adjacent carbon atoms on the ring together with unsubstituted or halogen-substituted —OCH$_2$CH$_2$— or —OCH$_2$O— form a fused ring;

R$_7$, R$_8$, R$_7$', R$_8$', R$_9$, R$_{19}$, R$_{20}$, R$_{21}$, R$_{23}$, R$_{24}$, R$_{26}$, R$_{27}$, R$_{28}$, R$_{29}$, R$_{30}$, R$_{31}$, R$_{32}$, R$_{34}$, R$_{35}$, R$_{36}$, R$_{37}$, R$_{38}$, R$_{39}$, R$_{40}$, R$_{41}$, R$_{42}$, R$_{43}$, R$_{44}$, R$_{45}$, R$_{46}$, R$_{47}$, R$_{48}$, R$_{49}$, R$_{50}$, R$_{51}$ each independently represent H, halogen, hydroxy, mercapto, formyl, hydroxy C1-C8 alkyl, nitro, cyano, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, —OR$_{11}$, —SR$_{11}$, —(SO)R$_{11}$, —(SO$_2$)R$_{11}$, —(SO$_2$)OR$_{11}$, —O(SO$_2$)R$_{11}$, —N(R$_{12}$)$_2$, phenyl or benzyl, wherein, the groups "C1-C8 alkyl", "C2-C8 alkenyl", "C2-C8 alkynyl", "C3-C8 cycloalkyl", "C3-C8 cycloalkyl C1-C8 alkyl", "C3-C8 cycloalkenyl" and "C3-C8 cycloalkenyl C1-C8 alkyl" are each independently unsubstituted or substituted by halogen, the groups "phenyl" and "benzyl" are each independently unsubstituted or substituted by at least one group selected from halogen, cyano, nitro, C1-C8 alkyl, halo C1-C8 alkyl, C1-C8 alkoxy carbonyl, C1-C8 alkylthio, C1-C8 alkyl sulfonyl, C1-C8 alkoxy or halo C1-C8 alkoxy;

or R$_7$, R$_8$, taken together, form —CH$_2$CH$_2$CH$_2$CH$_2$— or —CH═CH—CH═CH— that is unsubstituted or substituted by at least one group selected from halogen, C1-C8 alkyl or halo C1-C8 alkyl;

or R$_{19}$, R$_{20}$, taken together, form —CH$_2$CH$_2$CH$_2$CH$_2$— or —CH$_2$CH═CHCH$_2$— that is unsubstituted or substituted by at least one group selected from halogen, C1-C8 alkyl or halo C1-C8 alkyl;

or R$_{21}$, R$_{22}$, taken together, form —CH$_2$CH$_2$CH$_2$—, —CH$_2$OCH$_2$CH$_2$— or —CH$_2$CH$_2$CH$_2$CH$_2$— that is unsubstituted or substituted by at least one group selected from halogen, C1-C8 alkyl or halo C1-C8 alkyl;

R$_{11}$ independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, phenyl or benzyl; wherein, the groups "C1-C8 alkyl", "C2-C8 alkenyl" and "C2-C8 alkynyl" are each independently unsubstituted or substituted by halogen; the groups "phenyl" and "benzyl" are each independently unsubstituted or substituted by at least one group selected from halogen, cyano, nitro, C1-C8 alkyl, halo C1-C8 alkyl, C1-C8 alkoxy carbonyl, C1-C8 alkylthio, C1-C8 alkyl sulfonyl, C1-C8 alkoxy or halo C1-C8 alkoxy;

R$_{12}$ independently represents H, C1-C8 alkyl, C2-C8 alkenyl, C2-C8 alkynyl, C1-C8 alkoxy, C1-C8 alkyl sulfonyl, C3-C8 cycloalkyl, C3-C8 cycloalkyl C1-C8 alkyl, C3-C8 cycloalkenyl or C3-C8 cycloalkenyl C1-C8 alkyl, or the group N(R$_{12}$)$_2$ in —(CO)N(R$_{12}$)$_2$ or —(SO$_2$)N(R$_{12}$)$_2$ independently represents

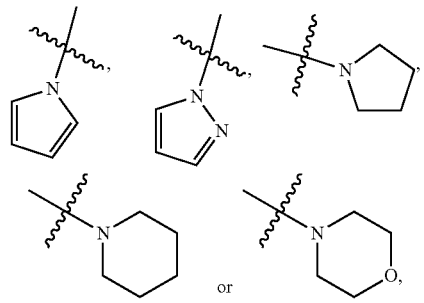

which is unsubstituted or substituted by at least one group selected from oxo, C1-C8 alkyl or C1-C8 alkoxy carbonyl;

R$_{13}$ independently represents C1-C8 alkyl, C2-C8 alkenyl, C2-C8 alkynyl, C3-C8 cycloalkyl, phenyl or phenyl substituted by at least one group selected from: halogen, cyano, nitro, C1-C8 alkyl, halo C1-C8 alkyl, C1-C8 alkoxy, halo C1-C8 alkoxy, C1-C8 alkoxy carbonyl, C1-C8 alkylthio, C1-C8 alkyl sulfonyl or phenoxy substituted by at least one group selected from halogen, cyano, nitro, C1-C8 alkyl, halo C1-C8 alkyl, C1-C8 alkoxy or halo C1-C8 alkoxy;

R$_{14}$ independently represents H, C1-C8 alkyl, halo C1-C8 alkyl, phenyl or phenyl substituted by at least one group selected from halogen, cyano, nitro, C1-C8 alkyl, halo C1-C8 alkyl, C1-C8 alkoxy carbonyl, C1-C8 alkylthio, C1-C8 alkyl sulfonyl, C1-C8 alkoxy or halo C1-C8 alkoxy;

R$_{15}$, R$_{16}$, R$_{52}$ each independently represent H, halogen, C1-C8 alkyl, C2-C8 alkenyl, C2-C8 alkynyl, C3-C8 cycloalkyl, C3-C8 cycloalkyl C1-C8 alkyl, C3-C8 cycloalkenyl or C3-C8 cycloalkenyl C1-C8 alkyl, wherein, the groups "C1-C8 alkyl", "C2-C8 alkenyl", "C2-C8 alkynyl", "C3-C8 cycloalkyl", "C3-C8 cycloalkyl C1-C8 alkyl", "C3-C8 cycloalkenyl" and "C3-C8 cycloalkenyl C1-C8 alkyl" are each independently unsubstituted or substituted by halogen.

3. The fused-ring substituted aromatic compound according to claim 1, which is characterized in that, Y represents halogen, halo C1-C6 alkyl, cyano, nitro or amino;

Het represents a cyclic structure that shares two carbon atoms at 4- and 5-positions with isoxazoline ring to form a fused ring; the cyclic structure is 3-8 member saturated or unsaturated carbocyclyl or saturated or unsaturated heterocyclyl containing 1, 2 or 3 heteroatoms selected from O, S, N, NH, CO, SO$_2$ or C═N—O—R$_{14}$; except for the 4- and 5-positions that are respectively substituted by X$_2$ or X$_1$, other positions on the Het are each independently unsubstituted or substituted by at least one group selected from halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —SOR$_{14}$, —(CO)OR$_{14}$, —(SO$_2$)R$_{14}$, —N(R$_{14}$)$_2$ or —O—(CO)OR$_{14}$;

X$_1$, X$_2$ each independently represent H, halogen, nitro, cyano, thiocyano, hydroxy, mercapto, sulfo, formyl, haloformyl, azido, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, —PO(OR')$_2$, —OR", —(CO)R", —SR", —(SO)R", —(SO$_2$)R", —Si(R")$_3$, —O(CO)R", —O—(SO$_2$)R", —S(CO)R", —(SO$_2$)OR", —O(CO)OR", —(CO)(CO)OR",

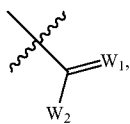

—CR'=N—OH, —CR'=N—O—R", heterocyclyl, heterocyclyl C1-C6 alkyl, aryl, aryl C1-C6 alkyl, amino, amino C1-C6 alkyl, amino carbonyl C1-C6 alkyl, amino carbonyloxy C1-C6 alkyl, amino thio carbonyloxy C1-C6 alkyl, amino sulfonyl or amino sulfonyloxy C1-C6 alkyl, wherein, the groups "C1-C6 alkyl", "C2-C6 alkenyl" and "C2-C6 alkynyl" are each independently unsubstituted or substituted by 1, 2 or 3 groups selected from halogen, cyano, hydroxy, mercapto, carboxyl, —OR", —(CO)R", —SR", —(SO$_2$)R", —O(CO)H, —O(CO)R", —O—(SO$_2$)R", —(CO)OR", —O(CO)OR", —O(CO)(CO)OH, —O(CO)(CO)OR", —O—(C1-C6 alkyl)-(CO)OH or —O—(C1-C6 alkyl)-(CO)OR", the groups "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" and "aryl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C6 alkyl)-(CO)OR$_{14}$, or two adjacent carbon atoms on the ring together with unsubstituted or halogen-substituted —OCH$_2$CH$_2$— or —OCH$_2$O— form a fused ring, the groups "amino", "amino C1-C6 alkyl", "amino carbonyl C1-C6 alkyl", "amino carbonyloxy C1-C6 alkyl", "amino thio carbonyloxy C1-C6 alkyl", "amino sulfonyl" and "amino sulfonyloxy C1-C6 alkyl" are each independently unsubstituted or substituted by one or two groups selected from —R$_{11}$, —OR$_{11}$, —(CO)R$_{11}$, —(CO)OR$_{11}$, —(C1-C6 alkyl)-(CO)OR$_{11}$, —(SO$_2$)R$_{11}$, —(SO$_2$)OR$_{11}$, —(C1-C6 alkyl)-(SO$_2$)R$_{11}$, —(CO)N(R$_{12}$)$_2$ or —(SO$_2$)N(R$_{12}$)$_2$;

R' independently represents H, halogen, C1-C6 alkoxy, C1-C6 alkoxy C1-C6 alkyl, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, heterocyclyl or heterocyclyl C1-C6 alkyl; wherein, the groups "C1-C6 alkyl", "C2-C6 alkenyl" and "C2-C6 alkynyl" are each independently unsubstituted or substituted by halogen; the groups "C3-C6 cycloalkyl", "C3-C6 cycloalkyl C1-C6 alkyl", "C3-C6 cycloalkenyl", "C3-C6 cycloalkenyl C1-C6 alkyl", "aryl", "aryl C1-C6 alkyl", "heterocyclyl" and "heterocyclyl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C6 alkyl)-(CO)OR$_{14}$, or two adjacent carbon atoms on the ring together with unsubstituted or halogen-substituted —OCH$_2$CH$_2$— or —OCH$_2$O— form a fused ring;

R" independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, aryl C2-C6 alkenyl, heterocyclyl, heterocyclyl C1-C6 alkyl or heterocyclyl C2-C6 alkenyl; wherein, the groups "C1-C6 alkyl", "C2-C6 alkenyl" and "C2-C6 alkynyl" are each independently unsubstituted or substituted by 1, 2 or 3 groups selected from halogen, cyano, tri C1-C6 alkylsilyl, —OR$_{13}$, —SR$_{13}$, —O(CO)R$_{13}$, —(CO)R$_{13}$, —(CO)OR$_{13}$ or —O(CO)OR$_{13}$; the groups "C3-C6 cycloalkyl", "C3-C6 cycloalkyl C1-C6 alkyl", "C3-C6 cycloalkenyl", "C3-C6 cycloalkenyl C1-C6 alkyl", "aryl", "aryl C1-C6 alkyl", "aryl C2-C6 alkenyl", "heterocyclyl", "heterocyclyl C1-C6 alkyl" and "heterocyclyl C2-C6 alkenyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —(C1-C6 alkyl)-(CO)OR$_{14}$, or two adjacent carbon atoms on the ring together with unsubstituted or halogen-substituted —OCH$_2$CH$_2$— or —OCH$_2$O— form a fused ring;

W$_1$ represents O, S, NH or N—(C1-C6 alkyl);

W independently represents H, C1-C6 alkyl, C2-C6 alkenyl, C2-C6 alkynyl, C3-C6 cycloalkyl, C3-C6 cycloalkenyl, heterocyclyl, aryl,

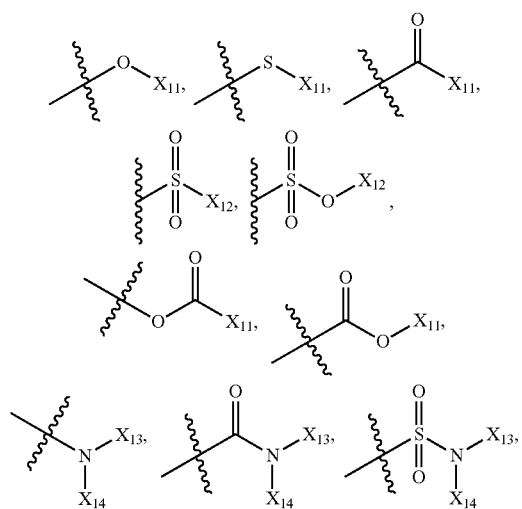

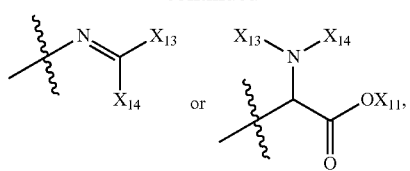

wherein, the groups "C1-C6 alkyl", "C2-C6 alkenyl" and "C2-C6 alkynyl" are each independently unsubstituted or substituted by 1, 2 or 3 groups selected from halogen, cyano, nitro, C3-C6 cycloalkyl, tri C1-C6 alkylsilyl, C3-C6 cycloalkenyl, heterocyclyl, aryl,

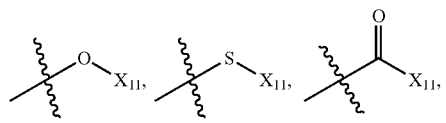

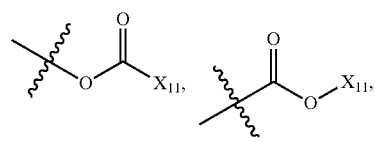

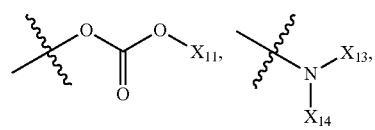

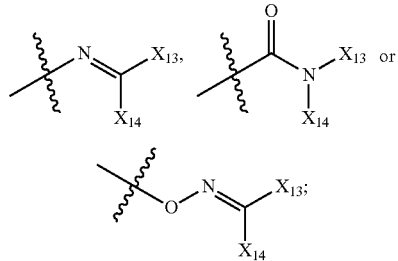

the groups "C3-C6 cycloalkyl", "C3-C6 cycloalkenyl", "heterocyclyl" and "aryl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C6 alkyl)-(CO)OR$_{14}$, or two adjacent carbon atoms on the ring together with unsubstituted or halogen-substituted —OCH$_2$CH$_2$— or —OCH$_2$O— form a fused ring;

or N(W$_3$)$_2$ represents

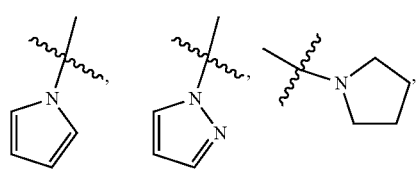

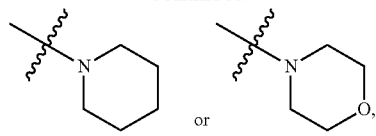

or which is unsubstituted or substituted by 1, 2 or 3 groups selected from oxo, C1-C6 alkyl or C1-C6 alkoxy carbonyl;

X$_{11}$ independently represents H, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl or aryl C1-C6 alkyl, wherein, the groups "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" and "aryl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C6 alkyl)-(CO)OR$_{14}$, or two adjacent carbon atoms on the ring together with unsubstituted or halogen-substituted —OCH$_2$CH$_2$— or —OCH$_2$O— form a fused ring;

X$_{12}$ independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl or aryl C1-C6 alkyl; wherein, the groups "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" and "aryl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C6 alkyl)-(CO)OR$_{14}$, or two adjacent carbon atoms on the ring together with unsubstituted or halogen-substituted —OCH$_2$CH$_2$— or —OCH$_2$O— form a fused ring;

X$_{13}$, X$_{14}$ each independently represent H, halogen, cyano, C1-C6 alkoxy, C1-C6 alkoxy C1-C6 alkyl, C1-C6 alkyl carbonyl, C1-C6 alkoxy carbonyl, C1-C6 alkyl sulfonyl, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, heterocyclyl or heterocyclyl C1-C6 alkyl, or the group CX$_{13}$X$_{14}$, taken together, forms 5-8 membered saturated carbocyclyl,

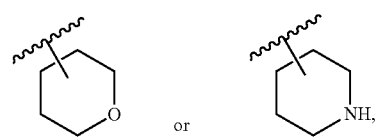

or the group NX₁₃X₁₄, taken together, forms

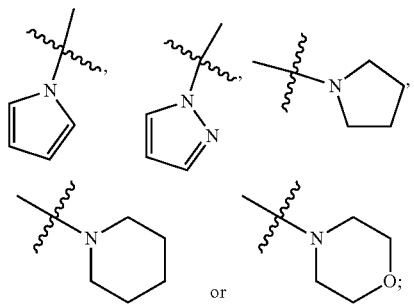

or wherein, the groups "C1-C6 alkyl", "C2-C6 alkenyl" and "C2-C6 alkynyl" are each independently unsubstituted or substituted by halogen; the groups "C3-C6 cycloalkyl", "C3-C6 cycloalkyl C1-C6 alkyl", "C3-C6 cycloalkenyl", "C3-C6 cycloalkenyl C1-C6 alkyl", "aryl", "aryl C1-C6 alkyl", "heterocyclyl" and "heterocyclyl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR₁₄, —SR₁₄, —(CO)OR₁₄, —(SO₂)R₁₄, —N(R₁₄)₂ or —O—(C1-C6 alkyl)-(CO)OR₁₄, or two adjacent carbon atoms on the ring together with unsubstituted or halogen-substituted —OCH₂CH₂— or —OCH₂O— form a fused ring; the groups "5~8 membered saturated carbocyclyl,

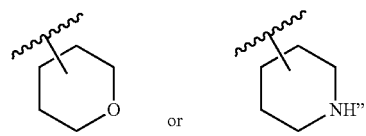

or are unsubstituted or substituted by 1, 2 or 3 groups selected from C1-C6 alkyl, C1-C6 alkoxy carbonyl or benzyl, or together with aryl or heterocyclyl form a fused ring; the groups

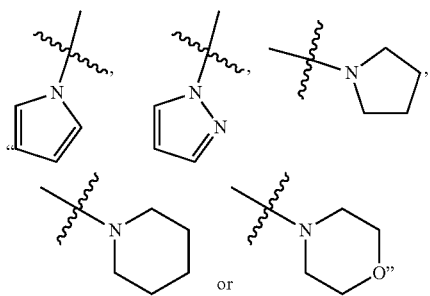

or are unsubstituted or substituted by 1, 2 or 3 groups selected from oxo, C1-C6 alkyl or C1-C6 alkoxy carbonyl;

R₁, R₂, R₆, R₁₀, R₁₇, R₁₈, R₂₂, R₂₅, R₃₂ each independently represent H, cyano, C1-C6 alkyl, C2-C6 alkenyl, C2-C6 alkynyl, formyl C1-C6 alkyl, cyano C1-C6 alkyl, amino, amino C1-C6 alkyl, amino carbonyl, amino carbonyl C1-C6 alkyl, amino sulfonyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl, aryl C1-C6 alkyl, R₄R₅N—(CO)—NR₃—,

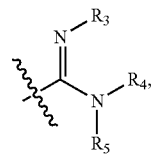

R₃—S(O)ₘ—(C1-C6 alkyl)ₙ-, R₃—O—(C1-C6 alkyl)ₙ-, R₃—(CO)—(C1-C6 alkyl)ₙ-, R₃—O—(C1-C6 alkyl)ₙ-(CO)—, R₃—(CO)—O—(C1-C6 alkyl)ₙ-, R₃—S—(CO)—(C1-C6 alkyl)ₙ-, R₃—O—(CO)—(C1-C6 alkyl)- or R₃—O—(CO)—O—(C1-C6 alkyl)-,
wherein,
the groups "C1-C6 alkyl", "C2-C6 alkenyl" and "C2-C6 alkynyl" are each independently unsubstituted or substituted by halogen,
the groups "amino", "amino C1-C6 alkyl", "amino carbonyl", "amino carbonyl C1-C6 alkyl" and "amino sulfonyl" are each independently unsubstituted or substituted by one or two groups selected from —R₁₁, —OR₁₁, —(CO)R₁₁, —(CO)OR₁₁, —(C1-C6 alkyl)-(CO)OR₁₁, —(SO₂)R₁₁, —(SO₂)OR₁₁, —(C1-C6 alkyl)-(SO₂)R₁₁, —(CO)N(R₁₂)₂ or —(SO₂)N(R₁₂)₂,
the groups "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" and "aryl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR₁₄, —SR₁₄, —(CO)OR₁₄, —(SO₂)R₁₄, —N(R₁₄)₂ or —O—(C1-C6 alkyl)-(CO)OR₁₄, or two adjacent carbon atoms on the ring together with unsubstituted or halogen-substituted —OCH₂CH₂— or —OCH₂O— form a fused ring;
or R₁₇, R₁, taken together, form —CH₂CH₂CH₂CH₂— or —CH₂CH₂OCH₂— that is unsubstituted or substituted by at least one group selected from halogen, C1-C6 alkyl or halo C1-C6 alkyl;
R₃, R₄, R₅ each independently represent H, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl or aryl C1-C6 alkyl; wherein, the groups "C1-C6 alkyl", "C2-C6 alkenyl" and "C2-C6 alkynyl" are each independently unsubstituted or substituted by halogen; the groups "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" and "aryl C1-C6 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR₁₄, —SR₁₄, —(CO)OR₁₄, —(SO₂)R₁₄, —N(R$_{14}$)$_2$ or —O—(C1-C6 alkyl)-(CO)OR$_{14}$, or two adjacent carbon atoms on the ring together with unsubstituted or halogen-substituted —OCH$_2$CH$_2$— or —OCH$_2$O— form a fused ring;

R$_7$, R$_8$, R$_7'$, R$_8'$, R$_9$, R$_{19}$, R$_{20}$, R$_{21}$, R$_{23}$, R$_{24}$, R$_{25}$, R$_{27}$, R$_{28}$, R$_{29}$, R$_{30}$, R$_{31}$, R$_{32}$, R$_{34}$, R$_{35}$, R$_{36}$, R$_{37}$, R$_{38}$, R$_{39}$, R$_{40}$, R$_{41}$, R$_{42}$, R$_{43}$, R$_{44}$, R$_{45}$, R$_{46}$, R$_{47}$, R$_{48}$, R$_{49}$, R$_{50}$, R$_{51}$ each independently represent H, halogen, hydroxy, mercapto, formyl, hydroxy C1-C6 alkyl, nitro, cyano, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, —OR$_{11}$, —SR$_{11}$, —(SO)R$_{11}$, —(SO$_2$)R$_{11}$, —(SO$_2$)OR$_{11}$, —O(SO$_2$)R$_{11}$, —N(R$_{12}$)$_2$, phenyl or benzyl, wherein, the groups "C1-C6 alkyl", "C2-C6 alkenyl", "C2-C6 alkynyl", "C3-C6 cycloalkyl", "C3-C6 cycloalkyl C1-C6 alkyl", "C3-C6 cycloalkenyl" and "C3-C6 cycloalkenyl C1-C6 alkyl" are each independently unsubstituted or substituted by halogen; the groups "phenyl" and "benzyl" are each independently unsubstituted or substituted by at least one group selected from halogen, cyano, nitro, C1-C6 alkyl, halo C1-C6 alkyl, C1-C6 alkoxy carbonyl, C1-C6 alkylthio, C1-C6 alkyl sulfonyl, C1-C6 alkoxy or halo C1-C6 alkoxy;

or R$_7$, R$_8$, taken together, form —CH$_2$CH$_2$CH$_2$CH$_2$— or —CH═CH—CH═CH— that is unsubstituted or substituted by at least one group selected from halogen, C1-C6 alkyl or halo C1-C6 alkyl;

or R$_{19}$, R$_{20}$, taken together, form —CH$_2$CH$_2$CH$_2$CH$_2$— or —CH$_2$CH═CHCH$_2$— that is unsubstituted or substituted by at least one group selected from halogen, C1-C6 alkyl or halo C1-C6 alkyl;

or R$_{21}$, R$_{22}$, taken together, form —CH$_2$CH$_2$CH$_2$—, —CH$_2$OCH$_2$CH$_2$— or —CH$_2$CH$_2$CH$_2$CH$_2$— that is unsubstituted or substituted by at least one group selected from halogen, C1-C6 alkyl or halo C1-C6 alkyl;

R$_1$ independently represents C1-C6 alkyl, C2-C6 alkenyl C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, phenyl or benzyl; wherein, the groups "C1-C6 alkyl", "C2-C6 alkenyl" and "C2-C6 alkynyl" are each independently unsubstituted or substituted by halogen; the groups "phenyl" and "benzyl" are each independently unsubstituted or substituted by 1, 2 or 3 groups selected from halogen, cyano, nitro, C1-C6 alkyl, halo C1-C6 alkyl, C1-C6 alkoxy carbonyl, C1-C6 alkylthio, C1-C6 alkyl sulfonyl, C1-C6 alkoxy or halo C1-C6 alkoxy;

R$_{12}$ independently represents H, C1-C6 alkyl, C2-C6 alkenyl, C2-C6 alkynyl, C1-C6 alkoxy, C1-C6 alkyl sulfonyl, C3-C6 cycloalkyl, C3-C6 cycloalkyl C1-C6 alkyl, C3-C6 cycloalkenyl or C3-C6 cycloalkenyl C1-C6 alkyl, or the group N(R$_{12}$)$_2$ in —(CO)N(R$_{12}$)$_2$ or —(SO$_2$)N(R$_{12}$)$_2$ independently represents

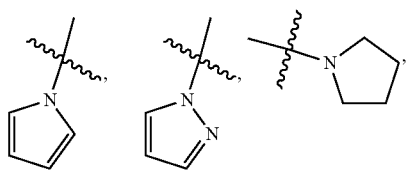

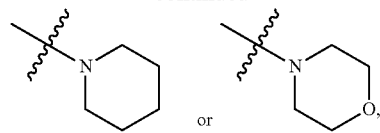

or which is unsubstituted or substituted by 1, 2 or 3 groups selected from oxo, C1-C6 alkyl or C1-C6 alkoxy carbonyl;

R$_{13}$ independently represents C1-C6 alkyl, C2-C6 alkenyl, C2-C6 alkynyl, C3-C6 cycloalkyl, phenyl or phenyl substituted by 1, 2 or 3 groups selected from: halogen, cyano, nitro, C1-C6 alkyl, halo C1-C6 alkyl, C1-C6 alkoxy, halo C1-C6 alkoxy, C1-C6 alkoxy carbonyl, C1-C6 alkylthio, C1-C6 alkyl sulfonyl or phenoxy substituted by 1, 2 or 3 groups selected from halogen, cyano, nitro, C1-C6 alkyl, halo C1-C6 alkyl, C1-C6 alkoxy or halo C1-C6 alkoxy;

R$_{14}$ independently represents H, C1-C6 alkyl, halo C1-C6 alkyl, phenyl or phenyl substituted by 1, 2 or 3 groups selected from halogen, cyano, nitro, C1-C6 alkyl, halo C1-C6 alkyl, C1-C6 alkoxy carbonyl, C1-C6 alkylthio, C1-C6 alkyl sulfonyl, C1-C6 alkoxy or halo C1-C6 alkoxy;

R$_{15}$, R$_{16}$, R$_{52}$ each independently represent H, halogen, C1-C6 alkyl, C2-C6 alkenyl, C2-C6 alkynyl, C3-C6 cycloalkyl, C3-C6 cycloalkyl C1-C6 alkyl, C3-C6 cycloalkenyl or C3-C6 cycloalkenyl C1-C6 alkyl, wherein, the groups "C1-C6 alkyl", "C2-C6 alkenyl", "C2-C6 alkynyl", "C3-C6 cycloalkyl", "C3-C6 cycloalkyl C1-C6 alkyl", "C3-C6 cycloalkenyl" and "C3-C6 cycloalkenyl C1-C6 alkyl" are each independently unsubstituted or substituted by halogen.

4. The fused-ring substituted aromatic compound according to claim 1, which is characterized in that, X$_1$, X$_2$ each independently represent H, halogen, nitro, cyano, thiocyano, hydroxy, mercapto, sulfo, formyl, haloformyl, azido, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, —PO(OR')$_2$, —OR", —(CO)R", —SR", —(SO)R", —(SO$_2$)R", —Si(R")$_3$, —O(CO)R", —O—(SO$_2$)R", —S(CO)R", —(SO$_2$)OR", —O(CO)OR", —(CO)(CO)OR",

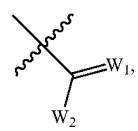

—CR'═N—OH, —CR'═N—O—R", heterocyclyl, heterocyclyl C1-C3 alkyl, aryl, aryl C1-C3 alkyl, amino, amino C1-C3 alkyl, amino carbonyl C1-C3 alkyl, amino carbonyloxy C1-C3 alkyl, amino thio carbonyloxy C1-C3 alkyl, amino sulfonyl or amino sulfonyloxy C1-C3 alkyl, wherein, the groups "C1-C6 alkyl", "C2-C6 alkenyl" and "C2-C6 alkynyl" are each independently unsubstituted or substituted by 1, 2 or 3 groups selected from halogen, cyano, hydroxy, mercapto, carboxyl, —OR", —(CO)R", —SR", —(SO$_2$)R", —O(CO)H, —O(CO)R", —O—(SO$_2$)R", —(CO)OR", —O(CO)OR", —O(CO)

(CO)OH, —O(CO)(CO)OR″, —O—(C1-C3 alkyl)-(CO)OH or —O—(C1-C3 alkyl)-(CO)OR″,
the groups "C3-C6 cycloalkyl", "C3-C6 cycloalkyl C1-C3 alkyl", "C3-C6 cycloalkenyl", "C3-C6 cycloalkenyl C1-C3 alkyl", "heterocyclyl", "heterocyclyl C1-C3 alkyl", "aryl" and "aryl C1-C3 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —$OR_{14}$, —$SR_{14}$, —$(CO)OR_{14}$, —$(SO_2)R_{14}$, —$N(R_{14})_2$ or —O—(C1-C3 alkyl)-$(CO)OR_{14}$, or two adjacent carbon atoms on the ring together with unsubstituted or halogen-substituted —$OCH_2CH_2$— or —$OCH_2O$— form a fused ring,
the groups "amino", "amino C1-C3 alkyl", "amino carbonyl C1-C3 alkyl", "amino carbonyloxy C1-C3 alkyl", "amino thio carbonyloxy C1-C3 alkyl", "amino sulfonyl" and "amino sulfonyloxy C1-C3 alkyl" are each independently unsubstituted or substituted by one or two groups selected from —$R_{11}$, —$OR_{11}$, —$(CO)R_{11}$, —$(CO)OR_{11}$, —(C1-C3 alkyl)-$(CO)OR_{11}$, —$(SO_2)R_{11}$, —$(SO_2)OR_{11}$, —(C1-C3 alkyl)-$(SO_2)R_{11}$, —$(CO)N(R_{12})_2$ or —$(SO_2)N(R_{12})_2$;
R′ independently represents H, halogen, C1-C6 alkoxy, C1-C6 alkoxy C1-C3 alkyl, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, aryl, aryl C1-C3 alkyl, heterocyclyl or heterocyclyl C1-C3 alkyl; wherein, the groups "C1-C6 alkyl", "C2-C6 alkenyl" and "C2-C6 alkynyl" are each independently unsubstituted or substituted by halogen; the groups "C3-C6 cycloalkyl", "C3-C6 cycloalkyl C1-C3 alkyl", "C3-C6 cycloalkenyl", "C3-C6 cycloalkenyl C1-C3 alkyl", "aryl", "aryl C1-C3 alkyl", "heterocyclyl" and "heterocyclyl C1-C3 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —$OR_{14}$, —$SR_{14}$, —$(CO)OR_{14}$, —$(SO_2)R_{14}$, —$N(R_{14})_2$ or —O—(C1-C3 alkyl)-$(CO)OR_{14}$, or two adjacent carbon atoms on the ring together with unsubstituted or halogen-substituted —$OCH_2CH_2$— or —$OCH_2O$— form a fused ring;
R″ independently represents C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, aryl, aryl C1-C3 alkyl, aryl C2-C3 alkenyl, heterocyclyl, heterocyclyl C1-C3 alkyl or heterocyclyl C2-C3 alkenyl; wherein, the groups "C1-C6 alkyl", "C2-C6 alkenyl" and "C2-C6 alkynyl" are each independently unsubstituted or substituted by 1, 2 or 3 groups selected from halogen, cyano, tri C1-C6 alkylsilyl, —$OR_{13}$, —$SR_{13}$, —$O(CO)R_{13}$, —$(CO)R_{13}$, —$(CO)OR_{13}$ or —$O(CO)OR_{13}$; the groups "C3-C6 cycloalkyl", "C3-C6 cycloalkyl C1-C3 alkyl", "C3-C6 cycloalkenyl", "C3-C6 cycloalkenyl C1-C3 alkyl", "aryl", "aryl C1-C3 alkyl", "aryl C2-C3 alkenyl", "heterocyclyl", "heterocyclyl C1-C3 alkyl" and "heterocyclyl C2-C3 alkenyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —$OR_{14}$, —$SR_{14}$, —$(CO)OR_{14}$, —$(SO_2)R_{14}$, —$N(R_{14})_2$ or —O—(C1-C3 alkyl)-$(CO)OR_{14}$, or two adjacent carbon atoms on the ring together with unsubstituted or halogen-substituted —$OCH_2CH_2$— or —$OCH_2O$— form a fused ring;

$W_3$ independently represents H, C1-C6 alkyl, C2-C6 alkenyl, C2-C6 alkynyl, C3-C6 cycloalkyl, C3-C6 cycloalkenyl, heterocyclyl, aryl,

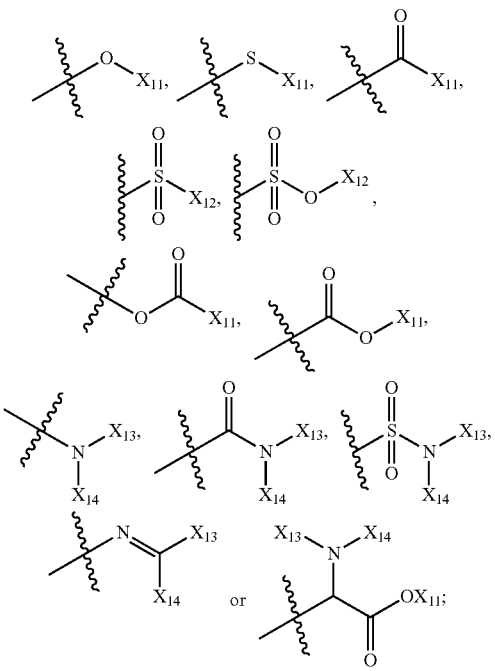

wherein, the groups "C1-C6 alkyl", "C2-C6 alkenyl" and "C2-C6 alkynyl" are each independently unsubstituted or substituted by 1, 2 or 3 groups selected from halogen, cyano, nitro, C3-C6 cycloalkyl, tri C1-C6 alkylsilyl, C3-C6 cycloalkenyl, heterocyclyl, aryl,

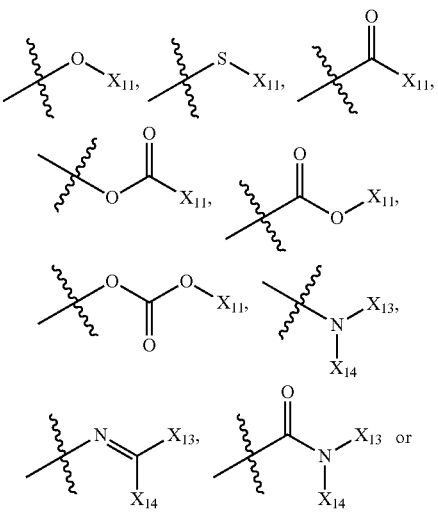

-continued

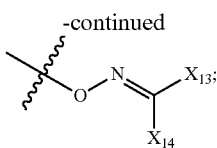

the groups "C3-C6 cycloalkyl", "C3-C6 cycloalkenyl", "heterocyclyl" and "aryl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C3 alkyl)-(CO)OR$_{14}$, or two adjacent carbon atoms on the ring together with unsubstituted or halogen-substituted —OCH$_2$CH$_2$— or —OCH$_2$O— form a fused ring;

or N(W$_3$)$_2$ represents

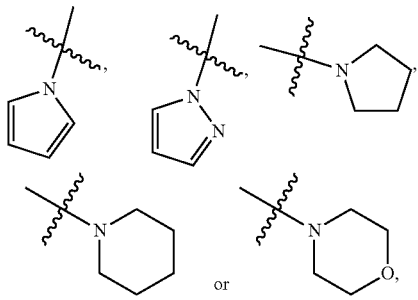

which is unsubstituted or substituted by 1, 2 or 3 groups selected from oxo, C1-C6 alkyl or C1-C6 alkoxy carbonyl;

$X_{11}$ independently represents H, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, heterocyclyl, heterocyclyl C1-C3 alkyl, aryl or aryl C1-C3 alkyl; wherein, the groups "C3-C6 cycloalkyl", "C3-C6 cycloalkyl C1-C3 alkyl", "C3-C6 cycloalkenyl", "C3-C6 cycloalkenyl C1-C3 alkyl", "heterocyclyl", "heterocyclyl C1-C3 alkyl", "aryl" and "aryl C1-C3 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C3 alkyl)-(CO)OR$_{14}$, or two adjacent carbon atoms on the ring together with unsubstituted or halogen-substituted —OCH$_2$CH$_2$— or —OCH$_2$O— form a fused ring;

$X_{12}$ independently represents C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, heterocyclyl, heterocyclyl C1-C3 alkyl, aryl or aryl C1-C3 alkyl; wherein, the groups "C3-C6 cycloalkyl", "C3-C6 cycloalkyl C1-C3 alkyl", "C3-C6 cycloalkenyl", "C3-C6 cycloalkenyl C1-C3 alkyl", "heterocyclyl", "heterocyclyl C1-C3 alkyl", "aryl" and "aryl C1-C3 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C3 alkyl)-(CO)OR$_{14}$, or two adjacent carbon atoms on the ring together with unsubstituted or halogen-substituted —OCH$_2$CH$_2$— or —OCH$_2$O— form a fused ring;

$X_{13}$, $X_{14}$ each independently represent H, halogen, cyano, C1-C6 alkoxy, C1-C6 alkoxy C1-C3 alkyl, C1-C6 alkyl carbonyl, C1-C6 alkoxy carbonyl, C1-C6 alkyl sulfonyl, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, aryl, aryl C1-C3 alkyl, heterocyclyl or heterocyclyl C1-C3 alkyl, or the group CX$_{13}$X$_{14}$, taken together, forms 5~8 membered saturated carbocyclyl,

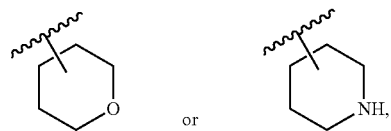

or the group NX$_{13}$X$_{14}$, taken together, forms

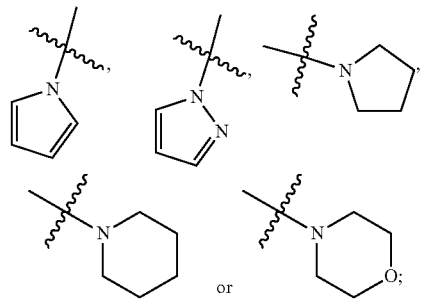

wherein, the groups "C1-C6 alkyl", "C2-C6 alkenyl" and "C2-C6 alkynyl" are each independently unsubstituted or substituted by halogen; the groups "C3-C6 cycloalkyl", "C3-C6 cycloalkyl C1-C3 alkyl", "C3-C6 cycloalkenyl", "C3-C6 cycloalkenyl C1-C3 alkyl", "aryl", "aryl C1-C3 alkyl", "heterocyclyl" and "heterocyclyl C1-C3 alkyl" are each independently unsubstituted or substituted by 1, 2 or 3 groups selected from oxo, halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —(CO)OR$_{14}$, —(SO$_2$)R$_{14}$, —N(R$_{14}$)$_2$ or —O—(C1-C3 alkyl)-(CO)OR$_{14}$, or two adjacent carbon atoms on the ring together with unsubstituted or halogen-substituted —OCH$_2$CH$_2$— or —OCH$_2$O— form a fused ring; the groups "5~8 membered saturated carbocyclyl,

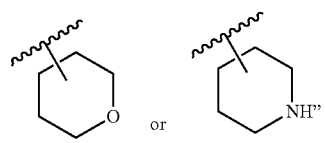

are unsubstituted or substituted by 1, 2 or 3 groups selected from C1-C6 alkyl, C1-C6 alkoxy carbonyl or benzyl, or together with phenyl or thienyl form a fused ring; the groups

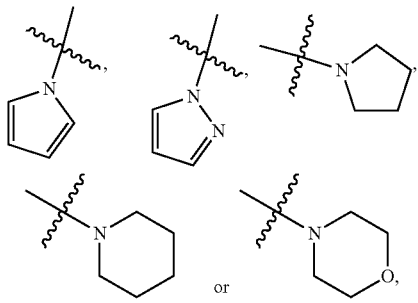

are unsubstituted or substituted by 1, 2 or 3 groups selected from oxo, C1-C6 alkyl or C1-C6 alkoxy carbonyl;

$R_{11}$ independently represents C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, phenyl, benzyl; wherein, the groups "C1-C6 alkyl", "C2-C6 alkenyl" and "C2-C6 alkynyl" are each independently unsubstituted or substituted by halogen; the groups "phenyl" and "benzyl" are each independently unsubstituted or substituted by 1, 2 or 3 groups selected from halogen, cyano, nitro, C1-C6 alkyl, halo C1-C6 alkyl, C1-C6 alkoxy carbonyl, C1-C6 alkylthio, C1-C6 alkyl sulfonyl, C1-C6 alkoxy or halo C1-C6 alkoxy;

$R_{12}$ independently represents H, C1-C6 alkyl, C2-C6 alkenyl, C2-C6 alkynyl, C1-C6 alkoxy, C1-C6 alkyl sulfonyl, C3-C6 cycloalkyl, C3-C6 cycloalkyl C1-C3 alkyl, C3-C6 cycloalkenyl or C3-C6 cycloalkenyl C1-C3 alkyl, or the group $N(R_{12})_2$ in —(CO)N$(R_{12})_2$ or —(SO$_2$)N$(R_{12})_2$ independently represents

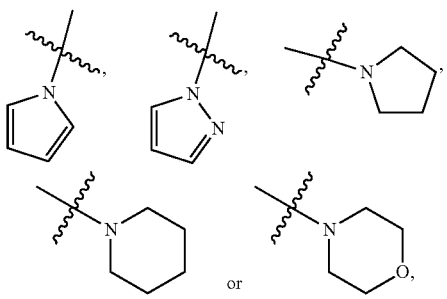

which is unsubstituted or substituted by 1, 2 or 3 groups selected from oxo, C1-C6 alkyl or C1-C6 alkoxy carbonyl;

$R_{13}$ independently represents C1-C6 alkyl, C2-C6 alkenyl, C2-C6 alkynyl, C3-C6 cycloalkyl, phenyl or phenyl substituted by 1, 2 or 3 groups selected from: halogen, cyano, nitro, C1-C6 alkyl, halo C1-C6 alkyl, C1-C6 alkoxy, halo C1-C6 alkoxy, C1-C6 alkoxy carbonyl, C1-C6 alkylthio, C1-C6 alkyl sulfonyl or phenoxy substituted by 1, 2 or 3 groups selected from halogen, cyano, nitro, C1-C6 alkyl, halo C1-C6 alkyl, C1-C6 alkoxy or halo C1-C6 alkoxy;

$R_{14}$ independently represents H, C1-C6 alkyl, halo C1-C6 alkyl, phenyl or phenyl substituted by 1, 2 or 3 groups selected from halogen, cyano, nitro, C1-C6 alkyl, halo C1-C6 alkyl, C1-C6 alkoxy carbonyl, C1-C6 alkylthio, C1-C6 alkyl sulfonyl, C1-C6 alkoxy or halo C1-C6 alkoxy.

5. The fused-ring substituted aromatic compound according to claim 1, which is characterized in that, Het represents

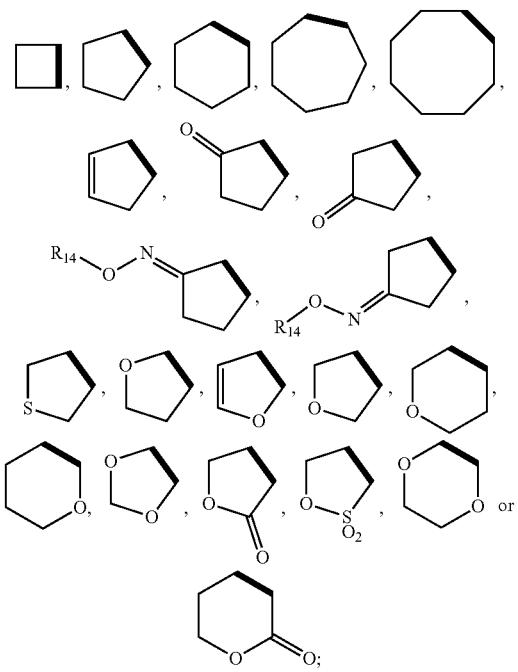

except for the 4- and 5-positions that are respectively substituted by $X_2$ or $X_1$ in the general formula I, other positions on the Het are each independently unsubstituted or substituted by 1, 2 or 3 groups selected from halogen, cyano, nitro, C1-C6 alkyl, C2-C6 alkenyl, C2-C6 alkynyl, C3-C6 cycloalkyl, halo C1-C6 alkyl, halo C2-C6 alkenyl, halo C2-C6 alkynyl, halo C3-C6 cycloalkyl, C1-C6 alkyl-substituted C3-C6 cycloalkyl, —OR$_{14}$, —SR$_{14}$, —SOR$_{14}$, —(CO)OR$_{14}$, —(SO$_2$)R$_{14}$, —N(R$_{14}$)$_2$ or —O—(C1-C3 alkyl)-(CO)OR$_{14}$.

6. The fused-ring substituted aromatic compound according to claim 1, which is characterized in that, Q represents

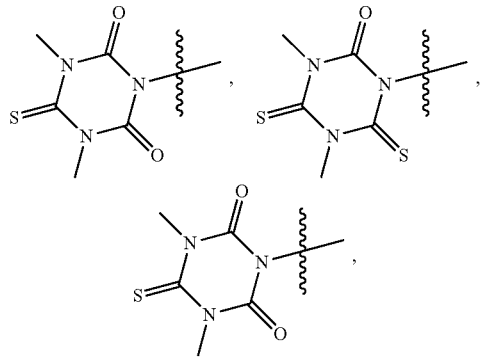

397
-continued

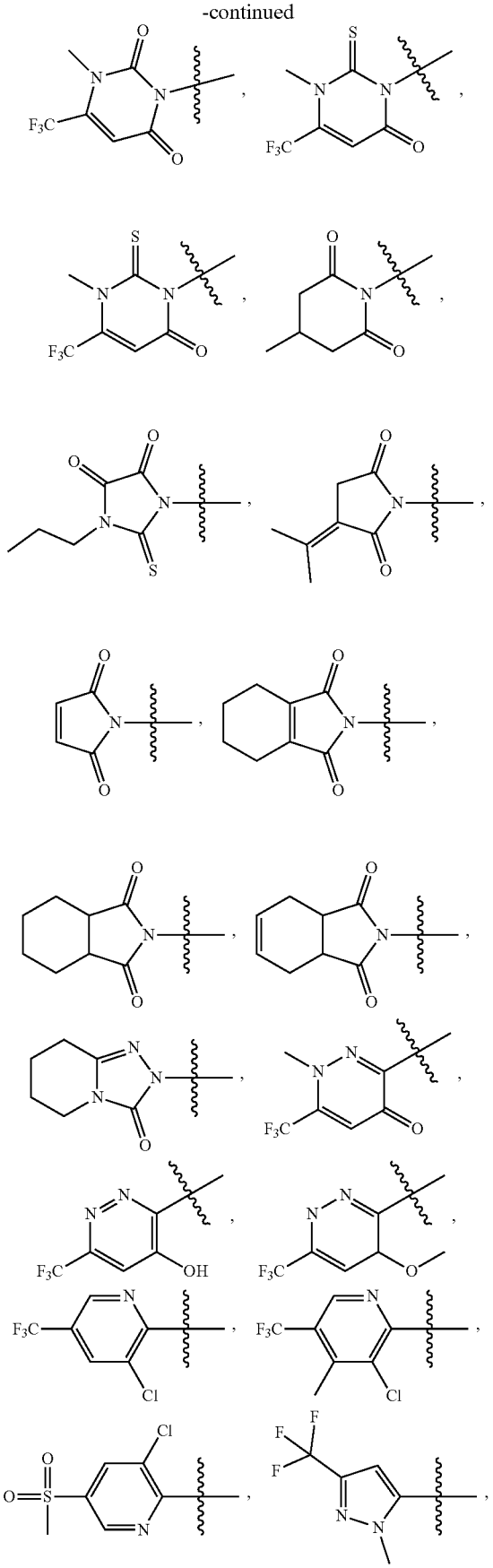

398
-continued

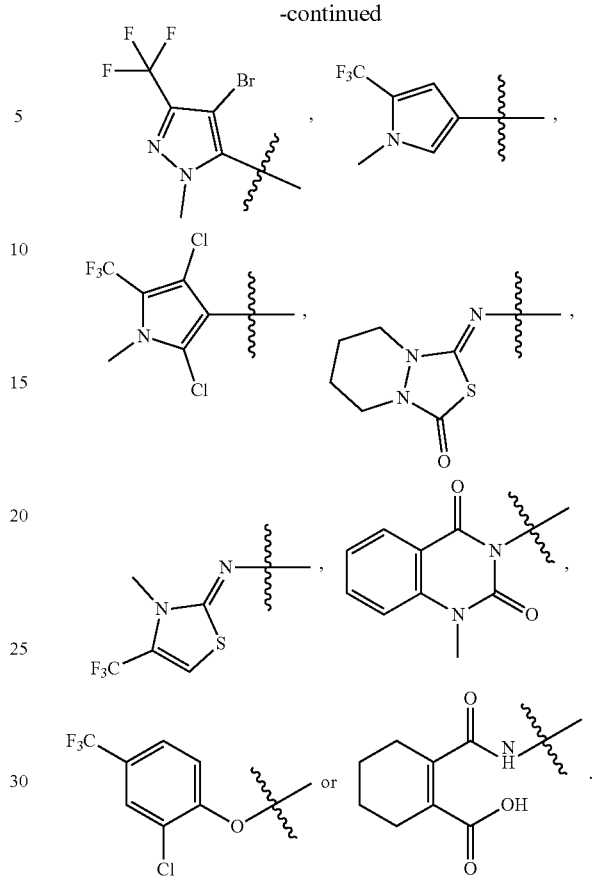

7. A method for preparing the fused-ring substituted aromatic compound according to claim 1, which comprises the following step:

converting the compound represented by general formula II

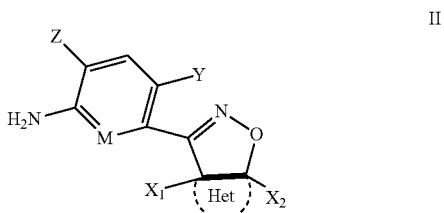

II into the compound represented by general formula I; the substituents $X_1$, $X_2$, Het, Q, Y, Z and M are as defined in claim 1.

8. A herbicidal composition comprising a herbicidally effective dose of at least one of the fused-ring substituted aromatic compound according to claim 1.

9. A method for controlling a weed which includes applying a herbicidally effective dose of at least one of the fused-ring substituted aromatic compound according to claim 1 to a plant or a weed area.

10. The fused-ring substituted aromatic compound according to claim 1, which is selected from the compounds of formula I as follows:

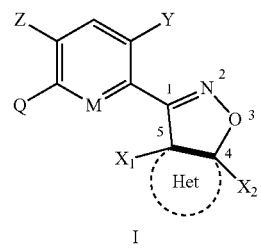
| No. | M | 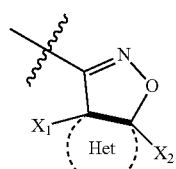 | Y | Z | Q |
|---|---|---|---|---|---|
| 2 | CH | 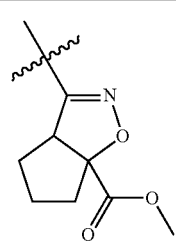 [SMILES: *C1=NOC2(C(=O)OC)CCCC12] | Cl | F | 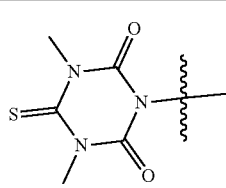 [SMILES: *n1c(=O)n(C)c(=S)n(C)c1=O] |
| 3 | CH | 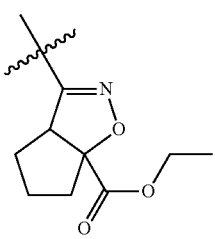 [SMILES: *C1=NOC2(C(=O)OCC)CCCC12] | Cl | F | 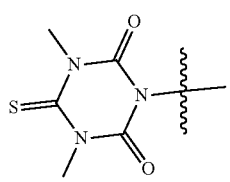 [SMILES: *n1c(=O)n(C)c(=S)n(C)c1=O] |
| 4 | CH | 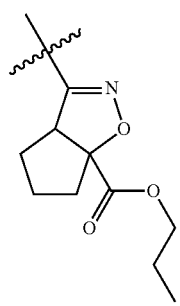 [SMILES: *C1=NOC2(C(=O)OCCC)CCCC12] | Cl | F | 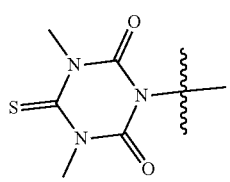 [SMILES: *n1c(=O)n(C)c(=S)n(C)c1=O] |
| 10 | CH | 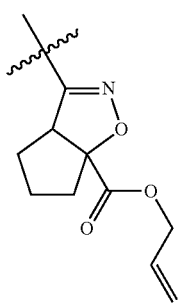 [SMILES: *C1=NOC2(C(=O)OCC=C)CCCC12] | Cl | F | 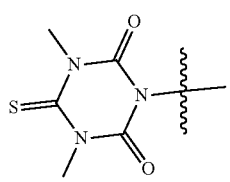 [SMILES: *n1c(=O)n(C)c(=S)n(C)c1=O] |

-continued
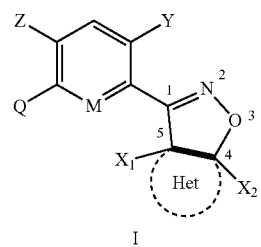
I
| No. | M | | Y | Z | Q |
|---|---|---|---|---|---|
| 13 | CH | 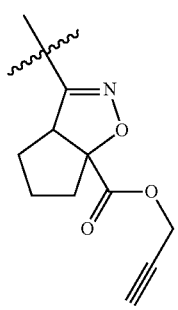 [SMILES: *C1=NOC2(C(=O)OCC#C)CCCC12] | Cl | F | 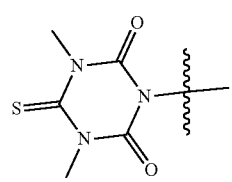 [SMILES: *n1c(=O)n(C)c(=S)n(C)c1=O] |
| 49 | CH | 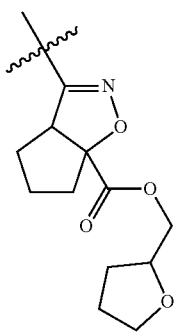 [SMILES: *C1=NOC2(C(=O)OCC3CCCO3)CCCC12] | Cl | F | 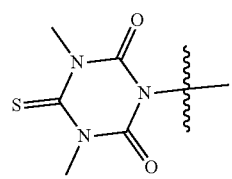 [SMILES: *n1c(=O)n(C)c(=S)n(C)c1=O] |
| 51 | CH | 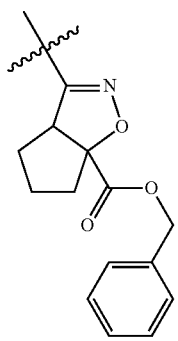 [SMILES: *C1=NOC2(C(=O)OCc3ccccc3)CCCC12] | Cl | F | 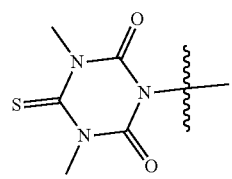 [SMILES: *n1c(=O)n(C)c(=S)n(C)c1=O] |

-continued
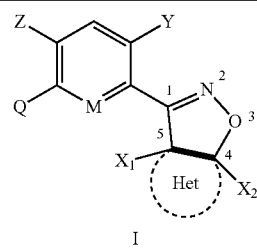
I
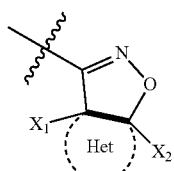
| No. | M | | Y | Z | Q |
|---|---|---|---|---|---|
| 66 | CH | 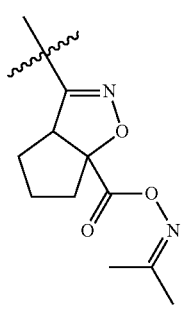 [SMILES: *C1=NOC2(C(=O)ON=C(C)C)CCCC12] | Cl | F | 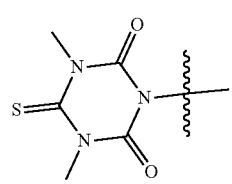 [SMILES: *n1c(=O)n(C)c(=S)n(C)c1=O] |
| 160 | CH | 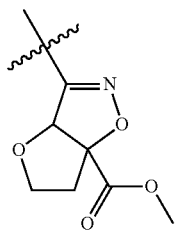 [SMILES: *C1=NOC2(C(=O)OC)CCOC12] | Cl | F | 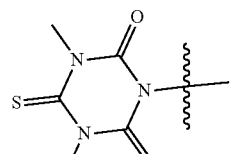 |
| 162 | CH | 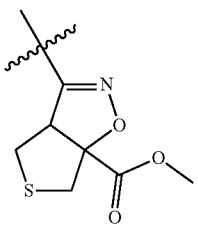 [SMILES: *C1=NOC2(C(=O)OC)CSCC12] | Cl | F | 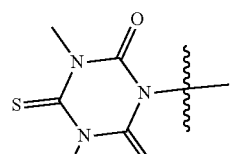 |
| 209 | CH | 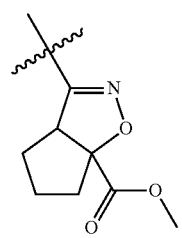 [SMILES: *C1=NOC2(C(=O)OC)CCCC12] | Cl | F | 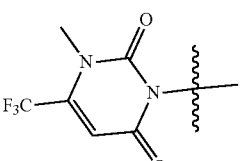 |

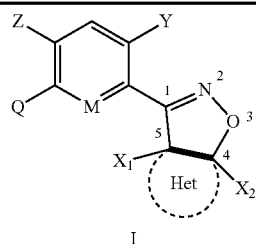

I

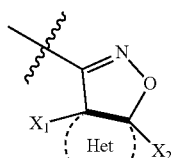

| No. | M | | Y | Z | Q |
|---|---|---|---|---|---|
| 210 | CH | methyl 3a-linked hexahydrocyclopenta[c]isoxazole-6a-carboxylate | Br | F | 1-methyl-6-(trifluoromethyl)-2,4-dioxopyrimidin-3-yl |
| 211 | CH | methyl 3a-linked hexahydrocyclopenta[c]isoxazole-6a-carboxylate | CF3 | F | 1-methyl-6-(trifluoromethyl)-2,4-dioxopyrimidin-3-yl |
| 212 | CH | methyl 3a-linked hexahydrocyclopenta[c]isoxazole-6a-carboxylate | CN | F | 1-methyl-6-(trifluoromethyl)-2,4-dioxopyrimidin-3-yl |
| 213 | CH | 3a-linked hexahydrocyclopenta[c]isoxazole-6a-carboxylic acid | Cl | F | 1-methyl-6-(trifluoromethyl)-2,4-dioxopyrimidin-3-yl |
| 214 | CH | methyl 3a-linked hexahydrocyclopenta[c]isoxazole-6a-carboxylate | Cl | F | 1-methyl-6-(trifluoromethyl)-2,4-dioxopyrimidin-3-yl |

-continued
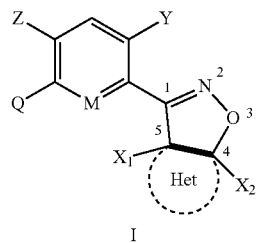
I
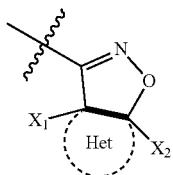
| No. | M | | Y | Z | Q |
|---|---|---|---|---|---|
| 215 | CH | 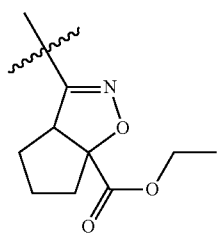 [SMILES: *C1=NOC2(C(=O)OCC)CCCC12] | Cl | F | 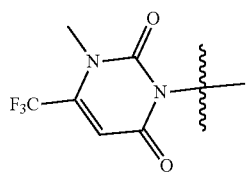 [SMILES: *n1c(=O)cc(C(F)(F)F)n(C)c1=O] |
| 216 | CH | 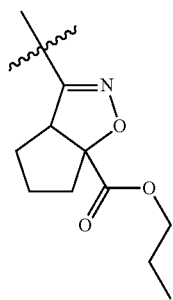 [SMILES: *C1=NOC2(C(=O)OCCC)CCCC12] | Cl | F | 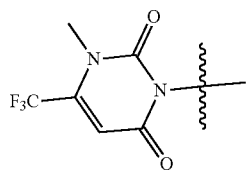 [SMILES: *n1c(=O)cc(C(F)(F)F)n(C)c1=O] |
| 217 | CH | 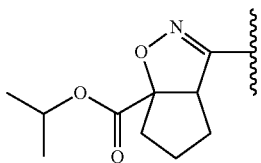 [SMILES: *C1=NOC2(C(=O)OC(C)C)CCCC12] | Cl | F | 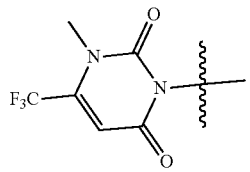 [SMILES: *n1c(=O)cc(C(F)(F)F)n(C)c1=O] |
| 222 | CH | 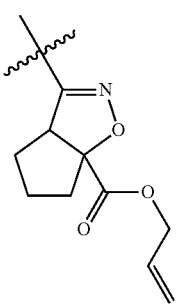 [SMILES: *C1=NOC2(C(=O)OCC=C)CCCC12] | Cl | F | 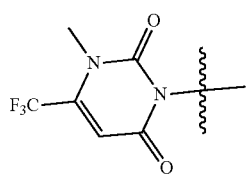 [SMILES: *n1c(=O)cc(C(F)(F)F)n(C)c1=O] |

-continued
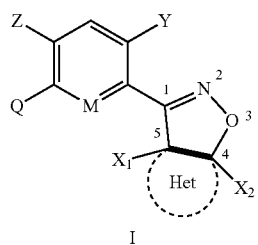
I
| No. | M | | Y | Z | Q |
|---|---|---|---|---|---|
| 225 | CH | 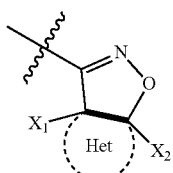 | Cl | F | 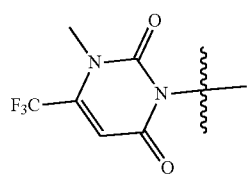 |
| 231 | CH | 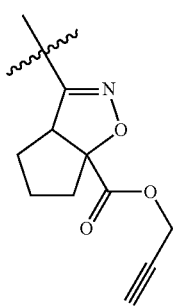 [SMILES: *C1=NOC2(C(=O)OCC#C)CCCC12] | Cl | F | 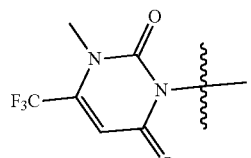 |
| 245 | CH | 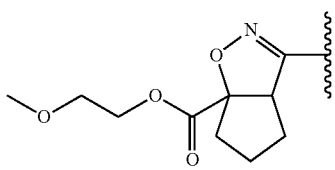 | Cl | F | 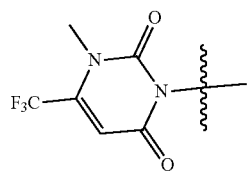 [SMILES: *n1c(=O)cc(C(F)(F)F)n(C)c1=O] |
| 261 | CH | 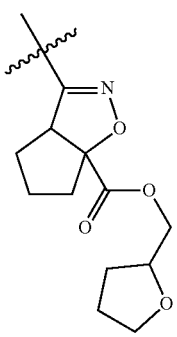 [SMILES: *C1=NOC2(C(=O)OCC3CCCO3)CCCC12] | Cl | F | 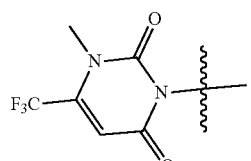 |

-continued
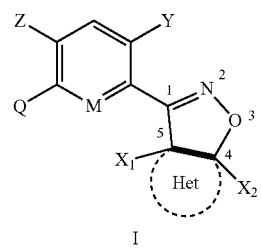
I
| No. | M | 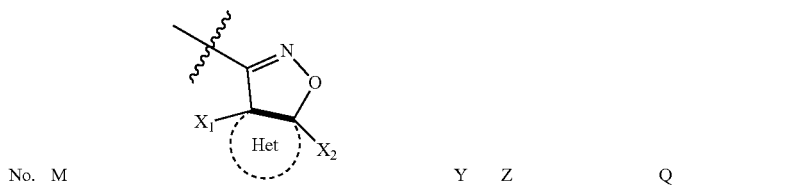 | Y | Z | Q |
|---|---|---|---|---|---|
| 264 | CH | 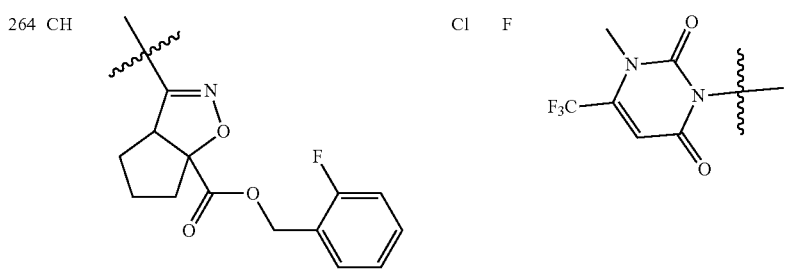 | Cl | F | |
| 278 | CH | 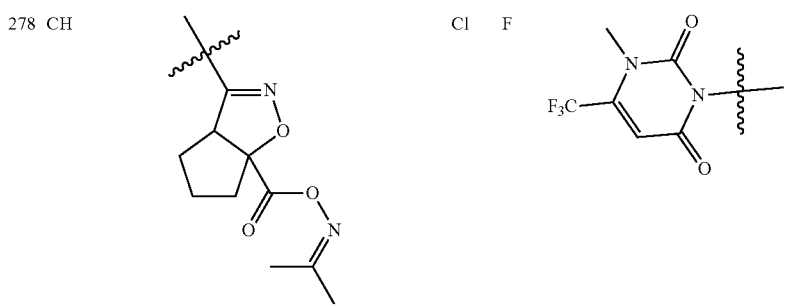 | Cl | F | |
| 333 | CH | 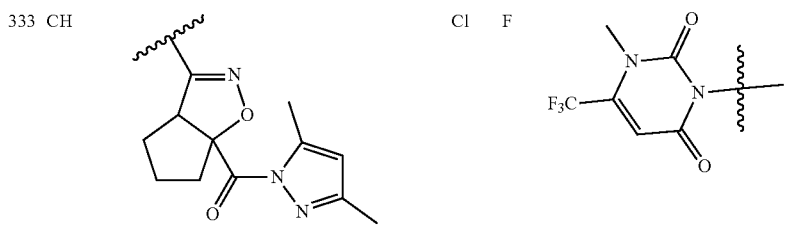 | Cl | F | |
| 334 | CH | 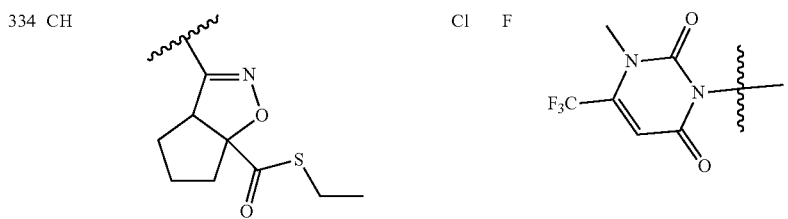 | Cl | F | |

-continued

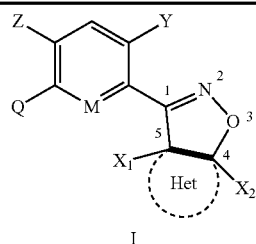

I

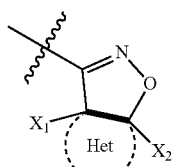

| No. | M | | Y | Z | Q |
|---|---|---|---|---|---|
| 341 | CH | (methyl-substituted cyclopentane-fused isoxazoline with methyl ester) | Cl | F | (1-methyl-6-trifluoromethyl-2,4-dioxopyrimidin-3-yl) |
| 351 | CH | (hydroxy-substituted cyclopentane-fused isoxazoline with methyl ester) | Cl | F | (1-methyl-6-trifluoromethyl-2,4-dioxopyrimidin-3-yl) |
| 370 | CH | (cyclohexane-fused isoxazoline with methyl ester) | Cl | F | (1-methyl-6-trifluoromethyl-2,4-dioxopyrimidin-3-yl) |
| 372 | CH | (tetrahydrofuran-fused isoxazoline with methyl ester) | Cl | F | (1-methyl-6-trifluoromethyl-2,4-dioxopyrimidin-3-yl) |
| 374 | CH | (tetrahydrothiophene-fused isoxazoline with methyl ester) | Cl | F | (1-methyl-6-trifluoromethyl-2,4-dioxopyrimidin-3-yl) |

-continued
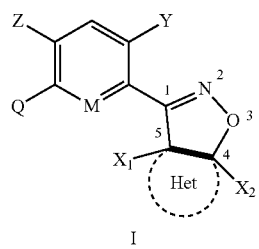
I
| No. | M | | Y | Z | Q |
|---|---|---|---|---|---|
| 395 | CH | 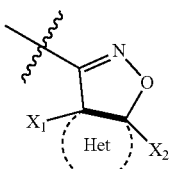 | Cl | F | 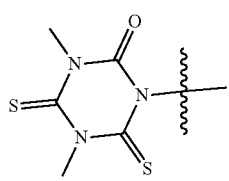 |
| 424 | CH | 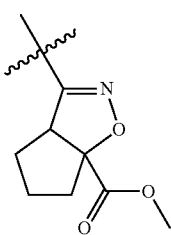 | Cl | F | 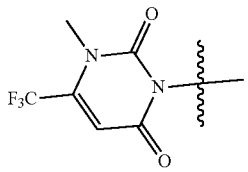 [SMILES: *n1c(=O)cc(C(F)(F)F)n(C)c1=O] |
| 425 | CH | 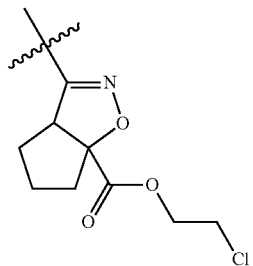 [SMILES: *C1=NOC2(C(=O)OCCCl)CCCC12] | Cl | F | 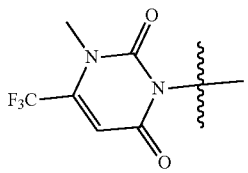 |
| 426 | CH | 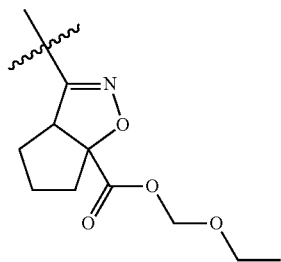 [SMILES: *C1=NOC2(C(=O)OCOCC)CCCC12] | Cl | F | 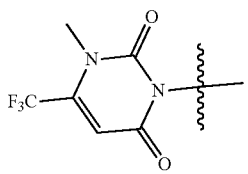 [SMILES: *n1c(=O)cc(C(F)(F)F)n(C)c1=O] |

-continued
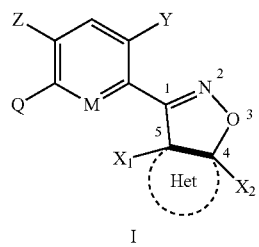
I
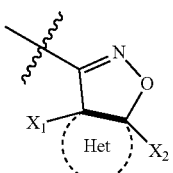
| No. | M | | Y | Z | Q |
|---|---|---|---|---|---|
| 427 | CH | 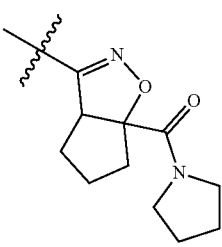 [SMILES: *C1=NOC2(C(=O)N3CCCC3)CCCC12] | Cl | F | 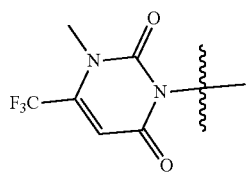 [SMILES: *n1c(=O)cc(C(F)(F)F)n(C)c1=O] |
| 433 | CH | 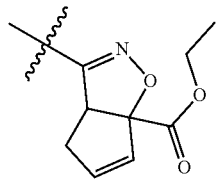 [SMILES: *C1=NOC2(C(=O)OCC)C=CCC12] | Cl | F | 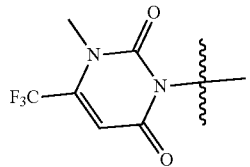 [SMILES: *n1c(=O)cc(C(F)(F)F)n(C)c1=O] |
| 434 | CH | 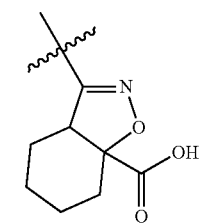 [SMILES: *C1=NOC2(C(=O)O)CCCCC12] | Cl | F | 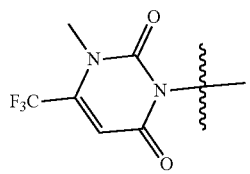 [SMILES: *n1c(=O)cc(C(F)(F)F)n(C)c1=O] |
| 435 | CH | 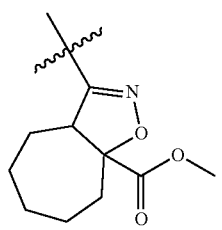 [SMILES: *C1=NOC2(C(=O)OC)CCCCCC12] | Cl | F | 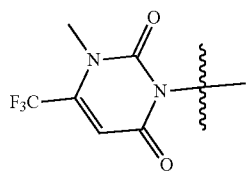 [SMILES: *n1c(=O)cc(C(F)(F)F)n(C)c1=O] |
| 436 | CH | 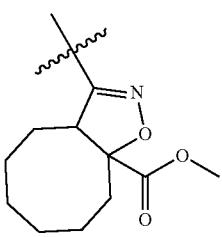 [SMILES: *C1=NOC2(C(=O)OC)CCCCCCC12] | Cl | F | 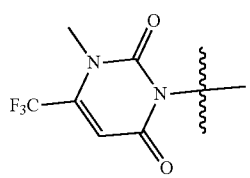 [SMILES: *n1c(=O)cc(C(F)(F)F)n(C)c1=O] |

-continued
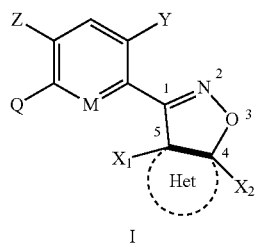
I
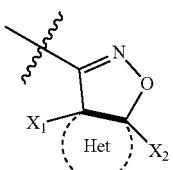
| No. | M | | Y | Z | Q |
|---|---|---|---|---|---|
| 438 | CH | 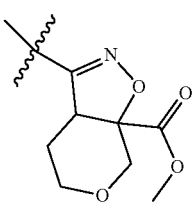 [SMILES: *C1=NOC2(C(=O)OC)COCCC12] | Cl | F | 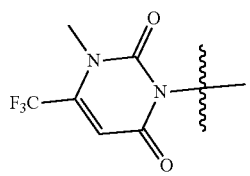 [SMILES: *n1c(=O)cc(C(F)(F)F)n(C)c1=O] |
| 440 | CH | 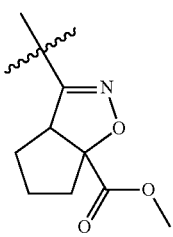 [SMILES: *C1=NOC2(C(=O)OC)CCCC12] | Cl | Cl | 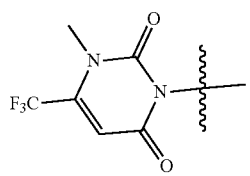 |
| 441 | CH | 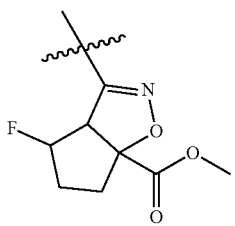 [SMILES: *C1=NOC2(C(=O)OC)CCC(F)C12] | Cl | F | 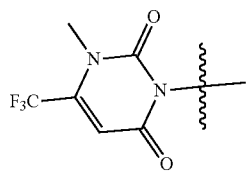 [SMILES: *n1c(=O)cc(C(F)(F)F)n(C)c1=O] |
| 443 | CH | 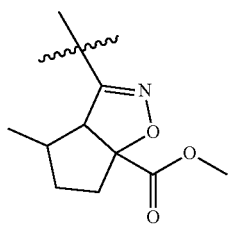 | Cl | F | 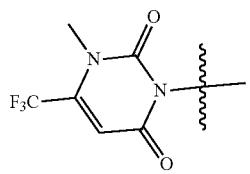 |
| 444 | CH | 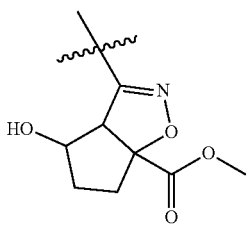 [SMILES: *C1=NOC2(C(=O)OC)CCC(O)C12] | Cl | F | 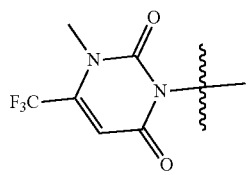 [SMILES: *n1c(=O)cc(C(F)(F)F)n(C)c1=O] |

-continued
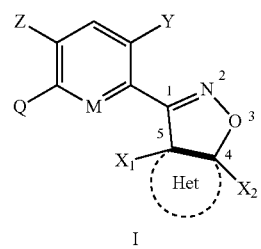
I
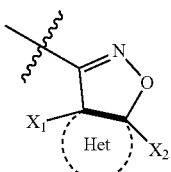
| No. | M | | Y | Z | Q |
|---|---|---|---|---|---|
| 451 | CH | 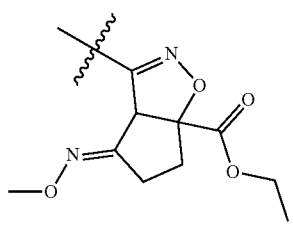 [SMILES: *C1=NOC2(C(=O)OCC)CC/C(=N\OC)C12] | Cl | F | 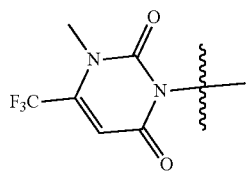 |
| 456 | CH | 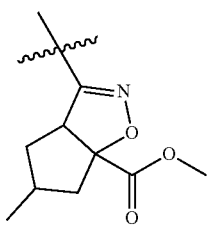 | Cl | F | 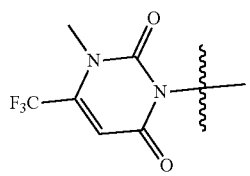 [SMILES: *n1c(=O)cc(C(F)(F)F)n(C)c1=O] |
| 464 | CH | 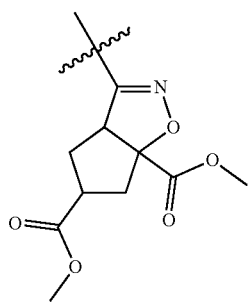 [SMILES: *C1=NOC2(C(=O)OC)CC(C(=O)OC)CC12] | Cl | F | 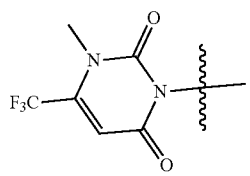 [SMILES: *n1c(=O)cc(C(F)(F)F)n(C)c1=O] |
| 472 | CH | 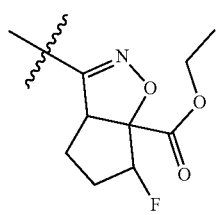 [SMILES: *C1=NOC2(C(=O)OCC)C(F)CCC12] | Cl | F | 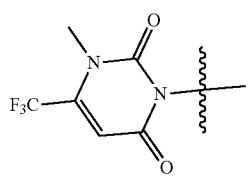 [SMILES: *n1c(=O)cc(C(F)(F)F)n(C)c1=O] |

-continued
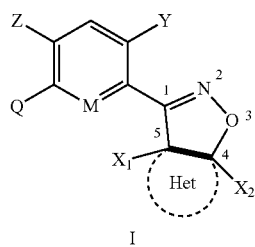
I
| No. | M | 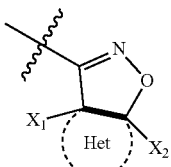 | Y | Z | Q |
|---|---|---|---|---|---|
| 474 | CH | 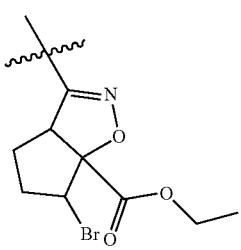 [SMILES: *C1=NOC2(C(=O)OCC)C(Br)CCC12] | Cl | F | 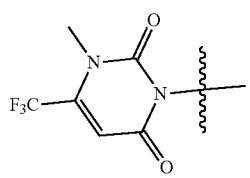 [SMILES: *n1c(=O)cc(C(F)(F)F)n(C)c1=O] |
| 475 | CH | 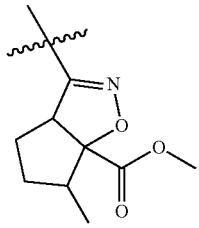 [SMILES: *C1=NOC2(C(=O)OC)C(C)CCC12] | Cl | F | 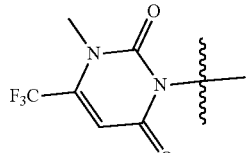 |
| 476 | CH | 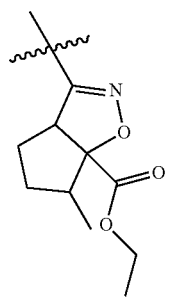 [SMILES: *C1=NOC2(C(=O)OCC)C(C)CCC12] | Cl | F | 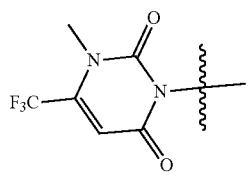 [SMILES: *n1c(=O)cc(C(F)(F)F)n(C)c1=O] |
| 477 | CH | 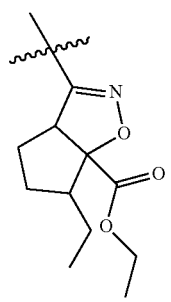 [SMILES: *C1=NOC2(C(=O)OCC)C(CC)CCC12] | Cl | F | 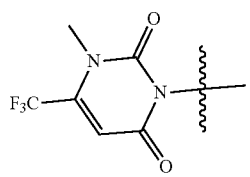 [SMILES: *n1c(=O)cc(C(F)(F)F)n(C)c1=O] |

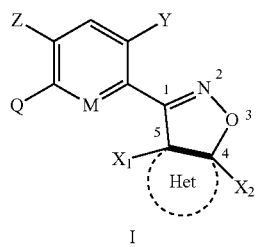
I
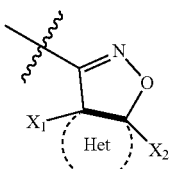
| No. | M | | Y | Z | Q |
|---|---|---|---|---|---|
| 480 | CH | 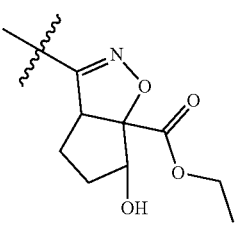 [SMILES: *C1=NOC2(C(=O)OCC)C(O)CCC12] | Cl | F | 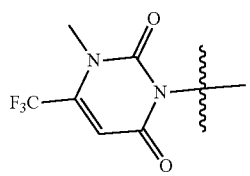 [SMILES: *n1c(=O)cc(C(F)(F)F)n(C)c1=O] |
| 490 | CH | 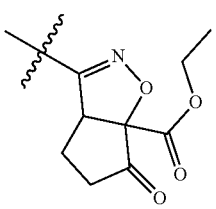 [SMILES: *C1=NOC2(C(=O)OCC)C(=O)CCC12] | Cl | F | 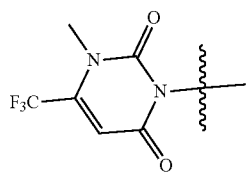 [SMILES: *n1c(=O)cc(C(F)(F)F)n(C)c1=O] |
| 491 | CH | 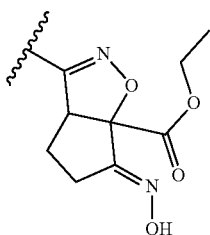 [SMILES: *C1=NOC2(C(=O)OCC)/C(=N/O)CCC12] | Cl | F | 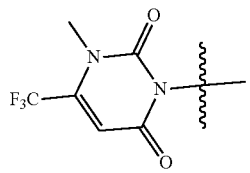 [SMILES: *n1c(=O)cc(C(F)(F)F)n(C)c1=O] |
| 493 | CH | 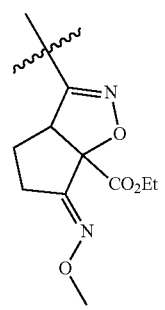 [SMILES: *C1=NOC2(C(=O)OCC)/C(=N/OC)CCC12] | Cl | F | 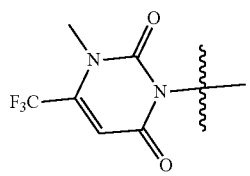 [SMILES: *n1c(=O)cc(C(F)(F)F)n(C)c1=O] |

-continued
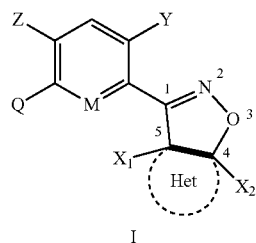
I
| No. | M | 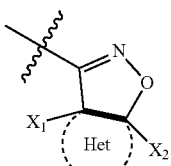 | Y | Z | Q |
|---|---|---|---|---|---|
| 497 | CH | 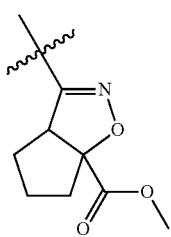 [SMILES: *C1=NOC2(C(=O)OC)CCCC12] | Cl | F | 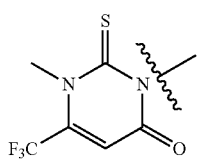 |
| 498 | CH | 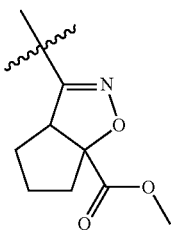 [SMILES: *C1=NOC2(C(=O)OC)CCCC12] | Cl | F | 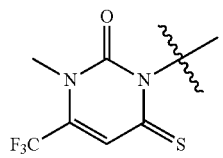 |
| 521 | N | 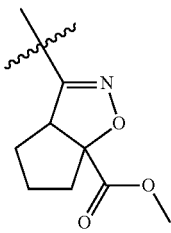 [SMILES: *C1=NOC2(C(=O)OC)CCCC12] | Cl | F | 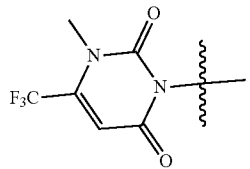 [SMILES: *n1c(=O)cc(C(F)(F)F)n(C)c1=O] |
| 530 | CH | 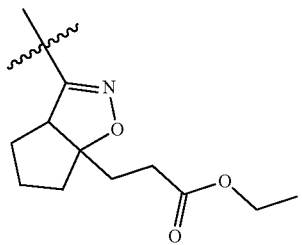 [SMILES: *C1=NOC2(CCC(=O)OCC)CCCC12] | Cl | F | 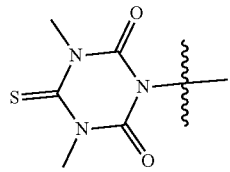 [SMILES: *n1c(=O)n(C)c(=S)n(C)c1=O] |

-continued
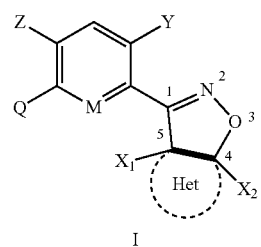
I
| No. | M | | Y | Z | Q |
|---|---|---|---|---|---|
| 533 | CH | 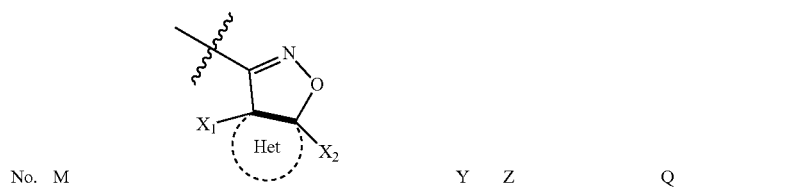 | Cl | F | |
| 534 | CH | 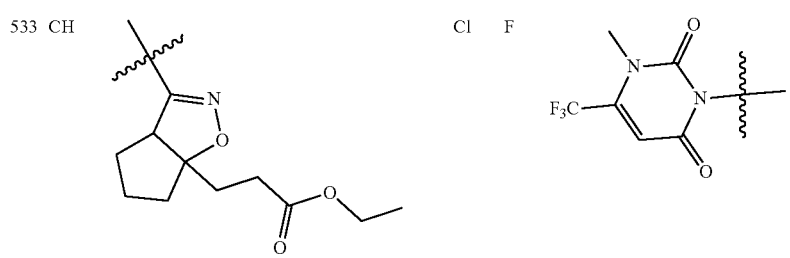 | Cl | F | |
| 536 | CH | 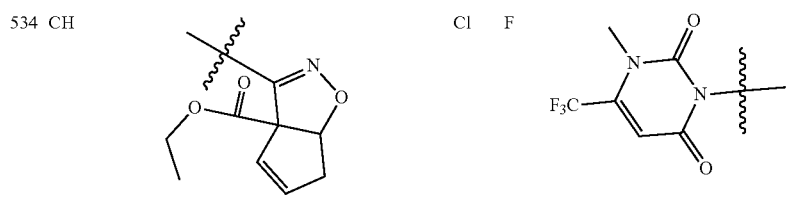 | Cl | F | |
| 537 | CH | 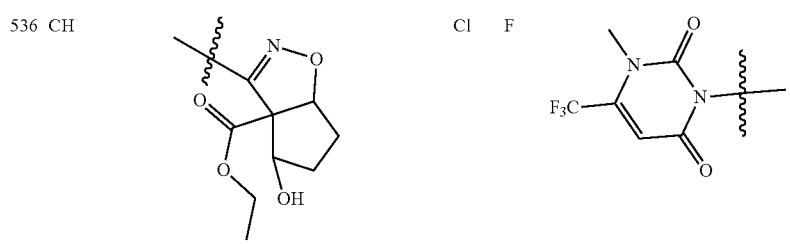 | Cl | F | |

-continued
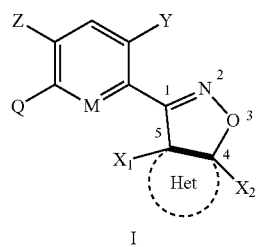
I
| No. | M | 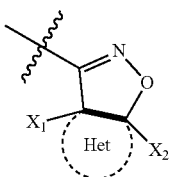 | Y | Z | Q |
|---|---|---|---|---|---|
| 539 | CH | 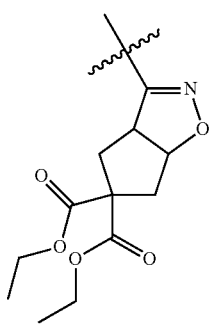 [SMILES: *C1=NOC2CC(C(=O)OCC)(C(=O)OCC)CC12] | Cl | F | 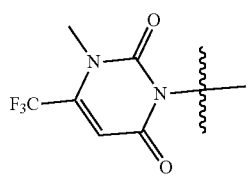 [SMILES: *n1c(=O)cc(C(F)(F)F)n(C)c1=O] |
| 540 | CH | 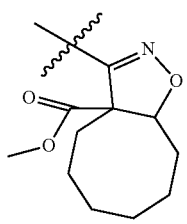 [SMILES: *C1=NOC2CCCCCCC12C(=O)OC] | Cl | F | 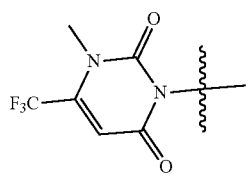 [SMILES: *n1c(=O)cc(C(F)(F)F)n(C)c1=O] |
| 541 | CH | 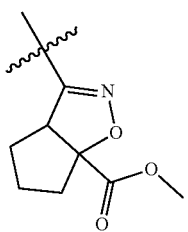 [SMILES: *C1=NOC2(C(=O)OC)CCCC12] | Cl | F | 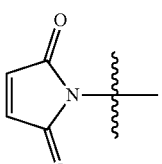 |
| 542 | CH | 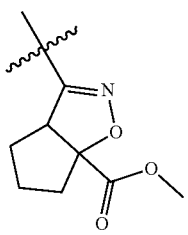 [SMILES: *C1=NOC2(C(=O)OC)CCCC12] | Cl | F | 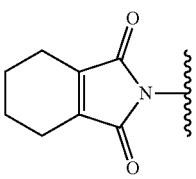 [SMILES: *N1C(=O)C2=C(CCCC2)C1=O] |

-continued

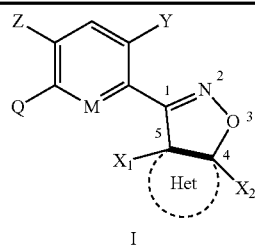

I

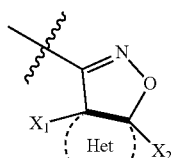

| No. | M | | Y | Z | Q |
|---|---|---|---|---|---|
| 544 | CH | (methyl ester bicyclic isoxazoline) | Cl | F | (3-isopropylidene-2,5-dioxopyrrolidin-1-yl) |
| 545 | CH | (methyl ester bicyclic isoxazoline) | Cl | F | (hexahydro-1,3-dioxoisoindol-2-yl) |
| 546 | CH | (carboxylic acid bicyclic isoxazoline) | Cl | F | (tetrahydro-1,3-dioxoisoindol-2-yl, with one double bond) |
| 547 | CH | (methyl ester bicyclic isoxazoline) | Cl | F | (4-methyl-2,6-dioxopiperidin-1-yl) |
| 551 | CH | (methyl ester bicyclic isoxazoline) | Cl | F | (1-methyl-2,4-dioxo-1,2,3,4-tetrahydroquinazolin-3-yl) |

-continued
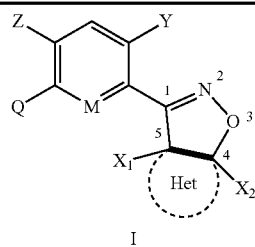
I
| No. | M | 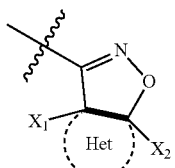 | Y | Z | Q |
|---|---|---|---|---|---|
| 552 | CH | 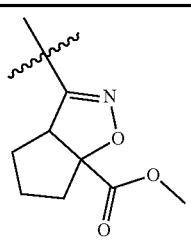 | Cl | F | 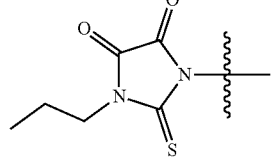 |
| 553 | CH | 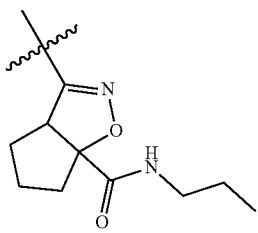 [SMILES: *C1=NOC2(C(=O)NCCC)CCCC12] | Cl | F | 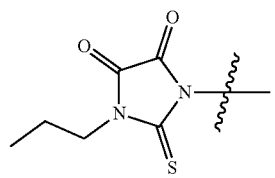 [SMILES: *N1C(=O)C(=O)N(CCC)C1=S] |
| 561 | CH | 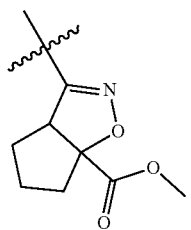 [SMILES: *C1=NOC2(C(=O)OC)CCCC12] | Cl | F | 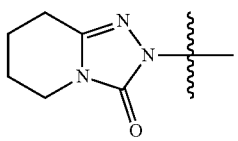 [SMILES: *n1nc2n(c1=O)CCCC2] |
| 574 | CH | 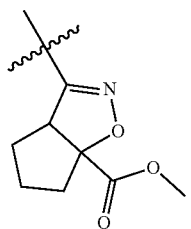 [SMILES: *C1=NOC2(C(=O)OC)CCCC12] | Cl | F | 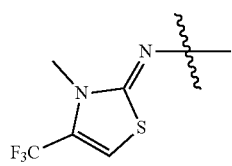 |
| 575 | CH | 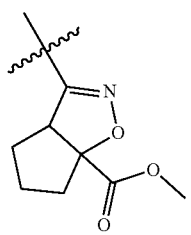 [SMILES: *C1=NOC2(C(=O)OC)CCCC12] | Cl | F | 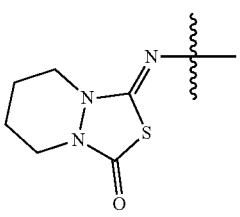 [SMILES: */N=c1\sc(=O)n2n1CCCC2] |

-continued
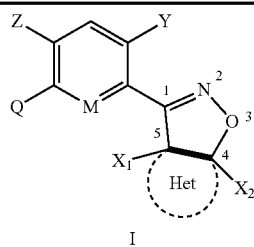
I
| No. | M | | Y | Z | Q |
|---|---|---|---|---|---|
| 577 | CH | 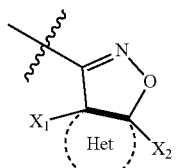 | Cl | F | 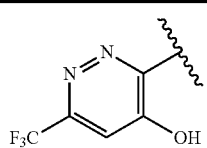 |
| 578 | CH | 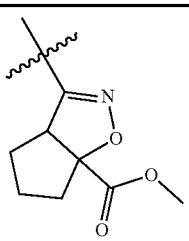 | Cl | F | 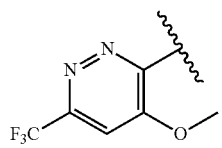 |
| 579 | CH | 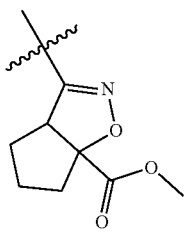 [SMILES: *C1=NOC2(C(=O)OC)CCCC12] | Cl | F | 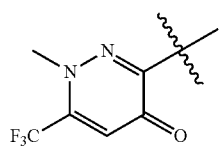 |
| 584 | CH | 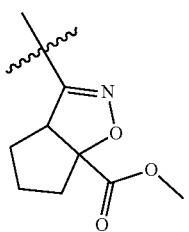 [SMILES: *C1=NOC2(C(=O)OC)CCCC12] | Cl | F | 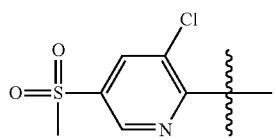 [SMILES: *c1ncc(S(C)(=O)=O)cc1Cl] |
| 585 | CH | 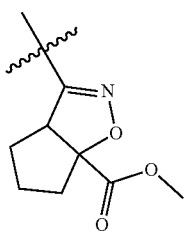 [SMILES: *C1=NOC2(C(=O)OC)CCCC12] | Cl | F | 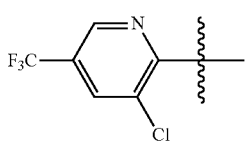 [SMILES: *c1ncc(C(F)(F)F)cc1Cl] |

-continued
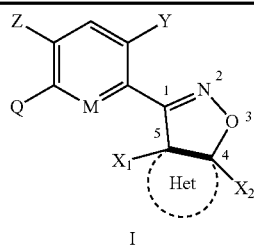
I
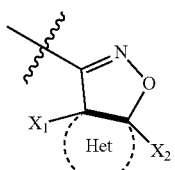
| No. | M | | Y | Z | Q |
|---|---|---|---|---|---|
| 586 | CH | 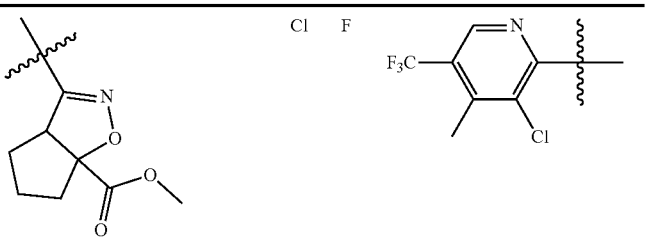 | Cl | F | |
| 588 | CH | 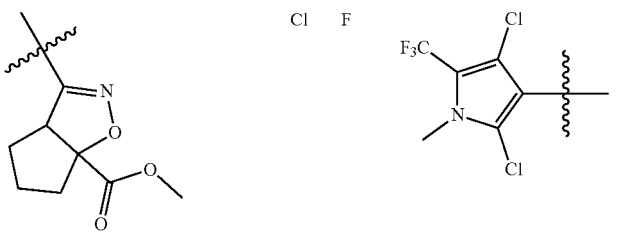 | Cl | F | |
| 589 | CH | 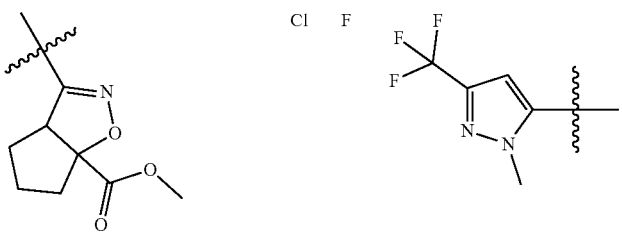 | Cl | F | |
| 590 | CH | 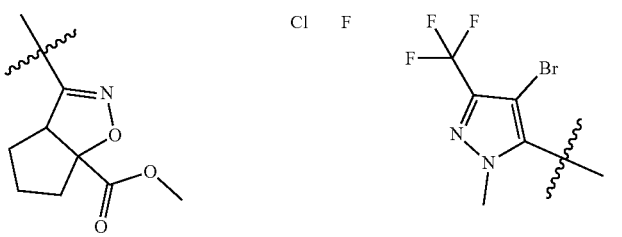 | Cl | F | |
| 596 | CH | 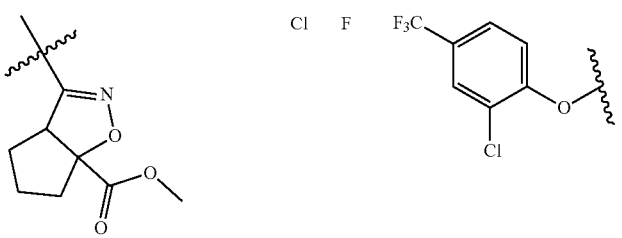 | Cl | F | |

-continued

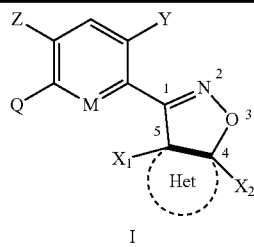

I

| No. | M | 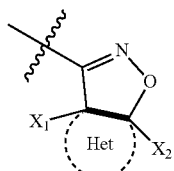 | Y | Z | Q |
|---|---|---|---|---|---|
| 597 | CH | 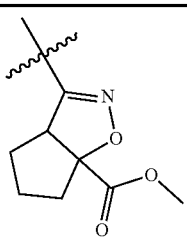 | Cl | F | ![Q structure] |

11. The herbicidal composition of claim 8, wherein the herbicidal composition also comprises a preparation auxiliary.

12. A method for controlling a weed which includes applying a herbicidally effective dose of at least one of the herbicidal composition according to claim 8 to a plant or a weed area.

13. A method for preventing and/or controlling a weed in a useful crop comprising applying at least one of the fused-ring substituted aromatic compound according to claim 1.

14. A method for preventing and/or controlling a weed in a useful crop comprising applying at least one of the herbicidal composition according to claim 8.

15. The method of claim 13, wherein the useful crop is a transgenic crop or a crop treated by gene editing technique.

16. The method of claim 14, wherein the useful crop is a transgenic crop or a crop treated by gene editing technique.

* * * * *